US012006350B2

(12) United States Patent
Ulery et al.

(10) Patent No.: US 12,006,350 B2

(45) Date of Patent: Jun. 11, 2024

(54) TRIBLOCK PEPTIDE AMPHIPHILES, MICELLES AND METHODS OF USE

(71) Applicants: Bret Ulery, Columbia, MO (US); Rui Zhang, Columbia, MO (US); Caitlin Leeper, Columbia, MO (US); Josiah Smith, Columbia, MO (US); Logan Morton, Columbia, MO (US)

(72) Inventors: Bret Ulery, Columbia, MO (US); Rui Zhang, Columbia, MO (US); Caitlin Leeper, Columbia, MO (US); Josiah Smith, Columbia, MO (US); Logan Morton, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/760,329

(22) PCT Filed: Oct. 30, 2018

(86) PCT No.: PCT/US2018/058200

§ 371 (c)(1),
(2) Date: Apr. 29, 2020

(87) PCT Pub. No.: WO2019/089584

PCT Pub. Date: May 9, 2019

(65) Prior Publication Data

US 2020/0339661 A1 Oct. 29, 2020

Related U.S. Application Data

(60) Provisional application No. 62/578,843, filed on Oct. 30, 2017.

(51) Int. Cl.

| | |
|---|---|
| ***C07K 14/77*** | (2006.01) |
| ***A61P 29/00*** | (2006.01) |
| ***A61P 31/16*** | (2006.01) |
| ***C07K 14/575*** | (2006.01) |
| *A61K 38/00* | (2006.01) |

(52) U.S. Cl.

CPC .............. *C07K 14/77* (2013.01); *A61P 29/00* (2018.01); *A61P 31/16* (2018.01); *C07K 14/57563* (2013.01); *A61K 38/00* (2013.01)

(58) Field of Classification Search

CPC .............. C07K 14/77; C07K 14/57563; C07K 14/001; A61P 29/00; A61P 31/16; A61K 38/00

See application file for complete search history.

(56) References Cited

U.S. PATENT DOCUMENTS 7,371,719 B2 * 5/2008 Stupp .................... C07K 14/78 424/1.65
7,683,025 B2 3/2010 Stupp et al.

FOREIGN PATENT DOCUMENTS

WO WO 03-070749 A2 8/2003
WO WO 2017-139746 A1 8/2017

OTHER PUBLICATIONS

Black et al (Advanced Materials, 2012, 24, 3845-3849) (Year: 2012).*
Tsonchev et al (Nano Letters, 2004, vol. 4, No. 3, 427-431) (Year: 2004).*
Arnold et al (Langmuir, 2005, 21, 4705-4709) (Year: 2005).*
Ye et al (ACS Applied Materials & Interfaces, 2015, 7, 22448-22457) (Year: 2015).*
Nowinski et al (J.Am.Chem.Soc., 2012, 134, 6000-6006) (Year: 2012).*
Zheng et al (Polymer Degradation and Stability, 2017, 139, 1-19) (Year: 2017).*
Lui, Y., et al., "Triblock Peptide-Linker-Lipid Molecular Design Improves Potency of Peptide Ligands Targeting Family B G Protein-coupled Receptors", Chemical Communications, 2015, vol. 51, No. 28, pp. 6157-6160 (4 pgs).
Pinchuck, P., et al., "Antigenicity of Polypeptides (poly alpha amino acids): XVI. Genetic control of immunogenicity of synthetic polypeptides in mice", Journal of Experimental Medicine, 1965, vol. 122, No. 4, pp. 673-679 (7 pgs).
Zhang, R., et al., "Vaccine Adjuvant Incorporation Strategy Dictates Peptide Amphiphile Micelle Immunostimulatory Capacity", The AAPS Journal, Jun. 1, 2018 (published online), vol. 20, Article No. 73, pp. 1-10 (10 pgs).
Zhang, R., et al., "Instructive Design of Triblock Peptide Amphiphiles for Structurally Complex Micelle Fabrication", ACS Biomaterials Science & Engineering, Apr. 24, 2018, vol. 4 (10 pgs).
International Search Report and Written Opinion dated May 3, 2019 in related PCT application, PCT/US2018/058200 (12 pgs).

* cited by examiner

*Primary Examiner* — Sudhakar Katakam
(74) *Attorney, Agent, or Firm* — Stinson LLP

(57) ABSTRACT

One aspect of the present invention is directed to triblock peptides comprising a lipid moiety, a peptide block and a zwitterion-like block. Another aspect of the invention is directed to pharmaceutical compositions comprising the triblock peptides of the present in invention arranged in micelles in a pharmaceutically acceptable carrier. In certain embodiments, the pharmaceutical compositions of the present invention are vaccine compositions, which may further comprise an adjuvant. Another aspect of the invention is directed to methods of using the triblock peptides and compositions of the invention to treat a disease or condition.

34 Claims, 66 Drawing Sheets

Specification includes a Sequence Listing.

PalmK:

$Palm_2K$:

$A_1 B_1 C$: PalmK-$OVA_{BT}$-$(KE)_4$ $A_1 B_2 C$: PalmK-$OVA_{CytoT}$-$(KE)_4$ $A_1 C B_1$: PalmK-$(EK)_4$-$OVA_{BT}$ $A_1 C B_2$: PalmK-$(EK)_4$-$OVA_{CytoT}$ $A_2 B_1 C$: $Palm_2K$-$OVA_{BT}$-$(KE)_4$ $A_2 B_2 C$: $Palm_2K$-$OVA_{CytoT}$-$(KE)_4$ $A_2 C B_1$: $Palm_2K$-$(EK)_4$-$OVA_{BT}$ $A_2 C B_2$: $Palm_2K$-$(EK)_4$-$OVA_{CytoT}$

| | pH=2 | pH=7 | pH=11 |
|---|---|---|---|
| α-Helix | 15.0% | 0.0% | 0.0% |
| β-Sheet | 27.7% | 100.0% | 100.0% |
| Random Coil | 57.3% | 0.0% | 0.0% |

| | pH=2 | pH=3 | pH=7 | pH=11 | pH=12 |
|---|---|---|---|---|---|
| α-helix | 15.0% | 1.4% | 0.0% | 0.0% | 0.0% |
| β-sheet | 27.7% | 54.7% | 100.0% | 100.0% | 100.0% |
| Random Coil | 57.3% | 43.9% | 0.0% | 0.0% | 0.0% |

e

| | pH=3 | pH=7 | pH=11 |
|---|---|---|---|
| α-Helix | 29.9% | 5.8% | 21.6% |
| β-Sheet | 41.9% | 94.2% | 33.4% |
| Randon Coil | 28.2% | 0.0% | 45.0% |

b

| | pH=3 | pH=7 | pH=11 |
|---|---|---|---|
| α-Helix | 0.0% | 0.0% | 0.0% |
| β-Sheet | 86.3% | 91.4% | 83.4% |
| Random Coil | 13.7% | 8.6% | 16.7% |

| | pH=3 | pH=7 | pH=11 |
|---|---|---|---|
| α-helix | 29.9% | 5.8% | 21.6% |
| β-sheet | 41.9% | 94.2% | 33.40% |
| Random Coil | 28.2% | 0.0% | 45% |

(a) pVIPA: HSDAVFTDNYTRLRKQMAVKKYLNSILN 0.2 μm

| | VIP | pVIPA | pzVIPA |
|---|---|---|---|
| α - Helix | 0.1% | 0.0% | 25.2% |
| β - Sheet | 50.1% | 73.6% | 38.9% |
| Random Coil | 49.7% | 26.4% | 36.0% |

TRIBLOCK PEPTIDE AMPHIPHILES, MICELLES AND METHODS OF USE

CROSS-REFERENCE TO RELATED APPLICATIONS

This application is based on and claims priority to U.S. Provisional Application Ser. No. 62/578,843 filed on Oct. 30, 2017 and PCT Application PCT/US2018/058200 filed on Oct. 30, 2018, which are hereby incorporated herein by reference.

STATEMENT REGARDING FEDERALLY SPONSORED RESEARCH OR DEVELOPMENT

This invention was made with government support under grant number W81XWH-17-1-0596 awarded by the U.S. Army/MRMC. The government has certain rights in the invention.

INCORPORATION OF SEQUENCE LISTING

A paper copy of the Sequence Listing and a computer readable form of the Sequence Listing containing the file named "0800528.011601 Sequence Listing ST25," which is 20,706 bytes in size (as measured in MICROSOFT WINDOWS® EXPLORER) and was created on Apr. 29, 2022, are provided herein and are herein incorporated by reference. This Sequence Listing consists of SEQ ID NOs: 1-89.

FIELD OF THE INVENTION

The present disclosure relates to pharmaceutical compositions, such as vaccines and immunomodulatory therapies, comprising a triblock peptide and methods of use.

BACKGROUND OF THE INVENTION

Taking inspiration from biomolecules, specifically proteins, biomolecular materials have emerged as a promising bio-materials subfield. Peptide amphiphiles are diblock materials comprised of a hydrophilic peptide tethered to a hydrophobic lipid which self-assemble into micelles in water. These peptide amphiphile micelles (PAMs) possess several advantageous properties over peptides alone including increasing local concentration, preventing dissemination, and enhancing cellular interactions. These desirable characteristics have led to PAMs being studied as therapeutic systems for a variety of biomedical applications including regenerative medicine, cancer therapy, and vaccination. It is believed that micellar physical properties, such as size, shape, and surface charge significantly affect their bioactivity.

Over the past two decades, the fundamental thermodynamic principles that govern micelle formation have been characterized. This work has yielded useful tools like the critical packing parameter which can be utilized to predict first-order micellar structures making it much easier to create simple geometries such as spheres and cylinders. While useful, simple micelles are quite limited in their adaptability, functionality, and stability, which has prompted further research into the development of more architecturally complex micellar structures. Recently, twisted and helical micelles have been fabricated demonstrating the feasibility of accessing new structural domains. Understanding the structure—function relationships that govern these novel architectures would allow for the rational design of novel PAM systems capable of carrying out a variety of complex tasks.

Most commercial vaccines are whole-pathogen vaccines, which have some disadvantages. For example, there can be safety issues related to reversion to virulence and autoimmune diseases. In addition, production of whole-pathogen vaccines is complicated, including cell and pathogen culture, toxicity reduction, and purification. The vaccines require refrigerated or frozen storage.

BRIEF SUMMARY OF THE INVENTION

One aspect of the present disclosure is directed to a triblock peptide. The triblock peptide is of the formula:

A-B-C wherein A is a lipid moiety; and B and C are independently a peptide block or a zwitterion-like block.

Another aspect of the present disclosure is directed to a pharmaceutical composition. The pharmaceutical composition comprises a triblock peptide of the formula:

A-B-C wherein A is a lipid moiety; and B and C are independently a peptide block or a zwitterion-like block. The triblock peptides may be arranged in micelles in a pharmaceutically acceptable carrier. The pharmaceutical composition may be a vaccine composition, which optionally may additionally comprise an adjuvant.

An additional aspect of the present disclosure is directed to a method of treating a disease or condition in a subject. The method comprises administering a therapeutically effective amount of a triblock peptide to the subject, wherein the triblock peptide is of the formula:

A-B-C wherein A is a lipid moiety; and B and C are independently a peptide block or a zwitterion-like block. The triblock peptides may be arranged in micelles in a pharmaceutically acceptable carrier. The pharmaceutical composition may be a vaccine composition, which optionally may additionally comprise an adjuvant.

Other aspects and features of the present disclosure will be in part apparent and in part pointed out hereinafter.

DETAILED DESCRIPTION OF PREFERRED EMBODIMENT

One aspect of the present invention is directed to triblock peptides comprising a lipid moiety, a peptide block and a zwitterion-like block. The peptides of the invention are useful in forming micelles. It has been found that adding a zwitterion-like block to a peptide-lipid amphiphile provides benefits over use of the peptide-lipid amphiphiles alone.

Another aspect of the invention is directed to pharmaceutical compositions comprising the triblock peptides of the present in invention arranged in micelles in a pharmaceutically acceptable carrier. The physical properties, such as size, shape and charge of the resulting micelles may be modified by the selection and order of the lipid, peptide and zwitterion-like components of the triblock peptide. These properties are closely related to micelle immunogenicity. In certain embodiments, the pharmaceutical compositions of the present invention are vaccine compositions. The peptide block of the vaccine may comprise the immunogenic peptide epitope of the target pathogen. The vaccine compositions may further comprise an adjuvant, which may be carried by the vaccine micelles.

Another aspect of the invention is directed to methods of using the triblock peptides, pharmaceutical compositions and vaccine compositions of the present invention to treat a disease or condition in a subject.

I. Triblock Peptide

In an aspect, the present disclosure is directed to a triblock peptide of the formula:

A-B-C wherein:

A is a lipid moiety; and

B and C are independently a peptide block or a zwitterion-like block.

Figure 1:
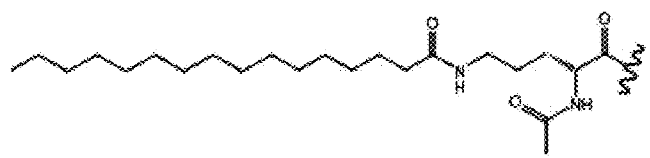
FIG. 1 depicts exemplary ABC triblock peptide amphiphiles of the present invention and exemplary lipids and zwitterion-like blocks.
Figure 1:
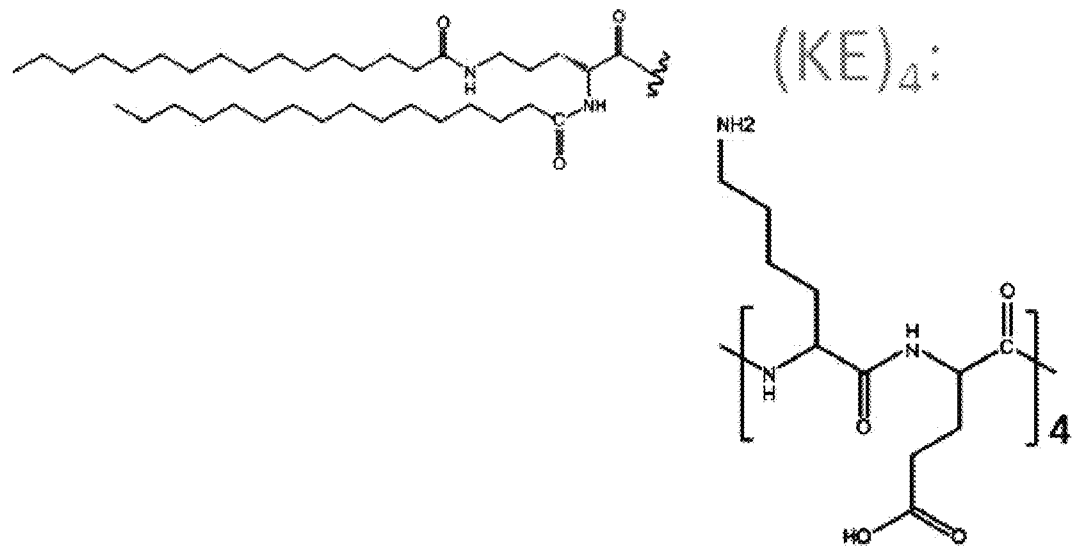

The unique ABC triblock peptides of the present invention are capable of forming complex nanostructures. As noted above, this is an improvement over traditional peptide amphiphiles that do not include a zwitterion-like block. These complex nanostructures are discussed in more detail in section II(A), below. Exemplary triblock peptides of the present invention are depicted in FIG. 1, along with exemplary lipids and zwitterion-like blocks.

In some embodiments, the lipid moiety may be a $C_2$-$C_{38}$ saturated fatty acid, for example, $C_2$, $C_4$, $C_6$, $C_8$, $C_{10}$, $C_{12}$, $C_{14}$, $C_{16}$, $C_{18}$, $C_{20}$, $C_{22}$, $C_{24}$, $C_{26}$, $C_{28}$, $C_{30}$, $C_{32}$, $C_{34}$, $C_{36}$, and $C_{38}$ any number or range of carbon atoms there between. In some embodiments, the lipid moiety may include linkers (e.g., lysine, glutamic acid, aspartic acid, citric acid, and glycerol) that allow for the attachment of one or two fatty acids, or even more, such as three, four, or any number up to eight fatty acids. Suitable lipid moieties include, without limit, acetic acid, propionic acid, butyric acid, valeric acid, caproic acid, enanthic acid, caprylic acid, pelargonic acid, capric acid, undecylic acid, lauric acid, tridecylic acid, myristic acid, pentadecanoic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatricontanoic acid, and their combinations. In certain embodiments discussed herein, the lipid moiety may be palmitic acid.

The lipid moiety may also be a $C_2$-$C_{38}$ unsaturated fatty acid, as discussed above with respect to saturated fatty acids, containing at least one carbon-carbon cis or trans double bond, for example $C_{18:3}$, $C_{18:4}$, $C_{20:5}$, $C_{22:6}$, $C_{18:2}$, $C_{20:3}$, $C_{20:4}$, $C_{22:4}$, $C_{16:1}$, $C_{18:1}$, $C_{20:1}$, $C_{22:1}$, and $C_{24:1}$. Similar to saturated fatty acids, the lipid moiety can consist of one to eight unsaturated fatty acids held together by suitable linker molecules. Suitable lipid moieties include, without limit, α-linolenic acid, stearidonic acid, eicosapentaenoic acid, docosahexaenoic acid, linoleic acid, linolelaidic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, mead acid, and their combinations. The lipid moiety can also be a bioactive lipid containing anywhere from one to eight saturated and/or unsaturated fatty acids ($C_2$-$C_{38}$, as discussed above with respect to saturated fatty acids), linked together. Suitable bioactive lipid moieties include, without limit, valproic acid, monophosphoryl lipid A (MPLA) and its analogs, dipalmityolcysteinylserinyltetralysine ($P_2CSK_4$), squalamine and its analogs, squalene and its analogs, leukotriene $B_4$, prostaglandin $E_2$, thromboxane $A_2$, prostacyclin $I_2$, phosphatidylserine, phosphatidylinositol, lysophosphatidic acid, sphingosine-1-phosphate, N-arachidonylethanolamine, 2-arachidonylglycerol, N-palmitoylethanolamine, eicosapentaenoic acid, lipoxin A4, docosahexaenoic acid, resolvin E1, resolvin D1, and maresin 1.

In some embodiments, the peptide block may be a peptide comprised of anywhere from one to fifty amino acids in length. In some embodiments, the lipid moiety may include linkers (e.g., lysine, glutamic acid, aspartic acid, citric acid, and glycerol) that allow for the attachment of one or two peptides, or even more, such as three, four, or any number up to eight peptides. In certain embodiments, the resulting peptide block may range from 75 g/mol to 80,000 g/mol in molecular weight. As used herein, the term peptide refers to one or more linked amino acids, which may comprise, without limit, a portion of a protein, a peptide epitope or a complete protein.

In certain embodiments, the peptide block comprises a peptide to treat or target a disease or condition. In some such embodiments, the peptide block comprises an immunogenic peptide epitope which can be used to produce micelle vaccines. Another embodiment includes a peptide comprised of an immunoactive peptide which can be used to make immunomodulatory micelles. Such vaccines and immunotherapeutics would be safe, cost and time effective, stable at room temperature and have low immugenicity. Other suitable peptides may include peptides to target and/or attack cancer cells (anti-cancer peptides).

Suitable peptide blocks include, without limit, ovalbumin and vasoactive intestinal peptide, for example $OVA_{BT}$ (ESLKISQAVHAAHAEINEAGRE) (SEQ ID NO: 1), $OVA_{CytoT}$ (EQLESIINFEKLTE) (SEQ ID NO: 2), as well as the immunogenic peptides, immunoactive peptides and anticancer peptides set forth in Tables 1, 2 and 3, below.

TABLE 1

Peptides for Vaccine Applications

| Name | Sequence | Reference (DOI) |
|---|---|---|
| TB10.4 | IMYNYPAM | 10.1038/s41598-018-31089-y |
| ESAT6 | QQWNFAGI | 10.1038/s41598-018-31089-y |
| Ag85B | FQDAYNAAGGHNAVF | 10.1038/s41598-018-31089-y |
| malaria peptide antigen | NANPNANPNANP | doi.org/10.1016/j.biomaterials.2012.05.041 |

TABLE 2

Peptides for Immune Regulation Applications

| Name | Sequence | Reference (DOI) |
|---|---|---|
| myelin oligodendrocyte glycoprotein Peptide | MEVGWYRSPFSRVVHLYRNGK | 10.1021/acsnano.6b04001 |
| Vasoactive Intestinal Peptide | HSDAVFTDNYTRLRKQMAVKKYLNSILN | 10.1039/c8bm00466h |
| TNF-alpha antigen | SSQNSSDKPVAHVVANHQVE | 10.1016/j.biomaterials.2017.09.031 |

TABLE 3

| Peptides for Cancer Applications | | |
|---|---|---|
| Name | Sequence | Reference (DOI) |
| MUC1 | (GVTSAPDTRPAPGSTAPPAH)5 | 101158/1940-6207.CAPR-12-0275 |
| Tyrosinase386-406 | FLLHHAFVDSIFEQWLQRHRP | 10.1158/1078-0432.CCR-15-0233 |
| Melan-A/MART151-73 | RNGYRALMDKSLHVGTQCALTRR | 10.1158/1078-0432.CCR-15-0233 |
| gp10044-59 | WNRQLYPEWTEAQRLD | 10.1158/1078-0432.CCR-15-0233 |
| Tyrosinase56-70 | AQNILLSNAPLGPQFP | 10.1158/1078-0432.CCR-15-0233 |
| MAGE-A3281-295 | TSYVKVLEIHMVKISG | 10.1158/1078-0432.CCR-15-0233 |
| MAGE-A1, 2, 3, 6121-134 | LLKYRAREPVTKAE | 10.1158/1078-0432.CCR-15-0233 |
| N/A | KIMDQVQQA | 10.1158/1078-0432.CCR-10-2614 |
| N/A | RLQEDPPAGV | 10.1158/1078-0432.CCR-10-2614 |
| N/A | KLDVGNAEV | 10.1158/1078-0432.CCR-10-2614 |
| N/A | YLMDTSGKV | 10.1158/1078-0432.CCR-10-2614 |
| N/A | ILDDIGHGV | 10.1158/1078-0432.CCR-10-2614 |
| N/A | LLDRFLATV | 10.1158/1078-0432.CCR-10-2614 |
| N/A | FLYDDNQRV | 10.1158/1078-0432.CCR-10-2614 |
| N/A | ALMEQQHYV | 10.1158/1078-0432.CCR-10-2614 |
| N/A | LLIDDKGTIKL | 10.1158/1078-0432.CCR-10-2614 |
| N/A | YLIELIDRV | 10.1158/1078-0432.CCR-10-2614 |
| N/A | NLMEQPIKV | 10.1158/1078-0432.CCR-10-2614 |
| N/A | FLAEDALNTV | 10.1158/1078-0432.CCR-10-2614 |
| NY-ESO-1 | SLLMWITQV | https ://www.iba-lifesciences.com/details/product/6-7013-901 html |
| HER1 | DTCPPLMLYNPTTYQMDVN | 10.7150/thno.14302 |
| HER2 | LHCPALVTYNTDTFESMPN | 10.7150/thno.14302 |
| HER3 | PRCPQPLVYNKLTFQLEPN | 10.7150/thno.14302 |
| HER4 | TQCPQTFVYNPTTFQLEHN | 10.7150/thno.14302 |
| PS1 | MLYNPTTYQMDVN | 10.7150/thno.14302 |
| PS2 | VTYNTDTFESMPN | 10.7150/thno.14302 |
| PS3 | LVYNKLTFQLEPN | 10.7150/thno.14302 |

TABLE 3-continued

| Peptides for Cancer Applications | | |
|---|---|---|
| Name | Sequence | Reference (DOI) |
| PS4 | FVYNPTTFQLEHN | 10 7150/thno.14302 |
| WP1 | DTCPPLMLYNPTTYQM | 10.7150/thno.14302 |
| WP2 | LHCPALVTYNTDTFES | 10 7150/thno.14302 |
| WP3 | PRCPQPLVYNKLTFQL | 10.7150/thno.14302 |
| WP4 | TQCPQTFVYNPTTFQL | 10.7150/thno.14302 |

In some embodiments, the peptides are selected for treatment of influenza. Exemplary peptides include, without limit, the peptides listed below:

Heterogeneous B Cell/Universal Helper T Cell Epitope Amphiphile Micelle Vaccines for Influenza Inhibition and/or Neutralization Cell Targeting Micelles that Also Enhance Micelle-Associated $P_2C$ Adjuvanticity B Cell Targeting Peptide—CD21-Specific P1—RMWPSSTVNLSAGRR (SEQ ID NO: 43)

B Cell Targeting Peptide—CD21-Specific B1—YILIHRN (SEQ ID NO: 44)

Alternative B Cell Targeting Peptide—CD21-Specific P2—PNLDFSPTCSFRFGC (SEQ ID NO: 45)

Alternative B Cell Targeting Peptide—CD21-Specific B2—PTLDPLP (SEQ ID NO: 46)

Alternative B Cell Targeting Peptide—A20-1 BCR—SAKTAVSQRVWLPSHRGGEP (SEQ ID NO: 47)

Alternative B Cell Targeting Peptide—A2036 BCR—EYVNCDNLVGNCVI (SEQ ID NO: 48)

Alternative B Cell Targeting Aptamer—CD19 Aptamer

B Cell Epitope Peptide—$M2_{(1)2-24}$—(M) SLLTEVETPIRNEWGCRCNDS SD (SEQ ID NO: 49)

B Cell Epitope Peptide—$HA2_{1-14(((16)20)23)}$—GLFGAIAGFIENGW (((EG) MIDG) WYG) (SEQ ID NO: 50)

B Cell Epitope Peptide—$NA_{222-230}$—ILRTQSEC (SEQ ID NO: 51)

Alternative B Cell Epitope Peptide—$NP_{147-155}$—TYQRTRALV (SEQ ID NO: 52)

Alternative B Cell Epitope Peptide—$NP_{243-251}$—RESRNPGNA (SEQ ID NO: 53)

Alternative B Cell Epitope Peptide—$HA_{268-84}$—KEFSEVEGRIQDLEKYV (SEQ ID NO: 54)

Universal Helper T Cell Epitope Peptide—$HBsAg_{19-33}$—FFLLTRILTIPQSLD (SEQ ID NO: 55)

Universal Helper T Cell Epitope Peptide—TpD ILMQYIKANSKFIGIPMGLPQSIALSSLMVAQ (SEQ ID NO: 56)

Alternative Helper T Cell Epitope Peptide—PADRE—A(a) KF(X)VAAWTLKAAA(a) (SEQ ID NO: 57)

Alternative Helper T Cell Epitope Peptide—$Pol_{711}$—EKVYLAWVPAHKGIG (SEQ ID NO: 58)

Cytotoxic T Cell Epitope Amphiphile Micelle Vaccines for Clearing Influenza Infected Host Cells DC targeting micelles that also enhance micelle-associated CpG adjuvanticity DC Targeting Peptide—NW—NWYLPWLGTNDW (SEQ ID NO: 59)

DC Targeting Peptide—h11c—ATPEDNGRSFS (SEQ ID NO: 60)

Alternative DC Targeting Peptide—WH—WPRFHSSVFHTH (SEQ ID NO: 61)

Alternative DC Targeting Peptide—TP—TPAFRYS (SEQ ID NO: 62)

Cytotoxic T Cell Epitope Peptide—$PB1_{590-599}$—LVSDGGPNLY (SEQ ID NO: 63)

Cytotoxic T Cell Epitope Peptide—$NP_{3047}$—FYIQMCTEL (SEQ ID NO: 64)

Cytotoxic T Cell Epitope Peptide—$NP_{366-374}$—ASNENMETM (SEQ ID NO: 65)

Cytotoxic T Cell Epitope Peptide—$PA_{224-233}$—SSLENFRAYV (SEQ ID NO: 66)

Alternative T Cell Epitope Peptide—$M1_{58-66}$—GILGFVFTL (SEQ ID NO: 67)

Alternative T Cell Epitope Peptide—$PA_{46-54}$—FMYSDFHFI (SEQ ID NO: 68)

Alternative T Cell Epitope Peptide—$NS1_{122-130}$—AIMDKNIIL (SEQ ID NO: 69)

Anti-Viral Peptide Amphiphile Micelles for Influenza Post-Exposure Treatment

Eepithelial Cell Targeting Micelles that Also Enhance Micelle-Associated Anti-Viral Bioactivity Epithelial Cell Targeting Peptide—Peptide E—SERSMNF (SEQ ID NO: 70)

Epithelial Cell Targeting Peptide—Peptide Y—YGLPHKF (SEQ ID NO: 71)

Alternative Epithelial Cell Targeting Peptide—Peptide G—PSGAARA (SEQ ID NO: 72)

Alternative Epithelial Cell Targeting Peptide—Peptide EPI—THALWHT (SEQ ID NO: 73)

Anti-Viral Peptide—FluPep4—RRKKWLVFFVIFYFFR (SEQ ID NO: 74)

Anti-Viral Peptide—LF C-$Lobe_{553-563}$—NGESSADWAKN (SEQ ID NO: 75)

Anti-Viral Peptide—$PB1_{1-25}$—MDVNPTLLFLKVPAQNAISTTFPYT (SEQ ID NO: 76)

Alternative Anti-Viral Peptide—FluPep3—WLVFFVIFYFFRRRKK (SEQ ID NO: 77)

Alternative Anti-Viral Peptide—LF C-$Lobe_{418-429}$—SKHSSLDCVLRP (SEQ ID NO: 78)

Alternative Anti-Viral Peptide—Derived EB Peptide—RRKKLAVLLALLA (SEQ ID NO: 79)

Alternative Anti-Viral Peptide—Peptide 6—CATCEQIADSQHRSHRQMV (SEQ ID NO: 80)

Immunomodulatory Amphiphile Micelles for Influenza Associated Sequelae Symptom Management Macrophage Targeting Micelles that Also Enhance Micelle-Associated Anti-Inflammatory Bioactivity Macrophage Targeting Peptide—MCP-1—YNFTNRKISVQRLASYRRITSSK (SEQ ID NO: 81)

Macrophage Targeting Peptide—LL-37—LLGDFFRKSKEKIGKEFKRIVQRIKDFLRNLVPRTES (SEQ ID NO: 82)

Alternative Macrophage Targeting Peptide—CD206—CSPGAKVRC (SEQ ID NO: 83)

Alternative Macrophage Targeting Peptide—fMLP—fMLP (SEQ ID NO: 84)

Immunomodulatory Peptide—VIP—HSDAVFTDNYTRLRKQMAVKKYLNSILN (SEQ ID NO: 3)

Immunomodulatory Peptide—AF10847 (IL-1 RANT)—ETPFTWEESNAYYWQPYALPL (SEQ ID NO: 85)

Immunomodulatory Peptide—IDR-1018—VRLIVAVRIWRR (SEQ ID NO: 86)

Alternative Immunomodulatory Peptide—KAF—KAFAKLAARLYRKALARQLGVAA (SEQ ID NO: 87)

Alternative Immunomodulatory Peptide—WP9QY—YCWSQYLCY (SEQ ID NO: 88)

In some embodiments, the peptide blocks may be synthesized using techniques known to those of skill in the art. Such methods include peptide coupling reagents, such as carbodiimides, aminium/uranium and phosphonium salts, solid supports, such as gel-type supports, surface-type supports, and composites, protecting group schemes, such as Boc/Bzl, Fmoc/tBu, benzyloxy-carbonyl, alloc, and regioselective disulfide bond formation, microwave-assisted synthesis, and on- and off-resin cyclization. Such methods may be used in combination with others, such as solid phase synthesis using Fmoc chemistry.

In some embodiments, the zwitterion-like block is generally comprised of a peptide comprised of a combination of positively charged, negatively charged, and neutral amino acids two to fifty amino acids in length that yields some local regions of positive and negative charge that can facilitate complexation. Suitable zwitterion-like blocks may include, without limit, $(\alpha_X\beta_Y\delta_Z)_B$ where α, β, and δ consists of a positively charged amino acid (K-lysine and/or R-arginine), a negatively charge amino acid (E-glutamic acid and/or D-aspartic acid), and a neutral amino acid (G-glycine and/or A-alanine) and X, Y, and Z, can be any number from 0-50, and B can be any number from 0-1.

In some embodiments, the zwitterion-like block may include linkers (e.g., lysine, glutamic acid, aspartic acid, citric acid, and glycerol) that allow for the attachment of one or two zwitterion-like peptides, or even more such as three, four, or any number up to eight zwitterion-like peptides. The resulting zwitterion-like block may range from 200 g/mol to 60,000 g/mol in molecular weight. Suitable zwitterion-like blocks may include, without limit, $(K_XE_YG_Z)_B$, $(K_XG_YE_Z)_B$, $(E_XK_YG_Z)_B$, $(E_XG_YK_Z)_B$, $(G_XK_YE_Z)_B$, $(G_XE_YK_Z)_B$, $(R_XE_YG_Z)_B$, $(R_XG_YE_Z)_B$, $(E_XR_YG_Z)_B$, $(E_XG_YR_Z)_B$, $(G_XR_YE_Z)_B$, $(G_XE_YR_Z)_B$, $(K_XD_YG_Z)_B$, $(K_XG_YD_Z)_B$, $(D_XK_YG_Z)_B$, $(D_XG_YK_Z)_B$, $(G_XK_YD_Z)_B$, $(G_XD_YK_Z)_B$, $(R_XD_YG_Z)_B$, $(R_XG_YD_Z)_B$, $(D_XR_YG_Z)_B$, $(D_XG_YR_Z)_B$, $(G_XR_YD_Z)_B$, $(G_XD_YR_Z)_B$, $(K_XE_YA_Z)_B$, $(K_XA_YE_Z)_B$, $(E_XK_YA_Z)_B$, $(E_XA_YK_Z)_B$, $(A_XK_YE_Z)_B$, $(A_XE_YK_Z)_B$, $(R_XE_YA_Z)_B$, $(R_XA_YE_Z)_B$, $(E_XR_YA_Z)_B$, $(E_XA_YR_Z)_B$, $(A_XR_YE_Z)_B$, $(A_XE_YR_Z)_B$, $(K_XD_YA_Z)_B$, $(K_XA_YD_Z)_B$, $(D_XK_YA_Z)_B$, $(D_XA_YK_Z)_B$, $(A_XK_YD_Z)_B$, $(A_XD_YK_Z)_B$, $(R_XD_YA_Z)_B$, $(R_XA_YD_Z)_B$, $(D_XR_YA_Z)_B$, $(D_XA_YR_Z)_B$, $(A_XR_YD_Z)_B$, and $(A_XD_YR_Z)_B$, for which X, Y, and Z, can be any number from 0-50, and B can be any number from 0-1 that results in a peptide from two to fifty amino acids in length.

In some embodiments, the zwitterion-like blocks may be $(KE)_X$, $(EG)_X$, $(KA)_X$, $(KG)_X$, including wherein X is 4.

In some embodiments, blocks A, B, and C may be arranged lipid-peptide-zwitterion, lipid-zwitterion-peptide, peptide-lipid-zwitterion, peptide-zwitterion-lipid, zwitterion-lipid-peptide, or zwitterion-peptide-lipid. Each of blocks A, B and C may contain complex, multiple component moieties as discussed above.

The peptide block may be synthesized using techniques known to those of skill in the art. In some embodiments, the peptide block may be synthesized using solid phase synthesis using Fmoc chemistry. During the solid phase synthesis, the Fmoc protecting group may be removed using piperidine in dimethylformamide (DMF).

In some embodiments, the peptide block may be modified by orthogonal deprotection with the aid of either Fmoc-Lys(Fmoc)-OH or Fmoc-Lys(Dde)-OH conjugated to the N terminus of the peptides depending on whether single or multiple lipid moiety conjugation is desired. In a further, embodiment, the two lysine chemistries can be used singularly or in multiple combinations to create from one to eight chemical handles on which lipids can be conjugated. Alternatively, a peptide can be initiated with either Fmoc-Lys(Fmoc)-OH or Fmoc-Lys(Dde)-OH on the C terminus for which a single or multiple amino acids can be included to allow from one to eight chemical handles on which peptides can be built. The same approach can be taken for the zwitterion-like block.

II. Pharmaceutical Composition

Another aspect of the present disclosure is directed to a pharmaceutical composition, the composition comprising a triblock peptide of the formula:

A-B-C wherein

A is a lipid moiety; and

B and C are independently a peptide block or a zwitterion-like block; and a pharmaceutically acceptable carrier, including any of the peptides discussed above.

Preferably, the triblock peptides are arranged in a micelle.

A. Micelles

In some embodiments, the triblock peptide may self-assemble into a micelle in the pharmaceutically acceptable carrier or other liquid.

Without being bound by theory, it is believed that electrostatic interactions, hydrogen bonding, hydrophobic/hydrophilic interactions, bioactive ligand matching, and hydrogen bonding influence the formation of complex micellar structures comprising the triblock polymers of the preset invention. Additionally, it is believed that hydrophobic self-assembly facilities individual micelle formation whereas dipole electrostatic interactions govern the association of micelle units into complex architectures.

The unique ABC triblock peptides of the present invention are capable of forming complex nanostructures. These include second-order (i.e., twines) and third-order (i.e., braids) micellar aggregates which are driven by intermolecular electrostatic complexation facilitated by the presence of a zwitterion-like peptide block. These interactions were found to be complementary of hydrophobically driven micellar self-assembly conveyed by the use of a fatty acid-based lipid provided these intramolecular forces were similar in strength. The present invention leverages zwitterion-like peptides and their electrostatic interactions to achieve unique, environmentally sensitive micelle aggregates comprised of a variety of interesting and complex architectures.

The inclusion of a zwitterion-like region has several advantages over comparable systems including their biocompatibility, solubility, and synthetic flexibility. Previous research has shown that zwitterionic materials are quite hydrophilic which can contribute to enhance micelle stability as well as favorable interactions with biological systems. Because of block length and PA location choice, considerable control over micelle size, aggregate shape, peptide secondary structure, and stimuli sensitivity can be achieved. When coupled with the fact that these facets were found to be application-specific peptide independent, triblock PAs have the potential to function as a unique platform technology for use in a wide variety of biomedical subfields.

Electrostatic interactions can act as a complementary driving force to hydrophobic self-assembly facilitating the formation of aggregated micellar structures. Like their polymeric analogs, triblock peptide amphiphiles with carefully selected components are believed to be able to yield a wide array of self-assembled nanostructures in solution. Multiple approaches such as changing block sequence, block ratio, and solvent conditions can possibly further alter their structure similarly to other comparable systems.

In certain embodiments, the individual micelles are spherical, cylindrical, or worm-like. These structures can range from 4 nm in diameter for small spherical micelles to 100 μm in length for worm-like micelles.

In some embodiments, micelles bearing a zwitterion-like block undergo electrostatic complexation yielding higher-order structures bearing complex architectures including, without limit, clusters, twines, braids, and nets. These structures can range from 10 nm in diameter for small cluster aggregates to 100 μm in each dimension for net-like aggregates.

Micelle morphology may be determined using techniques known to those of skill in the art. Such techniques include transmission electron microscopy (TEM). Micelle secondary structure may be determined using techniques known to those of skill in the art. Such techniques include circular dichroism (CD).

In some embodiments, the peptides confined within the micelles may form secondary structures including, without limit, α-helix, β-sheet, triple helix, 3-10 helix, and random coil. Without being bound by theory, it is believed that pH influences such secondary structure formation. At neutral and basic pH conditions, a β-sheet conformation has been observed and at acidic pH conditions, a random coil and some α-helix conformations has been observed for certain formulations.

The inclusion of a bioactive peptide and zwitterion-like block has direct impact on micelle charge. Based on zeta potential measurements, the charge of triblock peptide amphiphile micelles can be from −60 mV to 60 mV.

The critical micelle concentration (CMC) may be determined using techniques known to those of skill in the art. Such methods include 1,6-diphenyl-1,3,5-hexatriene (DPH) fluorescence. In some embodiments, the critical micelle concentration (CMC) may be from about 0.05 μM to about 50 μM. In other embodiments, the critical micelle concentration (CMC) may be about 0.05 μM, about 0.1 μM, about 0.15 μM, about 0.2 μM, about 0.25 μM, about 0.3 μM, about 0.35 μM, about 0.4 μM, about 0.45 μM, about 0.5 μM, about 0.55 μM, about 0.6 μM, about 0.65 μM, about 0.7 μM, about 0.75 μM, about 0.8 μM, about 0.85 μM, about 0.9 μM, about 1.0 μM, about 1.25 μM, about 1.5 μM, about 1.75 μM, about 2.0 μM, about 2.25 μM, about 2.5 μM, about 2.75 μM, about 3.0 μM, about 3.25 μM, about 3.5 μM, about 3.75 μM, about 4.0 μM, about 4.25 μM, about 4.5 μM, about 4.75 μM, about 5.0 μM, about 5.25 μM, about 5.5 μM, about 5.75 μM, about 6.0 μM, about 6.25 μM, about 6.5 μM, about 6.75 μM, about 7.0 μM, about 7.25 μM, about 7.5 μM, about 7.75 μM, about 8.0 μM, about 8.25 μM, about 8.5 μM, about 8.75 μM, about 9.0 μM, about 9.25 μM, about 9.5 μM, about 9.75 μM, about 10.0 μM, about 12.5 μM, about 15 μM, about 17.5 μM, about 20 μM, about 22.5 μM, about 25 μM, about 27.5 μM, about 30 μM, about 32.5 μM, about 35 μM, about 37.5 μM, about 40 μM, about 42.5 μM, about 45 μM, about 47.5 μM, and about 50 μM.

B. Vaccines

In some embodiments, the pharmaceutical composition may be a vaccine composition. The micelles formed from tribock peptides of the invention can be tailored for the vaccine composition. Vaccine size and shape can determine its ability to travel to lymph node and cell uptake ability. Vaccine charge may affect its ability to interact with cells. The morphology and charge of the micelles comprising the triblock peptide of the invention can be modulated to produce morphologies targeted for the intended use. Micelle morphology is discussed in more detail in Section II(A) above and the Examples. Exemplary immunogenic peptides are discussed in Section I, above.

In some embodiments, the vaccine composition may further include a pharmaceutically acceptable excipient such as a suitable adjuvant. Adjuvants can create an antigen depot or display danger signals to the host to generate stronger protection. The micelle vaccines of the present invention can be used in combination with adjuvants to enhance the benefits of the vaccine.

The adjuvant may include, without limit, an analgesic adjuvant, an inorganic compound, a mineral oil, a bacterial product, a delivery system, a cytokine, a food-based oil, a nonbacterial organic compound, an oligonucleotide, or a plant based saponin. In some embodiments, suitable adjuvants may include, without limit, an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, ceramide, monophosphoryl lipid A (MPLA), lipid A derivatives (e.g., of reduced toxicity), 3-O-deacylated MPL [3D-MPL], quit A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, poly(I:C), bioadhesives and mucoadhesives, microparticles, liposomes, polyoxyethylene ether formulations, polyoxyethylene ester formulations, muramyl peptides, squalamine and its derivatives, squalene and its derivatives, or imidazoquinolone compounds (e.g., imiquamod and its homologues). Human immunomodulators suitable for use as adjuvants in the invention include cytokines such as interleukins (e.g., IL-1, IL-2, IL-4, IL-5, IL-6, IL-7, IL-12, etc.), macrophage colony stimulating factor (M-CSF), tumour necrosis factor (TNF), granulocyte, macrophage colony stimulating factor (GM-CSF) may also be used as adjuvants.

Figure 2:
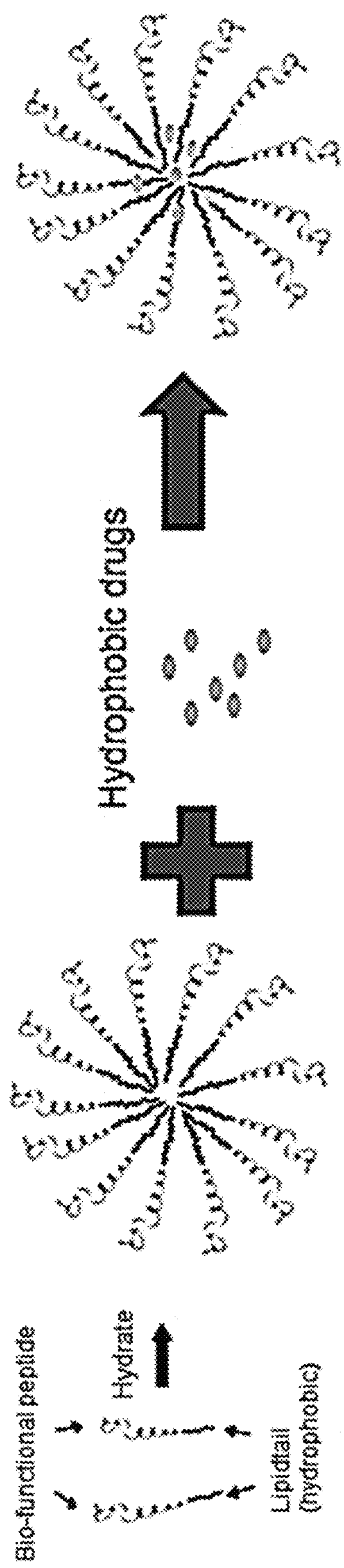
FIG. 2 depicts an exemplary micelle vaccine of the present invention carrying a lipid based adjuvant.
Figure 3:
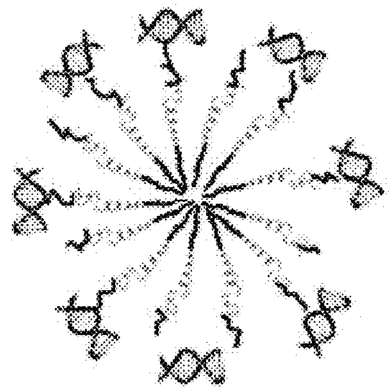
FIG. 3 depicts an exemplary micelle vaccine of the present invention carrying a nucleic acid based adjuvant.
Figure 3:
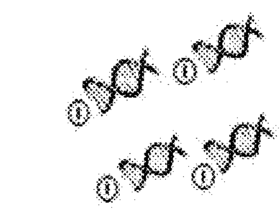
Figure 3:
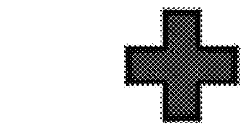
Figure 3:
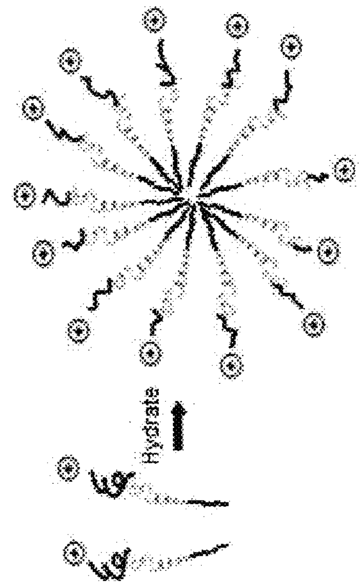

In certain embodiments, the micelle vaccines can be used as an adjuvant delivery vehicle. For example, a lipid based adjuvant, such a ceramide or MPLA, or a nucleic acid based adjuvant, such as CpG-ODN or Poly(I:C) can be carried by the micelle vaccine, as depicted in FIG. 2 and FIG. 3. Any of the lipid based, nucleic acid based, hydrophobic, and charged adjuvants discussed herein can be delivered by the micelle vaccines of the present invention. The adjuvants may be carried by electrostatic interactions.

C. Pharmaceutically Acceptable Carriers

Pharmaceutical compositions of the present invention will typically, in addition to the antigenic and adjuvant components mentioned above, comprise one or more pharmaceutically acceptable carriers or excipients, which include any excipient that does not itself induce the production of antibodies harmful to the individual receiving the composition. Suitable excipients are typically large, slowly metabolised macromolecules such as proteins, saccharides, polylactic acids, polyglycolic acids, polymeric amino acids, amino acid copolymers, sucrose, lactose and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, 20th edition, ISBN: 0683306472.

Compositions of the present disclosure may be lyophilized or in aqueous form, i.e., solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g., 2 doses).

Liquid compositions of the present disclosure are also suitable for reconstituting other compositions from a lyophilized form. Where a composition is to be used for such extemporaneous reconstitution, the invention provides a kit, which may comprise two vials, or may comprise one ready-filled syringe and one vial, with the contents of the syringe being used to reconstitute the contents of the vial prior to injection.

Compositions of the present disclosure may be packaged in unit dose form or in multiple dose form (e.g., 2 doses). For multiple dose forms, vials are preferred to pre-filled syringes. Effective dosage volumes can be routinely established, but a typical human dose of the composition for injection has a volume of 0.5 mL.

In one embodiment, compositions of the present disclosure may have a pH of between about 6.0 and about 8.0, in another embodiment, compositions of the invention have a pH of between 6.3 and 6.9, e.g., 6.6±0.2. Compositions may be buffered at this pH. Stable pH may be maintained by the use of a buffer. If a composition comprises an aluminum hydroxide salt, a histidine buffer may be used. The composition should be sterile and/or pyrogen free.

Compositions of the present disclosure may be isotonic with respect to humans.

Compositions of the present disclosure may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g., present as a preservative in pertussis antigens).

Compositions of the present disclosure may comprise a detergent, e.g., a TWEEN (polysorbate), such as TWEEN 80. Detergents are generally present at low levels e.g. <0.01%.

Compositions of the present disclosure may include sodium salts (e.g., sodium chloride) to give tonicity. The composition may comprise sodium chloride. In one embodiment, the concentration of sodium chloride in the composition of the invention is in the range of 0.1 to 100 mg/mL (e.g., 1-50 mg/mL, 2-20 mg/mL, 5-15 mg/mL) and in a further embodiment the concentration of sodium chloride may be 10±2 mg/mL NaCl e.g. about 9 mg/mL.

Compositions of the present disclosure will generally include a buffer. A phosphate or histidine buffer is typical.

Compositions of the present disclosure may include free phosphate ions in solution (e.g., by the use of a phosphate buffer) in order to favor non-adsorption of antigens. The concentration of free phosphate ions in the composition of the invention is in one embodiment between 0.1 and 10.0 mM, or in another embodiment between 1 and 5 mM, or in a further embodiment about 2.5 mM.

D. Dosage Forms

The pharmaceutical compositions disclosed herein may be formulated into various dosage forms and administered by a number of different means that will deliver a therapeutically effective amount of the antigen or antibody. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980). In a specific embodiment, a composition may be an intramuscular formulation.

Solid dosage forms for oral administration include capsules, tablets, caplets, pills, powders, pellets, and granules. In such solid dosage forms, the active ingredient is ordinarily combined with one or more pharmaceutically acceptable excipients. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfate; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, an antigen or antibody of the invention is encapsulated in a suitable vehicle to either aid in the delivery of the antigen or antibody to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of antigen or antibody in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, antigen may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), phosphatidylethanolamine (PE), and linear polyethylenimine (I-PEI). In a specific embodiment, the liposome may be comprised of linear polyethylenimine (I-PEI). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tetradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3 tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 Daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying antigen or antibody may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

III. Methods

In an additional aspect, the present disclosure is directed to a method a method of treating a disease or condition in a subject. The method comprises administering a therapeutically-effective amount of a triblock peptide to the subject, wherein the triblock peptide is of the formula: A-B-C wherein A is a lipid moiety; and B and C are independently a peptide block or a zwitterion-like block, including any of the peptides discussed above. The triblock peptide is preferably administered in a pharmaceutical composition of the present invention, including any of the pharmaceutical compositions discussed above. The pharmaceutical composition may be a vaccine composition of the present invention, including any of the vaccine compositions discussed above.

A. Administration

In certain aspects, a therapeutically-effective amount of a triblock peptide may be administered to a subject. Administration is performed using standard effective techniques.

B. Disease or Condition

In some embodiments, the disease or condition may be a pathogenic induced disease or condition, cancer or an autoimmune disease or condition. Such autoimmune diseases may include, without limit, rheumatoid arthritis, multiple sclerosis, type 1 diabetes, lupus, celiac disease, crohn's disease, ulcerative colitis, glomerulonephritis, chronic Lyme disease, Addison's disease, psoriasis, and scleroderma.

Without being bound by theory, it is believed that vasoactive intestinal peptide (VIP) has distinct anti-inflammatory effects including downregulating TNF-α by activated antigen presenting cells (APCs), specifically macrophages (MOs) and dendritic cells (DCs).

C. Dosage

Dosages of the triblock peptide can vary between wide limits, depending on the disease or condition to be treated, the age of the subject, and the condition of the subject to be treated.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days, or every 4 days. In a different embodiment, the frequency of dosing may be one, twice, three or four times monthly. For example, a dose may be administered every 1 week, every 2 weeks, every 3 weeks, or every 4 weeks.

D. Subject

As used herein, "subject" refers to, but are not limited to, a human, a livestock animal, a companion animal, a lab animal, and a zoological animal. In another embodiment, the subject may be a livestock animal. In some embodiments, the subject may be a bovine animal, a porcine animal, or a poultry animal. In other embodiments, the subject may be a cow, a pig, or a chicken. Non-limiting examples of suitable livestock animals may include pigs, cows, horses, goats, sheep, llamas, and alpacas. In yet another embodiment, the subject may be a companion animal. Non-limiting examples of companion animals may include pets such as dogs, cats, rabbits, and birds. In yet another embodiment, the subject may be a zoological animal. In an alternative embodiment, the subject may be a human.

The human subject may be of any age. In some embodiments, the human subject may be about 20, about 25, about 30, about 40, about 45, about 50, about 55, about 60, about 65, about 70, about 75, about 80, about 85, about 90, about 95 years of age or older. In some embodiments, the human subject is 30 years of age or older. In other embodiments, the human subject is 40 years of age or older. In other embodiments, the human subject is 45 years of age or older. In yet other embodiments, the human subject is 50 years of age or older. In still other embodiments, the human subject is 55 years of age or older. In other embodiments, the human subject is 60 years of age or older. In yet other embodiments, the human subject is 65 years of age or older. In still other embodiments, the human subject is 70 years of age or older. In other embodiments, the human subject is 75 years of age or older. In still other embodiments, the human subject is 80 years of age or older. In yet other embodiments, the human subject is 85 years of age or older. In still other embodiments, the human subject is 90 years of age or older.

DEFINITIONS

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As various changes could be made in the above-described materials and methods without departing from the scope of the invention, it is intended that all matter contained in the above description and in the examples given below, shall be interpreted as illustrative and not in a limiting sense.

The term "vaccine" as used herein means a composition that when administered to a subject, typically elicits a protective immune response, where a protective immune response is one that ameliorates one or more symptoms of the target disorder.

The terms "treat" or "treating" are meant to mean preventing or delaying an initial or subsequent occurrence of a disease or condition; increasing the disease-free survival time between the disappearance of a disease or condition and its reoccurrence; stabilizing or reducing an adverse symptom associated with a disease or condition; or inhibiting or stabilizing the progression of a disease or condition. This includes prophylactic treatment, in which treatment before the disease or condition is established, prevents or reduces the severity or duration of the disease or condition. In another embodiment, the length of time a patient survives after being diagnosed with a disease or condition and treated using a method of the invention is at least 20, 40, 60, 80, 100, 200, or even 500% greater than (i) the average amount of time an untreated patient survives, or (ii) the average amount of time a patient treated with another therapy survives.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following abbreviations are used throughout the Examples: DIPEA: N,N-diisopropylethylamine; Fmoc: 9-fluorenylmethyloxycarbonyl; HBTU: 2-(1H-benzotriazole-1-yl)-1,1,3,3-tetranethyluronium hexafluorophosphate; HOBt: 1-hydroxybenzotriazole; HPLC: high pressure liquid chromatography; LC-ESI-MS: liquid chromatography-Electro Spray Ionization-mass spectrometry; TFA: trifluoroacetic acid; Trt: Trityl; TIS: Triisopropylsilane; tBu: t-butyl, Pbf: 2,2,4,6,7-pentamethyl-dihydroben-zofurane-5-sulfonyl, Boc: t-Butoxy.

Example 1. Instructive Design of Triblock Peptide Amphiphiles for Structurally Complex Micelle Fabrication Introduction Although triblock peptide amphiphiles with a cationic region have been widely studied for nucleic acid therapeutic delivery, the use of electrostatic interactions for intermolecular attraction within a triblock peptide amphiphile has not previously been reported. Peptide amphiphiles were synthesized with a third region, $(KE)_4$: -Lys-Glu-Lys-Glu-Lys-Glu-Lys-Glu-, (SEQ ID NO: 89) a zwitterion-like peptide capable of participating in electrostatic interactions yielding triblock peptide amphiphiles capable of both hydrophobic and electrostatic interactions.

In this example, two model ovalbumin peptide sequences were explored: $OVA_{BT}$ (ESLKISQAVHAAHAEINEAGRE) (SEQ ID NO: 1), a linked recognition B cell and helper T cell immunogenic epitope, and OVACytoT (EQLESIIN-FEKLTE) (SEQ ID NO: 2), a cytotoxic T cell immunogenic epitope, in order to establish the flexibility of this foundational product for future biomedical applications. These peptides were individually linked to $(KE)_4$ and single or double fatty acid lipids to yield the eight ABC triblock peptide amphiphiles shown in FIG. 1 These materials were synthesized and then self-assembled in water for which their output micellar structures were characterized.

Experimental Section

Peptides were synthesized on Sieber amide resin (Chem-Impex International, SC Wood Dale, IL) by solid phase synthesis on a multiple peptide synthesizer (Advanced ChemTech 396 Omega, Louisville, KY) using Fmoc chemistry. The peptide chain was assembled by sequential acylation (20 minute coupling) with in situ activated Fmoc amino acids. Recoupling was automatically performed at every cycle. Fmoc amino acid activation was carried out using uronium salts (HBTU, 2.7 eq., HOBT 3 equiv) and DIEA (6 equiv). Amino acid side chain protecting groups were tBu (Glu, Ser), Boc (Lys), Trt (Gln, His, Asn), and Pbf (Arg). Fmoc protecting groups were removed at each amino acid addition cycle by treatment with 25% piperidine in dimethylformamide (DMF) for 15 minutes. Palmitic acid (Palm) tail modification was achieved by orthogonal deprotection with the aid of either Fmoc-Lys(Fmoc)-OH or Fmoc-Lys(Dde)-OH conjugated to the N terminus of the peptides depending on whether single or double fatty acid lipid conjugation was desired. Dde was removed by treating the peptide on resin with 2% Hydrazine in DMF. Fmoc-Lys (Fmoc)-OH, Fmoc-Lys(Dde)-OH, and Palm conjugation were conducted manually in a glass reaction vessel (Chemglass, Vineland, NJ). All peptides were cleavage from resin and their side groups deprotected via a single-step reaction consisting of 2 hour exposure to the following mixture: TFA, thioanisole, phenol, water, ethandithiol and triisopropylsilane (87.5:2.5:2.5:2.5:2.5). Precipitation and multiple washing with diethyl ether yielded crude peptide product. All products synthesized were characterized by analytical high-pressure liquid chromatography (HPLC, Beckmann Coulter, Fullerton, CA) and purified by mass spectrometry aided semipreparative high-pressure liquid chromatography (LC-MS) using either a C4 or C18 column (Milford, MA) and in-house optimized solvent gradients (FIG. 31, FIG. 32, FIG. 33, FIG. 34, FIG. 35, FIG. 36, FIG. 37, and FIG. 38). All reagents used were HPLC grade or peptide synthesis grade. TFA, HBTU, and HOBt were obtained from Oakwood Product INC, Estill, SC. The Fmoc amino acid derivatives and Sieber resin were obtained from Chem-Impex International, Wood Dale, IL. Solvents such as piperidine, DIEA, phenol, and triisopropylsilane were purchased from Sigma-Aldrich, St. Louis, MO.

Critical micelle concentration (CMC) was measured indirectly by 1,6-diphenyl-1,3,5-hexatriene (DPH) fluorescence. DPH becomes significantly brighter when trapped within a hydrophobic domain so a rapid change in fluorescence corresponds to the presence of micelles. Peptide amphiphile solutions were serially diluted in 1 μM 1,6-diphenyl-1,3,5 hexatriene (DPH) containing 0.01% THF and allowed to equilibrate for 1 hour prior to fluorescence measurement (ex. 350 nm, em. 428 nm) by a BioTek Cytation 5 fluorospectrophotometer. The resulting data was fit with two trend lines and the fluorescence inflection point was interpreted as the CMC (Table 4 and FIG. 23, FIG. 24, FIG. 25, FIG. 26, FIG. 27, FIG. 28, FIG. 29, and FIG. 30).

TABLE 4

CMC values of all peptide amphiphiles utilized at different pHs. In some groups there was no micelle formation observed at any concentration, so those groups are shown as not available (N/A)

| | pH | | | | | | |
|---|---|---|---|---|---|---|---|
| Unit (μM) | 2 | 3 | 7 | 9 | 11 | 12 | PBS |
| PalmK-$OVA_{BT}$-$(KE)_4$ | 0.33 | 0.27 | 0.25 | 0.41 | 0.19 | 0.26 | 0.22 |
| PalmK-$(EK)_4$-$OVA_{BT}$ | 0.26 | 0.45 | 0.32 | 0.27 | 0.2 | 0.28 | 0.35 |

TABLE 4-continued

CMC values of all peptide amphiphiles utilized at different pHs. In some groups there was no micelle formation observed at any concentration, so those groups are shown as not available (N/A)

| | pH | | | | | | |
|---|---|---|---|---|---|---|---|
| Unit (μM) | 2 | 3 | 7 | 9 | 11 | 12 | PBS |
| $Palm_2K$-$OVA_{BT}$-$(KE)_4$ | 0.31 | 0.33 | 0.21 | 0.2 | 0.21 | 0.35 | 0.27 |
| $Palm_2K$-$(EK)_4$-$OVA_{BT}$ | 0.44 | 0.32 | 0.35 | 0.29 | 0.27 | 0.23 | 0.31 |
| PalmK-$OVA_{cytoT}$-$(KE)_4$ | 0.19 | 0.31 | 0.17 | N/A | N/A | N/A | 0.16 |
| PalmK-$(EK)_4$-$OVA_{cytoT}$ | 0.24 | 0.3 | 0.16 | N/A | N/A | N/A | 0.29 |
| $Palm_2K$-$OVA_{cytoT}$-$(KE)_4$ | 0.45 | 0.17 | 0.21 | 0.28 | N/A | N/A | 0.29 |
| $Palm_2K$-$(EK)_4$-$OVA_{cytoT}$ | 0.33 | 0.2 | 0.3 | N/A | N/A | N/A | 0.28 |

Micelle morphology was assessed by negative stain transmission electron microscopy (TEM). TEM grids (200 mesh) with standard thickness carbon support films were purchased from Electron Microscopy Sciences and glow discharged for 45 seconds (Pelco Easiglow) to impart a negative charge. Product solutions (5 μL) were added to freshly glow-discharged films and incubated for 5 minutes. Filter paper was used to wick away excess solution and 5 μL of nano-tungsten (Nanoprobes, Inc.) was immediately added. After 5 minute of incubation, grids were blotted dried and stored for later use. Samples were imaged with a JEOL JEM-1400 TEM at 120 kV for shape assessment. Tilt series images were collected at 200 kV, spot size 4, gun lens of 5, and extraction voltage of 3950 sA at a nominal 23,000× magnification with an underfocus of 1 sm. Tilt increments were collected every 2 degrees with a tilt range of ±70°, starting at 0°, with the negative half of the tilt series collected using FEI Xplore3D. Frames were aligned using IMOD with the patch-tracking algorithm using the entire imaged area for frame alignment and reconstructed with the weighted back projection algorithm. Micellar diameters were measured using ImageJ software (NIH). Three different spots from each micelle were measured and the results from three separate micelles were averaged for each group.

Micelle secondary structure was investigated by circular dichroism using a circular dichroism spectrometer model 62DS (Aviv Biomedical, Inc., Lakewood, NJ). Micelle solutions (40 μM) were loaded into a 1 mm cuvette and measured a total of 10 times from 190 to 250 nm with an interval of 1 nm. The averaged data was curve fit using a linear combination of polylysine basis structures to calculate approximate α-helix, β-sheet, and random coil content.

Results and Discussion

Figure 4:
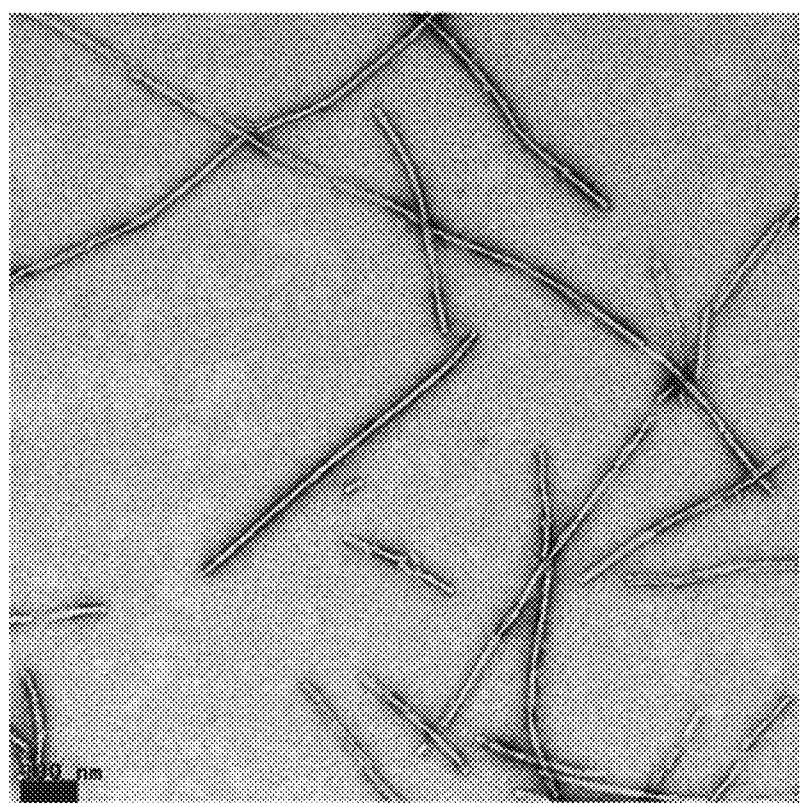
FIG. 4 depicts a micrograph of PalmK-$OVA_{BT}$ peptide amphiphile showing it self-assembles into cylindrical micelles in water.
Figure 5A:
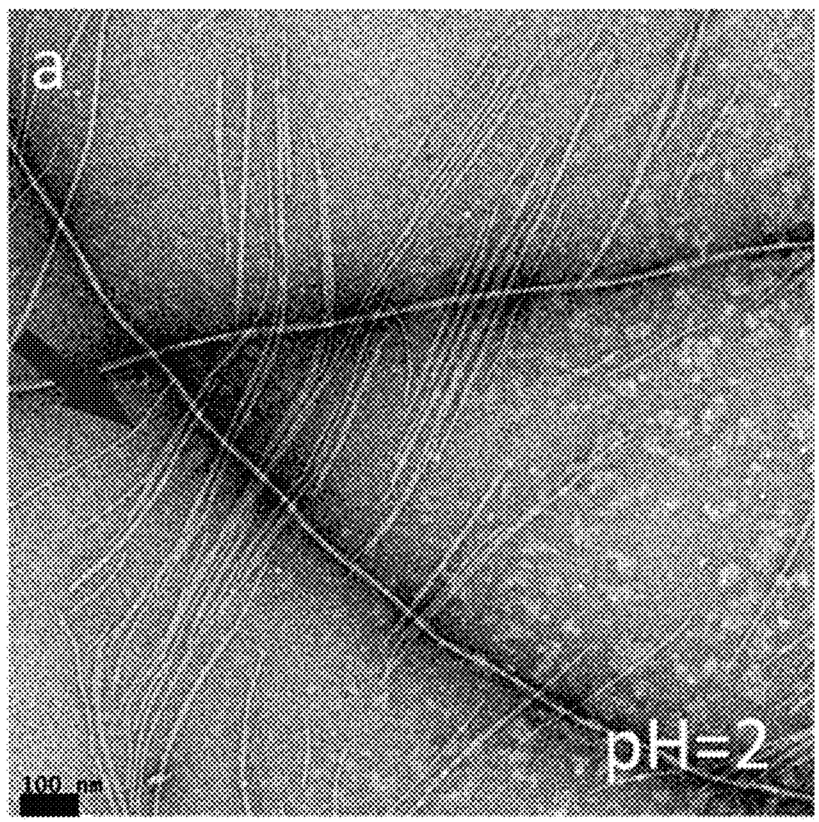
FIG. 5A, FIG. 5B, FIG. 5C, FIG. 5D, and FIG. 5E depict PalmK-$OVA_{BT}$-$(KE)_4$ complex micelle aggregation is pH-dependent. PalmK-$OVA_{BT}$-$(KE)_4$ was solubilized in different pH solutions to investigate the impact of this parameter on micelle formation as assessed by negative stain TEM ((FIG. 5A) 2, (FIG. 5B) 7, and (FIG. 5C) 11). The influence pH had on peptide secondary structure was also evaluated by obtaining (FIG. 5D) the CD spectra and using it to (FIG. 5E) estimate secondary structure.
Figure 5B:
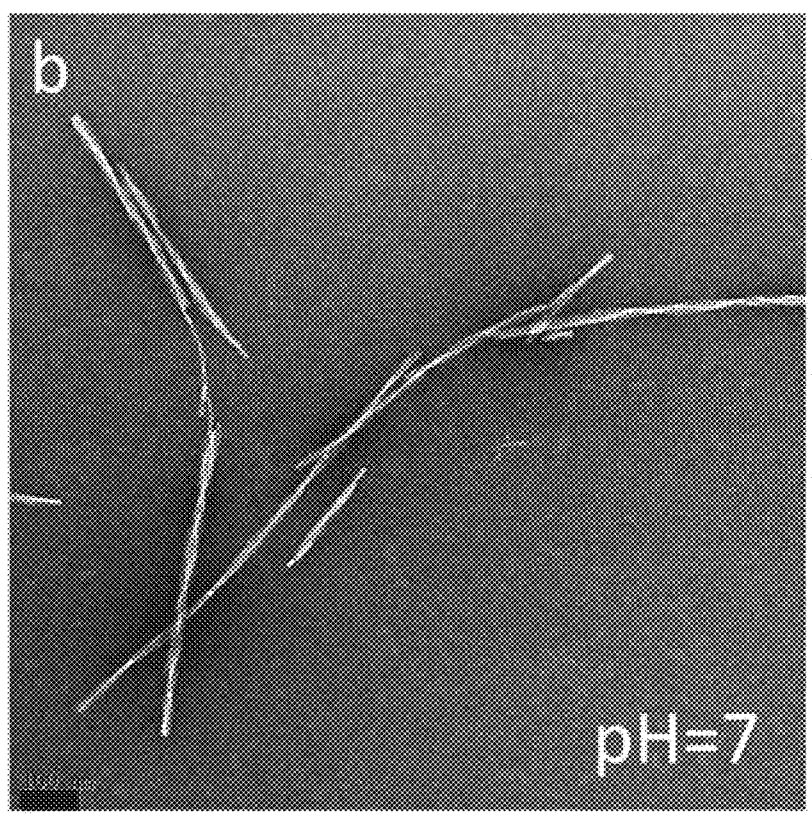
Figure 5C:
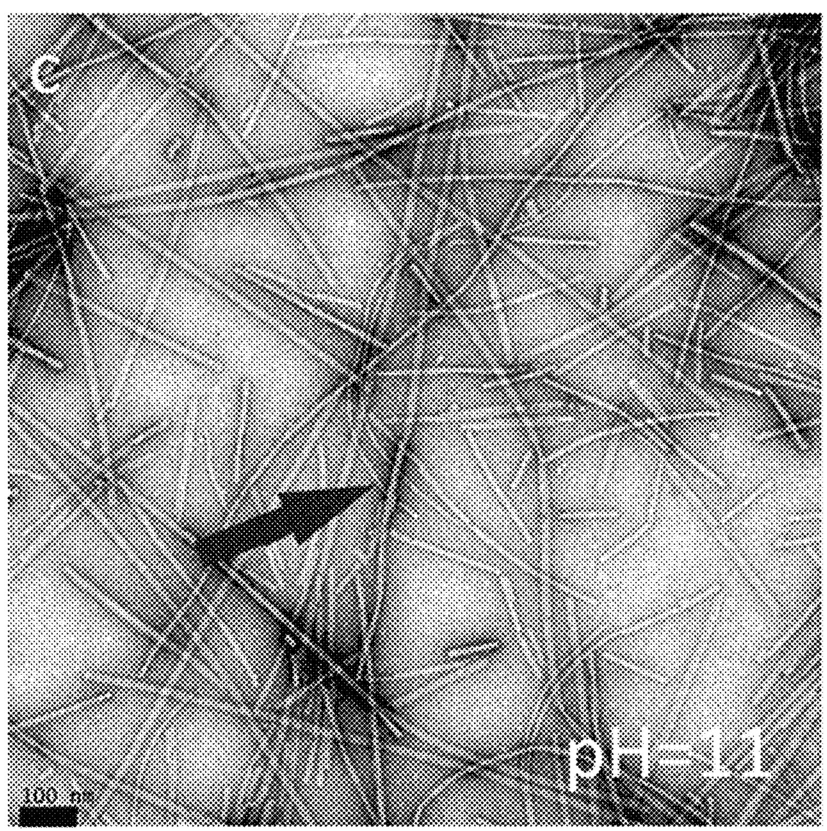
Figures 5D, 5E:
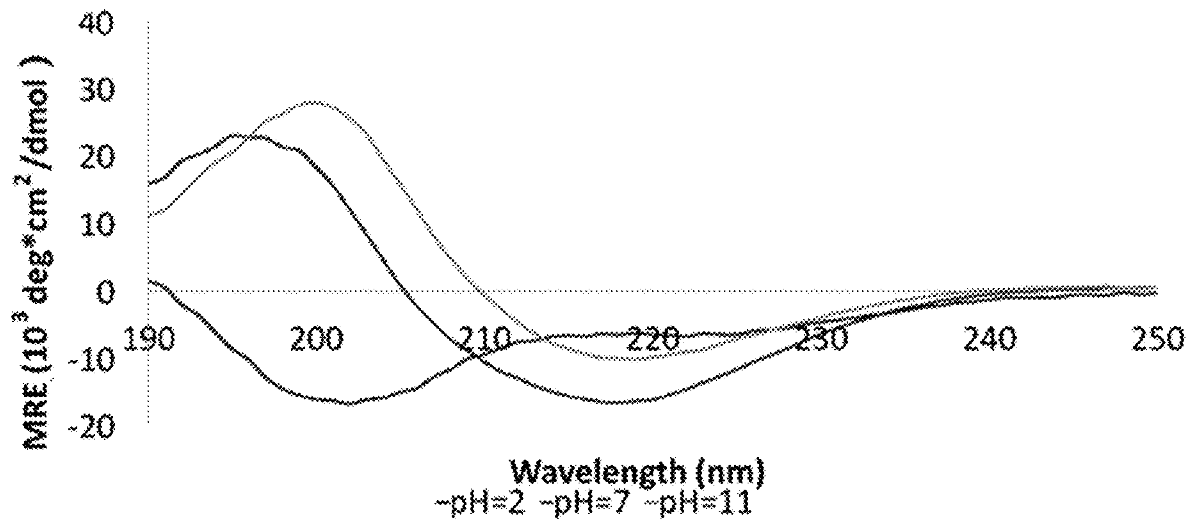
Figure 6A:
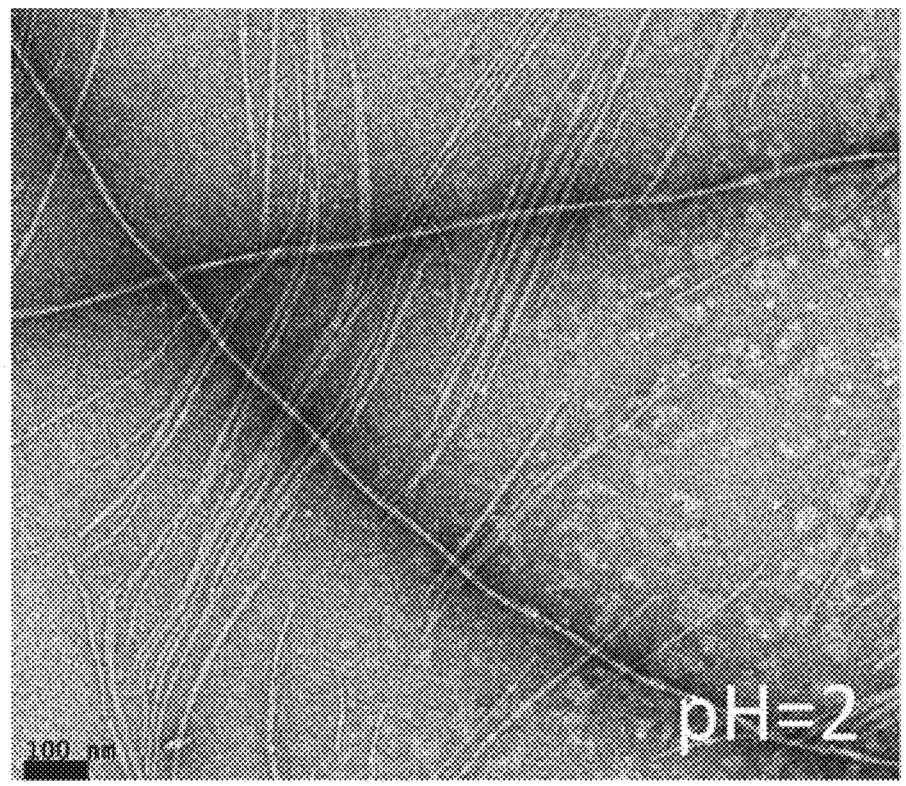
FIG. 6A, FIG. 6B, FIG. 6C, FIG. 6D, FIG. 6E, and FIG. 6F depict micrographs of PalmK-$OVA_{BT}$-$(KE)_4$ at pH=2, 3, 7, 9, 11, and 12, respectively.
Figure 6B:
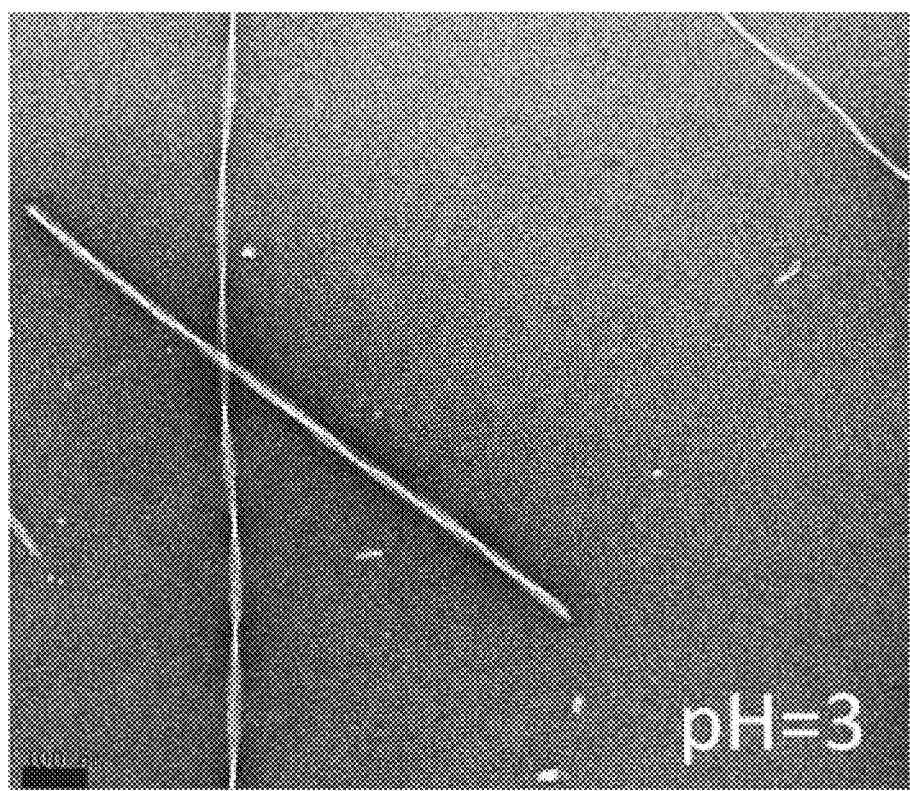
Figure 6C:
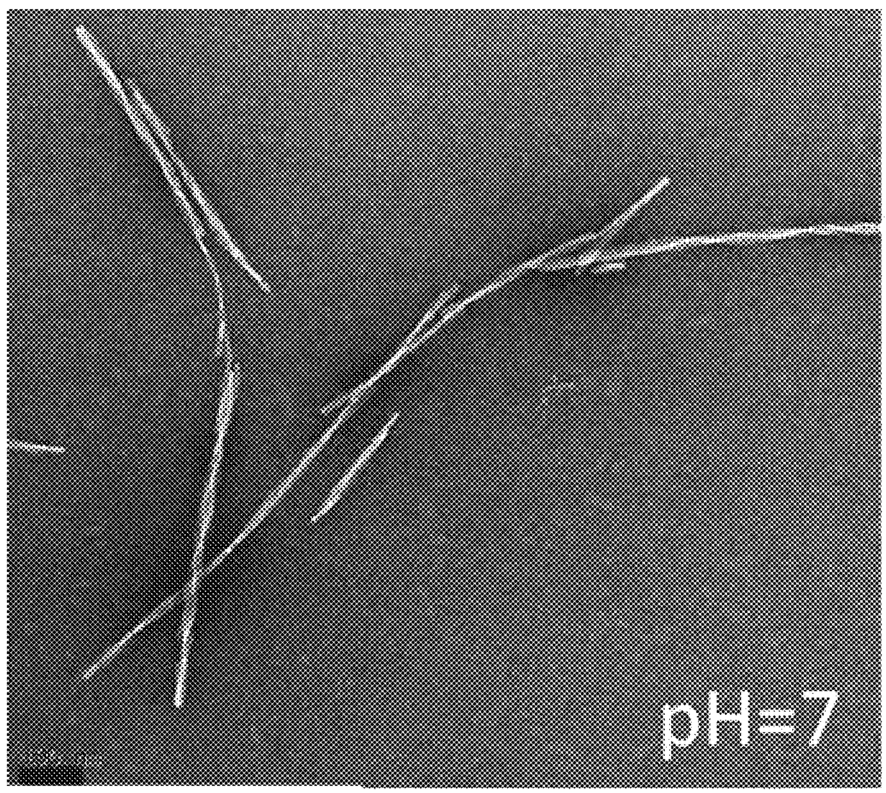
Figure 6D:
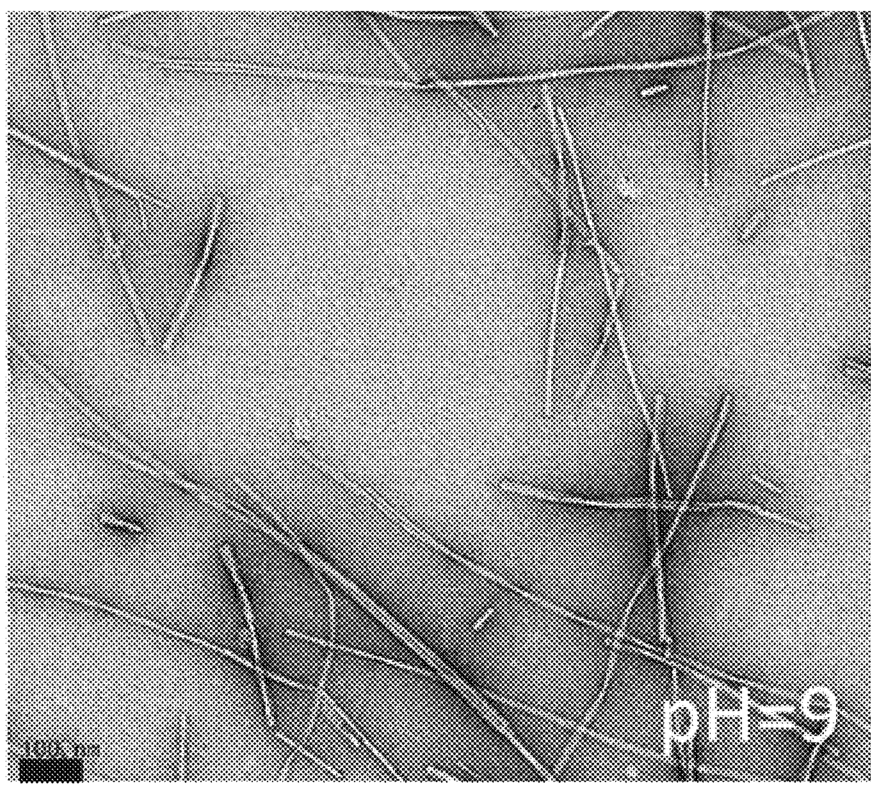
Figure 6E:
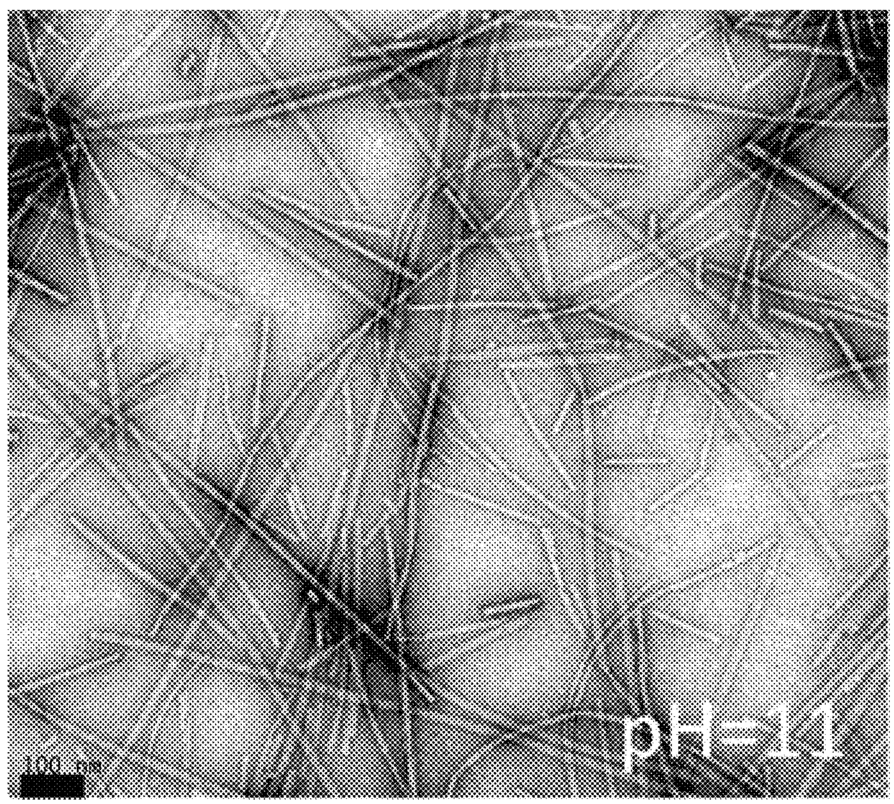
Figure 6F:
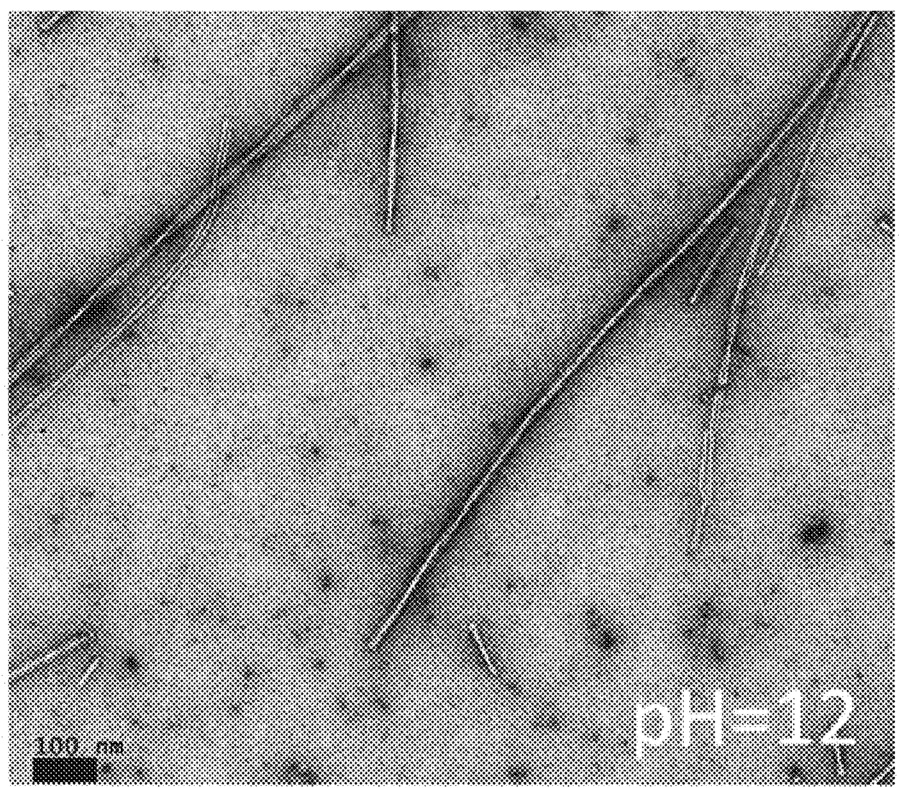
Figures 7A, 7B:
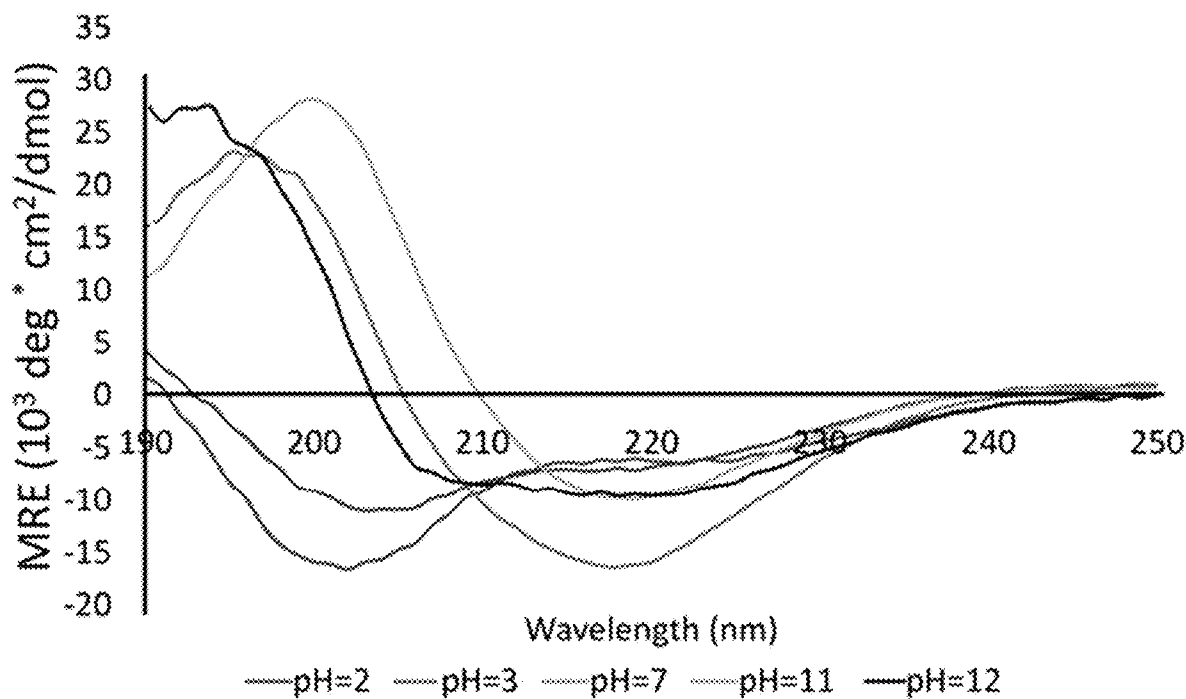
FIG. 7A and FIG. 7B depict CD spectra of PalmK-$OVA_{BT}$-$(KE)_4$ (FIG. 7A) and corresponding secondary structure estimation (FIG. 7B). PalmK-$OVA_{BT}$-$(KE)_4$ β-sheet content is more difficult to alter than PalmK-$(EK)_4$-$OVA_{BT}$ at very acidic or basic conditions. In the top figure spectra, though the fitting program predicts 100% β-sheet content at pH=12, there is a distinctive "dip" at around 205 nm (black rectangle) which indicates a likely conformational change away from β-sheet.

Electrostatic Interactions Effect. Cylindrical or worm-like micelles has been the most commonly observed ultrastructure for traditional diblock peptide amphiphile micelles. Thus, it was not surprising that the diblock peptide amphiphile micelle PalmK-$OVA_{BT}$ formed similar cylindrical micelles in water (FIG. 4). To investigate the impact that including a zwitterion-like block has on peptide amphiphile micelle structure, we first included the zwitterion-like region $(KE)_4$ at the C terminus of PalmK-$OVA_{BT}$ forming PalmK-$OVA_{BT}$-$(KE)_4$. TEM revealed that this triblock peptide amphiphile formed cylindrical micelles quite sensitive to changes in solution pH (FIG. 5A, FIG. 5B, FIG. 5C, FIG. 6A, FIG. 6B, FIG. 6C, FIG. 6D, FIG. 6E, and FIG. 6F). In specific, PalmK-$OVA_{BT}$-$(KE)_4$ micelles twisted together in pairs to form twine-like structures at neutral pH with an average length of 2.31±0.60 μm (FIG. 5B). These higher-order micelles mostly dissociated into individual thread-like, cylindrical micelles in highly acidic (pH=2, FIG. 5A) or highly basic (pH=11, FIG. 5C) solution conditions which are highlighted by red arrows. Peptide secondary structure was also affected by pH as evidenced by significant shifts in the sample CD spectra (FIG. 5D and FIG. 7A) and corresponding secondary structure content estimation (FIG. 5E and FIG. 7B). Neutral and basic pH conditions yielded 100% β-sheet conformation and acidic pH conditions caused a significant shift toward mostly random coil and some α-helical confirmation.

Figure 8:
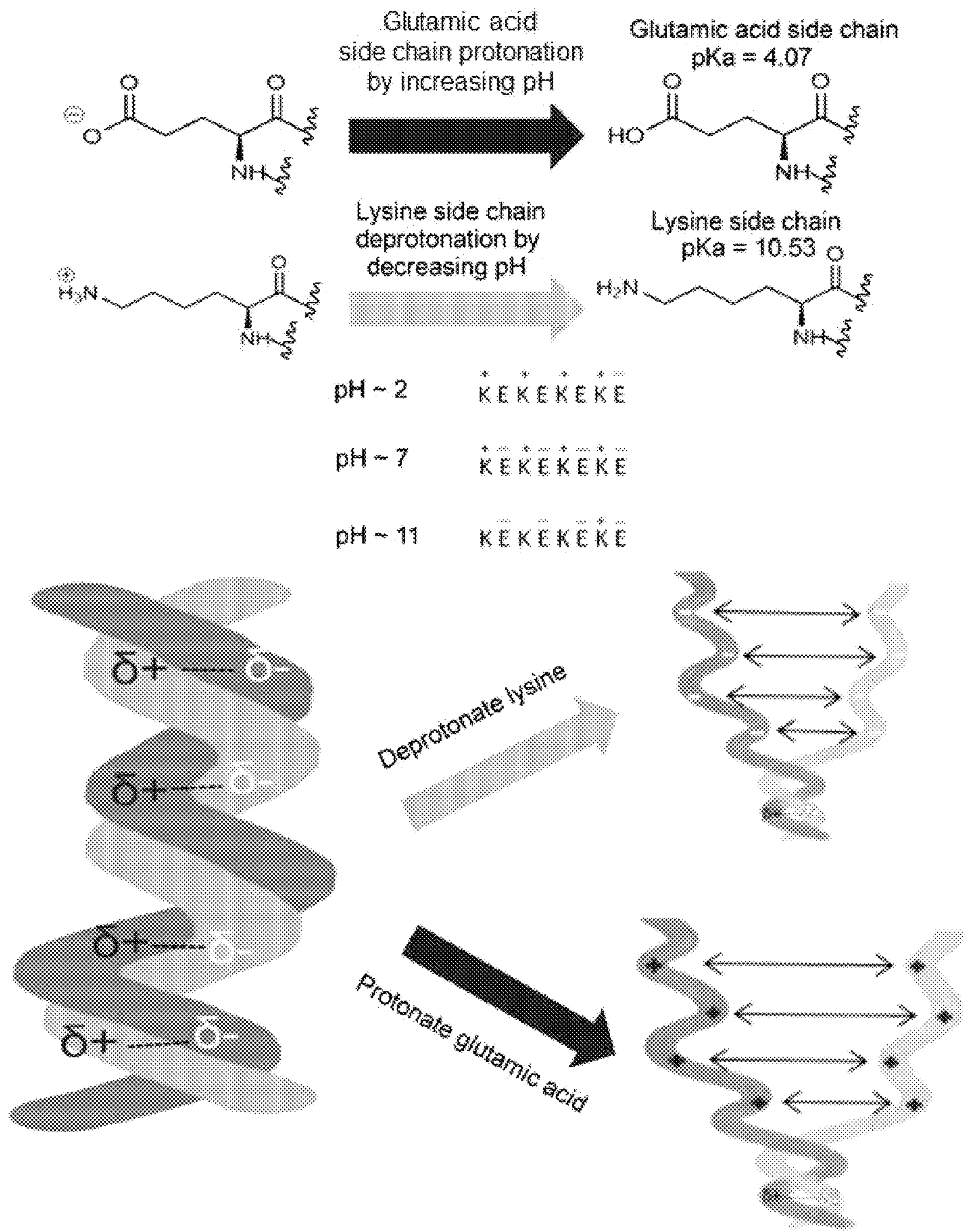
FIG. 8 depicts the disassociation of higher order micellar structures dependent on charge status changes in the zwitterion-like block due to lysine protonation or glutamic acid deprotonation. The formation or disassociation of aggregated twine-like micellar structures is dependent on the zwitterion-like block charge status. At neutral pH, charge complexation across multiple micelles due to local dipole moments is possible. At highly acidic or highly alkaline pH, the zwitterion-like block possesses a significant amount of non-charged glutamic acids or lysines, respectively, yielding electrostatically repulsive peptide segments that prevent complex micelle aggregation.
Figure 9A:
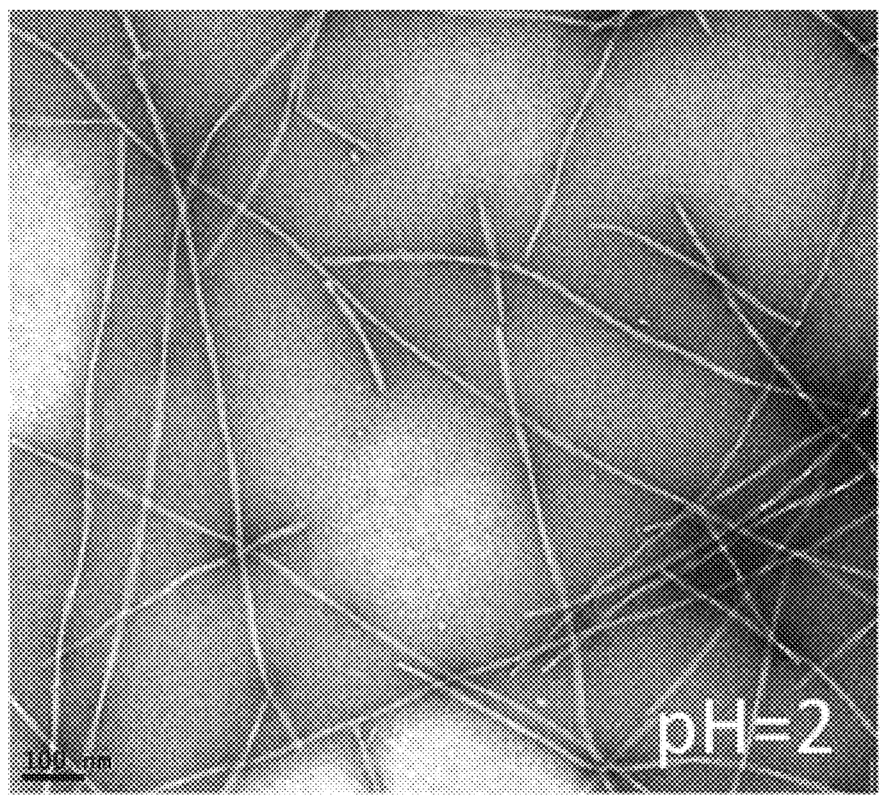
FIG. 9A, FIG. 9B, and FIG. 9C depict micrographs of PalmK-$OVA_{BT}$ at three different pHs (2 (FIG. 9A), 7 (FIG. 9B), and 11 (FIG. 9C)) showing no obvious morphological changes as a function of altering pH indicating the importance of the zwitterion-like region in complex micelle formation.
Figure 9B:
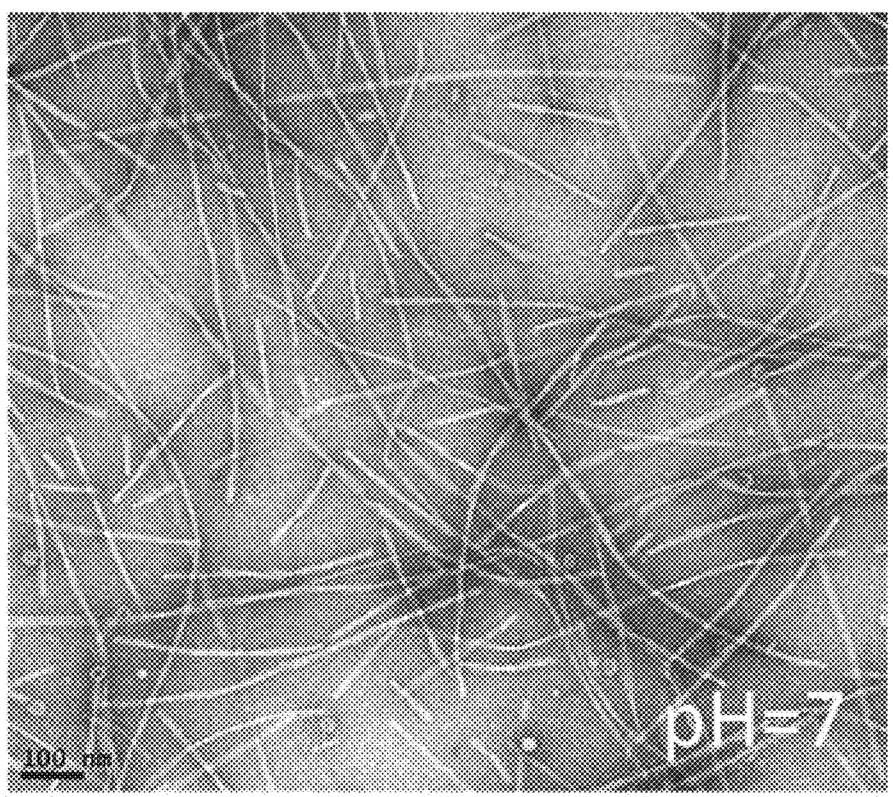
Figure 9C:
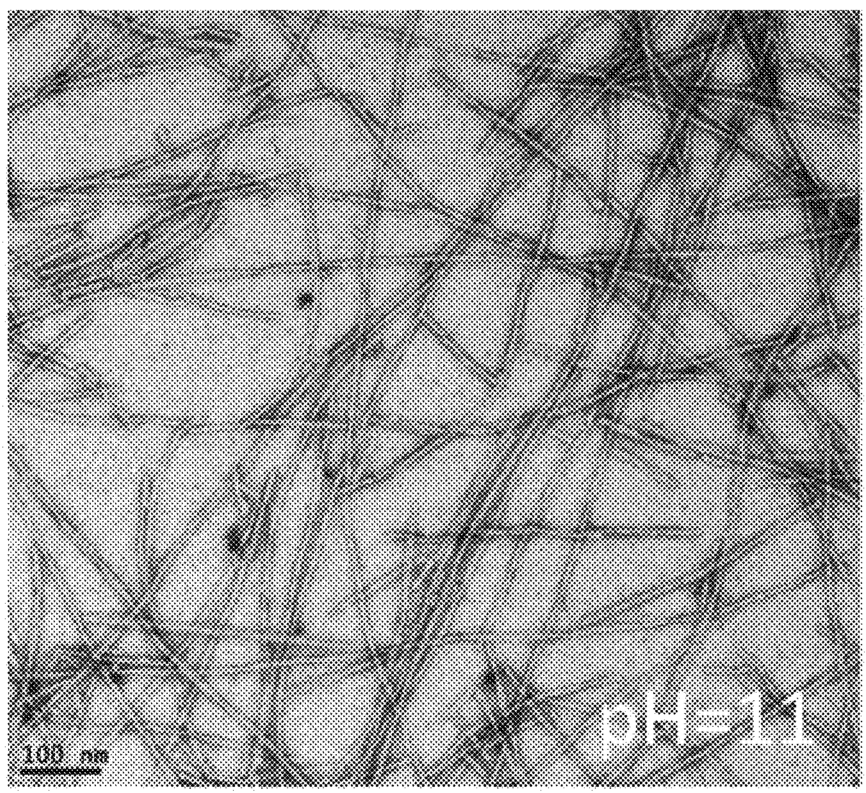

Since glutamic acid has a $pK_a$ of 4.07 and lysine has a $pK_a$ of 10.53, the zwitterion-like $(KE)_4$ block should possess a net positive charge at highly acidic pH, a near net zero charge at neutral pH, and a net negative charge at highly basic pH (FIG. 8). Zeta potential measurement of the $(KE)_4$ peptide region alone at neutral pH was found to be slightly negative that became highly positively or negatively charged under acidic or basic conditions, respectively (Table 5), confirming the pH sensitivity of the region. The alternating charge groups of $(KE)_4$ at neutral pH can create local dipole moments that allow for intermicellar complexation yielding the observed twining behavior. At low pH and high pH utilized, not all of the glutamic acids or lysines will be protonated or deprotonated, respectively, but the local change in $(KE)_4$ block charge is significant enough to repulse one another yielding individual thread-like micelles. By contrast, when the zwitterion-like region was excluded (i.e., PalmK-$OVA_{BT}$), no significant morphology changes were observed when pH was altered (FIG. 9A, FIG. 9B, and FIG. 9C) thereby revealing that the inclusion of the zwitterion-like region is key for twine-like micelle formation. Though twine-like micelles share some similar overall shape characteristics as previously reported ribbon-like micelles, those structures are individual micelles whose formation is governed by unevenly distributed hydrogen bonding and were found to be insensitive to changes in solution pH. When the hydrophobic region (i.e. PalmK) was excluded (i.e., $OVA_{BT}$-$(KE)_4$), no ultrastructure structure was detected using TEM (data not shown) revealing that the hydrophobic driving force is vital to the micelle formation necessary to achieve twine-like ultrastructure. These results together further indicated that the formation of twine-like micelles relies on the presence of both electrostatic attraction forces and hydrophobic interactions.

TABLE 5

Zeta potential measurement of the zwitterion-like peptide region alone (i.e. $(KE)_4$) under different pH conditions (i.e. 2, 7, and 11).

| pH | 2 | 7 | 11 |
|---|---|---|---|
| Zeta Potential (mV) | 31.4 ± 2.9 | −7.8 ± 1.2 | −18.1 ± 4.7 |

Since triblock peptide amphiphiles possess both a zwitterion-like peptide and an application-specific peptide, the overall secondary structure is expected to be dictated by synergy or competition between the constituents. An $(EK)_X$ peptide has been found to be weakly structured as mostly random coil with trace a-helical behavior. With lysine deprotonation, the sequence is similar to $(EG)_X$ which has been shown to be entirely β-sheet. In contrast, $(KA)_X$ and $(KG)_X$, sequences analogous to protonated glutamic acid $(KE)_4$, have been observed as possessing strong a-helical and some random coil secondary structure. $OVA_{BT}$ is part of a β-ladder within the ovalbumin protein and micellization has been previously shown to force peptides to reform their protein-based secondary structure, so it is expected to form a β-sheet within the micelle. At pH 11, it is unsurprising that PalmK-$OVA_{BT}$-$(KE)_4$ possessed β-sheet confirmation since both portions of the peptide independently possess this secondary structure. At pH 7, PalmK-$OVA_{BT}$-$(KE)_4$ was found to be entirely β-sheet indicating $OVA_{BT}$ dominated the overall secondary structure. At pH 2, the two peptide components have strong, competing structures which yielded a mix of α-helical, β-sheet, and random coil behavior.

Figure 10A:
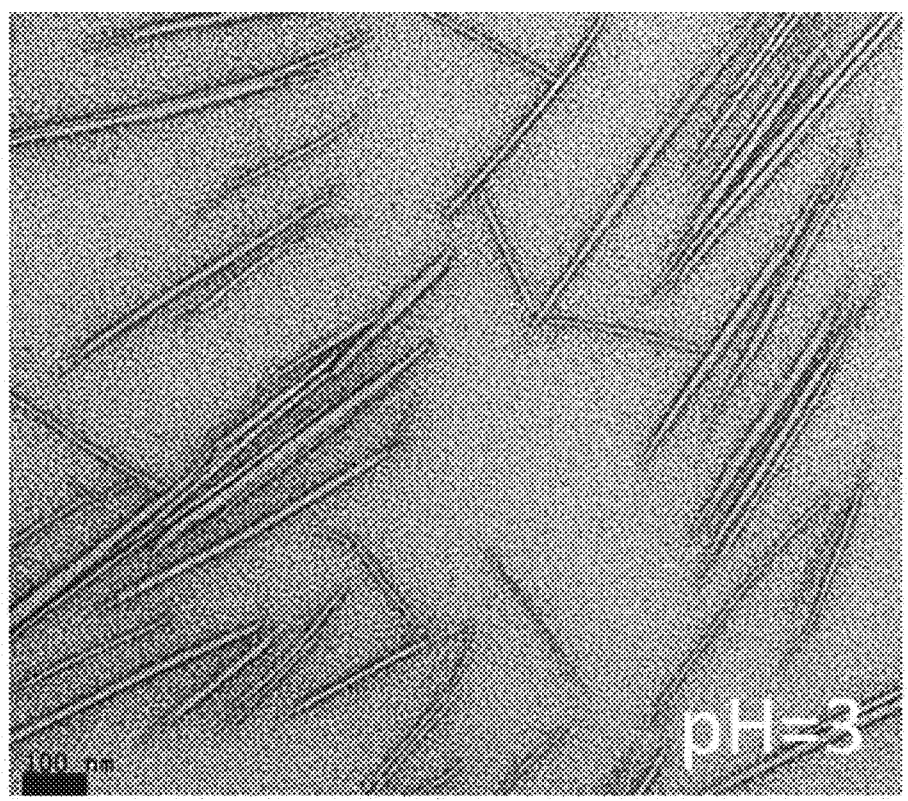
FIG. 10A, FIG. 10B, FIG. 10C, FIG. 10D, and FIG. 10E depict PalmK-$(EK)_4$-$OVA_{BT}$ complex micelle aggregation as pH-dependent. PalmK-$(EK)_4$-$OVA_{BT}$ was solubilized in different pH solutions to investigate the impact of this parameter on micelle formation as assessed by negative stain TEM ((FIG. 10A) 3, (FIG. 10B) 7, and (FIG. 10C) 11). The influence pH has on peptide secondary structure was also evaluated by (FIG. 10D) obtaining the CD spectra and using it to (FIG. 10E) estimate secondary structure.
Figure 10B:
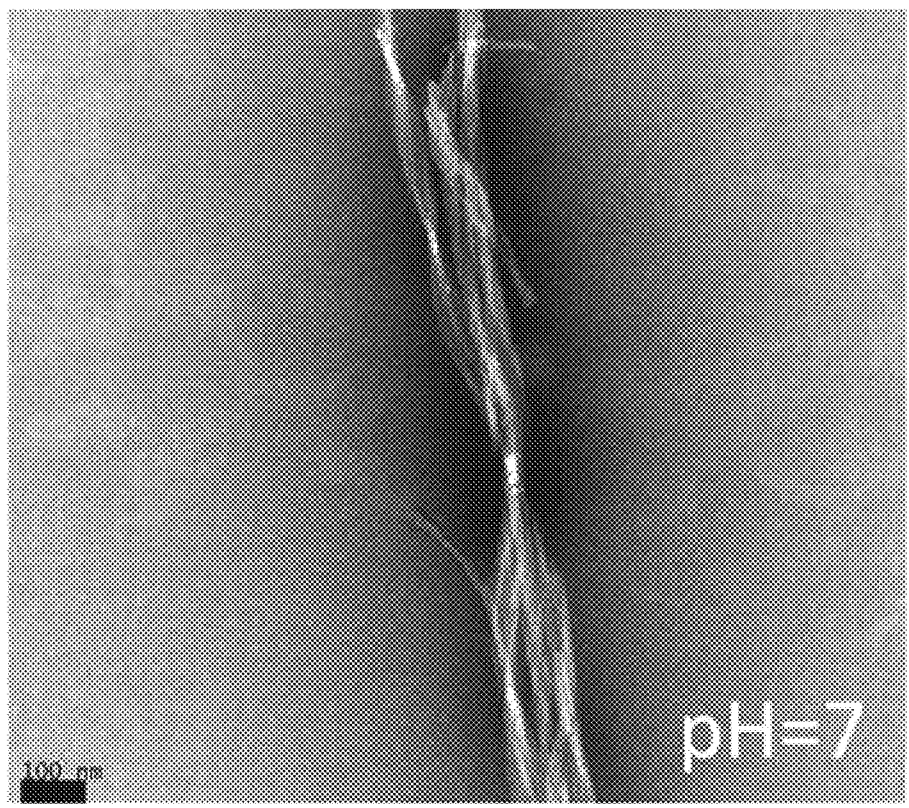
Figure 10C:
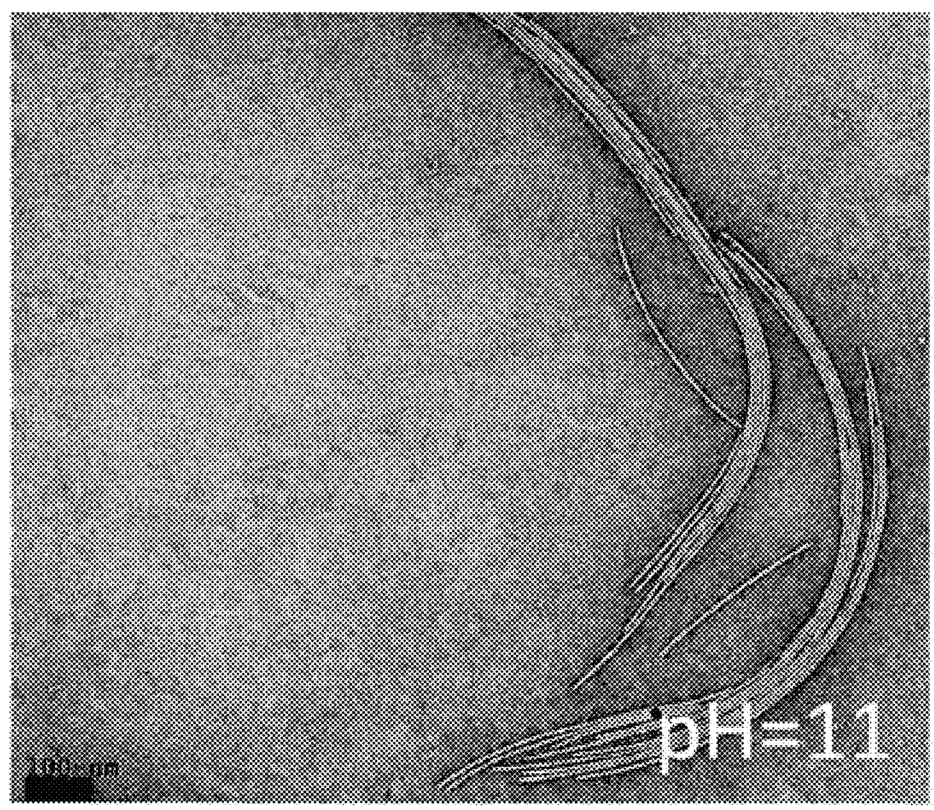
Figures 10D, 10E:
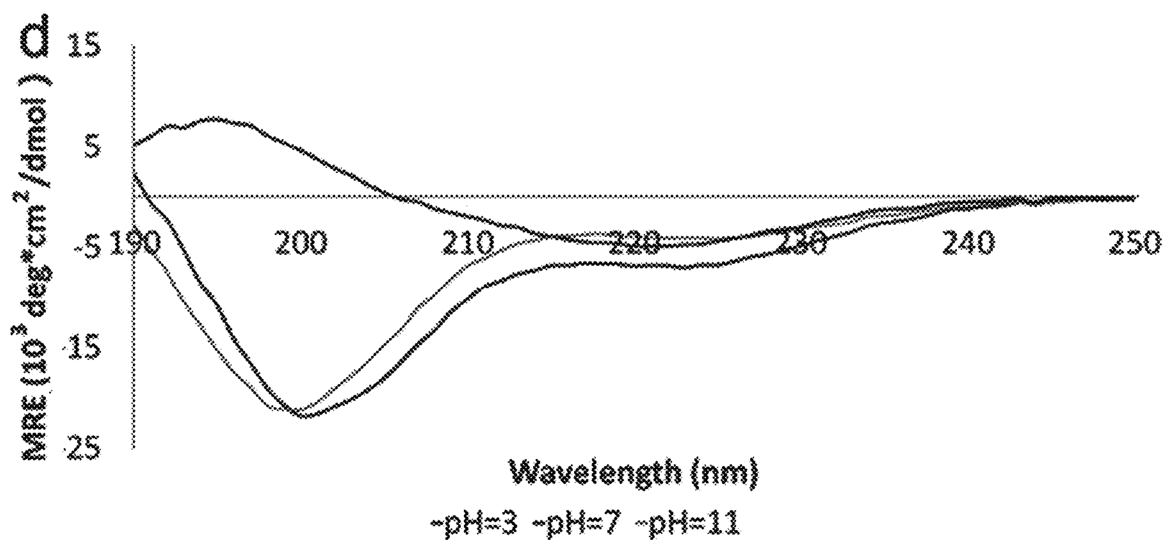

Zwitterion-Like Block Location Effect. In ABC triblock polymer research, it has been shown that block location plays an important role in determining material ultrastructure. It was hypothesized that changing the block position in the ABC triblock PAs could affect micellar properties prompting the design of PalmK-$(EK)_4$-$OVA_{BT}$ which, as expected, yielded a significant change in micelle morphology that was also found to be pH sensitive (FIG. 10A, FIG. 10B, and FIG. 10C). Interestingly, PalmK-$(EK)_4$-$OVA_{BT}$ individual micelles twined together like PalmK-$OVA_{BT}$-$(KE)_4$, but self-assembled further by wrapping together three twines to form higher order structures at neutral pH up to tens of microns in length (FIG. 10B, FIG. 11A, FIG. 11B, and FIG. 11C). These complex micelles were found to possess similar pH sensitivity to twine-like micelles as demonstrated by their dissociation into thread-like micelles in solution conditions that were highly acidic (pH=3, FIG. 10A) or highly basic (pH=11, FIG. 10C). Peptide secondary structure was similarly affected by pH as evidenced by changes in the CD spectra (FIG. 10D) and secondary structure content (FIG. 10E). Therefore, similarly to twine-like micelles, electrostatic attractive forces between individual cylinders are believed to be the driving force for forming braid-like micelles at moderate to neutral pH.

Figure 12A:
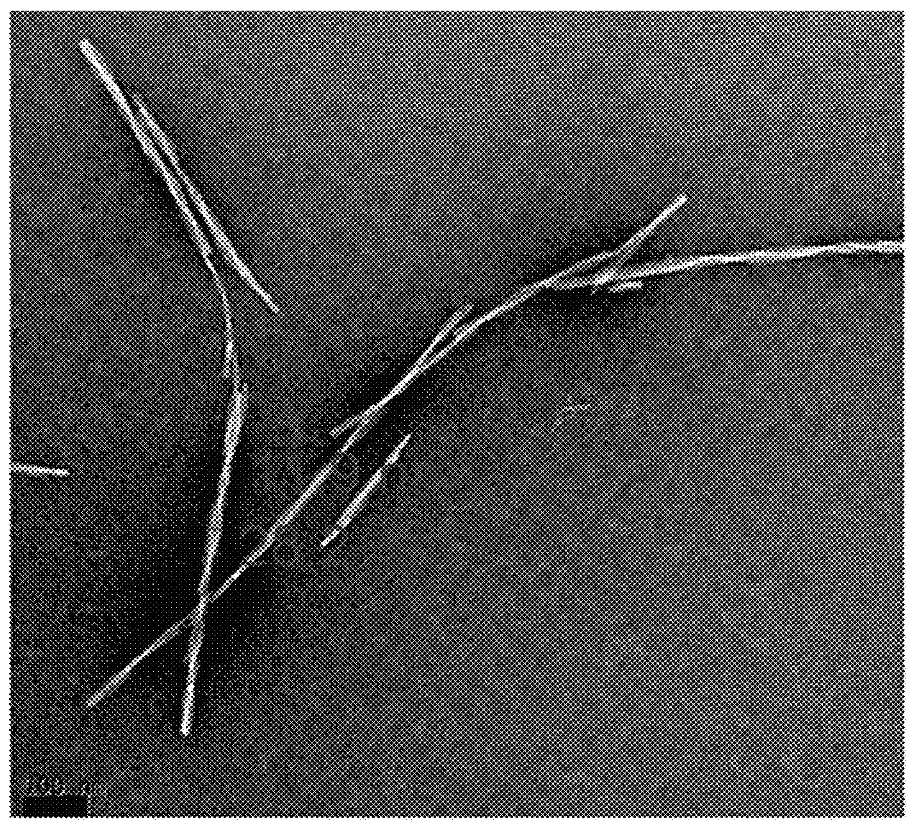
FIG. 12A and FIG. 12B depict a PalmK-$OVA_{BT}$-$(KE)_4$ micrograph (FIG. 12A) and a PalmK-$(EK)_4$-$OVA_{BT}$ micrograph (FIG. 12B) with micellar diameter measurements of 41.38 nm, 29.71 nm and 115.67 nm.
Figure 12B:
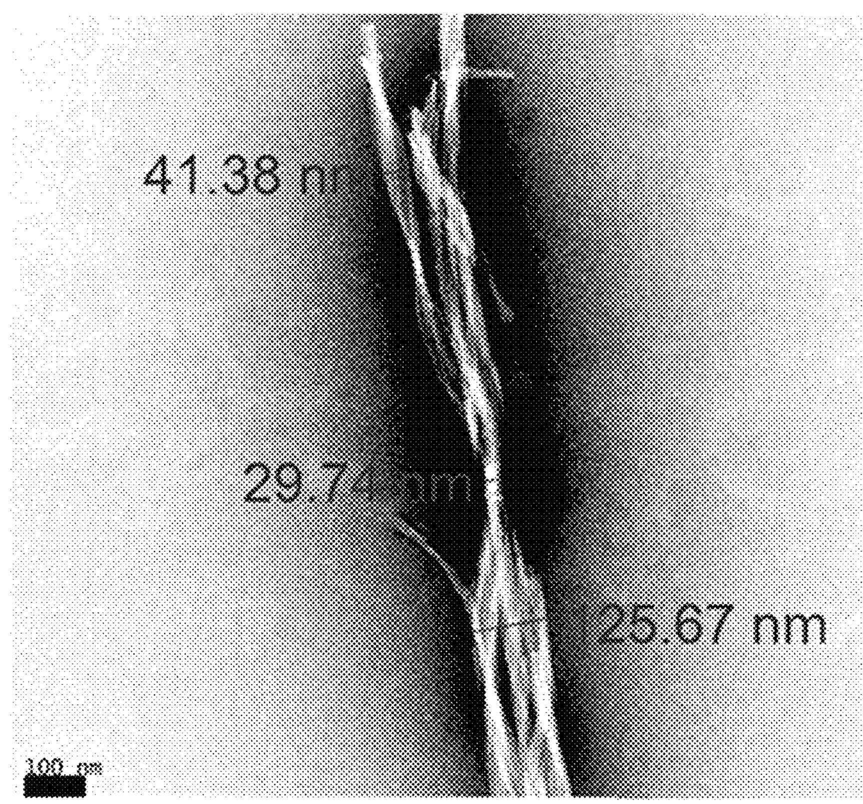
Figure 13:
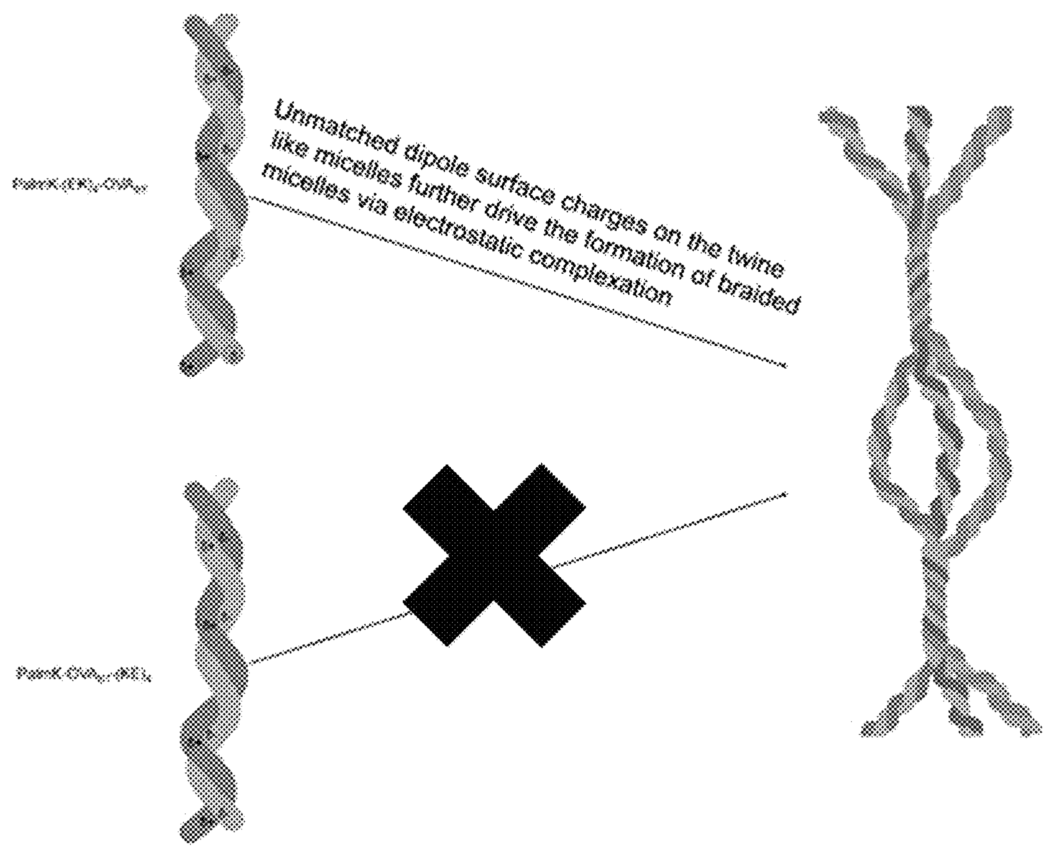
FIG. 13 depicts micelle braiding dependent on the zwitterion-like block location in PalmK-$OVA_{BT}$-$(KE)_4$ and PalmK-$(EK)_4$-$OVA_{BT}$. Micelle aggregation and its effect on the resulting final nanomaterial structure is dependent on how easily dipole surface charges can associate across micelles. For PalmK-$(EK)_4$-$OVA_{BT}$, unmatched dipole surface charges on the twine-like micelles further drive the formation of braided micelles via electrostatic complexation. PalmK-$(EK)_4$-$OVA_{BT}$ is expected to form flowerlike micelles to best position the zwitterion-like block in the corona, which significantly reduces amphiphile fluidity within the individual micelle. This limits the capacity for twining to match most or all charge dipoles allowing for the remaining unmated regions to further complex twines into braids.
Figure 14A:
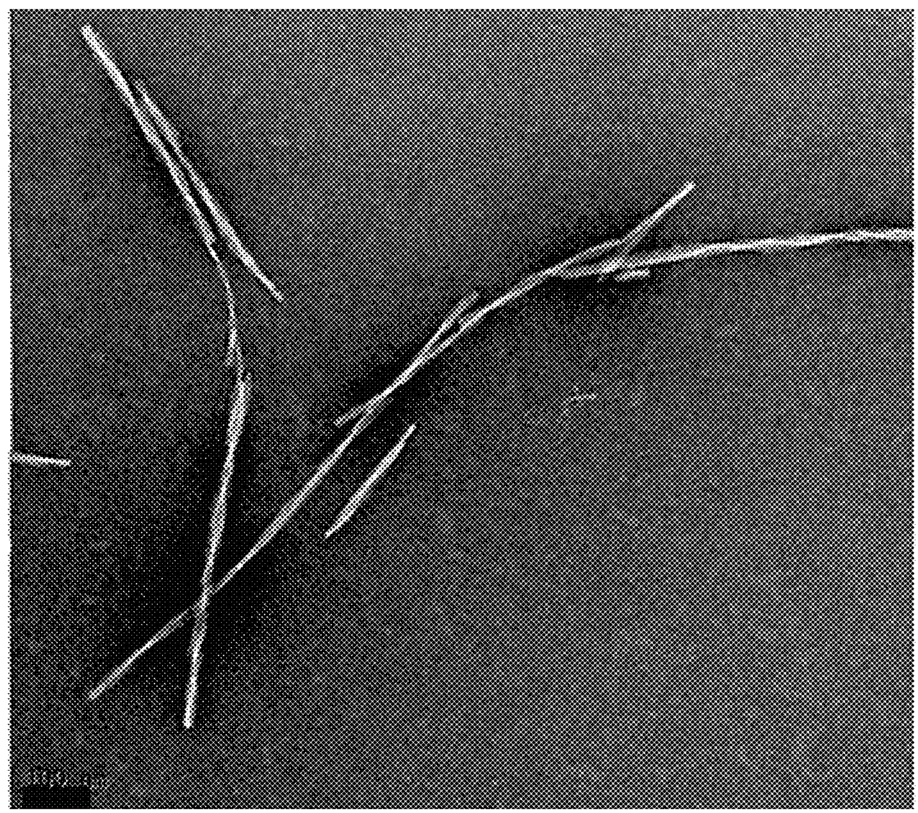
FIG. 14A, FIG. 14B, FIG. 14C, and FIG. 14D depict electrostatically driven micelle aggregation as insensitive to physiological ion content. Negative-stain TEM revealed that PalmK-$OVA_{BT}$-$(KE)_4$ and PalmK-$(EK)_4$-$OVA_{BT}$ form twinelike and braidlike micelles, respectively, regardless of whether the amphiphiles were exposed to low salt concentration (i.e., $ddH_2O$) or high salt concentration (i.e., PBS). $Palm_2K$-$OVA_{BT}$-$(KE)_4$ in $ddH_2O$ (FIG. 14A) and in PBS (FIG. 14B) and PalmK-$(EK)_4$-$OVA_{BT}$ in $ddH_2O$ (FIG. 14C) and in PBS (FIG. 14D).
Figure 14B:
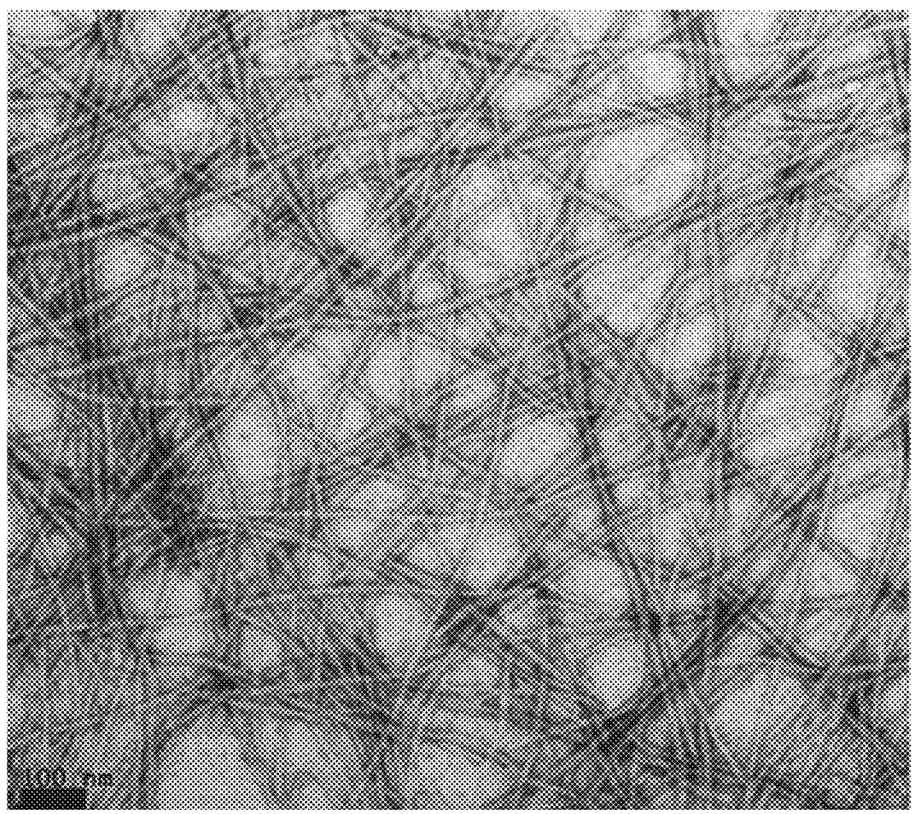
Figure 14C:
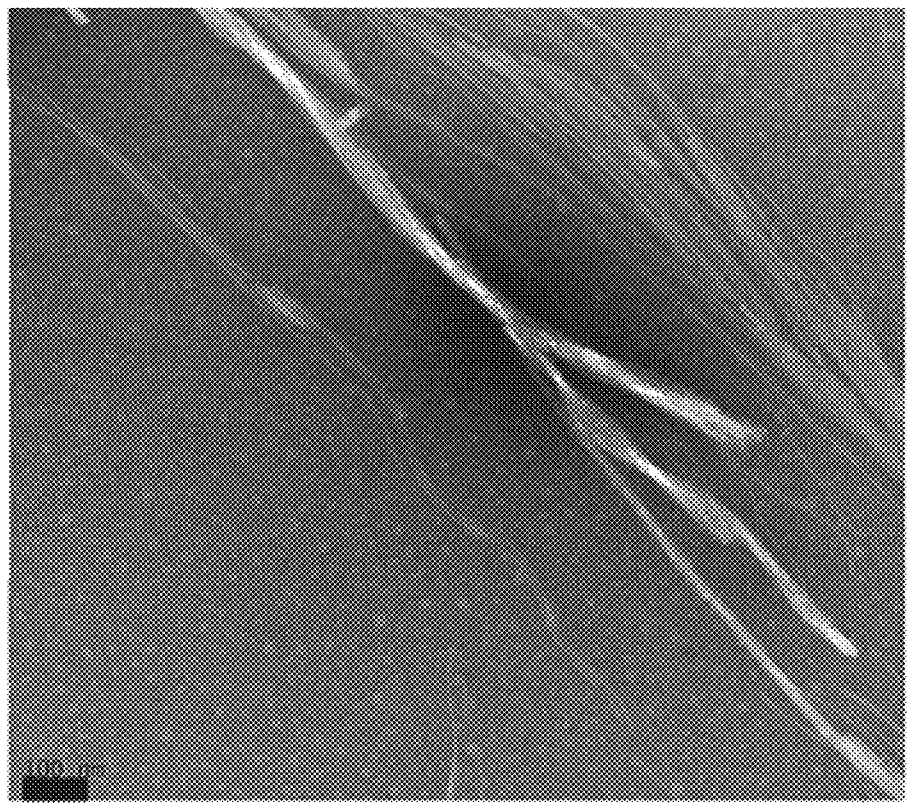
Figure 14D:
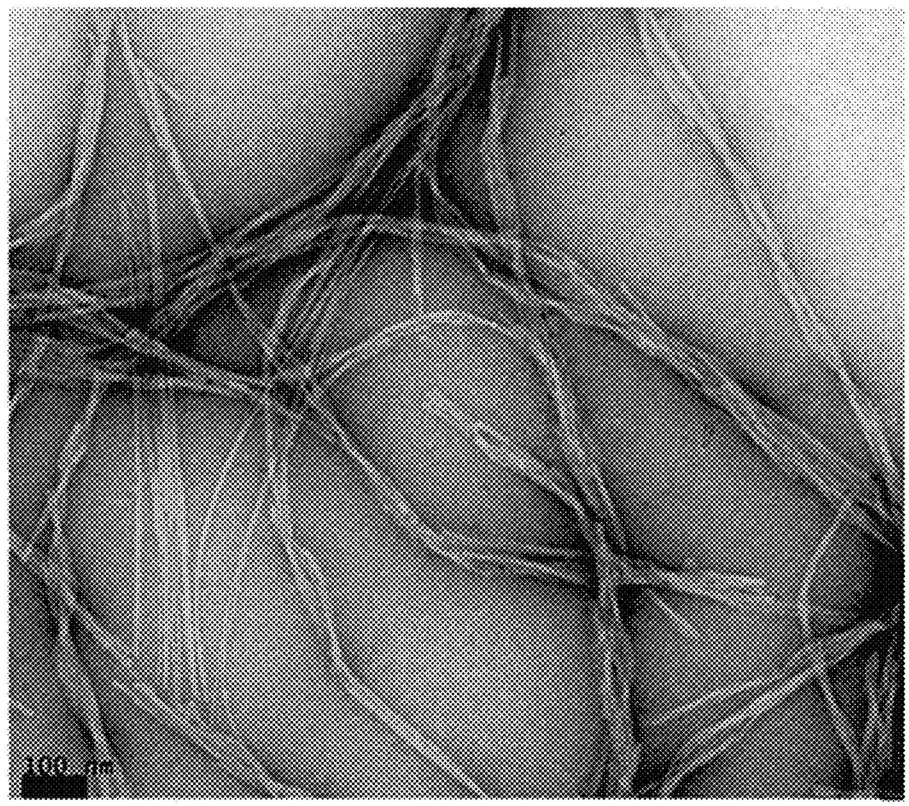
Figure 15A:
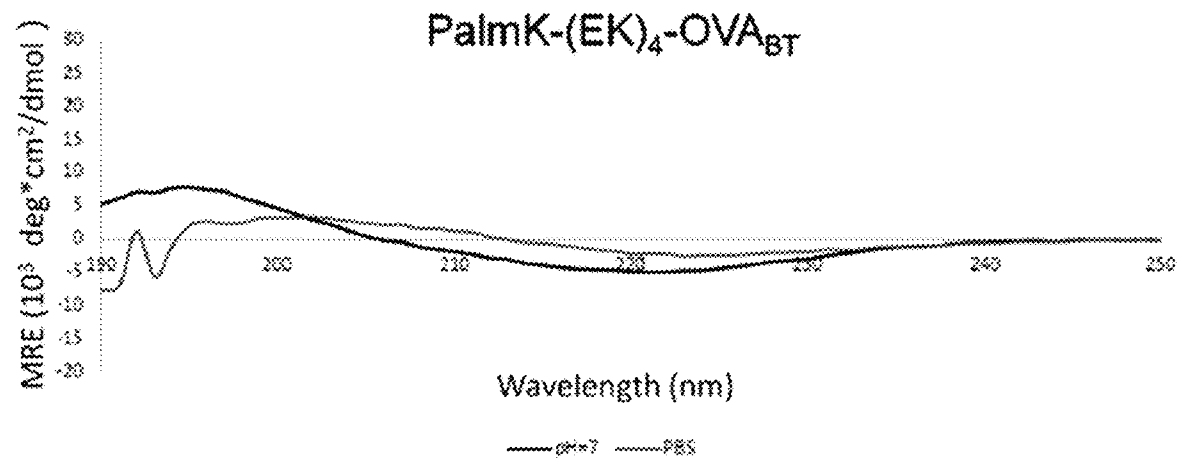
FIG. 15A, FIG. 15B, FIG. 15C, and FIG. 15D depict CD spectra of four different PA formulations (FIG. 15A—PalmK-$(EK)_4$-$OVA_{BT}$, FIG. 15B—$Palm_2K$-$(EK)_4$-$OVA_{BT}$, FIG. 15C—PalmK-$OVA_{BT}$-$(KE)_4$, and FIG. 15D—$Palm_2K$-$OVA_{BT}$-$(KE)_4$) in either $ddH_2O$ (pH adjusted to 7) or in PBS. Certain increases in ion concentration do not significantly alter micellar secondary structure. The CD spectra under 200 nm is variable in PBS solution due the high salt concentration interrupting absorbance at lower wavelengths.
Figure 15B:
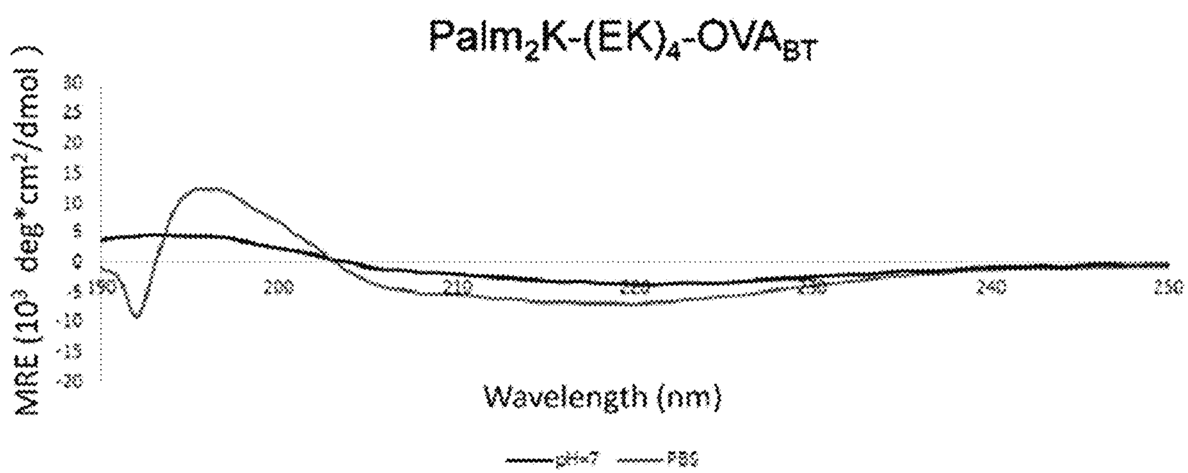
Figure 15C:
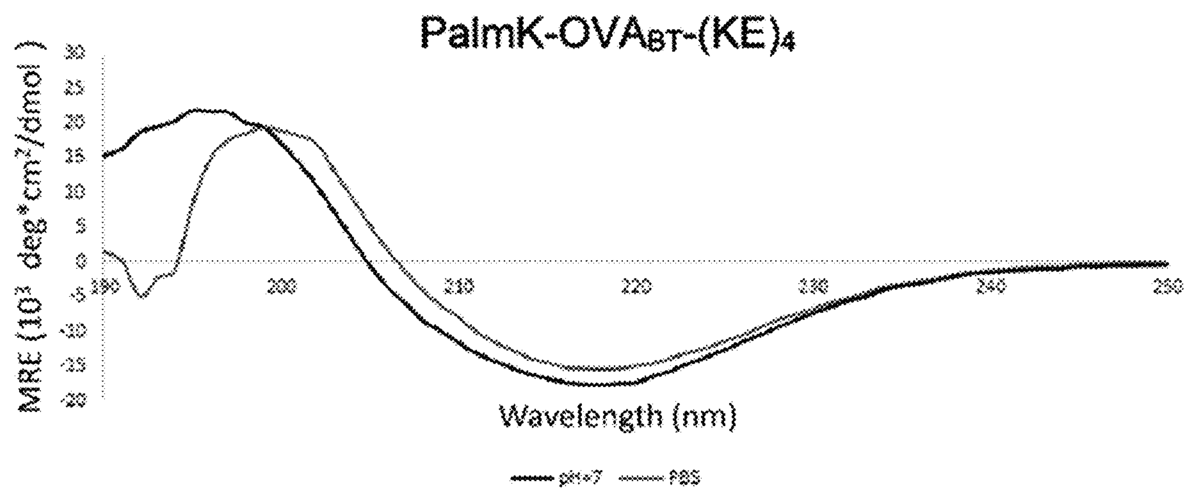
Figure 15D:
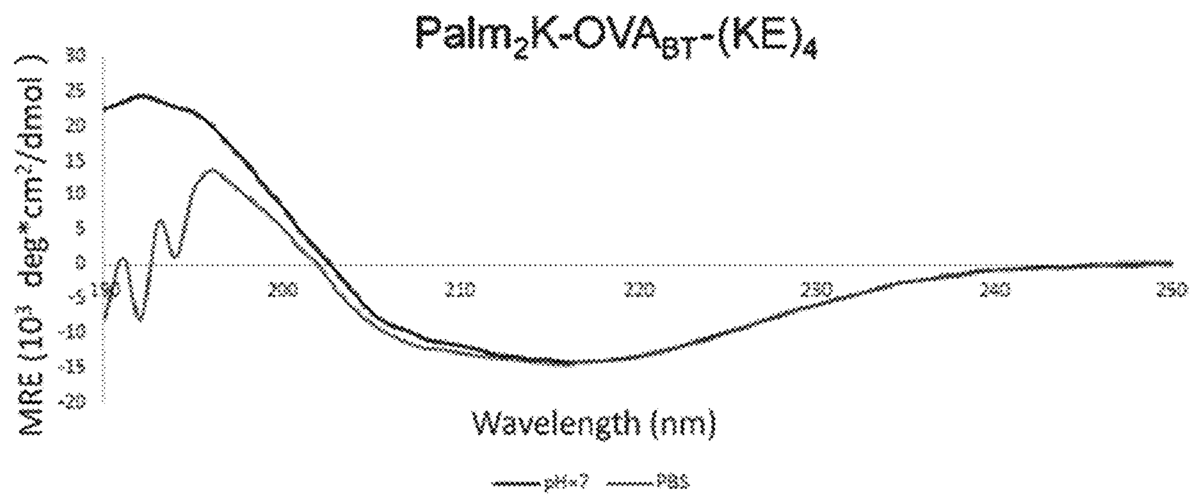

The diameter of the thread-like micelles in PalmK-$(EK)_4$-$OVA_{BT}$ were found to be similar in size to PalmK-$OVA_{BT}$-$(EK)_4$ thread-like micelles (FIG. 12A and FIG. 12B and Table 6). This indicates that individual cylindrical micelles are the building blocks of both complex micellar structures. However, these formulations yielded quite different final ultrastructures at neutral pH. While both PAs are believed to undergo intermicellar dipole moment matching, PalmK-$(EK)_4$-$OVA_{BT}$ is thought to be unable to pair all of its surface dipole moments during the twining process (FIG. 13). These unmatched dipole moments participate in further electrostatic interactions by twisting together several twine-like micelles to form braid-like micelles. This difference in dipole moment matching is supported by the molecular fluidity dissimilarities expected between the two PAs. Individual PalmK-$OVA_{BT}$-$(KE)_4$ PAs transition from very hydrophobic (PalmK) to modestly hydrophilic ($OVA_{BT}$) to highly hydrophilic ($(KE)_4$) likely aligning in this orientation from the core to the corona of the micelle allowing for significant PA mobility in the nanostructure. In contrast, confining the most hydrophilic block to the middle, PalmK-$(EK)_4$-$OVA_{BT}$ causes the PAs to bend the $OVA_{BT}$ block back toward the core exposing the more hydrophilic $(EK)_4$ block on the corona yielding flower-like micelles. This physical confinement makes PalmK-$(EK)_4$-$OVA_{BT}$ PAs less mobile and unable to rearrange in ways that fully charge match during the twining process therefore requiring further complexation through braiding to associate additional dipole moments. This extra complexation means fewer charge matches between each twine yielding overall weaker intermolecular forces holding them together. This theory is corroborated by the less extreme pH changes (i.e., 3/11 versus 2/12) required to break apart the individual micelles and the more significant extent of dissociation seen for PalmK-$(EK)_4$-$OVA_{BT}$ PAMs (FIG. 10A, FIG. 10B, FIG. 10C, FIG. 10D, and FIG. 10E) compared to PalmK-$OVA_{BT}$-$(KE)_4$ PAMs (FIG. 5A, FIG. 5B, FIG. 5C, FIG. 5D, and FIG. 5E).

TABLE 6

PalmK-$OVA_{BT}$-$(KE)_4$ and PalmK-$(EK)_4$-$OVA_{BT}$ thread-like micelle diameter measurements at highly acidic or basic conditions.

| PALMK-$OVA_{BT}$-$(KE)_4$ | Diameter (nm) |
|---|---|
| pH = 2 | 5.14 ± 0.75 |
| pH = 11 | 4.99 ± 0.63 |
| PALMK-$(EK)_4$-$OVA_{BT}$ | Diameter (nm) |
| pH = 3 | 4.87 ± 0.59 |
| pH = 11 | 4.22 ± 0.52 |

Figure 11A:
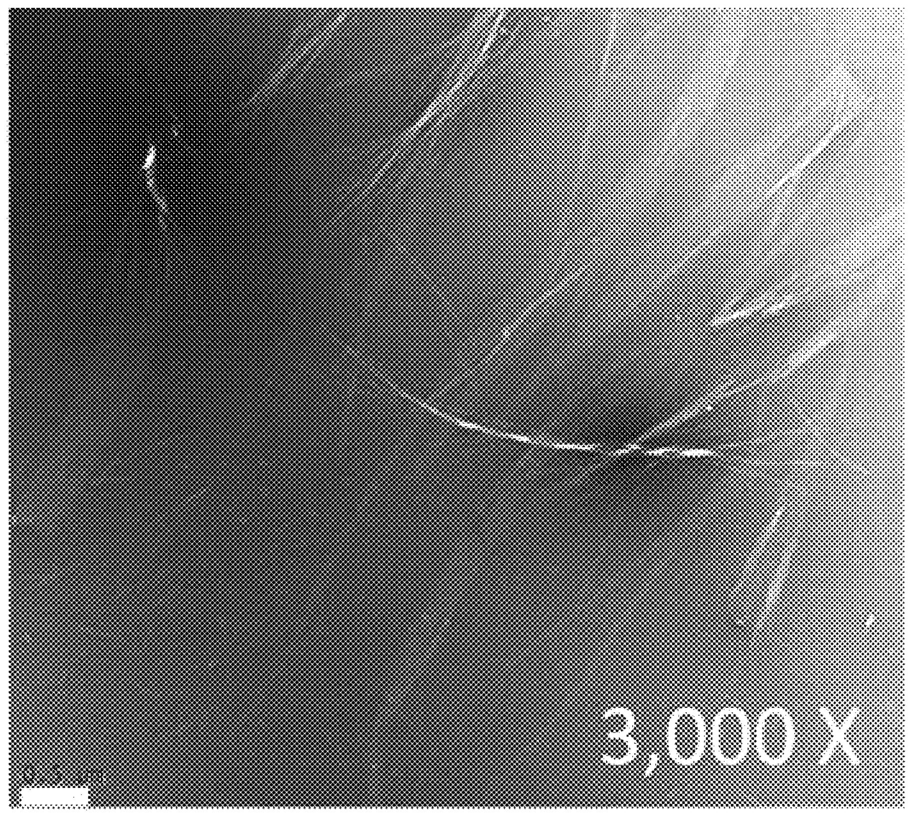
FIG. 11A, FIG. 11B, and FIG. 11C depict micrographs at three different magnifications (FIG. 11A—3,000×, FIG. 11B—8,000×, FIG. 11C—20,000×) showing PalmK-$(EK)_4$-$OVA_{BT}$ forms both thread-like and braided micelles at neutral pH.
Figure 11B:
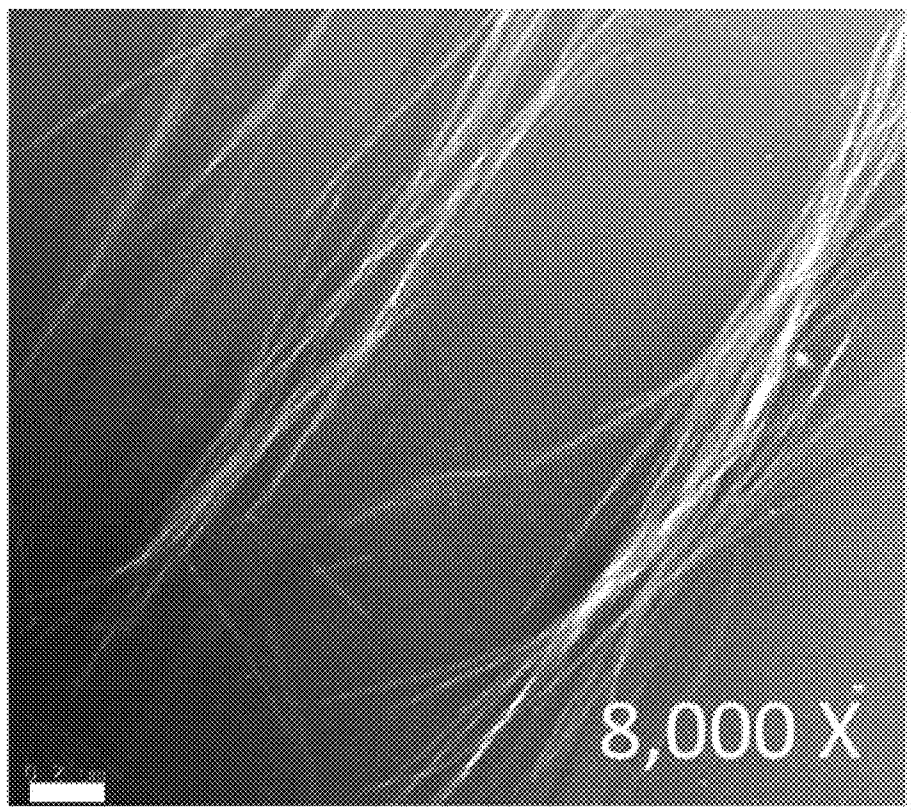
Figure 11C:
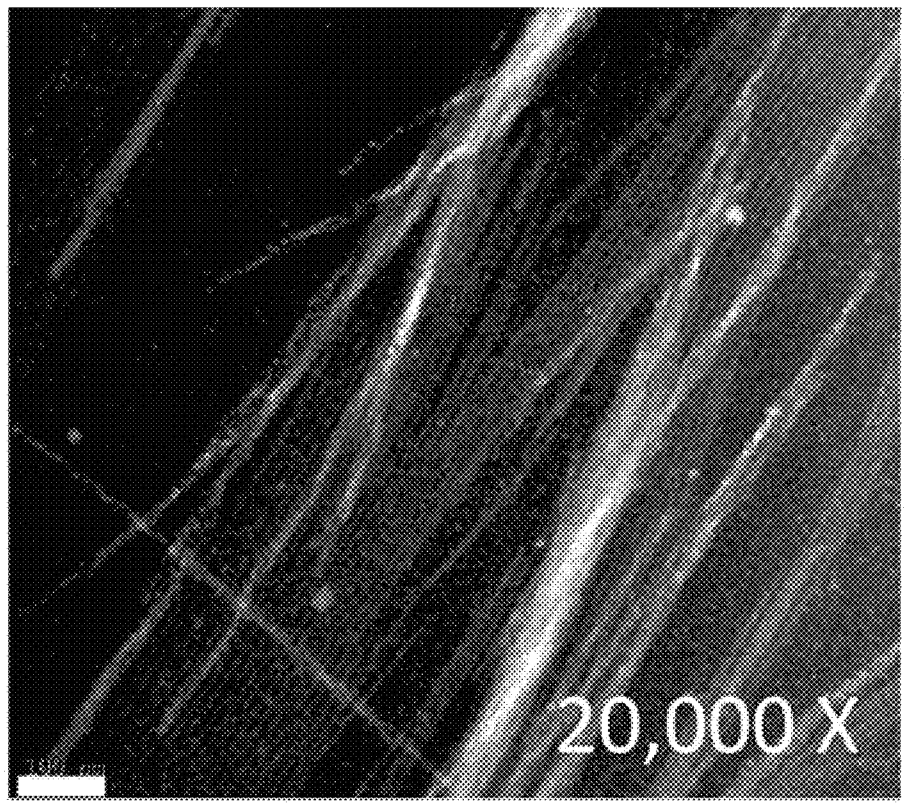

Similar to twine-like micelles, braided micelles not only dissociate into individual micelles at extreme pH but also saw changes to their peptide secondary structure. At extreme pHs, β-sheet content was largely decreased and was accompanied by a great increase in random coil content. This indicates weakened hydrogen bonding supporting the theory that electrostatic interactions play a role in these molecular interactions in addition to peptide backbone orientation. There are significant differences regarding secondary structure due to block position location, most notably less β-sheet formation in basic conditions and greater α-helical content in extreme pH conditions for PalmK-$(EK)_4$-$OVA_{BT}$ than PalmK-$OVA_{BT}$-$(KE)_4$. This behavior is expected due to the flower-like orientation of the PAs within the micelles where physical confinement makes intermolecular bonding more difficult and intramolecular bonding more favorable, the latter of which could explain the increase in α-helical content. Additionally, PalmK-$(EK)_4$-$OVA_{BT}$ thread-like micelles were occasionally observed as small fibers at neutral pH (FIG. 11A, FIG. 11B, and FIG. 11C). This indicates the existence of different types of β-sheet formation due to different orientations of carbonyl-amide stretching. Thread-like micelle fibers form when hydrogen bonding occurs in two parallel planes, in which case the stretching angle is 0°. However, as the angle increases up toward 90°, hydrogen bonding can take place at a variable pitch facilitating intermolecular bonds between individual micelles. While somewhat similar looking structures as braided micelles have been previously observed by leveraging hydrogen bonding through polar amino acids, the formation and final structure of braided micelles described here are fundamentally different. Dipole interactions created by the zwitterion-like block is the key driving force of these complex structures and something that has yet to be demonstrated in the literature.

Physiological Ion Concentration Effect. Modulating pH through the addition of hydrochloric acid (HCl) and sodium hydroxide (NaOH) also changed solution ion concentration. Since electrostatic interactions have been reported to be sensitive to ion content in some cases, it was worth investigating the impact ions have on complex micelle formation. In order to understand the ion effect on micelles for medical applications, PalmK-$OVA_{BT}$-$(KE)_4$ and PalmK-$(EK)_4$-$OVA_{BT}$ were dissolved in micelles in either neutral pH corrected milli-Q double distilled water ($ddH_2O$) or phosphate buffered saline (PBS). No significant differences were observed for either morphology (FIG. 14A, FIG. 14B, FIG. 14C, and FIG. 14D) or secondary structure (FIG. 15A, FIG. 15B, FIG. 15C, and FIG. 15D) regardless of which solution was used. This indicates that physiological ion interactions are unable to disrupt PA dipole interactions and also confirmed that the disassociation of the complex micelles was due to breaking dipole electrostatic interactions rather than ion charge shielding. Additionally, this revealed that complex micelle structures are expected to be stable in physiologic environments.

Figure 16A:
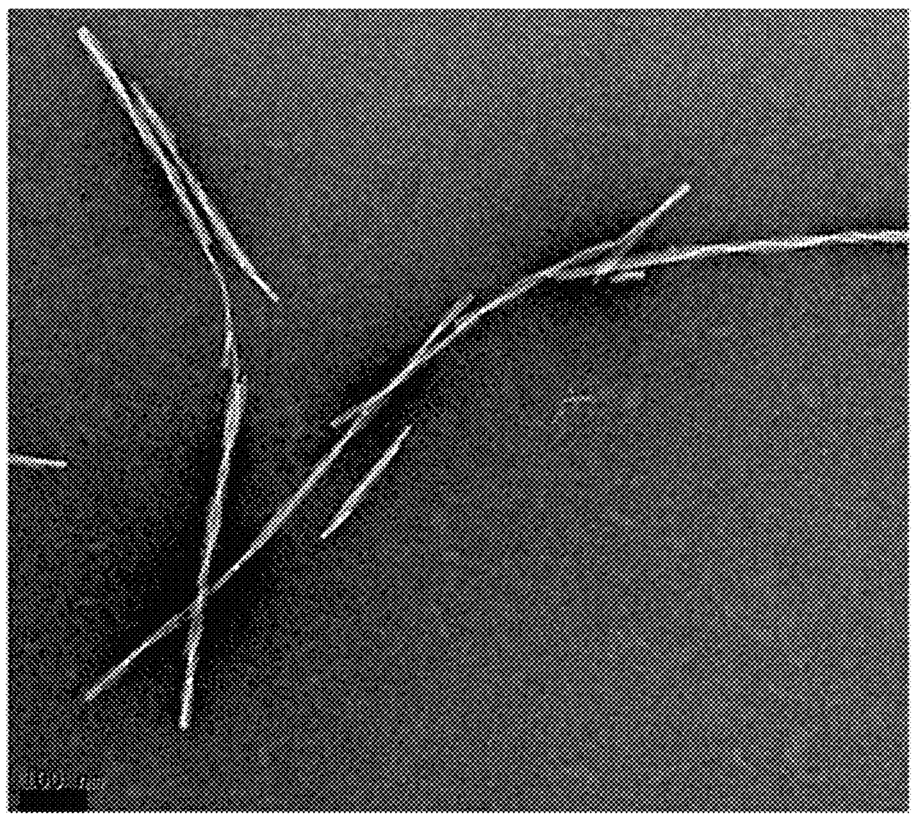
FIG. 16A, FIG. 16B, FIG. 16C, and FIG. 16D depict micelle shape and aggregation as dependent on hydrophobic content and zwitterion-like block location. Four different $OVA_{BT}$ amphiphile chemistries ((FIG. 16A) PalmK-$OVA_{BT}$-$(KE)_4$, (FIG. 16B) $Palm_2K$-$OVA_{BT}$-$(KE)_4$, (FIG. 16C) PalmK-$(EK)_4$-$OVA_{BT}$, and (FIG. 16D) $Palm_2K$-$(EK)_4$-$OVA_{BT}$) yielded significantly different micellar structures (i.e., (FIG. 16A) twines, (FIG. 16B) spheres/short cylinders, (FIG. 16C) braids, and (FIG. 16D) clusters) at pH 7 as determined by TEM. These results demonstrate that lipid tail number and component block order directly impact the resulting final micelle architecture yielding an array of resulting structures
Figure 16B:
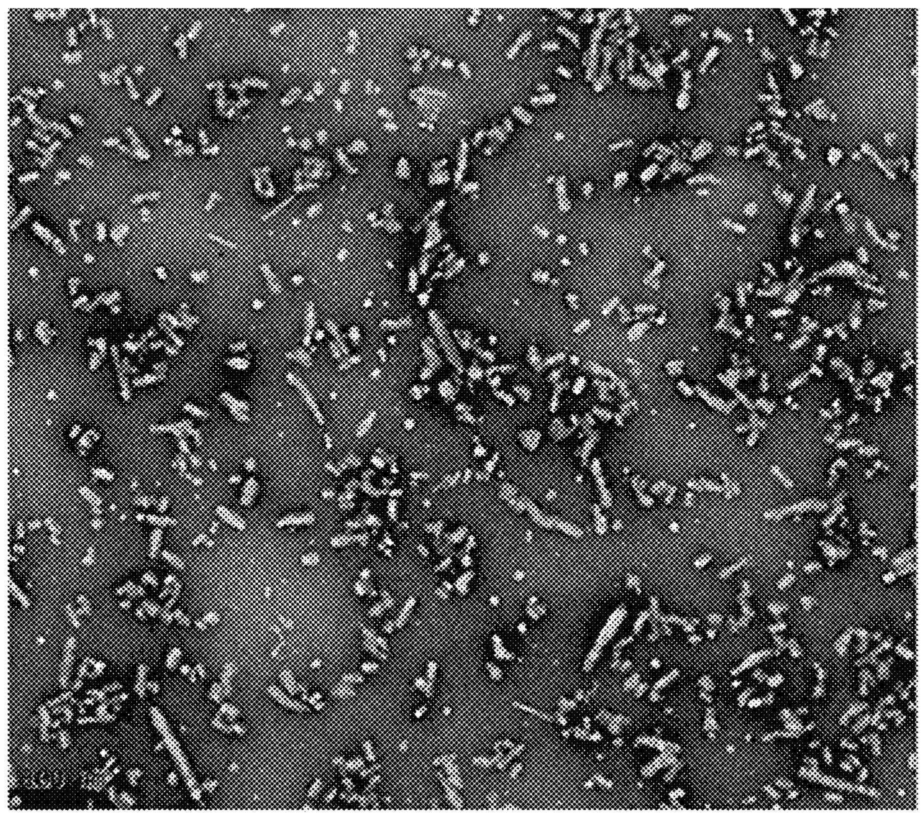
Figure 16C:
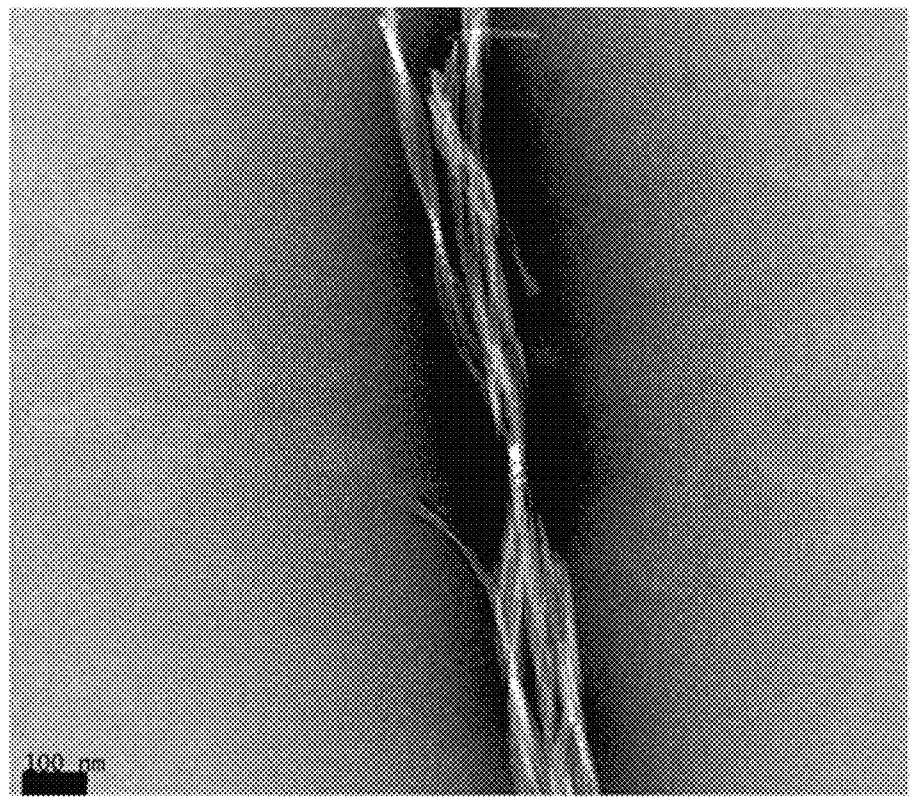
Figure 16D:
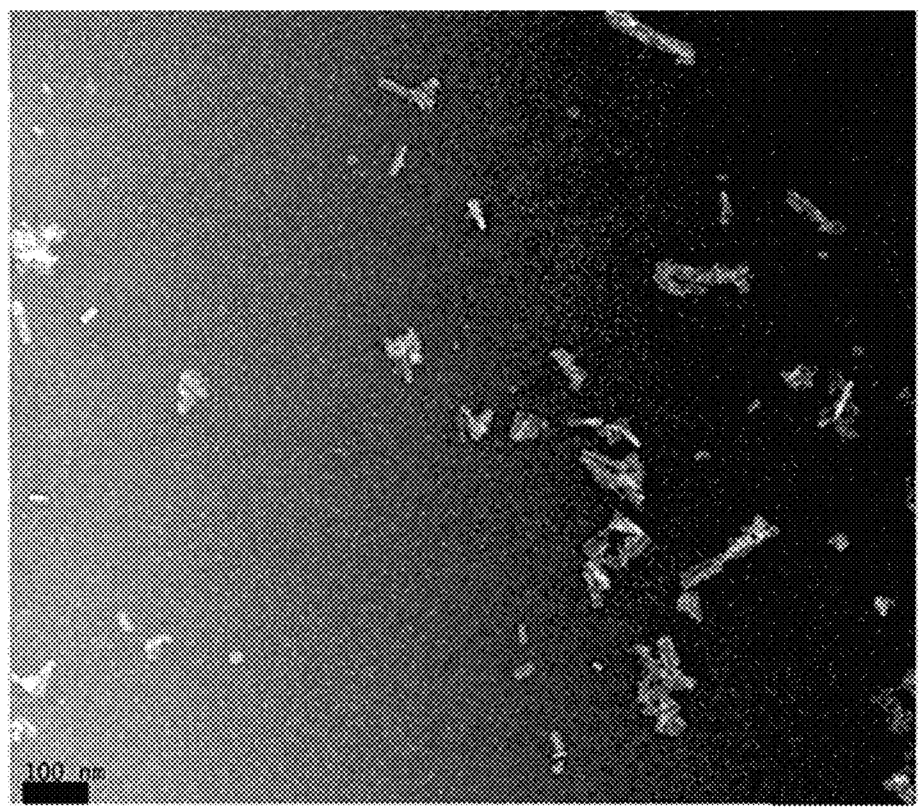
Figure 17:
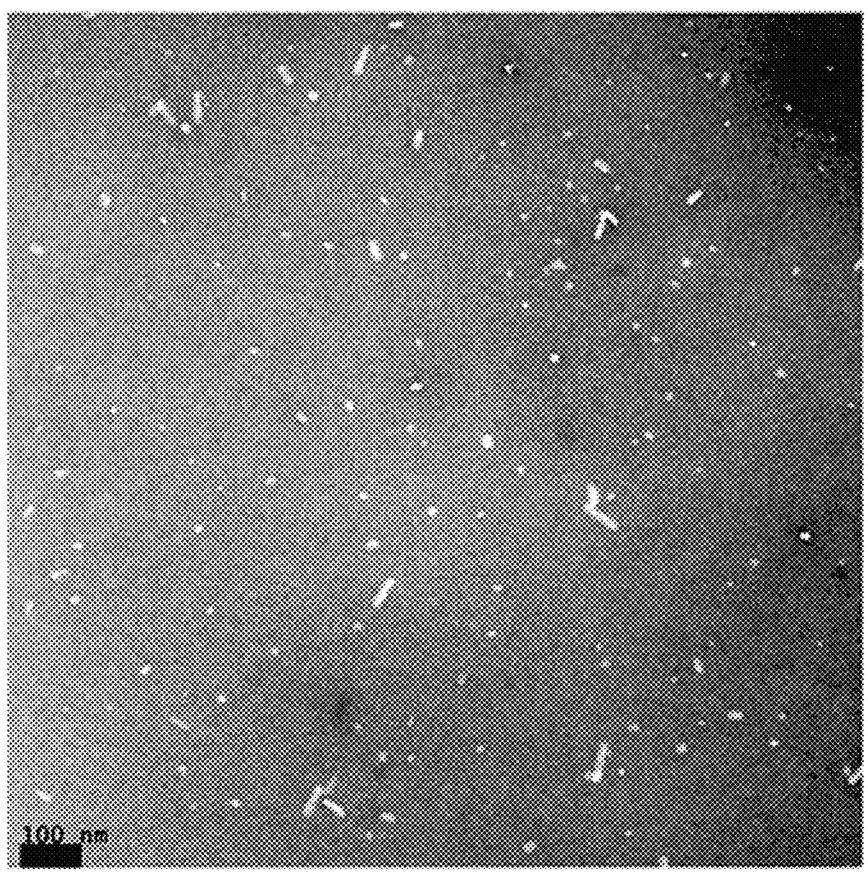
FIG. 17 depicts a micrograph of $Palm_2K$-$OVA_{BT}$ peptide amphiphile showing it self-assembles into spheres and cylindrical micelles in water.
Figure 18A:
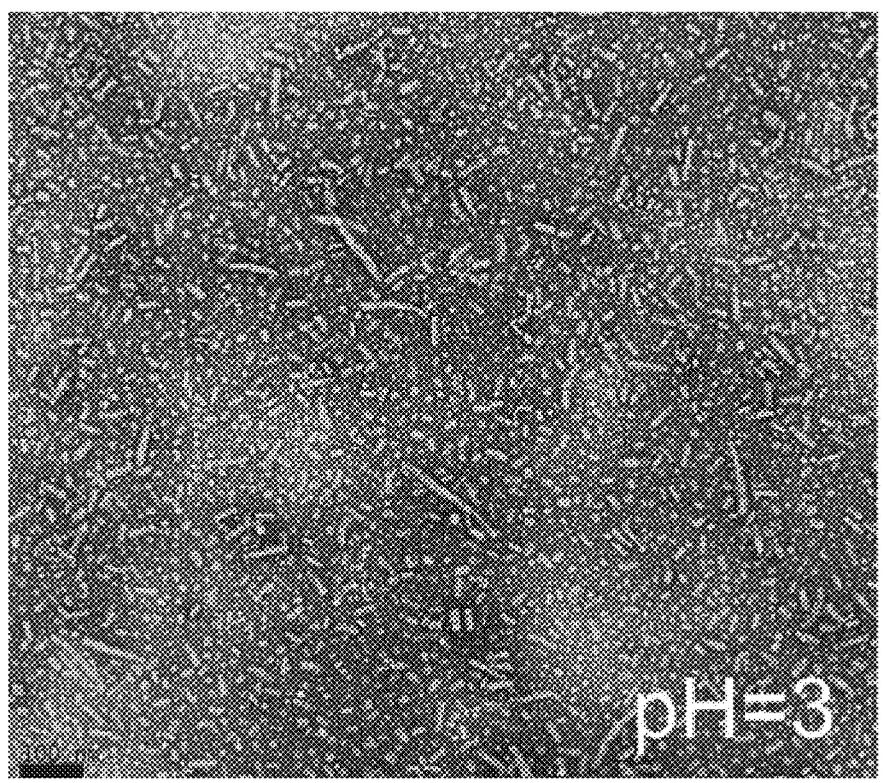
FIG. 18A, FIG. 18B, FIG. 18C, FIG. 18D, FIG. 18E, and FIG. 18F depict micrographs of $Palm_2K$-$OVA_{BT}$-$(KE)_4$ (FIG. 18A, FIG. 18B, and FIG. 18C) and $Palm_2K$-$(EK)_4$-$OVA_{BT}$ (FIG. 18D, FIG. 18E, and FIG. 18F) in $ddH_2O$ at three different pHs. While the micelles dissociated from one another at acidic or basic conditions, no other morphological changes were observed. This result is believed to be caused by hydrophobic interactions being more dominant than the electrostatic interactions.
Figure 18B:
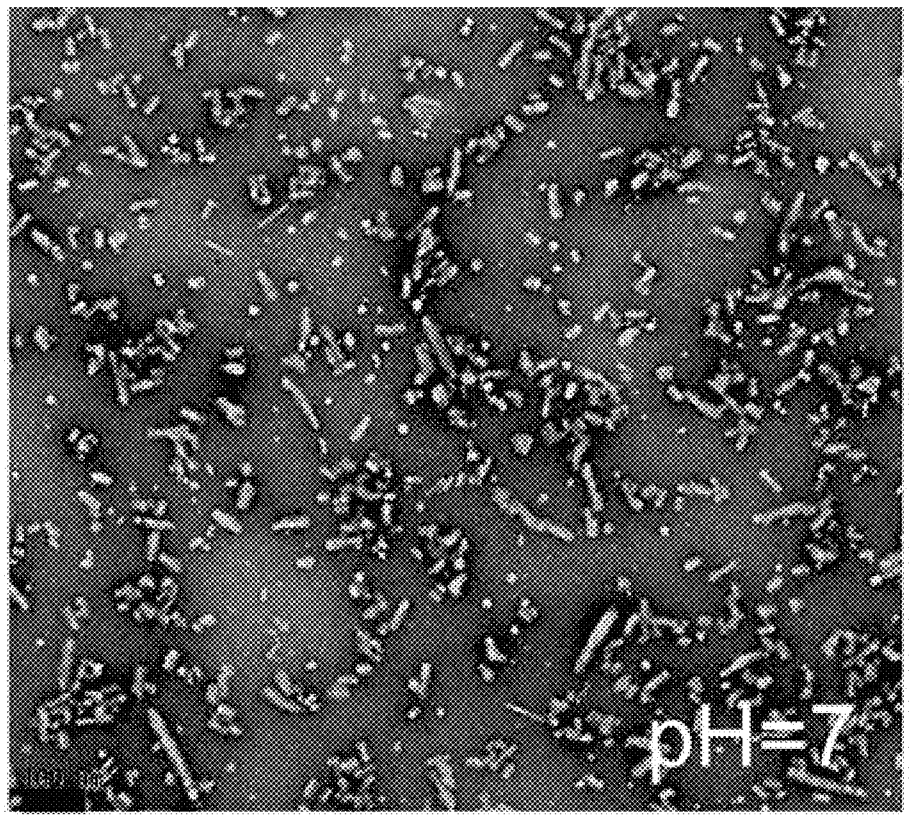
Figure 18C:
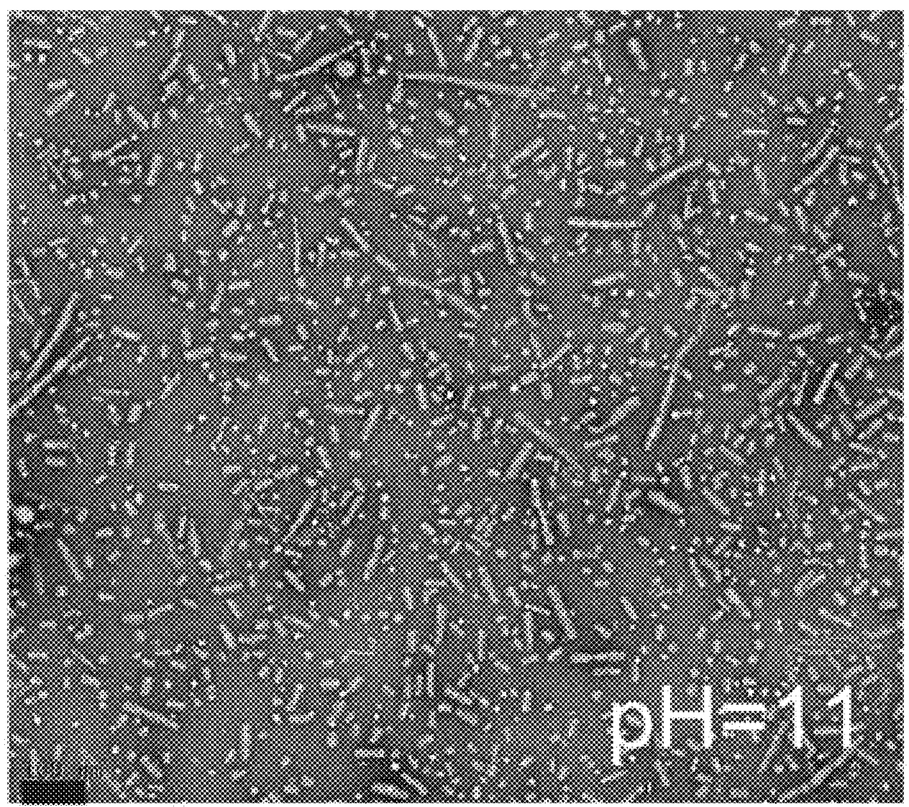
Figure 18D:
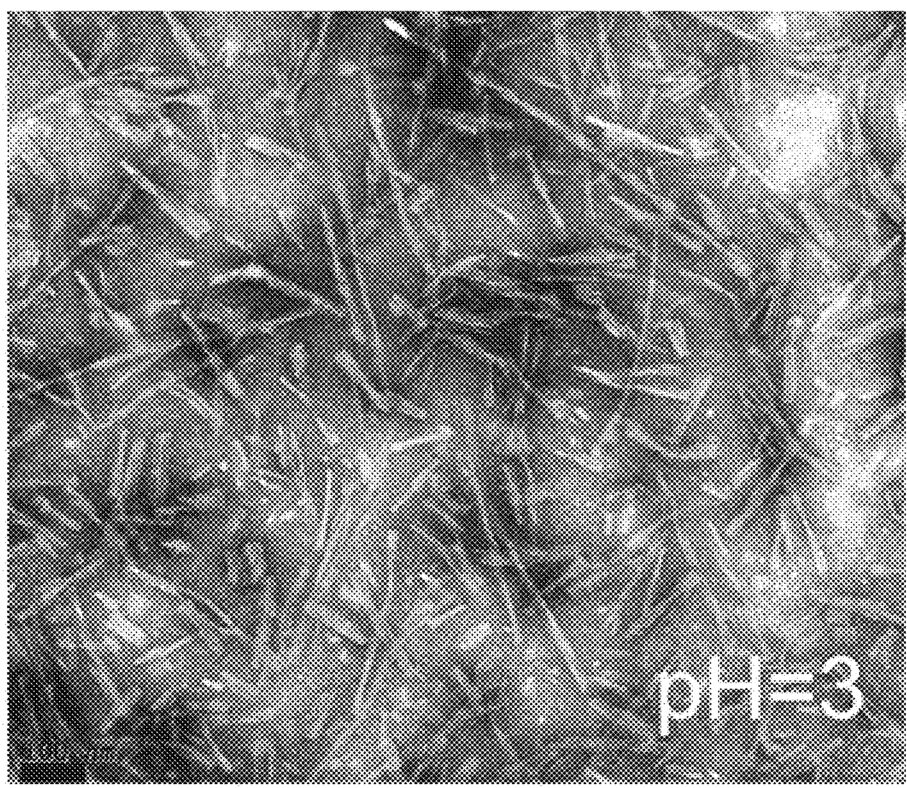
Figure 18E:
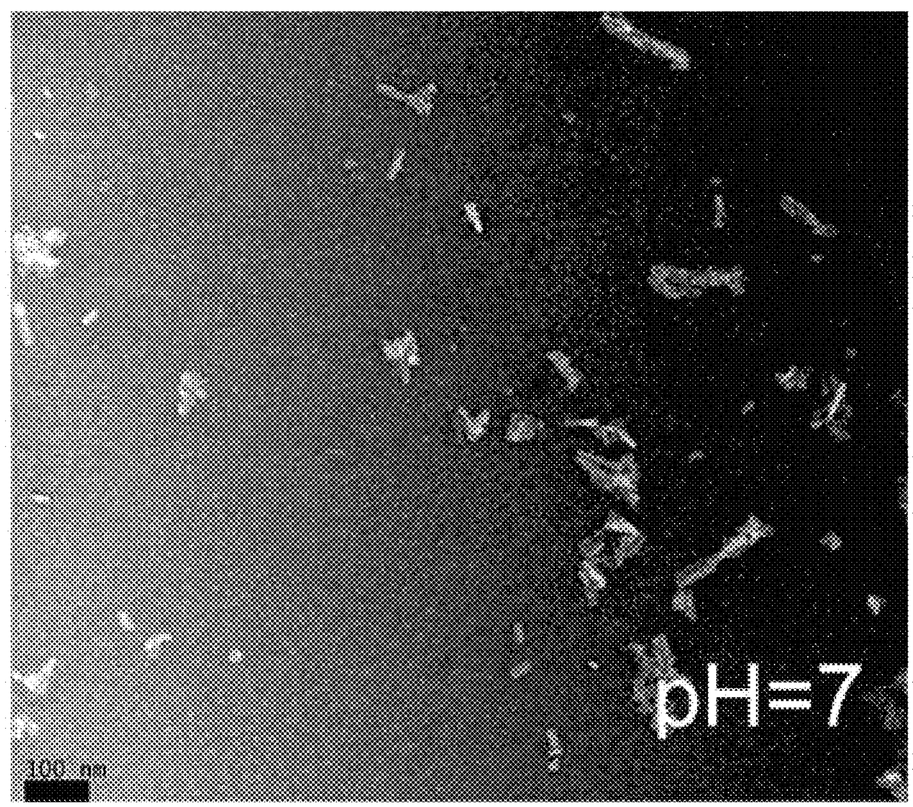
Figure 18F:
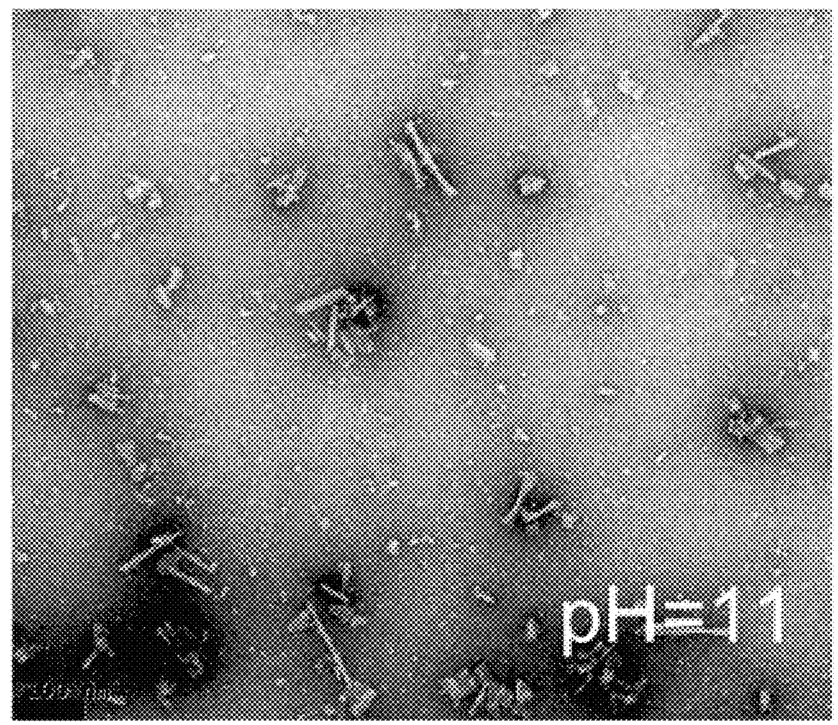
Figure 19A:
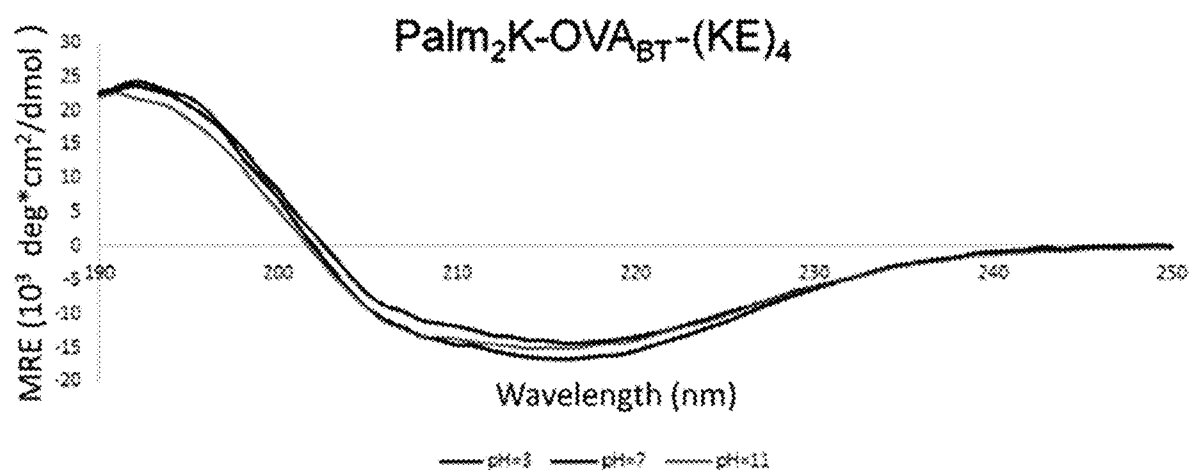
FIG. 19A, FIG. 19B, FIG. 19C, and FIG. 19D depict CD spectra of $Palm_2K$-$OVA_{BT}$-$(KE)_4$ (FIG. 19A) and $Palm_2K$-$(EK)_4$-$OVA_{BT}$ (FIG. 19C) with their respective secondary structure estimation (FIG. 19B and FIG. 19D, respectively).
Figures 19B, 19C:
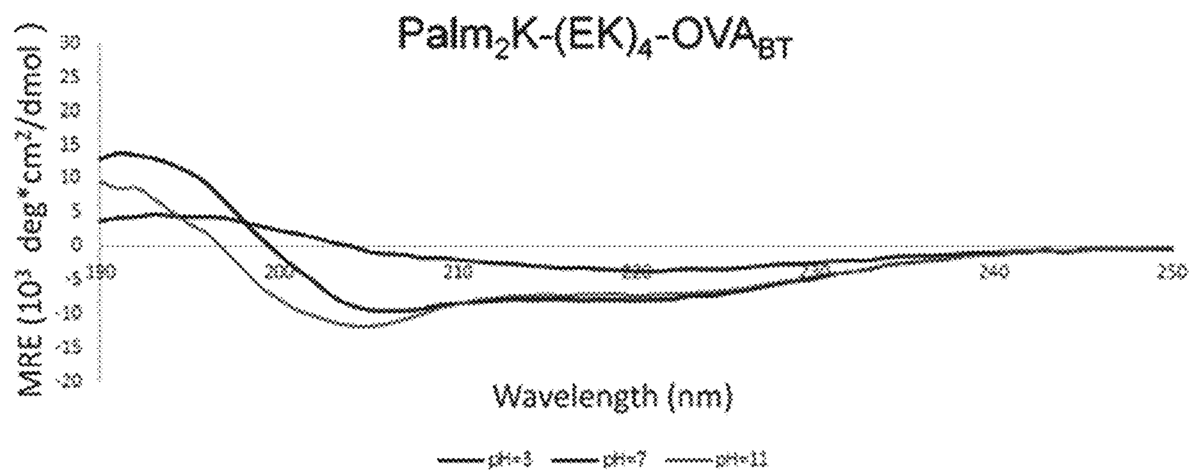
Figures 19D, 20A:
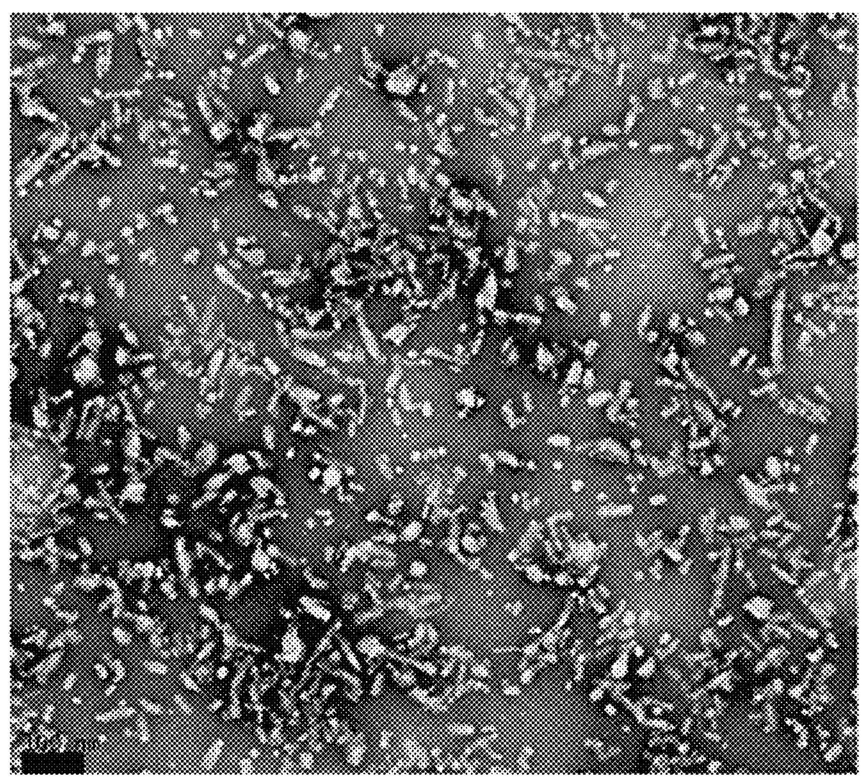
FIG. 20A and FIG. 20B depict micrographs of $Palm_2K$-$OVA_{BT}$-$(KE)_4$ (FIG. 20A) and $Palm_2K$-$(EK)_4$-$OVA_{BT}$ (FIG. 20B) in $ddH_2O$ (pH adjusted to 7). Significant aggregation of $Palm_2K$-$(EK)_4$-$OVA_{BT}$ was observed whereas only slight aggregation was shown for $Palm_2K$-$OVA_{BT}$-$(KE)_4$. It is hypothesized that double tail PAs have similar fluidity differences as their single tail counterparts so Palm2K-(EK) 4-$OVA_{BT}$ is less able to match dipoles within individual micelles allowing for greater multiple micelle complexation.
Figure 20B:
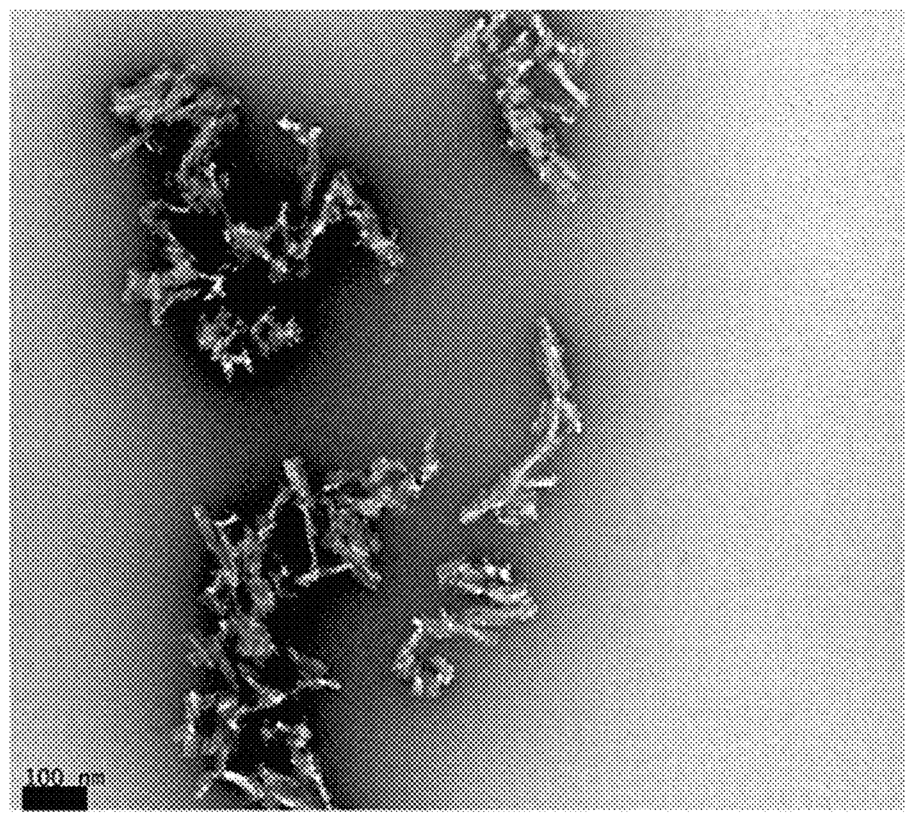
Figure 21A:
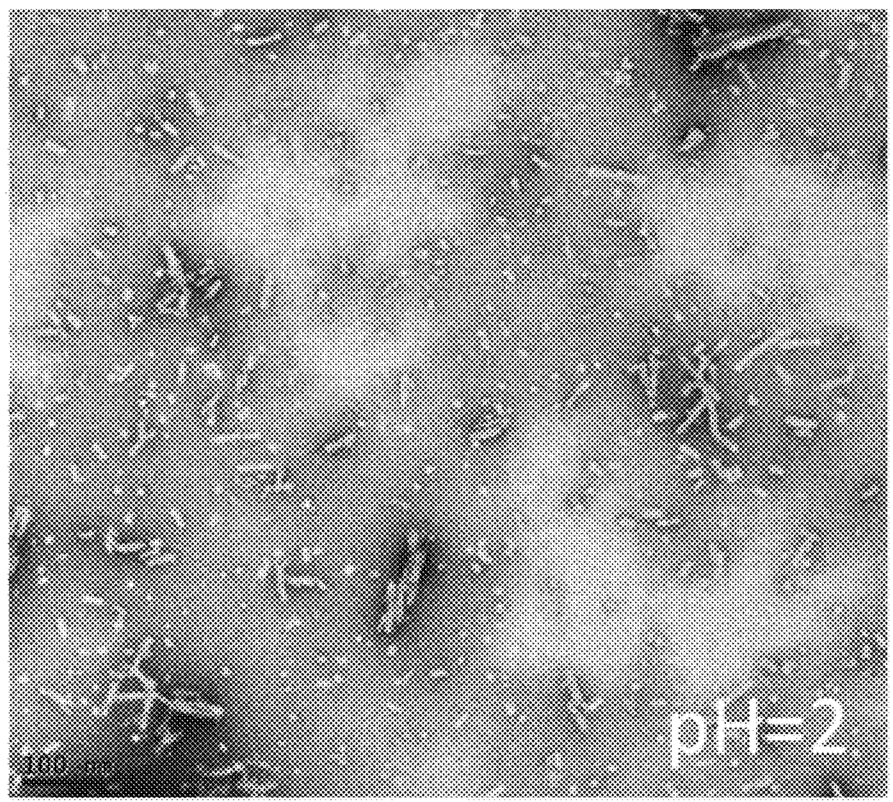
FIG. 21A, FIG. 21B, and FIG. 21C depict micrographs of $Palm_2K$-$OVA_{BT}$ (FIG. 21A, FIG. 21B, and FIG. 21C) at three different pHs (2, 7, and 11), showing no obvious morphological changes as a function of altering Ph, indicating the importance of the zwitterion-like region in complex micelle formation.
Figure 21B:
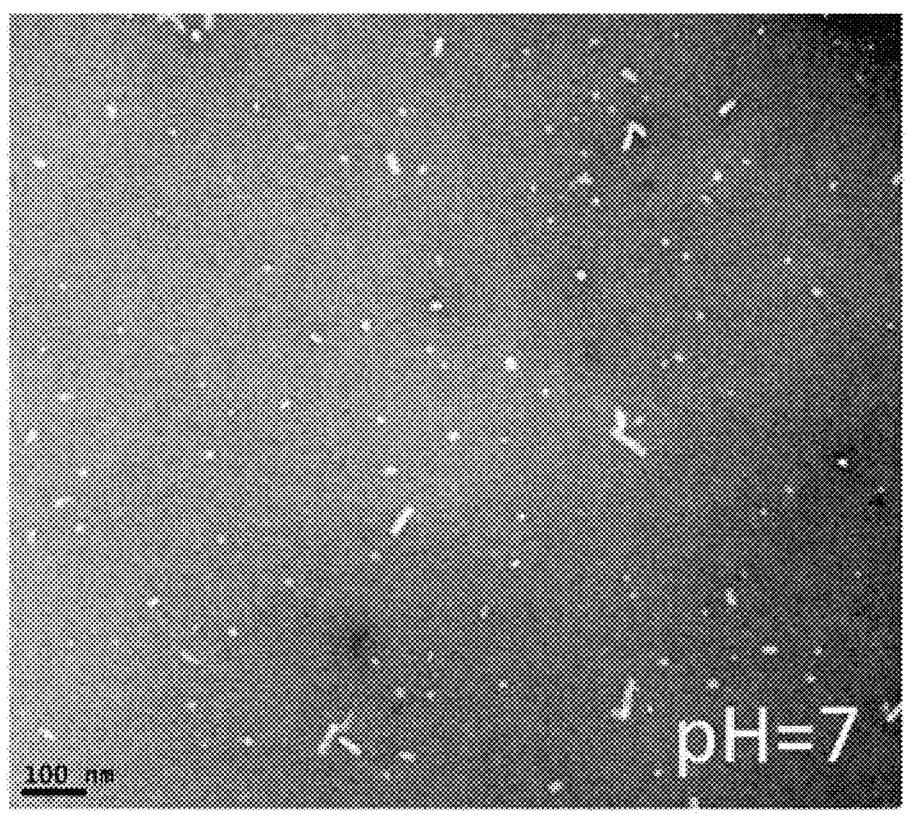
Figure 21C:
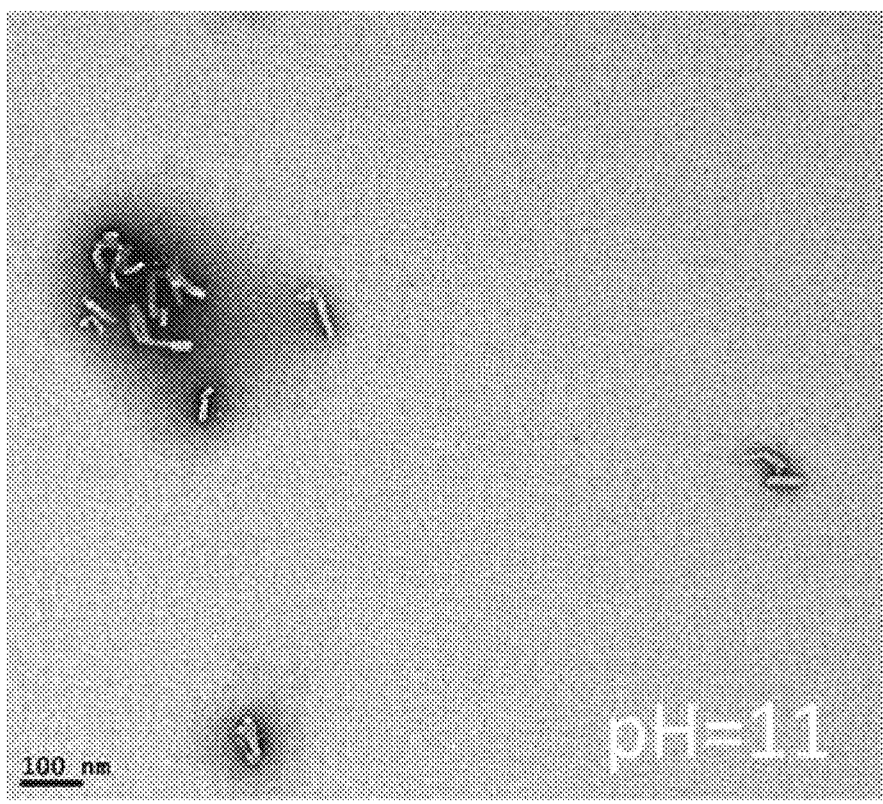
Figure 22A:
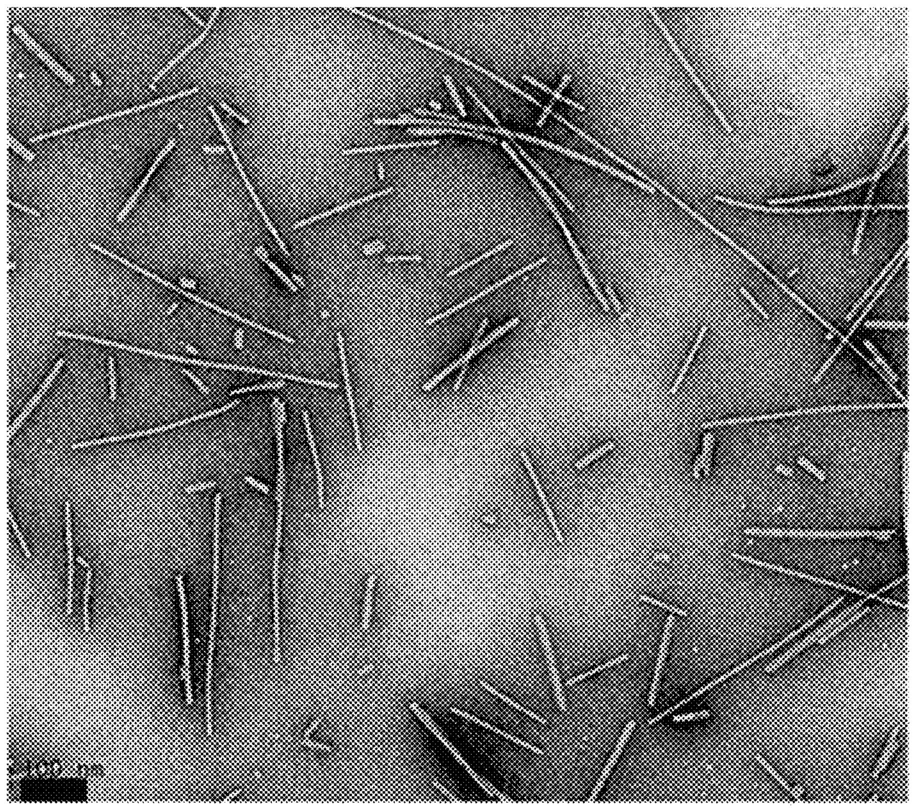
FIG. 22A, FIG. 22B, FIG. 22C, and FIG. 22D depict micelle shape and aggregation as application-specific peptide insensitive. Four $OVA_{cytoT}$ amphiphile chemistries ((FIG. 22A) PalmK-$OVA_{cytoT}$-$(KE)_4$, (FIG. 22B) $Palm_2K$-$OVA_{cytoT}$-$(KE)_4$, (FIG. 22C) PalmK-$(EK)_4$-$OVA_{cytoT}$, and (FIG. 22D) $Palm_2K$-$(EK)_4$-$OVA_{cytoT}$) similar to the $OVA_{BT}$ peptide amphiphiles yielded essentially identical structures (i.e., (FIG. 22A) twines, (FIG. 22B) spheres/short cylinders, (FIG. 22C) braids, and (FIG. 22D) clusters) at pH 7 as determined by TEM. These results provide evidence that the lipid and zwitterion-like regions dominate micelle formation and subsequent aggregation allowing micelle shape control to be independent of the application-specific peptide included.
Figure 22B:
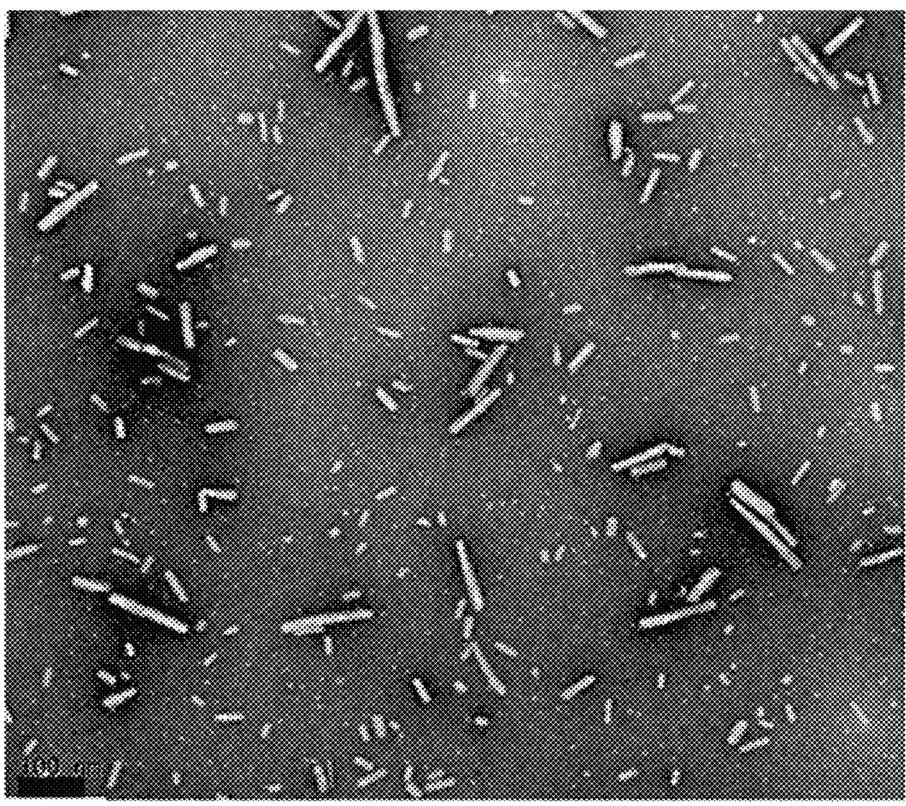
Figure 22C:
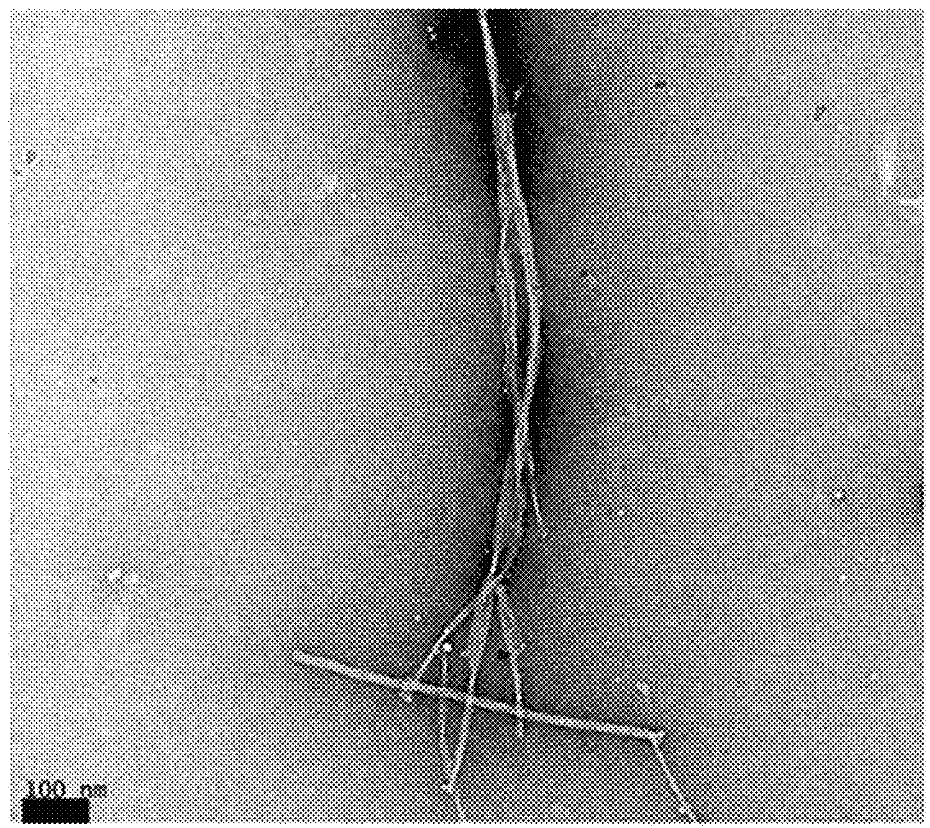
Figure 22D:
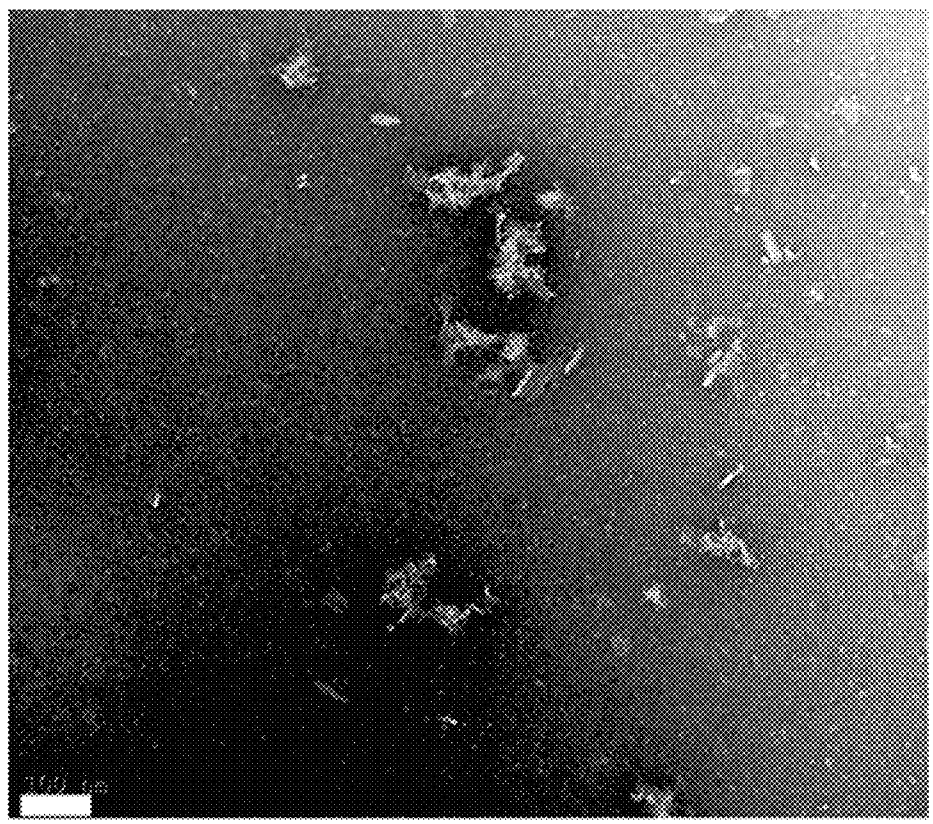
Figure 23:
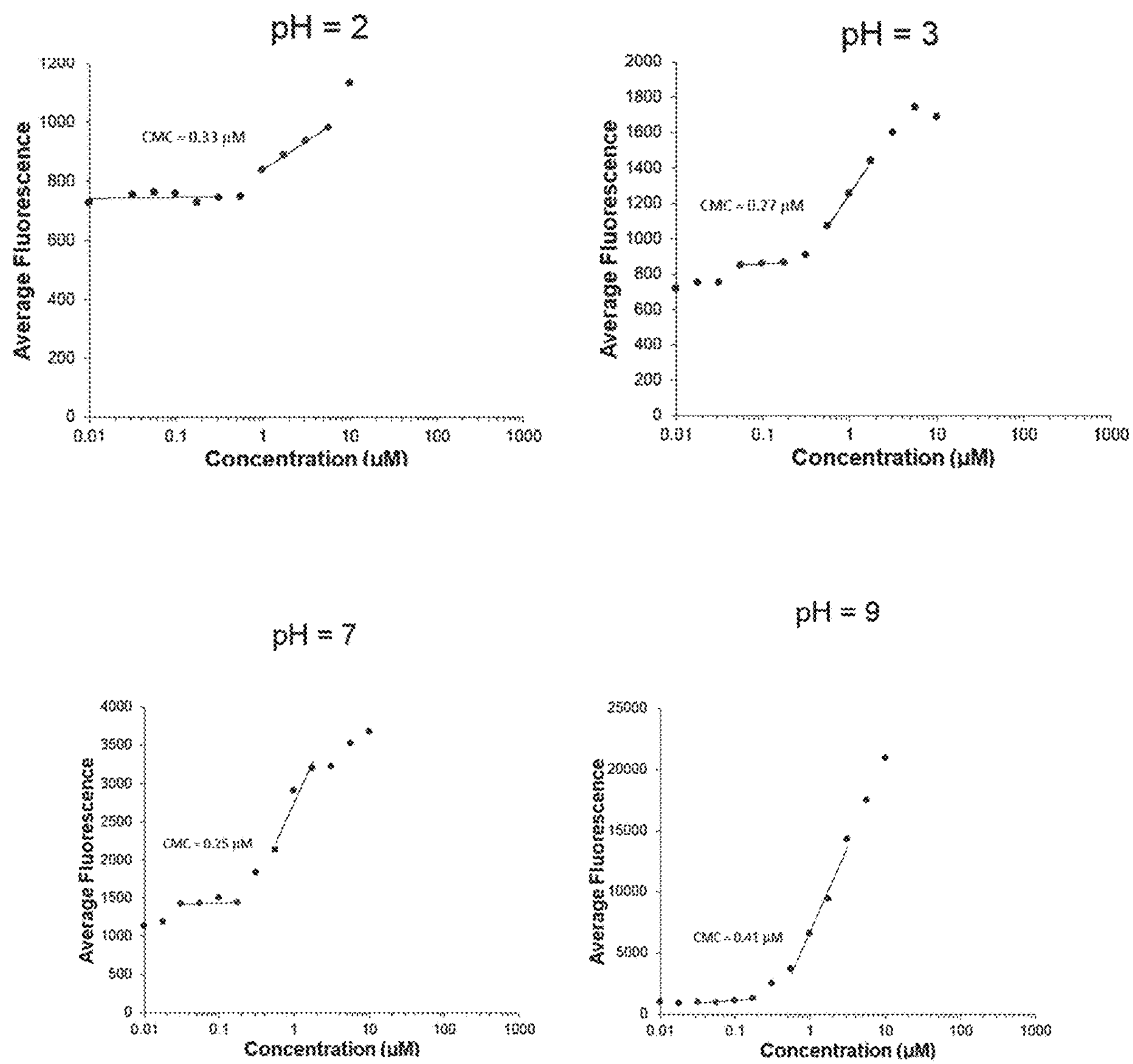
FIG. 23 depicts PalmK-$OVA_{BT}$-$(KE)_4$ CMC determination at different pH values.
Figure 23:
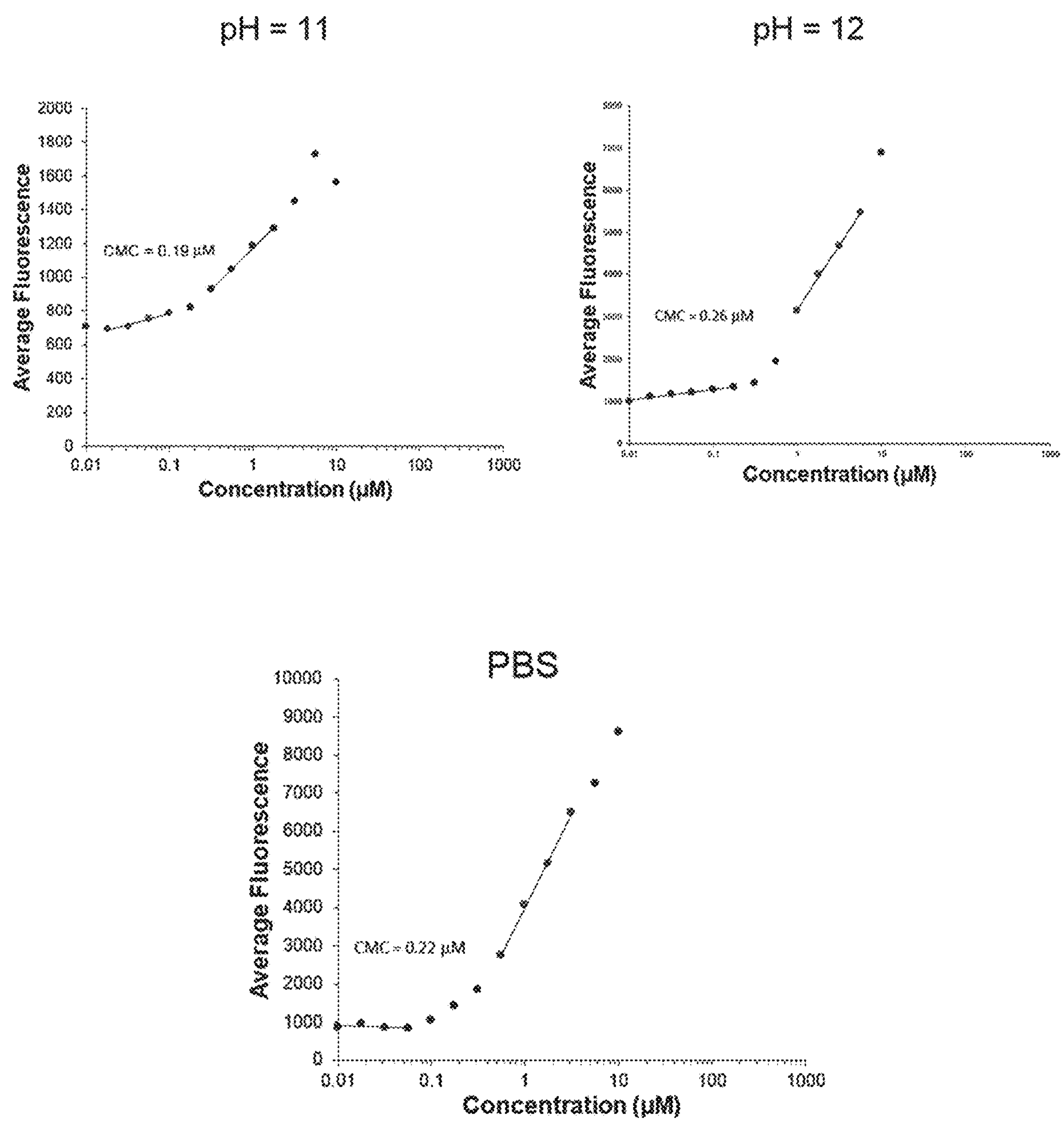
Figure 24:
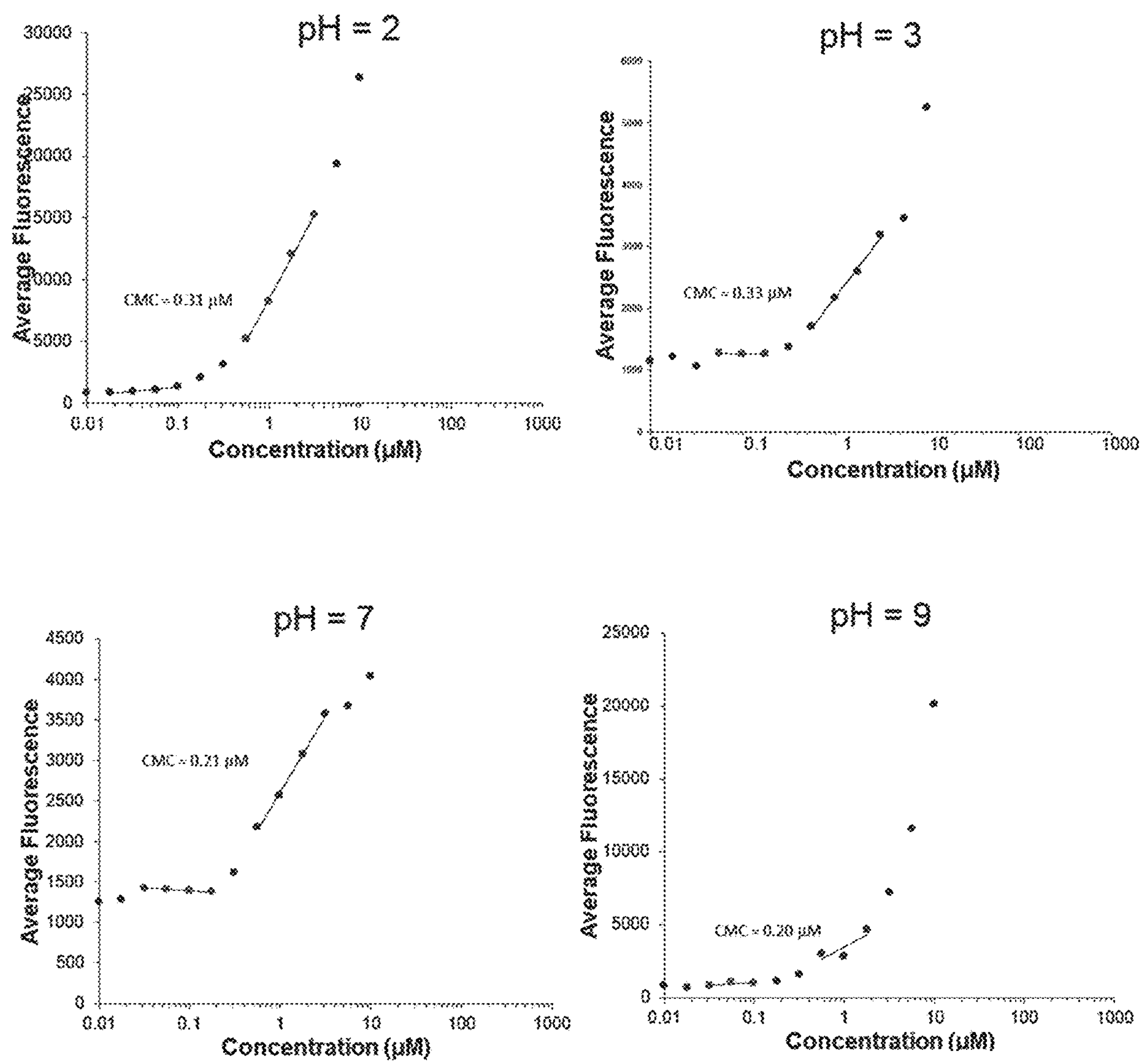
FIG. 24 depicts $Palm_2K$-$OVA_{BT}$-$(KE)_4$ CMC determination at different pH values.
Figure 24:
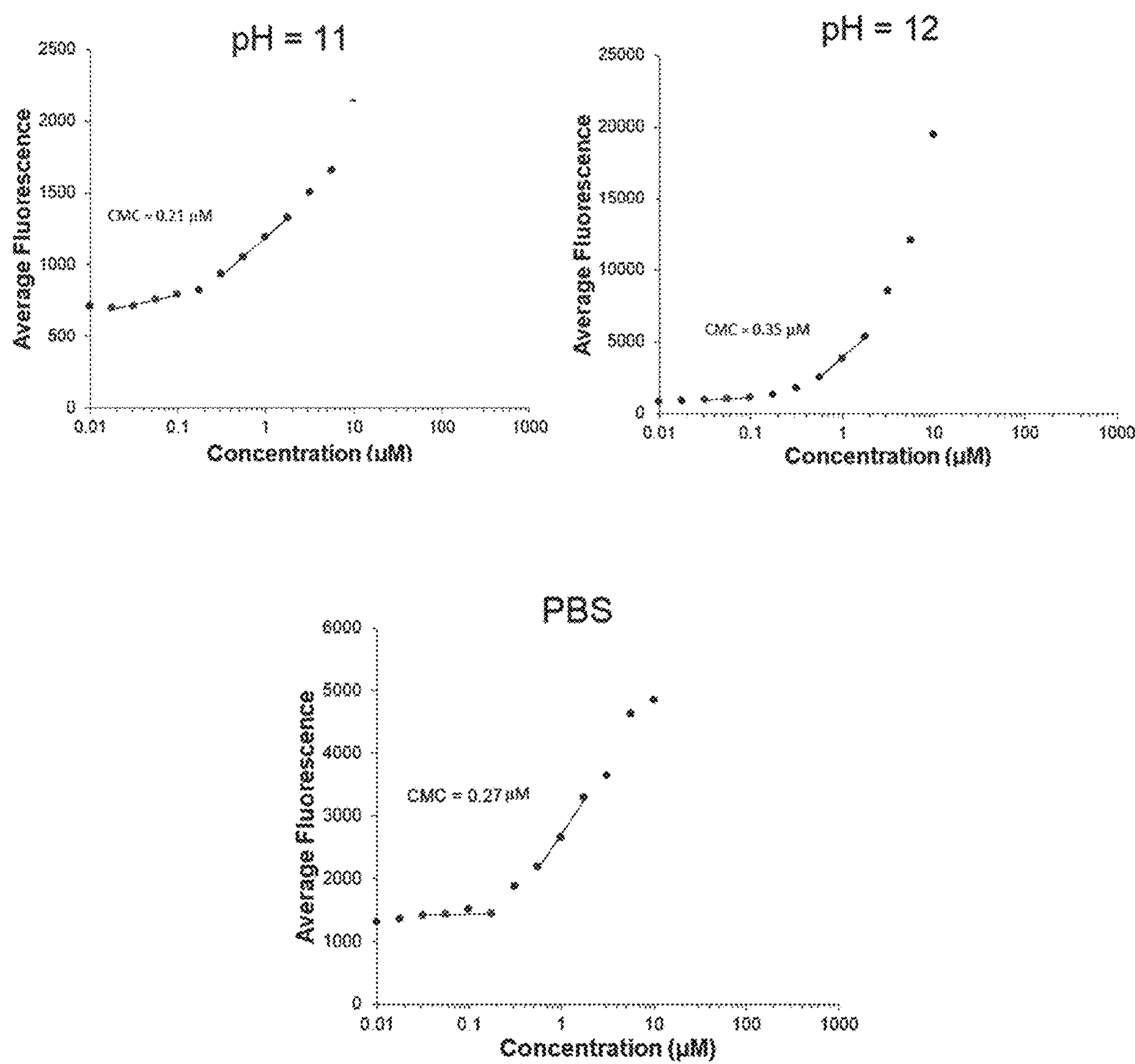
Figure 25:
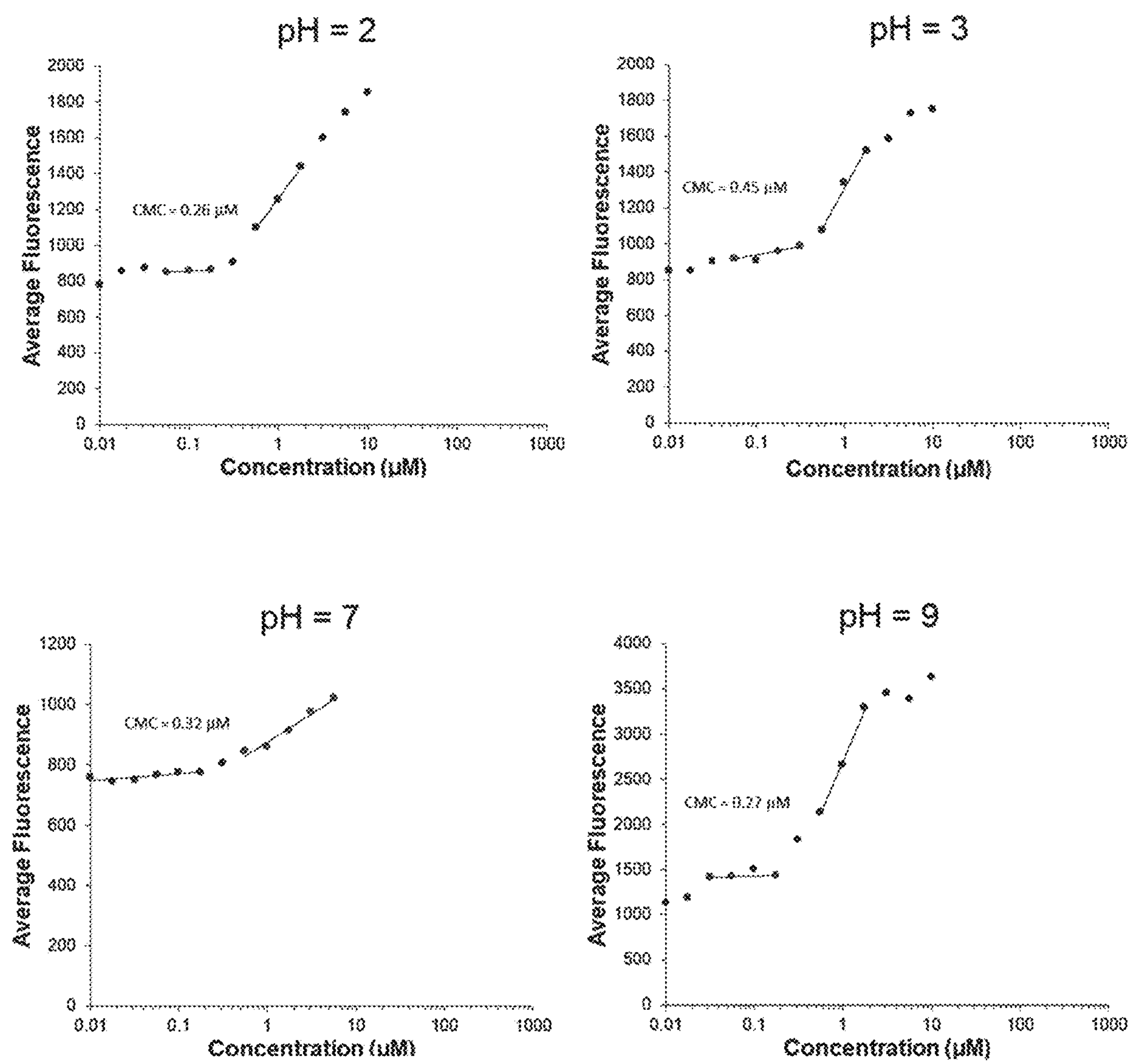
FIG. 25 depicts PalmK-$(KE)_4$-$OVA_{BT}$ CMC determination at different pH values.
Figure 25:
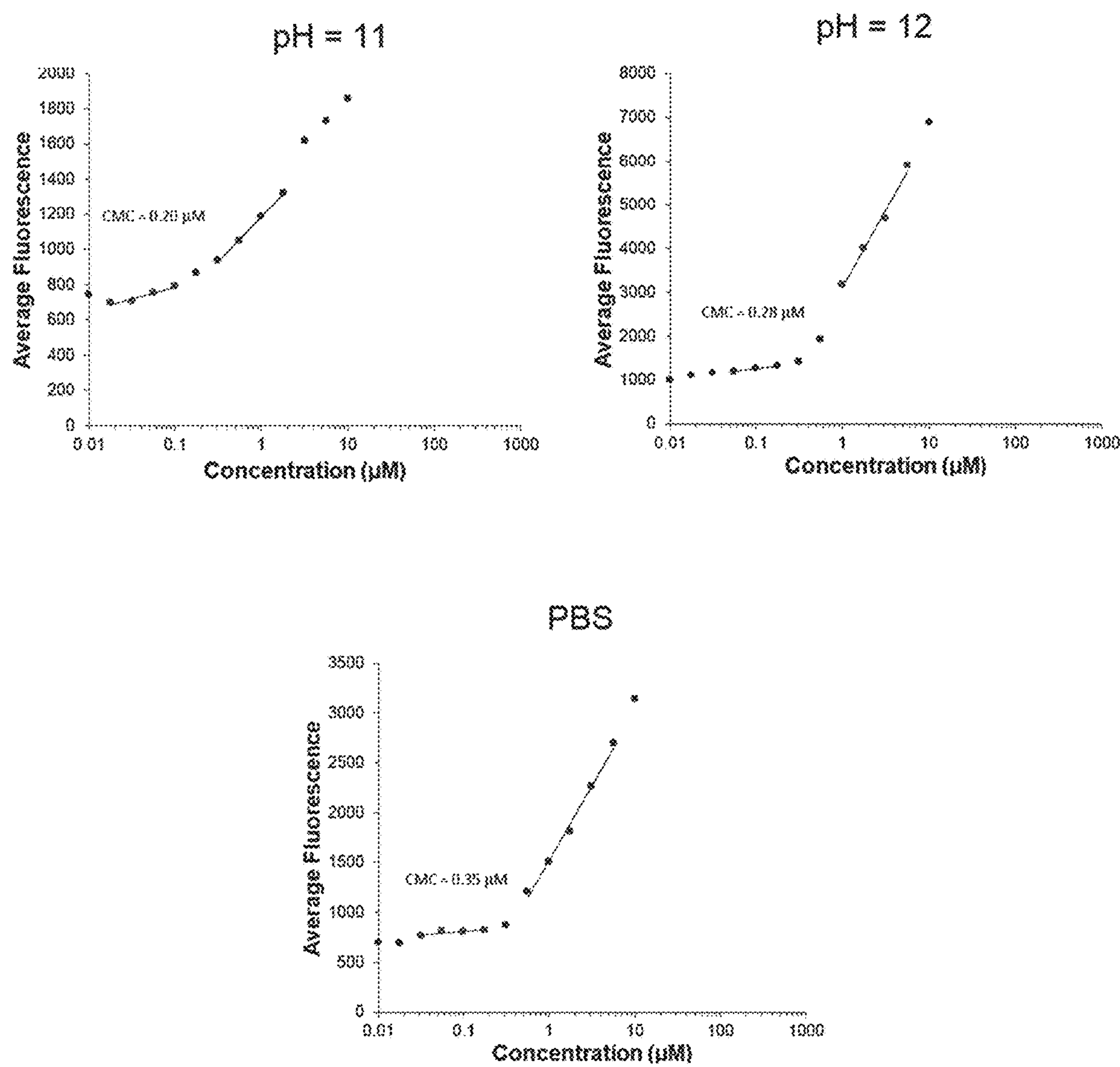
Figure 26:
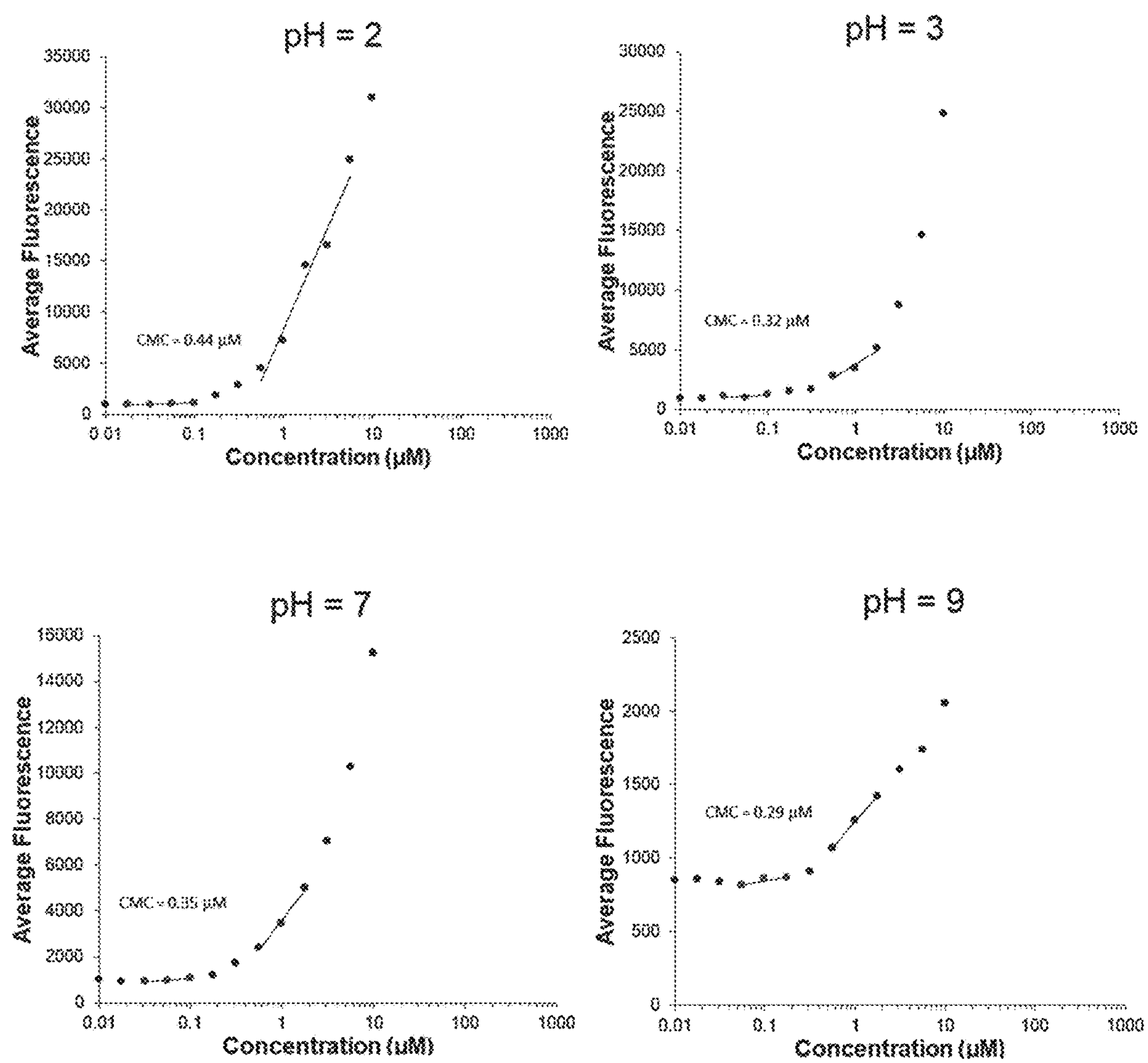
FIG. 26 depicts $Palm_2K$-$(KE)_4$-$OVA_{BT}$ CMC determination at different pH values.
Figure 26:
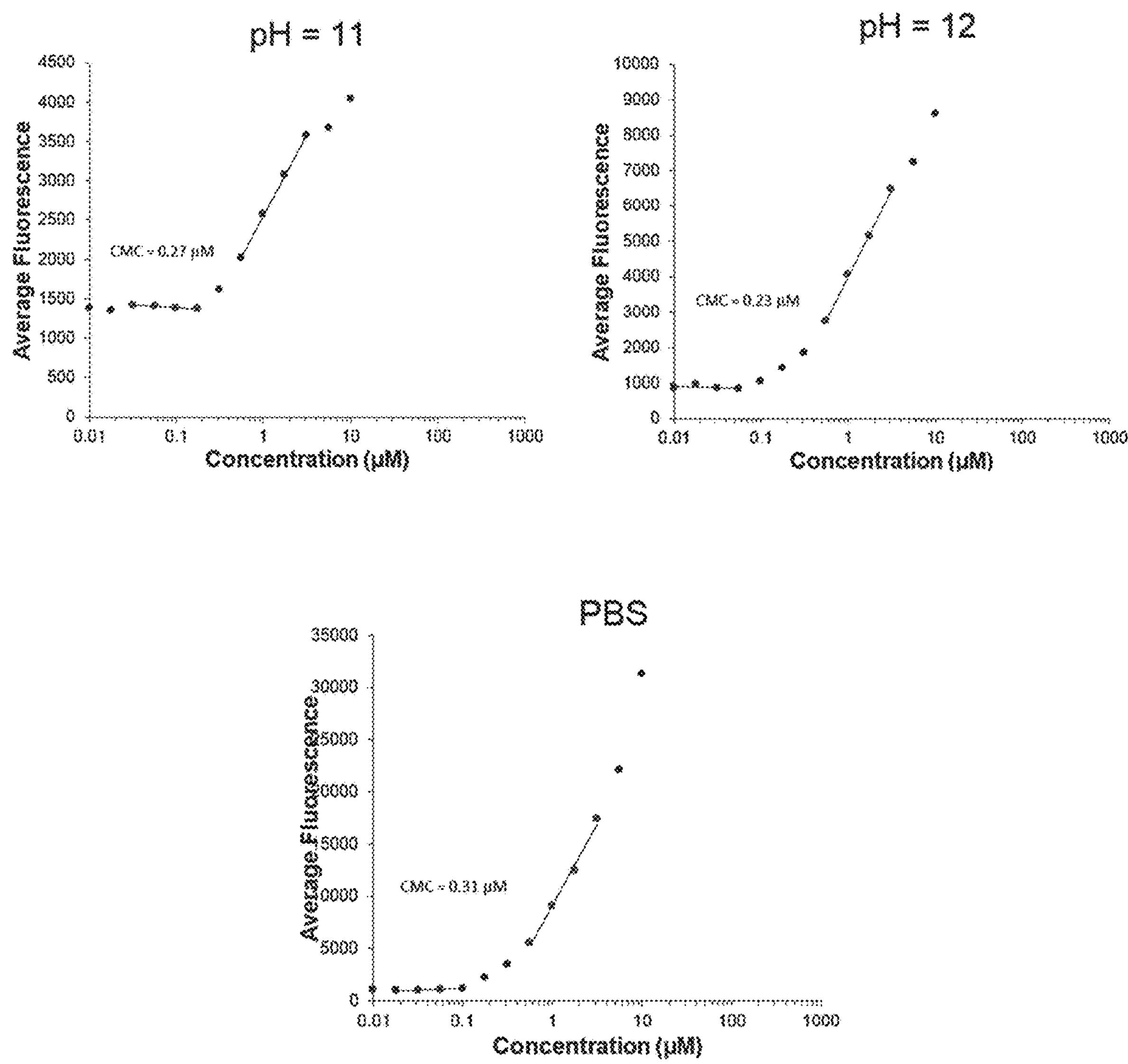
Figure 27:
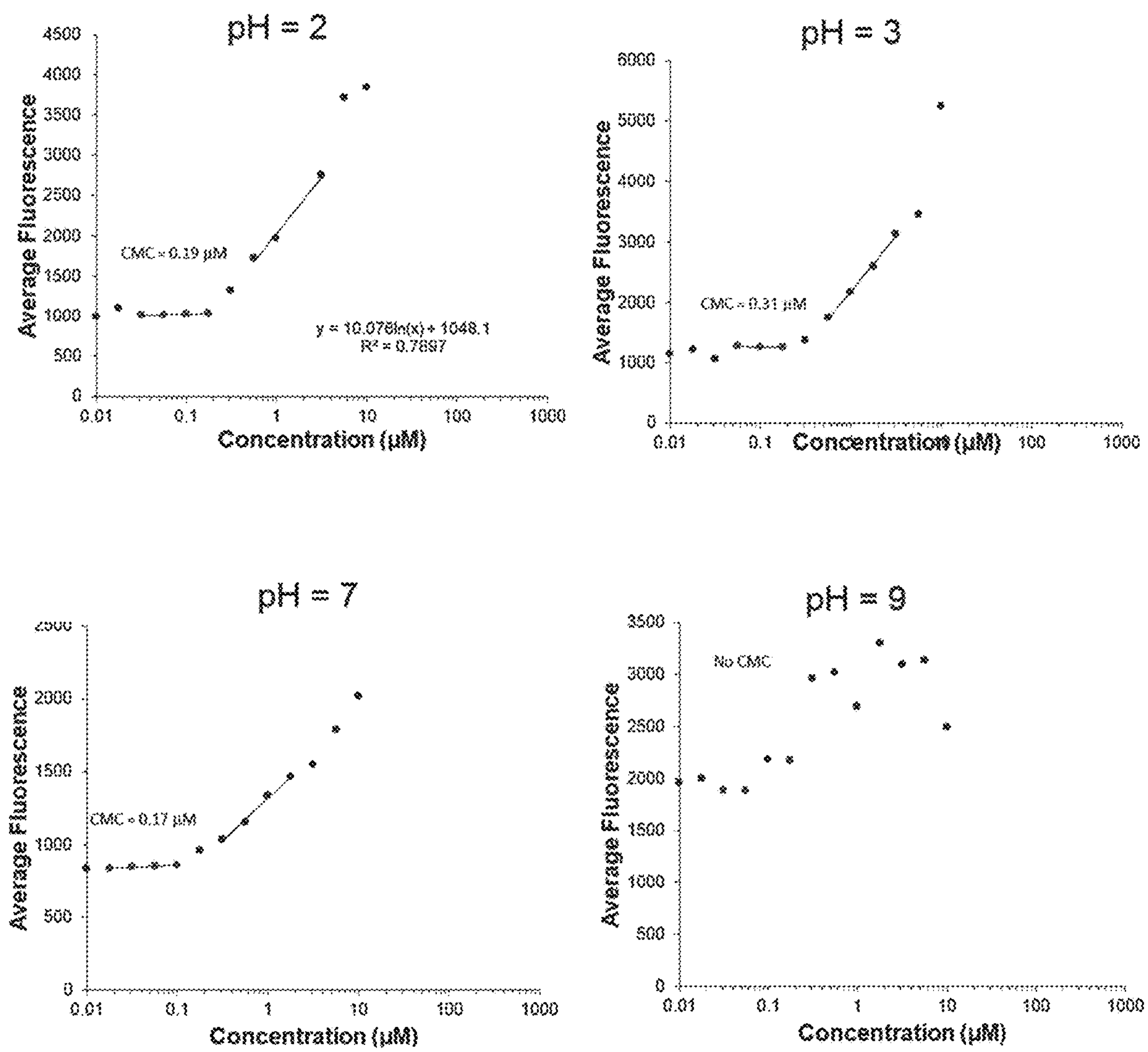
FIG. 27 depicts PalmK-$OVA_{cytoT}$-$(KE)_4$ CMC determination at different pH values.
Figure 27:
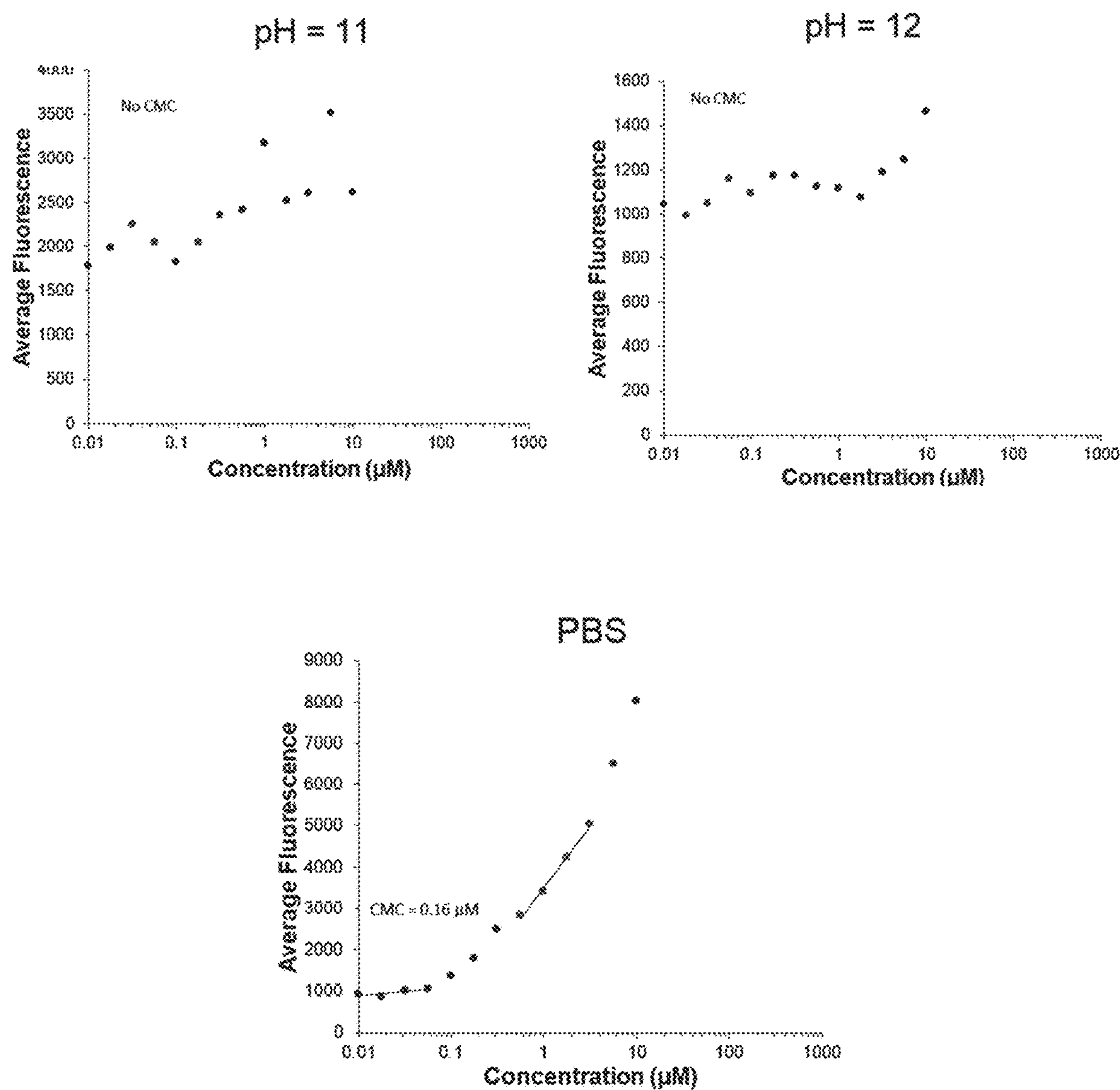
Figure 28:
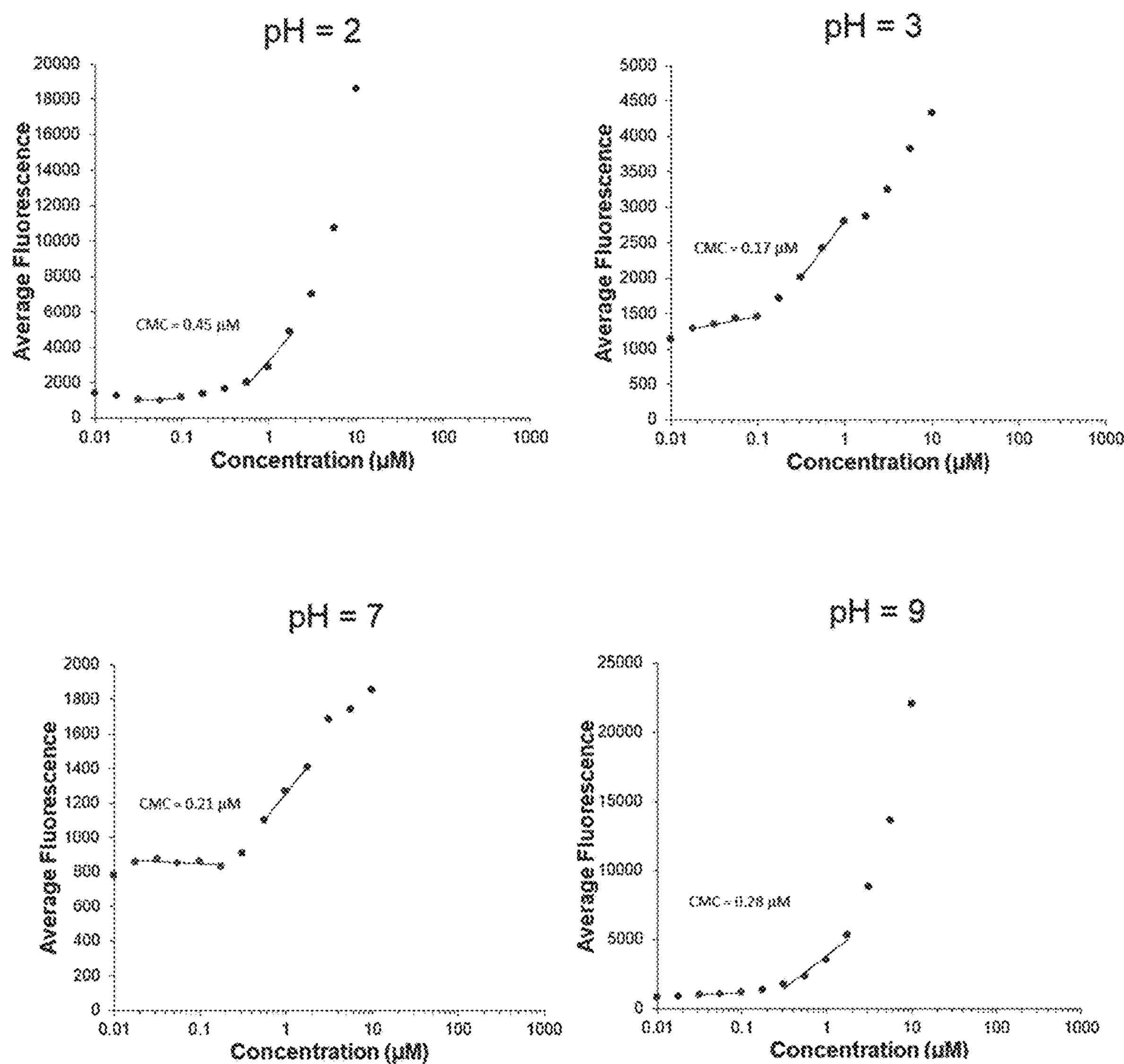
FIG. 28 depicts $Palm_2K$-$OVA_{cytoT}$-$(KE)_4$ CMC determination at different pH values.
Figure 28:
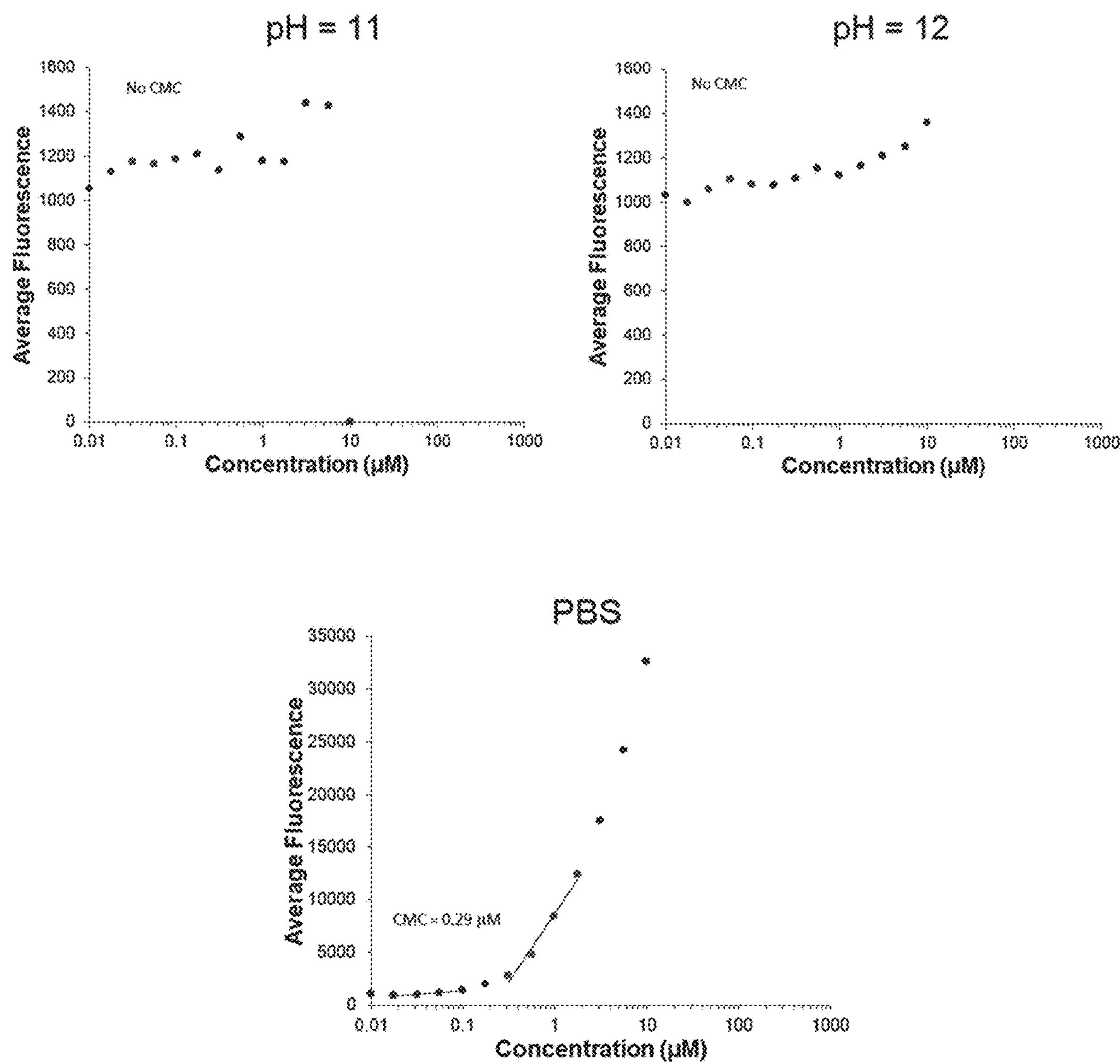
Figure 29:
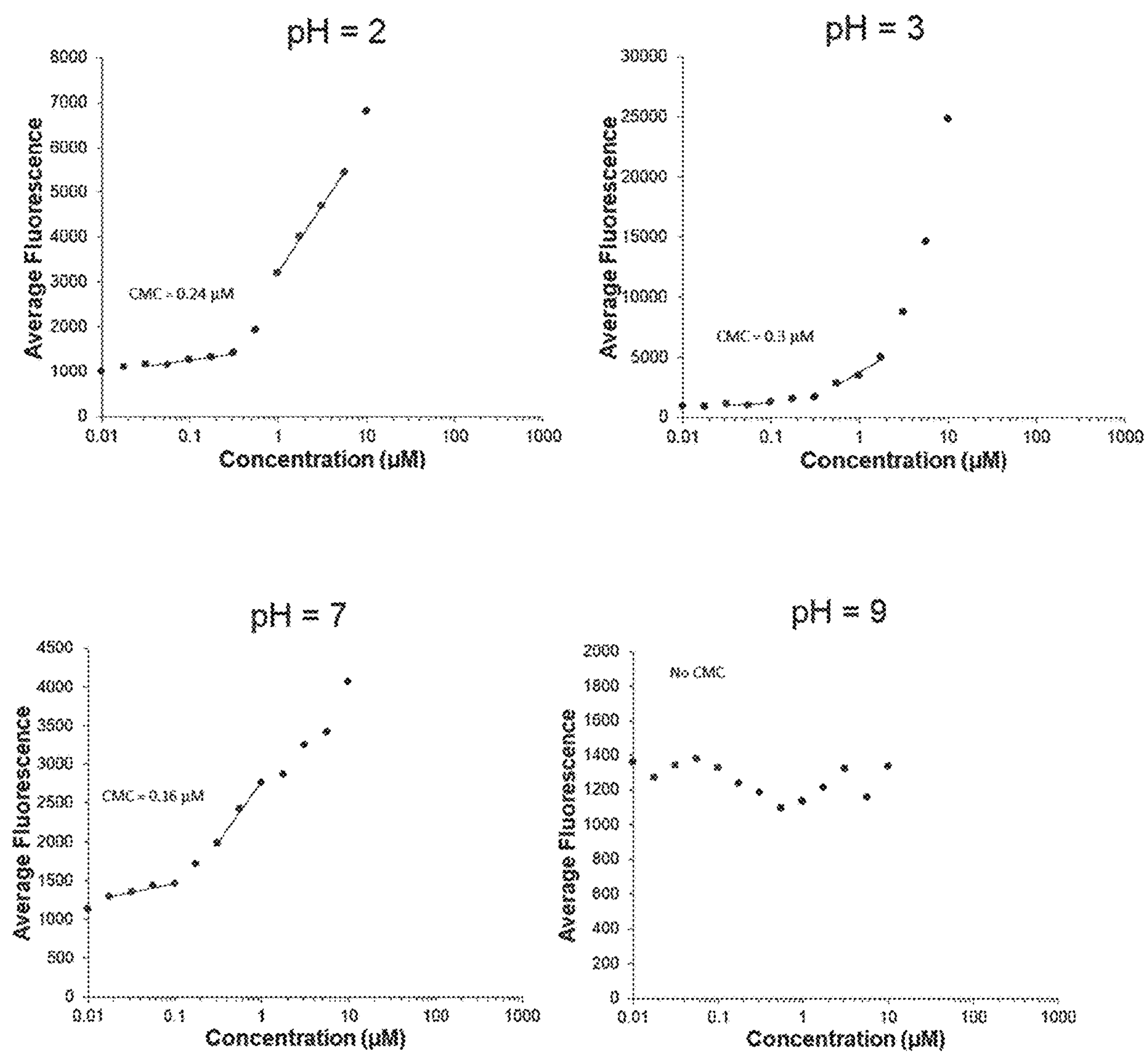
FIG. 29 depicts PalmK-$(KE)_4$-$OVA_{cytoT}$ CMC determination at different pH values.
Figure 29:
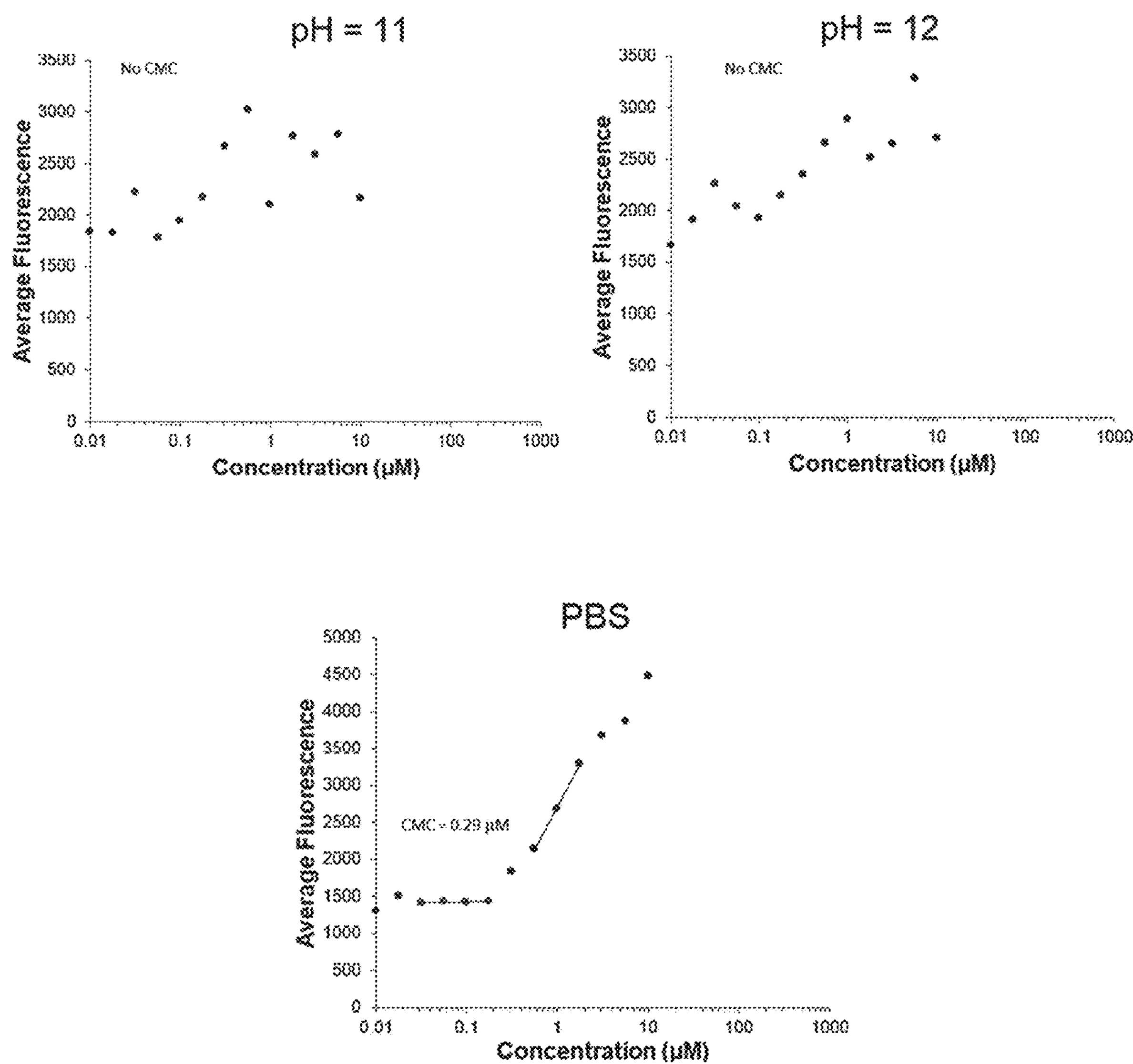
Figure 30:
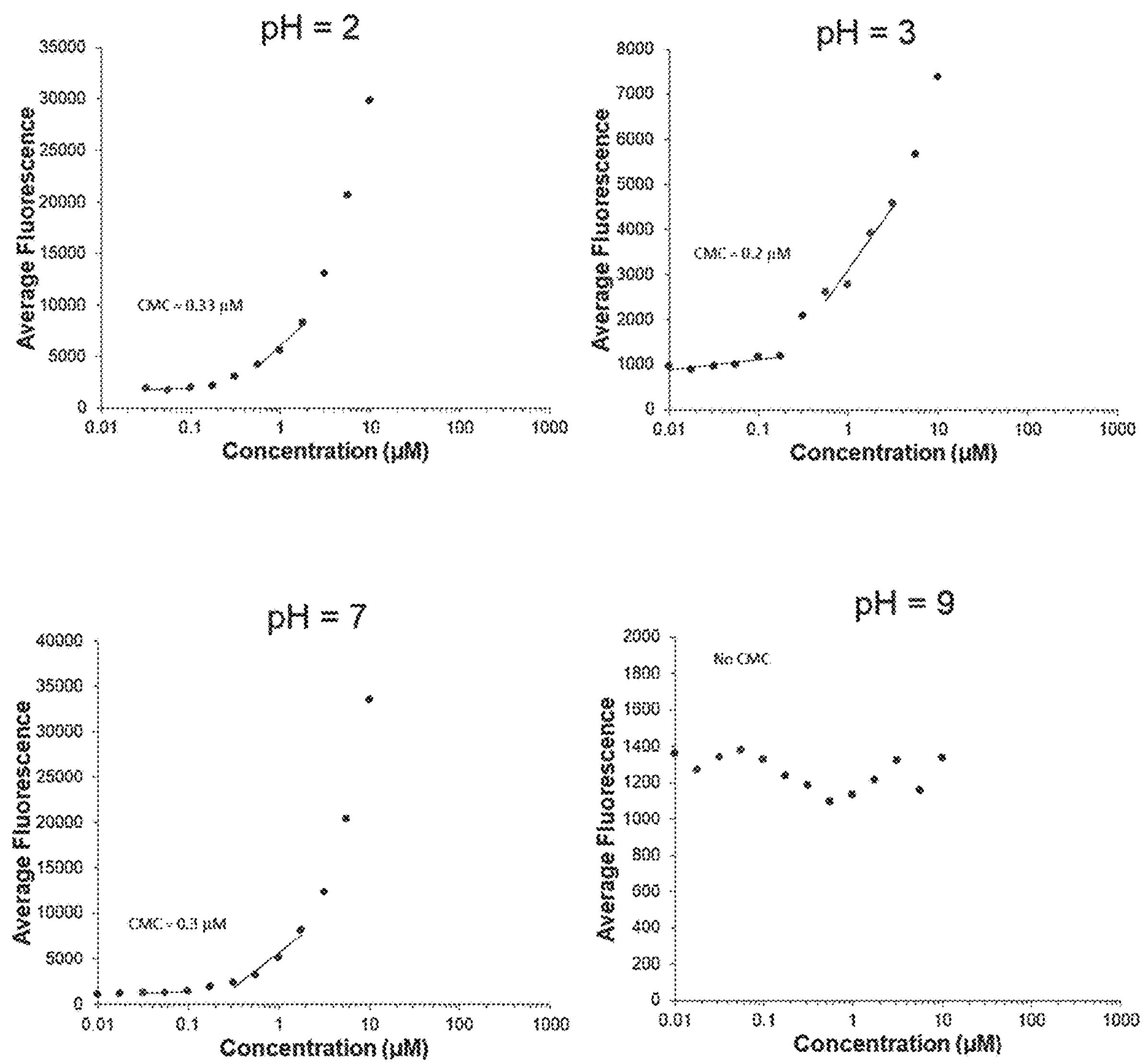
FIG. 30 depicts $Palm_2K$-$(KE)_4$-$OVA_{cytoT}$ CMC determination at different pH values.
Figure 30:
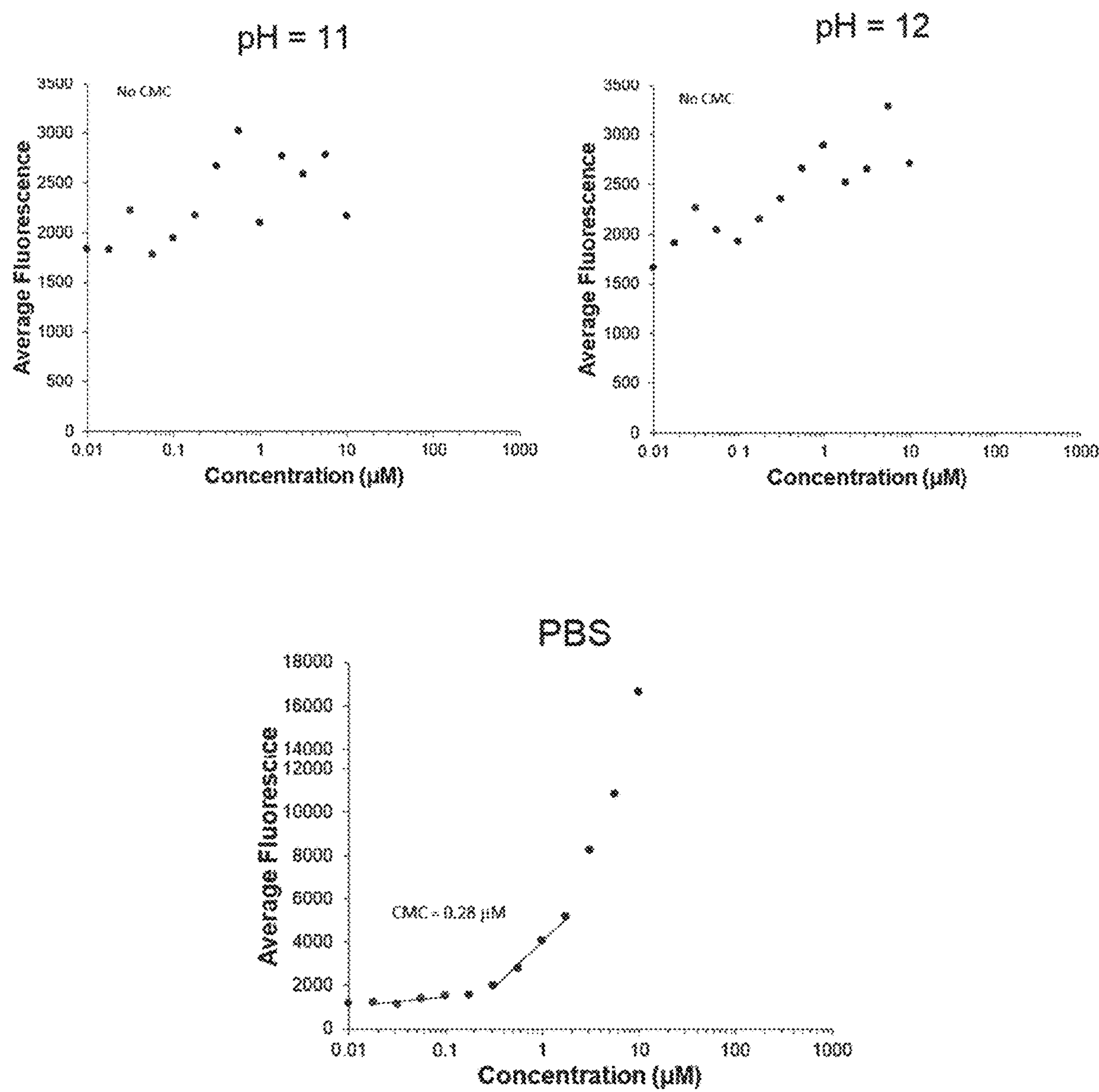
Figure 31A:
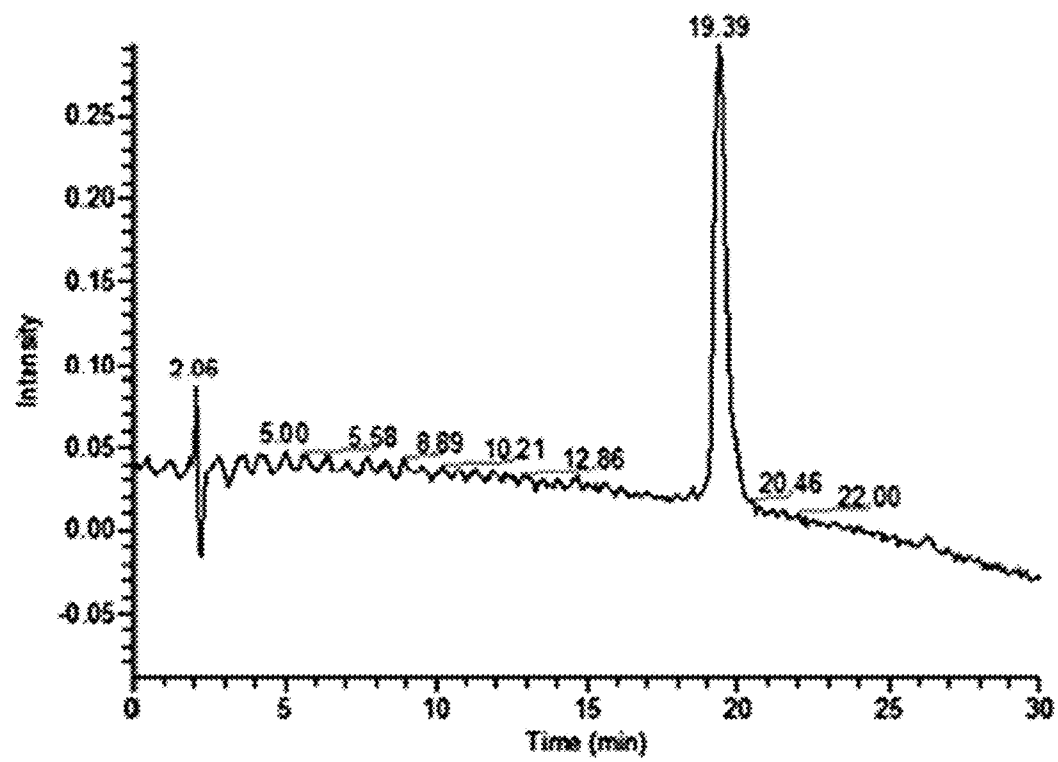
FIG. 31A and FIG. 31B depict HPLC photo diode array detection (FIG. 31A) and mass spectrometry analysis (FIG. 31B) of PalmK-$OVA_{BT}$-$(KE)_4$.
Figure 31B:
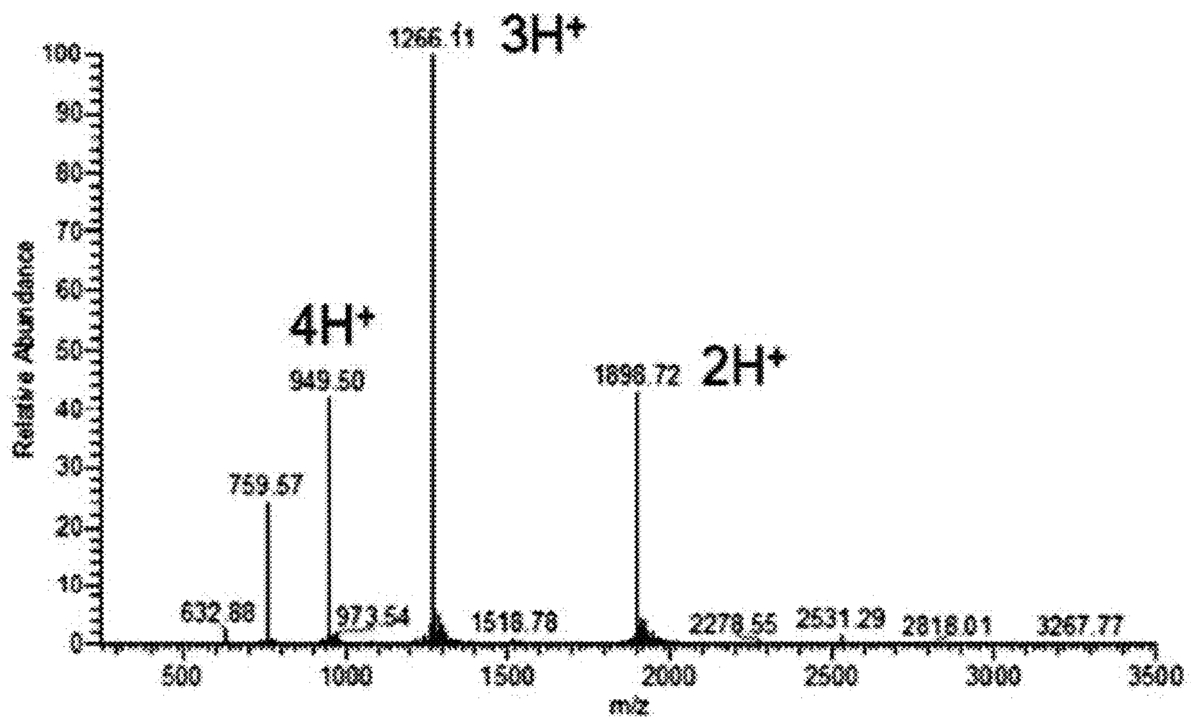
Figure 32A:
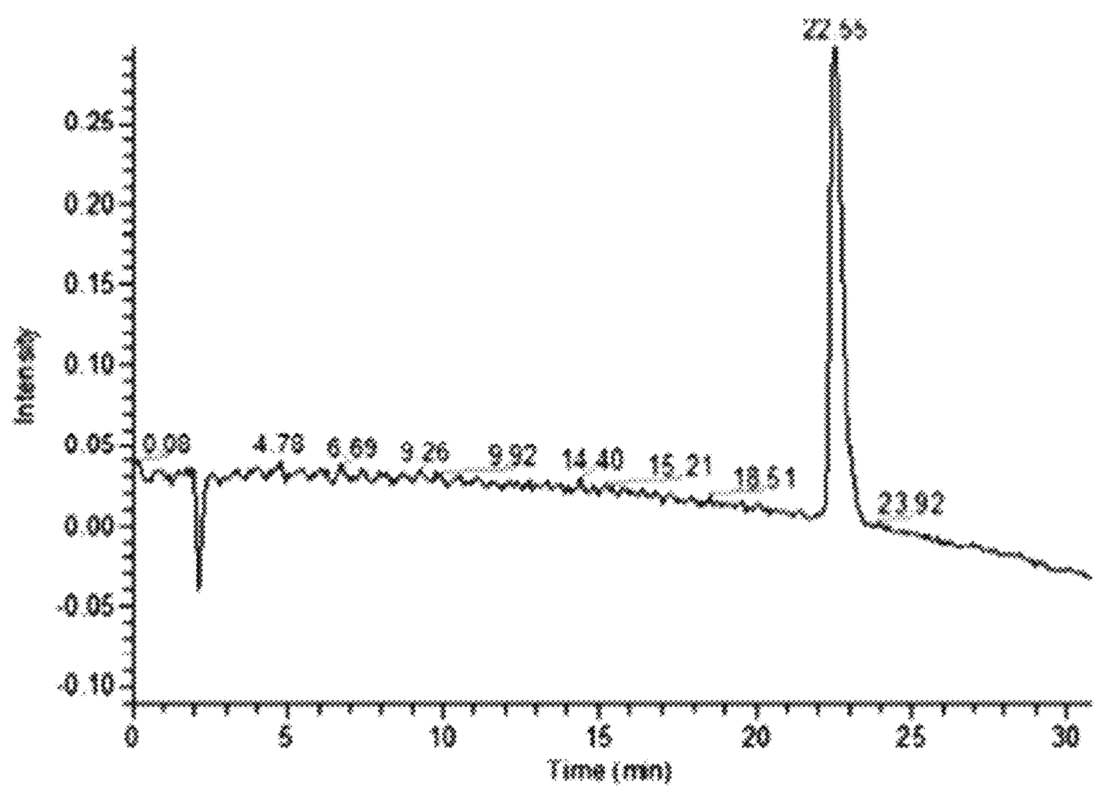
FIG. 32A and FIG. 32B depicts HPLC photo diode array detection (FIG. 32A) and mass spectrometry analysis (FIG. 32B) of $Palm_2K$-$OVA_{BT}$-$(KE)_4$.
Figure 32B:
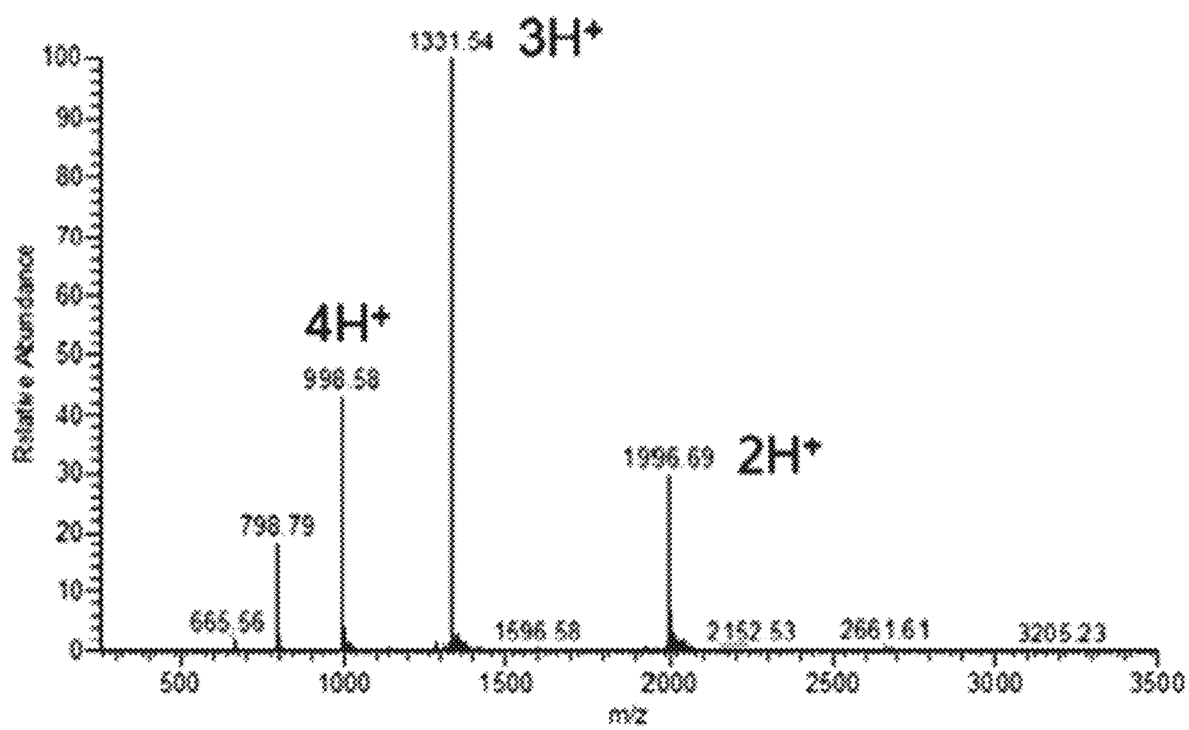
Figure 33A:
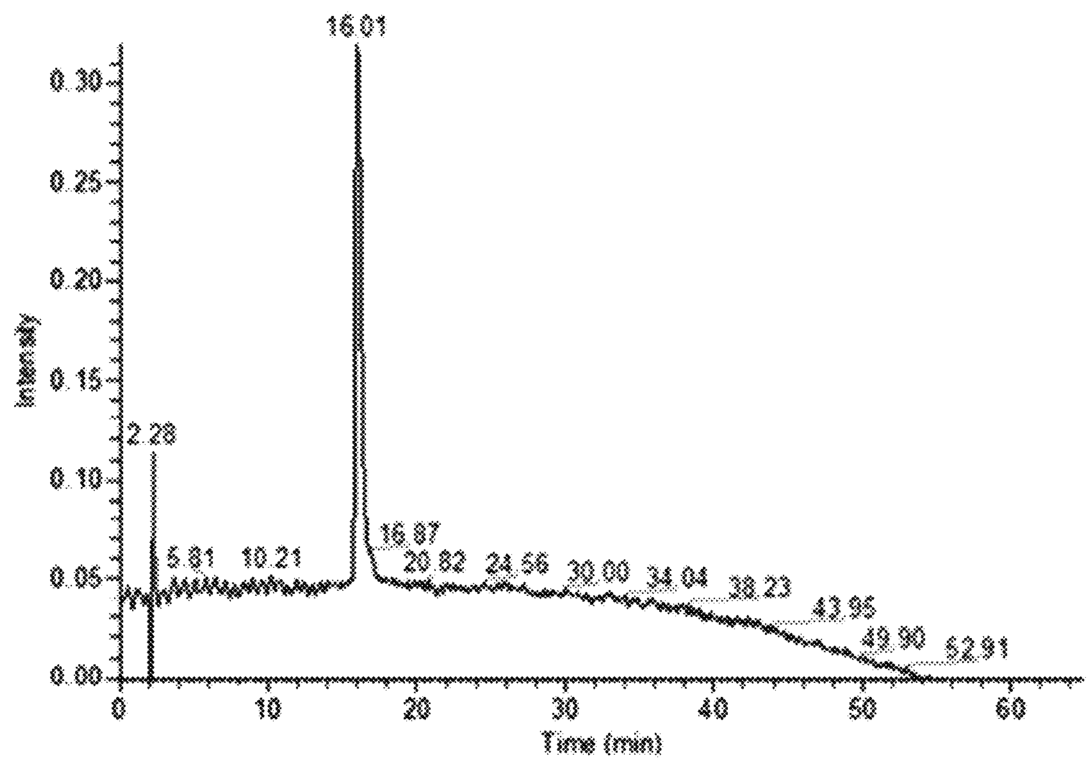
FIG. 33A and FIG. 33B depict HPLC photo diode array detection (FIG. 33A) and mass spectrometry analysis (FIG. 33B) of PalmK-$(EK)_4$-$OVA_{BT}$.
Figure 33B:
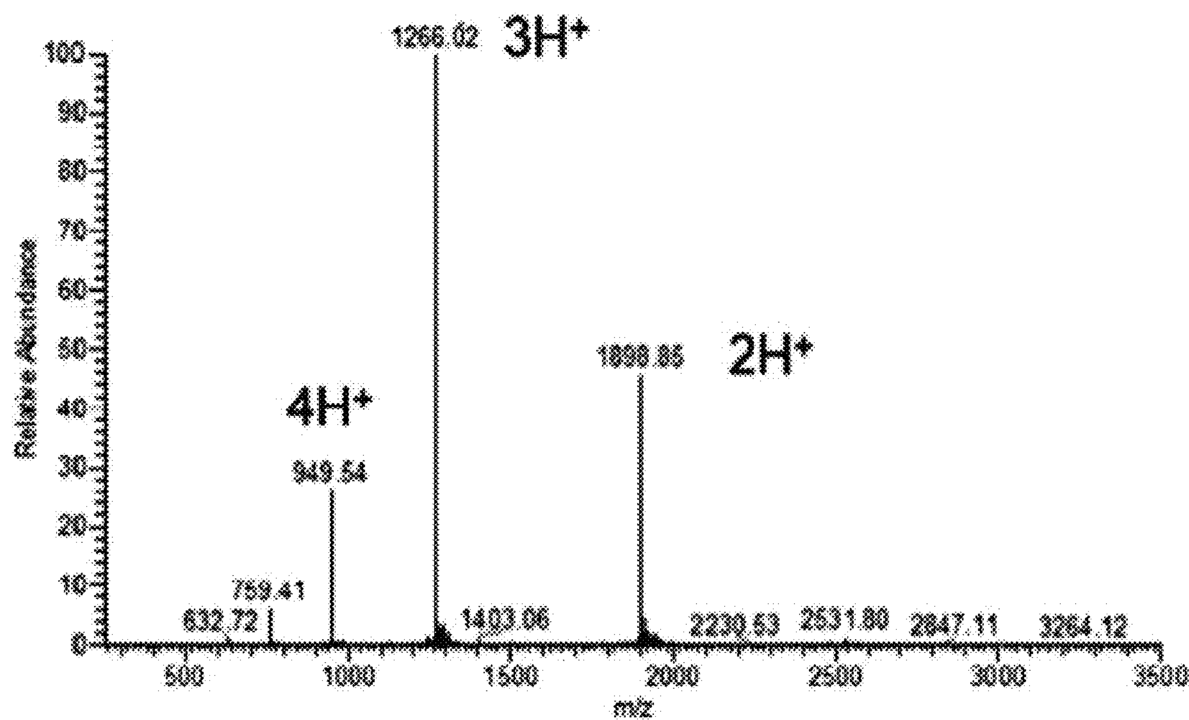
Figure 34A:
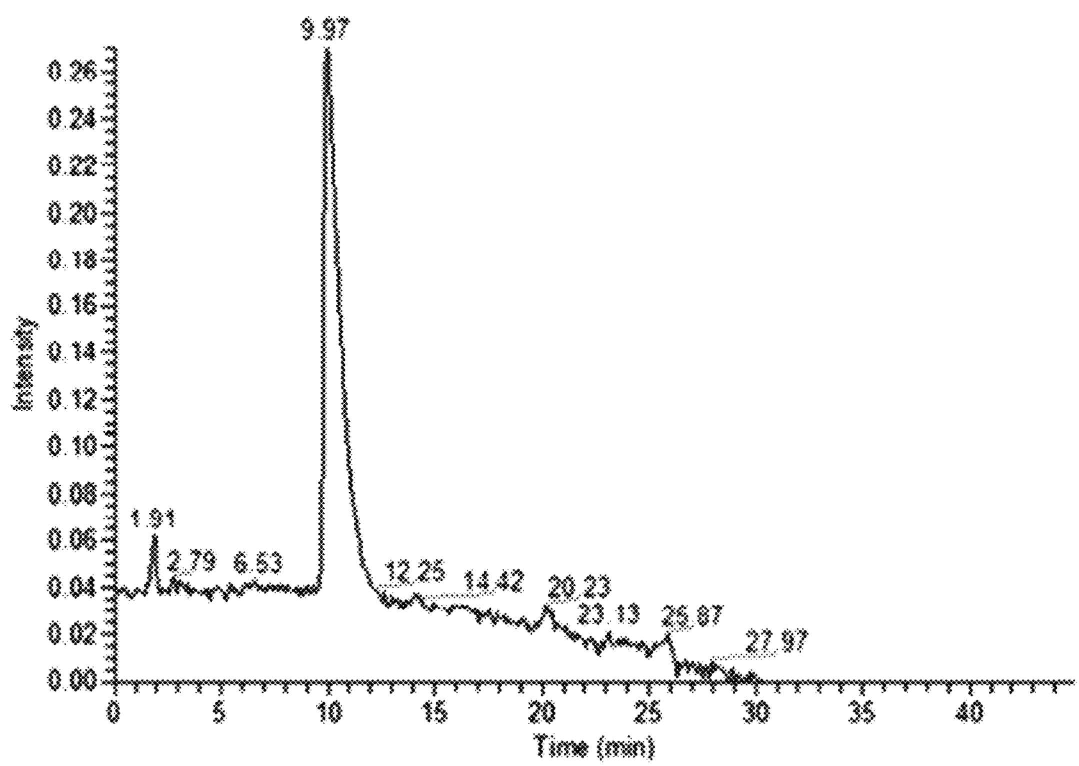
FIG. 34A and FIG. 34B depict HPLC photo diode array detection (FIG. 34A) and mass spectrometry analysis (FIG. 34B) of $Palm_2K$-$OVA_{BT}$-$(KE)_4$.
Figure 34B:
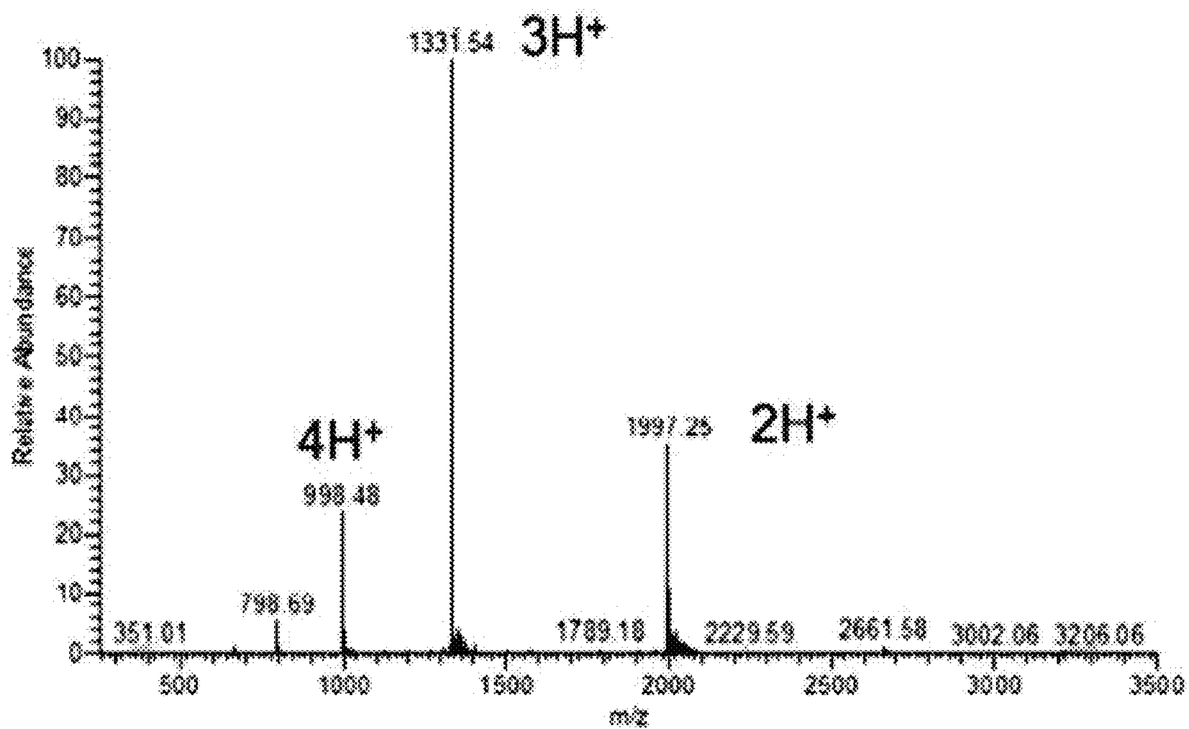
Figure 35A:
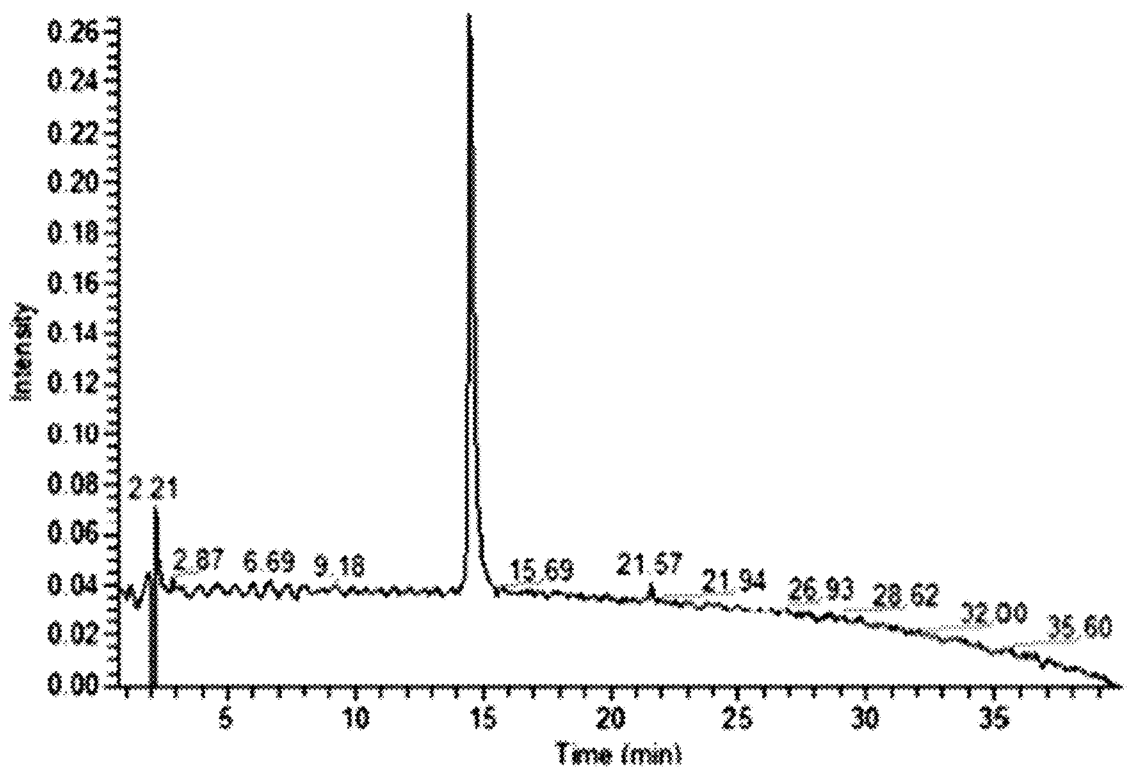
FIG. 35A and FIG. 35B depict HPLC photo diode array detection (FIG. 35A) and mass spectrometry analysis (FIG. 35B) of PalmK-$OVA_{cytoT}$-$(KE)_4$.
Figure 35B:
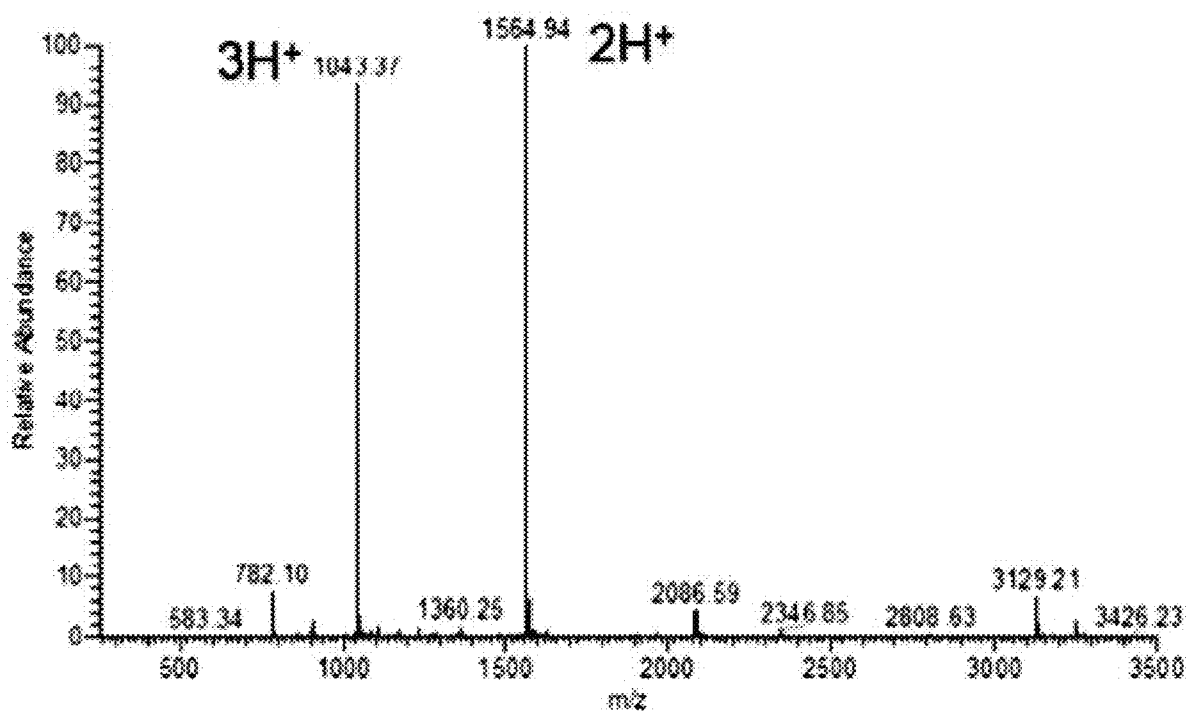
Figure 36A:
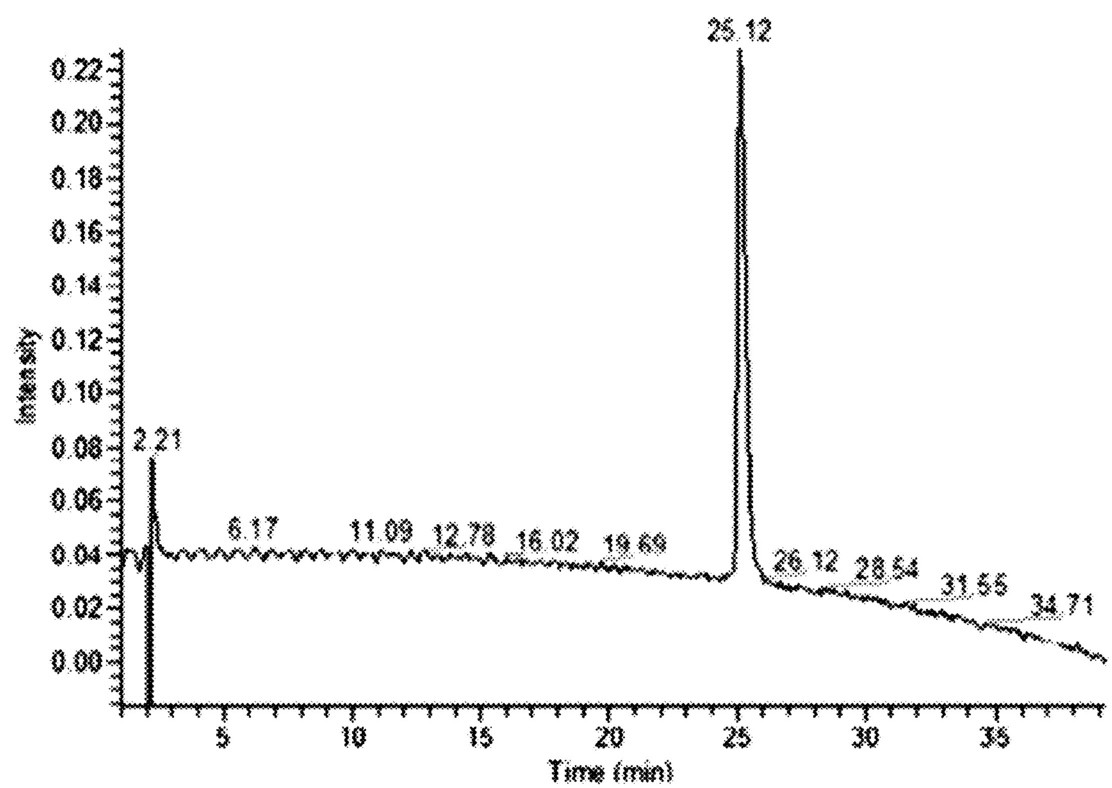
FIG. 36A and FIG. 36B depict HPLC photo diode array detection (FIG. 36A) and mass spectrometry analysis (FIG. 36B) of $Palm_2K$-$OVA_{cytoT}$-$(KE)_4$.
Figure 36B:
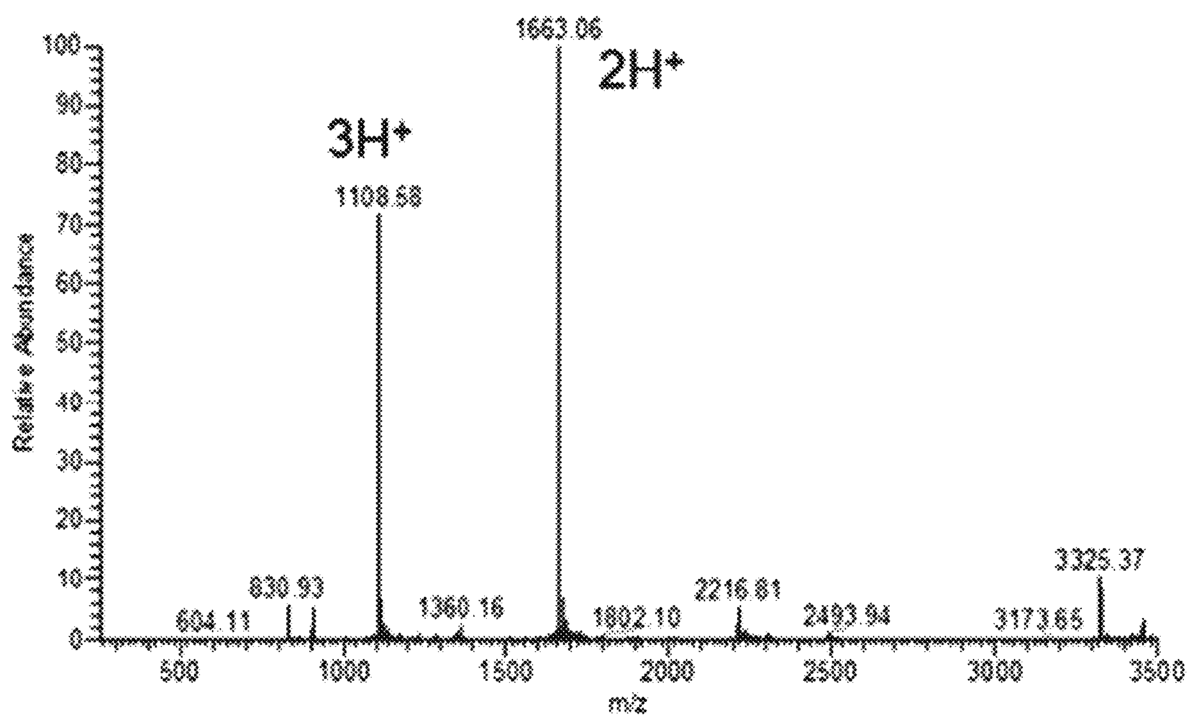
Figure 37A:
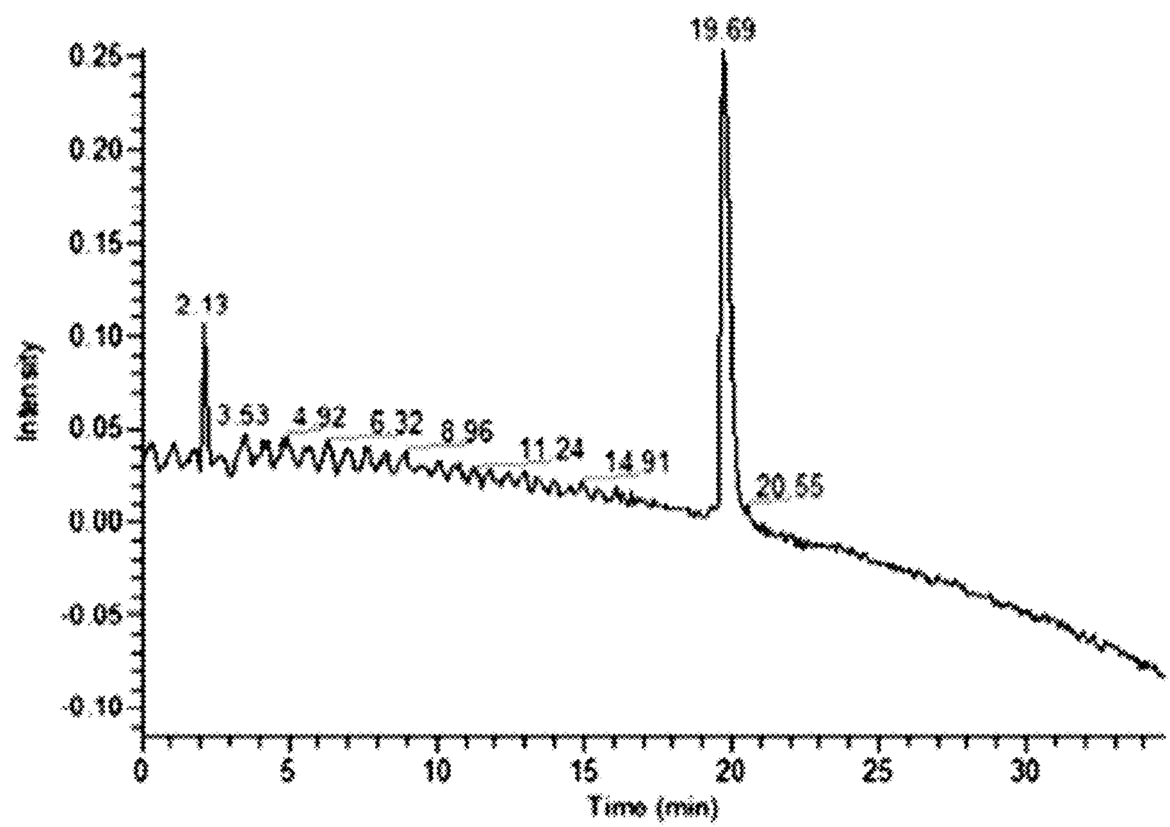
FIG. 37A and FIG. 37B depict HPLC photo diode array detection (FIG. 37A) and mass spectrometry analysis (FIG. 37B) of PalmK-$(EK)_4$-$OVA_{cytoT}$.
Figure 37B:
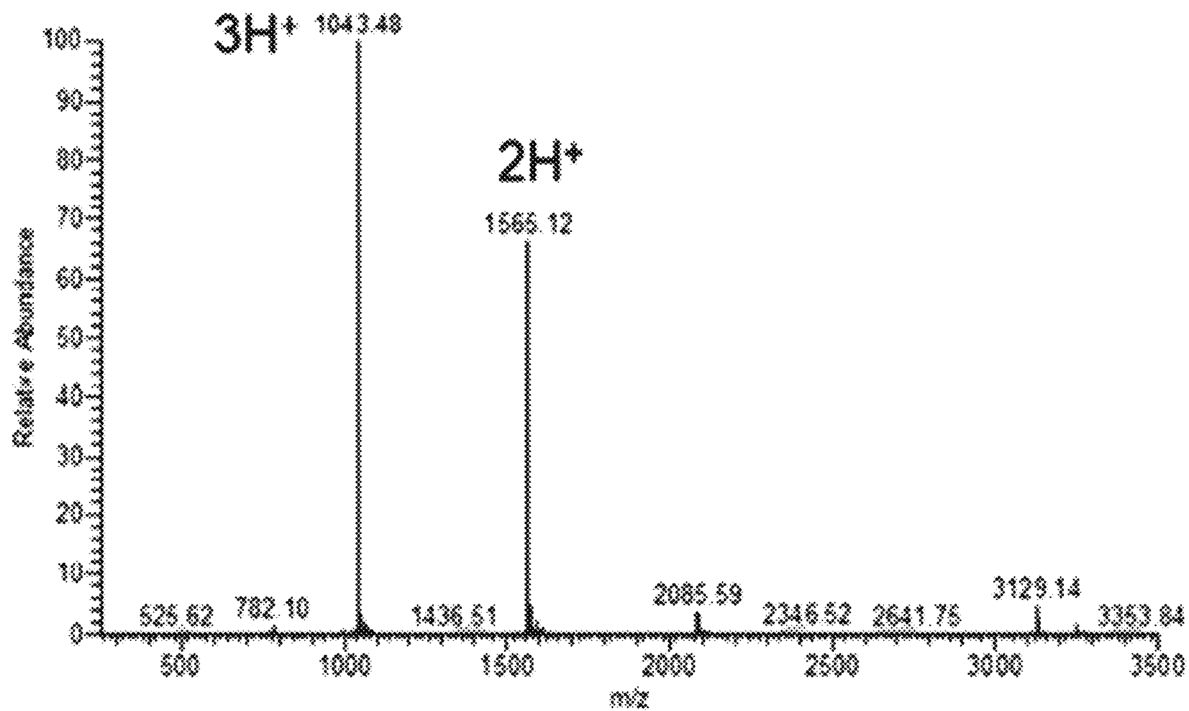
Figure 38A:
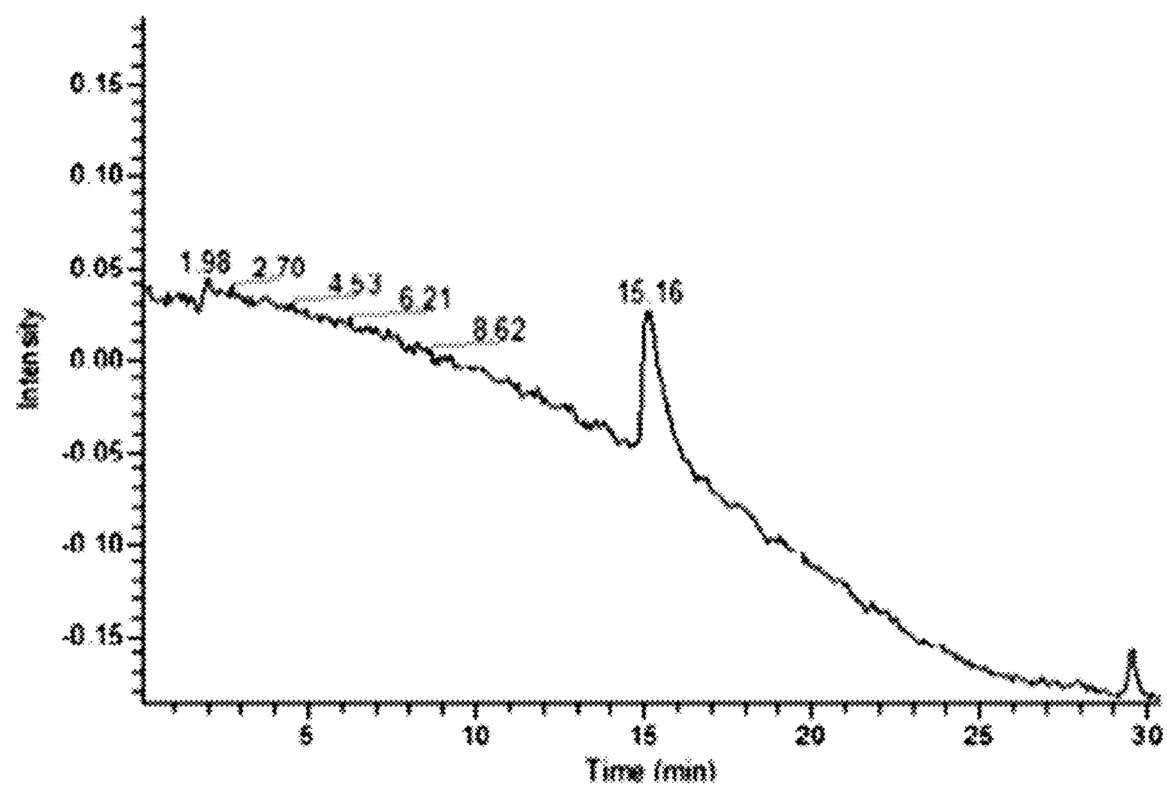
FIG. 38A and FIG. 38B depict HPLC photo diode array detection (FIG. 38A) and mass spectrometry analysis (FIG. 38B) of $Palm_2K$-$(EK)_4$-$OVA_{cytoT}$.
Figure 38B:
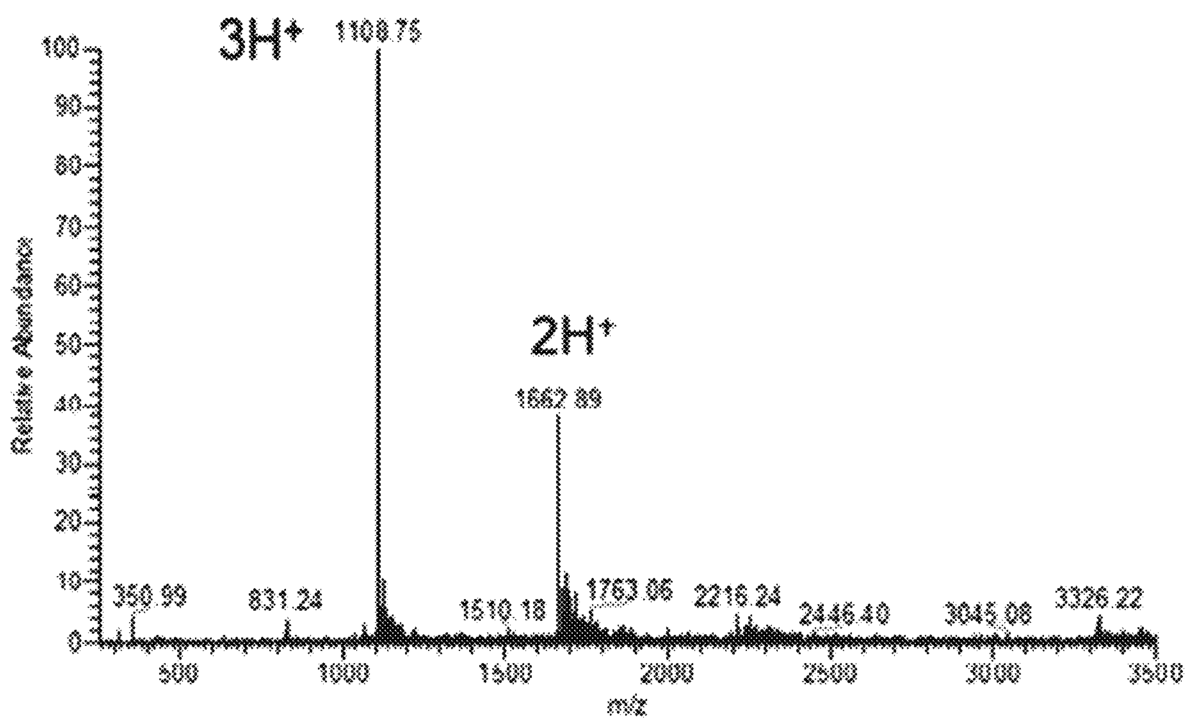

Hydrophobic Block Effect. The PA hydrophobic moiety has been found to play an important role in micellization, impacting the resulting nanomaterial properties. To investigate the effect of this region on triblock PAs, two different hydrophobic blocks possessing either one (PalmK) or two ($Palm_2K$) palmitic acid tails were tested. The ability to change the number of hydrophobic tails was achieved by orthogonally protecting the N-terminal non-native lysine so that either one or two palmitic acid tails could be conjugated. Adding a second tail was found to dramatically alter micellar morphology, both for micelles that with a zwitterion-like region (FIG. 16A, FIG. 16B, FIG. 16C, and FIG. 16D), and without a zwitterion-like region (FIG. 17). At neutral pH, the presence of a second palmitic acid for the external zwitterion-like block PAs (i.e., $Palm_2K$-$OVA_{BT}$-$(KE)_4$) changed the output micellar structure from twine-like (FIG. 16A) seen with its single palmitic acid counterpart (i.e., PalmK-$OVA_{BT}$-$(KE)_4$) to a mixture of spherical and short cylindrical micelles (FIG. 16B). A similar phenomenon was observed with internal zwitterion-like block PAs (i.e., $Palm_2K$-$(EK)_4$-$OVA_{BT}$) transitioned the resulting micelle structure from braid-like (FIG. 16C) created by its single palmitic acid counterpart (i.e., PalmK-$(EK)_4$-$OVA_{BT}$) to cluster micelles (FIG. 16D). Interestingly, the two hydrophobic tail products showed minimal morphological (FIG. 18A, FIG. 18B, FIG. 18C, FIG. 18D, FIG. 18E, and FIG. 18F) and secondary structure (FIG. 19A, FIG. 19B, FIG. 19C, and FIG. 19D) changes due to pH-controlled zwitterion-like block charge modification. Slight aggregation was observed for $Palm_2K$-$OVA_{BT}$-$(KE)_4$ and significant aggregation was seen for $Palm_2K$-$(EK)_4$-$OVA_{BT}$ at neutral pH (FIG. 20A and FIG. 20B), but this association was found to be more disorganized and pH sensitive (FIG. 18A, FIG. 18B, FIG. 18C, FIG. 18D, FIG. 18E, and FIG. 18F) than single tail PAMs. This result is believed to be caused by the increased hydrophobic content of the double tail PAMs acting as a much stronger molecular driving force than electrostatic interactions as compared to these forces being more equal in strength for single tail PAMs. Unsurprisingly, $Palm_2K$-$OVA_{BT}$, like PalmK-$OVA_{BT}$, showed no sensitivity to pH adjustment as no electrostatically sensitive region was included in this formulation (FIG. 21A, FIG. 21B, and FIG. 21C).

Peptide Block Effect. While the hydrophobic block and zwitterion-like block are clearly important in controlling micelle morphology and peptide secondary structure, it is unclear if the application-specific peptide plays a significant role in these properties. To investigate its importance, the $OVA_{BT}$ peptide sequence was replaced with a significantly different one (i.e., $OVA_{CytoT}$). Remarkedly, the four $OVA_{CytoT}$ micelle structures (FIG. 22A, FIG. 22B, FIG. 22C, and FIG. 22D) that correspond to the four $OVA_{BT}$ micelle structures (FIG. 16A, FIG. 16B, FIG. 16C, and FIG. 16D) showed no discernible differences in morphology. These results directly demonstrate the versatility of triblock PAMs to be utilized as a biomaterials platform for the controlled delivery of different bioactive peptides. In specific, complex micelle shape control is extremely valuable for isolating the effect of micelle morphology. For instance, when designing biomaterials-based devices for intravascular drug delivery, vehicle size is important for the prevention of vessel obstruction. By contrast, regenerative medicine applications require fiber or net-like structures as scaffolds for developing neotissue. By knowing the application requirements, micellar structures can be created that possess a wide range of desirable physical properties.

Example 2. Immunomodulatory Vasoactive Intestinal Peptide Amphiphile Micelles

Introduction

Vasoactive intestinal peptide (VIP) is a 28-amino acid neuropeptide that has distinct anti-inflammatory effects including downregulating TNF-α production by activated antigen presenting cells (APCs), specifically macrophages (MØs) and dendritic cells (DCs). It has also been shown to induce DCs to secrete CCL22 which recruit regulatory T cells ($T_{reg}$s) that can facilitate localized tolerance. These immunomodulatory effects have led to the extensive research of VIP as a treatment for a variety of autoimmune diseases such as rheumatoid arthritis, multiple sclerosis, and type 1 diabetes. Though exciting, VIP-based therapeutics possess drawbacks similar to other peptide-based therapies including a short-half life and minimal local retention when delivered in vivo. Thus, designing an appropriate delivery vehicle is crucial for optimizing the therapeutic efficacy of VIP.

In this study, VIP amphiphiles (VIPAs) were created to investigate their capacity to form micelles (VIPAMs) and potentiate the bioactivity of VIP. Physical and biological characterization experiments revealed unique properties for each formulation suggesting VIPAMs hold tremendous potential as a new treatment modality.

Experimental Section

Figure 39A:
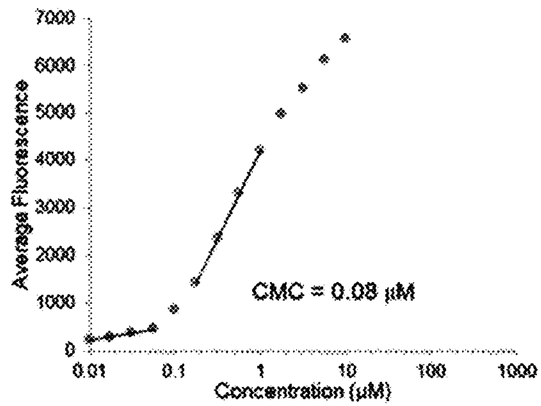
FIG. 39A and FIG. 39B depict chemical structure and physical characterization of different VIPAs. At concentrations above their respective CMC values, (FIG. 39A) pVIPA and (FIG. 39B) pzVIPA formed cylindrical micelles and braided micelles, respectively.
Figure 39B:
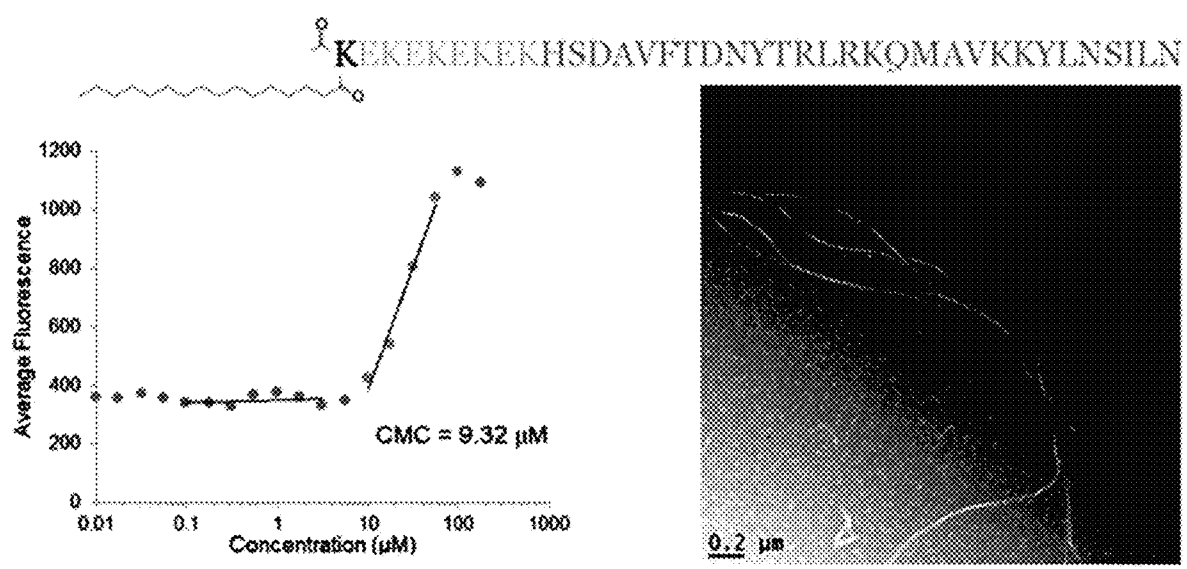
Figures 40A, 40B:
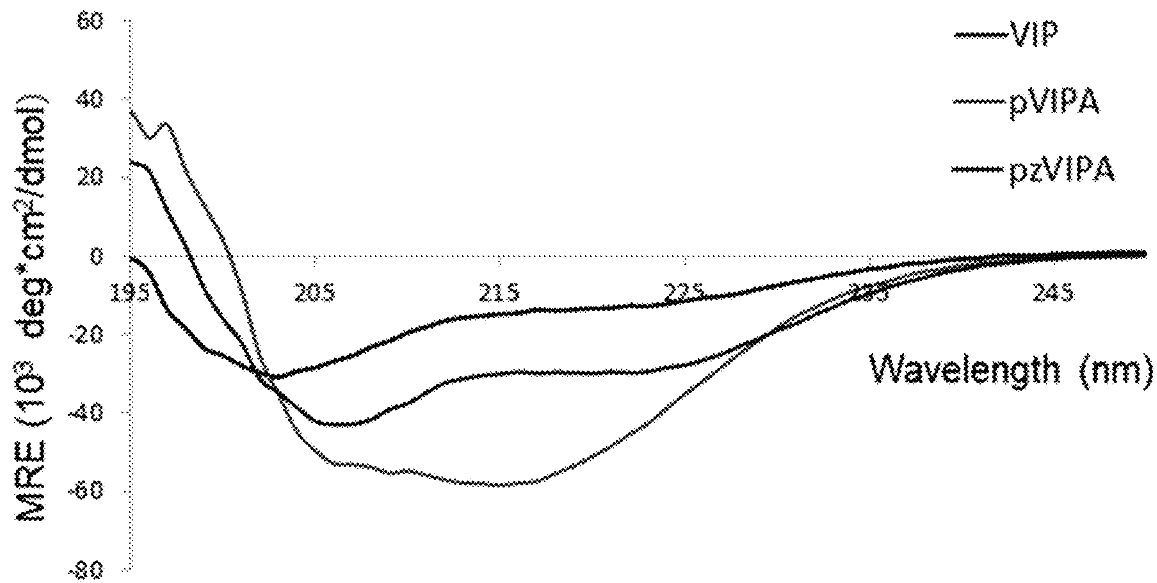
FIG. 40A and FIG. 40B depict peptide secondary structure analysis. The influence lipidation and zwitterion-like peptide block inclusion had on peptide secondary structure was evaluated by obtaining the CD spectra (FIG. 40A) and using it to estimate secondary structure (FIG. 40B).

VIPA design and physical characterization: Based on our recent research, two VIPA chemistries were produced. The first VIPA was synthesized by directly conjugating palmitic acid (Palm) to the N-terminus of VIP to form Palm-VIP, HSDAVFTDNYTRLRKQMAVKKYLNSILN (SEQ ID NO: 3), (pVIPA—FIG. 39A). The second VIPA included a zwitterion-like peptide region between Palm and VIP yielding PalmK-$(EK)_4$-VIP, KEKEKEKEKHSDAVFTDNYTRLRKQMAVKKYLNSILN (SEQ ID NO: 4) (pzVIPA—FIG. 39B). Micellization of each VIPA was characterized using a critical micelle (CMC) assay and negative-stain aided transmission electron microscopy (TEM). pVIPA was found to have a very low CMC (i.e. 0.08 NM) whereas pzVIPA possesses a CMC two orders of magnitude greater (i.e. 9.3 μM). While the addition of the hydrophilic block may have been expected to maintain or decrease the CMC, peptide folding to orient the most hydrophilic section externally can induce bending in the PA that may prevent straightforward micellar packing. This phenomenon has been previously observed by other researchers, and though it raises the CMC significantly, 9.3 μM is still likely low enough to be within the VIP therapeutic window. Interestingly, the two VIPAs yielded different micellar architectures with pVIPA and pzVIPA assembling into cylindrical and braided micelles, respectively. These results align with our previously published work showing that diblock PAs like pVIPA commonly form cylindrical micelles and triblock PAs with the same chemical orientation as pzVIPA self-assemble into braided micelles. The cylindrical micelles were found to be several hundred nanometers to a micron in length whereas the braided micelles were about an order of magnitude greater in length. This increased length is likely due to the intermicellar electrostatic complexation we have previously described for similar triblock PAs. Generally, particles in this size range have been found to be sterically hindered from interstitial transport facilitating their enhanced injection site retention and making them promising candidates for prolonged drug delivery applications. This is further supported by our previous findings that braided PAMs possess limited cell uptake and lymph node drainage capacity making them well suited for sustained, localized VIP delivery. The secondary structure of the three different VIP formulations was characterized by circular dichroism (CD, FIG. 40A and FIG. 40). Similar to previously reported observations, palmitic acid conjugation to VIP increased peptide β-sheet content. The addition of a zwitterion-like region (i.e. $(EK)_4$) increased overall α-helical content which is an expected phenomenon as oligoglutamyllysine is known to possess this secondary structure.

Results

VIPAM anti-inflammatory effects: Tumor necrosis factor alpha (TNF-α) is a monocyte-derived cytokine that plays a significant role in the inflammatory response. TNF-α is produced by MOs and DCs that are activated during infection, commonly due to the cell-based identification of pathogen associated molecule patterns, most notably lipopolysaccharide (LPS) found in the cell wall of gram-negative bacteria. Excessive TNF-α production has been shown to cause tissue injury, fever, atherosclerosis, and even death. Unlike activated MOs which accumulate at the site of inflammation, activated DCs tend to migrate to nearby lymph nodes where they activate naïve T helper cells. Activated effector T cells will migrate back to the inflammation site where they will recruit natural killer cells and additional MOs which further exacerbate the inflammatory response. The B7 ligand CD86 present on activated DCs plays an important role in this cascade acting as a co-stimulatory signal for T cell activation. A lack of co-stimulatory signaling often leads to T cell anergy. Conversely, the presence of CD86 on DCs without corresponding MHC II antigen presentation plays a role in $T_{reg}$ induction.

Figure 41A:
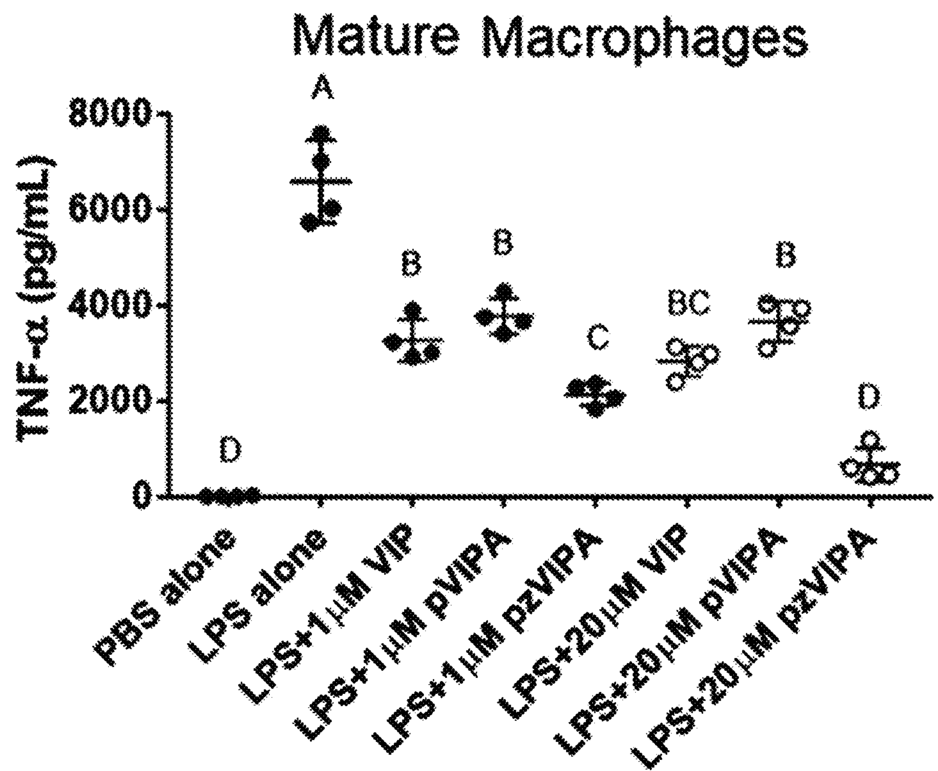
FIG. 41A, FIG. 41B, and FIG. 41C depict anti-inflammatory effects of different VIP formulations. TNF-α secretion from MOs (FIG. 41A) or DCs (FIG. 41B) as well as CD86 expression from DCs (FIG. 41C) were evaluated. LPS greatly increased each of these inflammatory correlates which were diminished to variable extents due to the presence of different concentrations and presentations of VIP. Within a graph, groups that possess different letters have statistically significant differences in mean ($p \leq 0.05$) whereas those that possess the same letter are similar ($p > 0.05$).
Figure 41B:
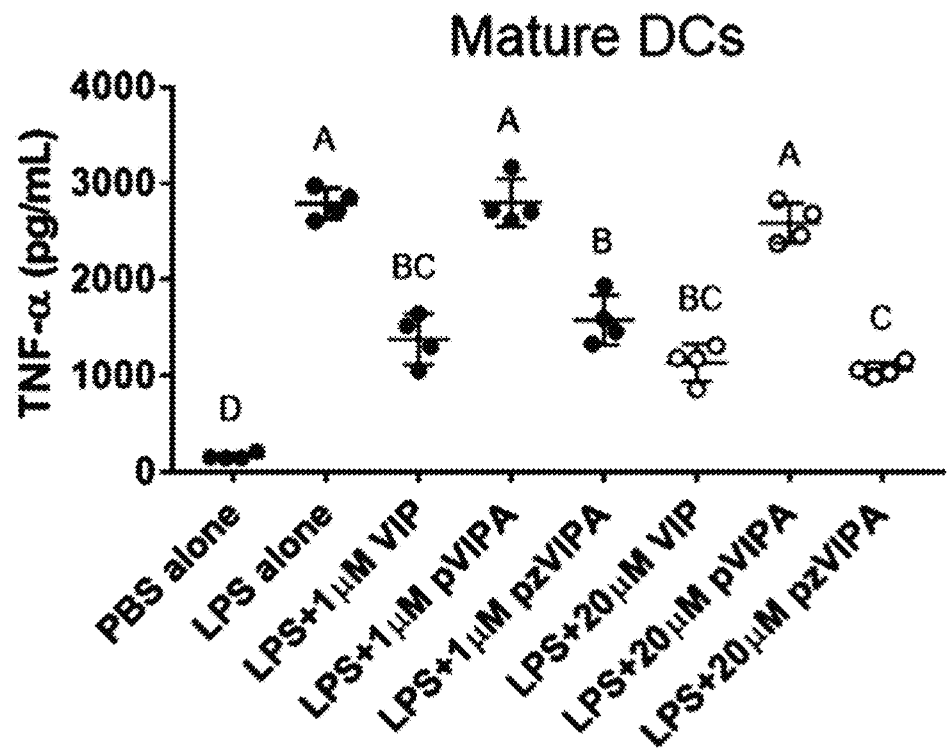
Figure 41C:
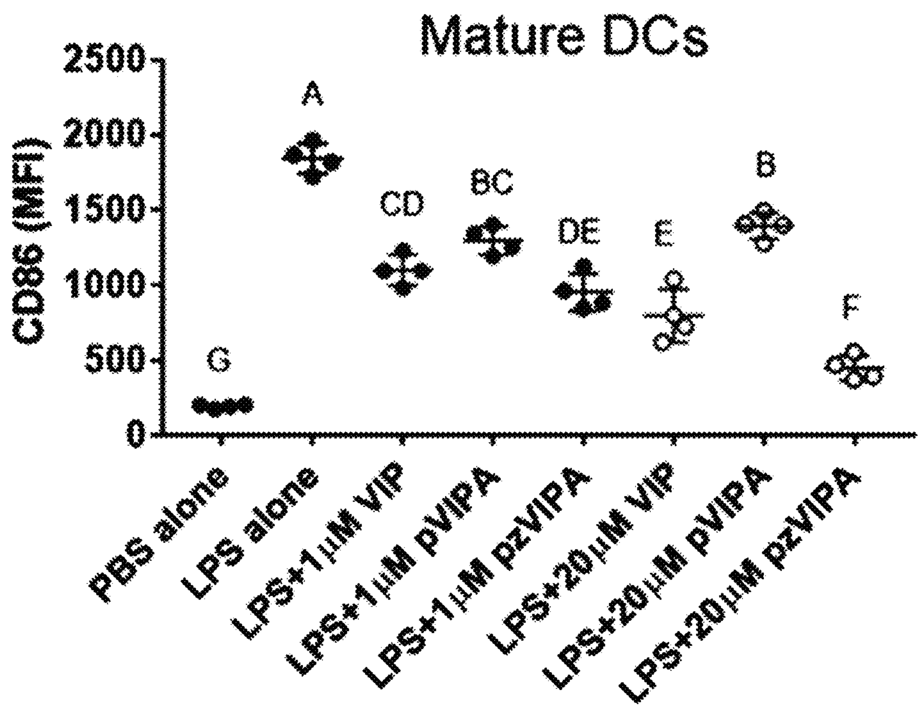

While the capacity to trigger a pro-inflammatory adaptive response is crucial for the host to clear unwanted pathogens, it is also responsible for transplant rejection and autoimmune-mediated tissue damage. One strategy to retard this inflammation loop is to limit TNF-α secretion from activated APCs and CD86 surface presentation on activated DCs. The anti-inflammatory effect of VIPAMs were explored by incubating MOs and DCs with LPS and different VIP materials at low (i.e. 1 μM) or high (20 μM) concentrations (FIG. 41A, FIG. 41B, and FIG. 41C). It was discovered that while VIP alone can modestly reduce TNF-α secretion and CD86 expression, this effect can be modulated through micellar delivery where chemical structure and micellar shape play a crucial role in bioactivity. pVIPA was unable to enhance the TNF-α suppressive effects of VIP in activated MOs (FIG. 41A) and completely nullified VIP effects on activated DC TNF-α secretion (FIG. 41B). The only statistically significant anti-inflammatory effect for pVIPA over VIP was found in DC CD86 expression at the high concentration where it was actually enhanced (FIG. 41C). In contrast, pzVIPA nearly completely abrogated TNF-α secretion in activated MØs (FIG. 41A), maintained VIP-based TNF-α secretion in activated DCs (FIG. 41B), and significantly limited CD86 surface expression on activated DCs (FIG. 41C). Interestingly, these enhancement effects were only observed at the high concentration and not at the low concentration. With a CMC of 9.3 μM (FIG. 39B), pzVIPA would likely exist as single biomolecules at the low dose (1 μM) and within braided micelles at the high dose (20 μM). In contrast, pVIPA would be confined in cylindrical micelles at both concentrations due to its very low CMC (0.08 μM, FIG. 39A). To provide further evidence that the observed bioactivity potentiation is a function of certain micelle structures and not the presence of lipid, inflammatory signals (i.e. TNF-α or CD86) were measured with Palm alone (FIG. 42A, FIG. 42B, FIG. 42C, FIG. 42D, FIG. 42E, and FIG. 42F) for which no TNF-α nor CD86 regulation were measured. Taken together, these results indicate that braided VIPAMs possess considerable intrinsic anti-inflammatory properties.

VIPAM $T_{reg}$ recruitment and induction potential: $T_{reg}$s are a unique type of suppressor T cell that facilitates peripheral immunological tolerance. Increasing the presence and development of $T_{reg}$s at the effector site of autoimmunity or inflammation has been suggested as a potential treatment for immune-related disorders or transplant rejection. $T_{reg}$ recruitment to the desirable tissue site can be guided by the presence of a gradient of the chemokine CCL22 (MDC). Previous research suggests that certain concentrations of and incubation times with VIP can induce DCs to produce CCL22 making it a desirable upstream bioactive molecule for $T_{reg}$ recruitment. Thus, CCL22 production from DCs treated with different VIP formulations was evaluated.

Figure 43A:
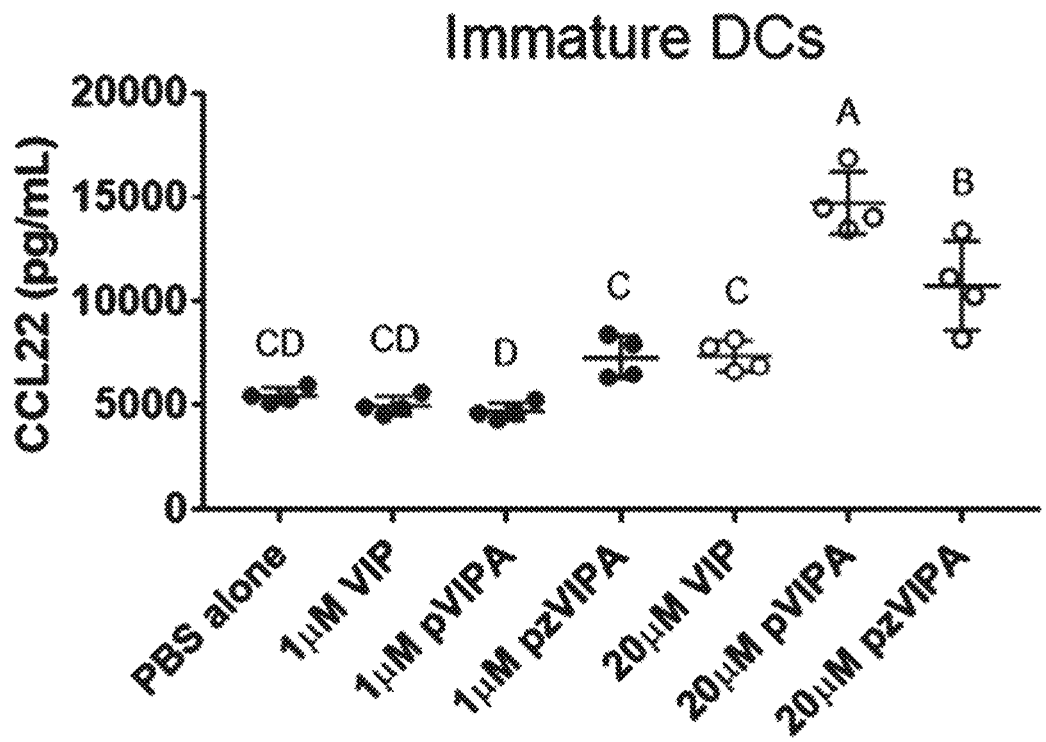
FIG. 43A, FIG. 43B, and FIG. 43C depict immunoregulatory effects of different VIP formulations. The secretion of CCL22 from immature DCs (FIG. 43A) and mature DCs (FIG. 43B) as well as the CD86 expression on DCs (FIG. 43C) was evaluated. The production of $T_{reg}$ recruiting CCL22 was enhanced for some VIPAM formulations. pVIPA significantly increased CD86 expression on immature DCs while the other two VIP formulations did not enhance CD86 expression. Within a graph, groups that possess different letters have statistically significant differences in mean ($p \leq 0.05$) whereas those that possess the same letter are similar ($p > 0.05$).
Figure 43B:
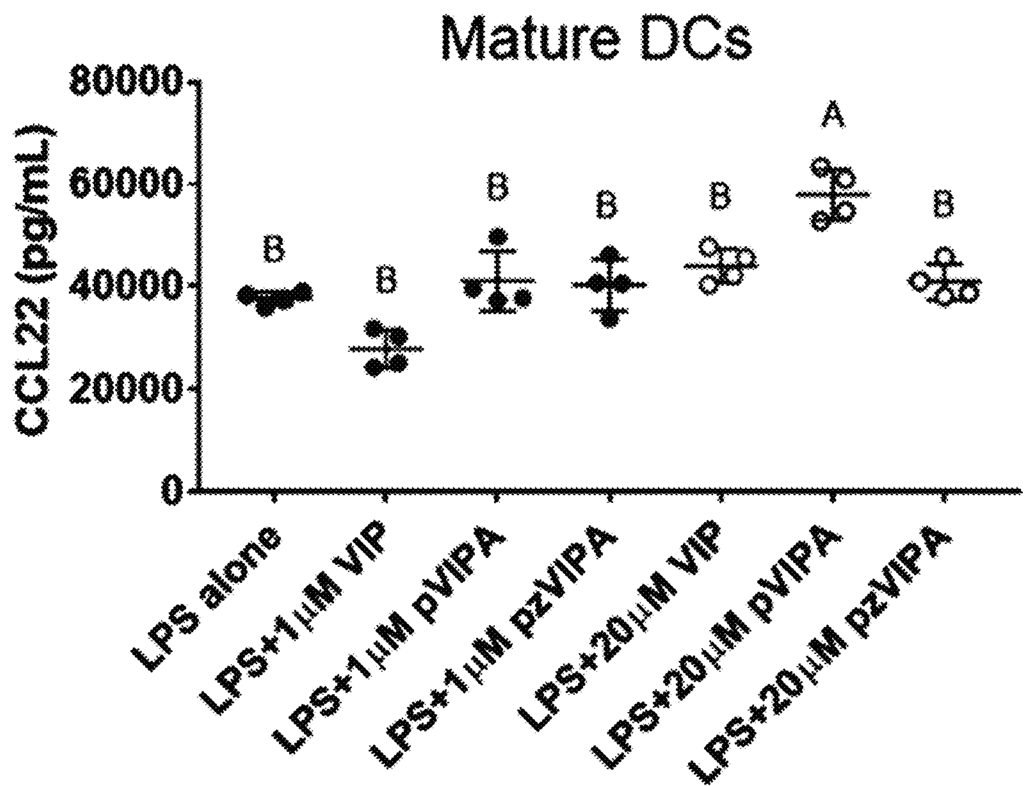
Figure 43C:
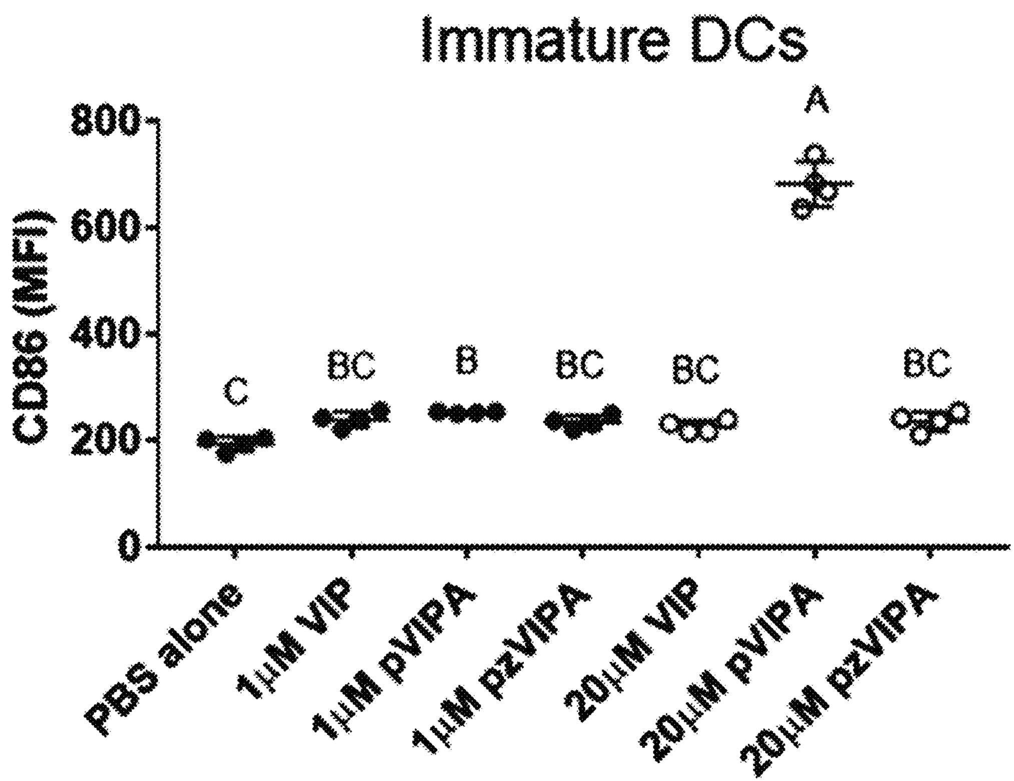
Figure 44A:
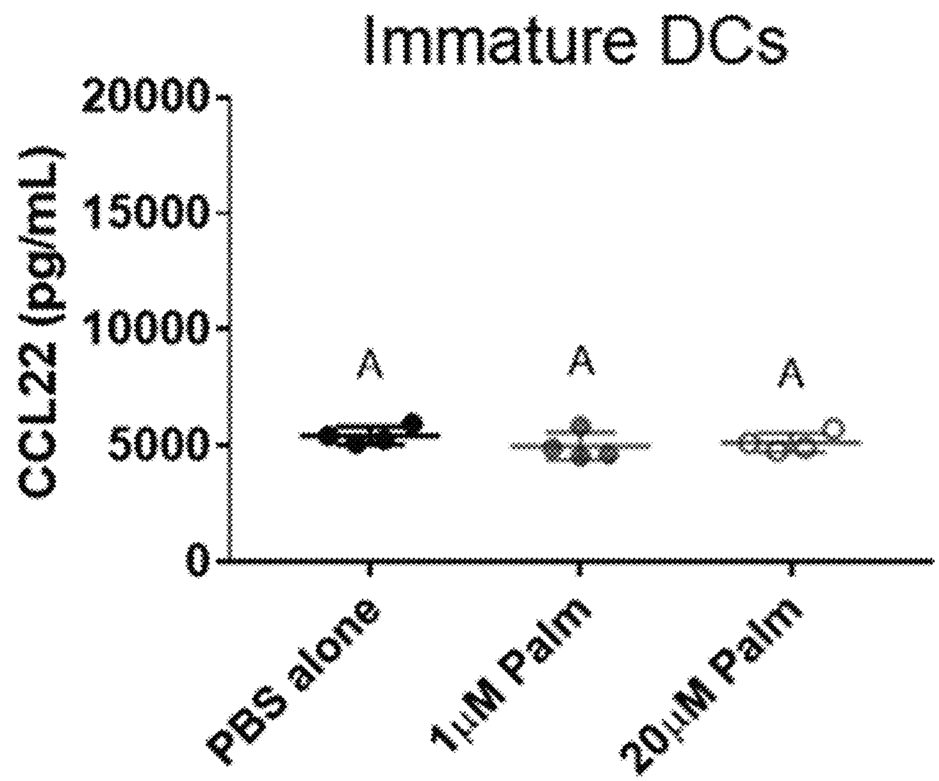
FIG. 44A and FIG. 44B depict CCL22 induction effects of the lipid moiety (i.e. palmitic acid—Palm). The secretion of CCL22 from immature DCs (FIG. 44A) and mature DCs (FIG. 44B) was evaluated. Palm was found to have no impact on CCL22 induction regardless of DC maturation state. Within a graph, groups that possess different letters have statistically significant differences in mean ($p \leq 0.05$) whereas those that possess the same letter are similar ($p > 0.05$).
Figure 44B:
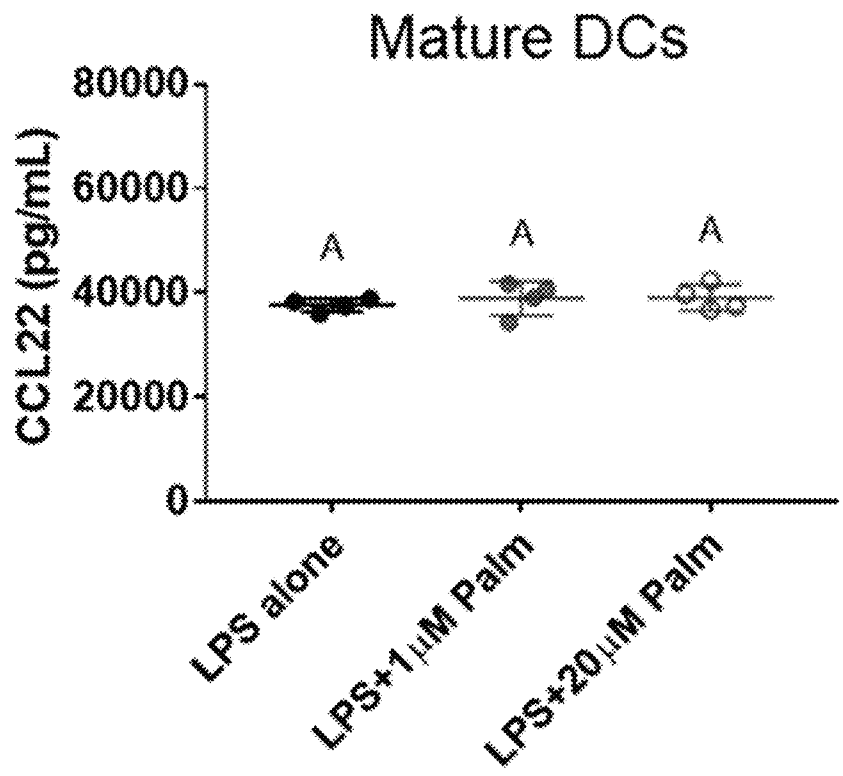

Previous results indicate that VIP peptide alone induces significant CCL22 production after 48 hours of incubation. While promising, prior research has shown that the more immediate presence of $T_{reg}$s is necessary to prevent or treat autoimmune disease and transplant rejection. Our results revealed that while VIP peptide was unable to induce DC CCL22 production at 24 hours, some VIPA formulations were able to provoke appreciable CCL22 increases at this early time point (FIG. 43A, FIG. 43B, and FIG. 43C). Specifically, the data indicate that high concentration pVIPA and pzVIPA induced greater CCL22 production from immature DCs than those given no stimulus (FIG. 43A). Interestingly, only high concentration pVIPA enhanced CCL22 production from mature DCs when compared to the LPS-stimulated mature DC control (FIG. 43B). Similar to the anti-inflammatory studies, lipid presence was found to not be the driving force behind CCL22 induction (FIG. 44A and FIG. 44B). These differences indicate that pVIPA possesses considerably more intrinsic $T_{reg}$ recruitment potential than VIP or pzVIPA. As VIP-mediated CCL22 induction has a very restricted therapeutic window with regards to both dose and incubation time, future studies are needed to complement this initial result.

Followed by $T_{reg}$ recruitment, the maintenance and expansion of those migrated $T_{reg}$s are essential for maintaining long term homeostasis. CD86 ligand presented by DCs is an important molecule that has been shown to induce $T_{reg}$ survival and expansion in peripheral tissue, especially in the absence of corresponding MHC II-presented antigen. Therefore, the enhanced expression of CD86 is a potential key factor that affects downstream immunoregulatory functions of CCL22-recruited $T_{reg}$s. It was discovered that high concentration pVIPA induced the highest CD86 expression of VIP treated groups or lipid control groups for both mature DCs (FIG. 32C) and immature DCs (FIG. 42A, FIG. 42B, FIG. 42C, FIG. 42D, FIG. 42E, FIG. 42F, and FIG. 43C). The CCL22 and CD86 data suggest that cylindrical VIPAMs possess potential immunoregulatory properties.

Figure 42A:
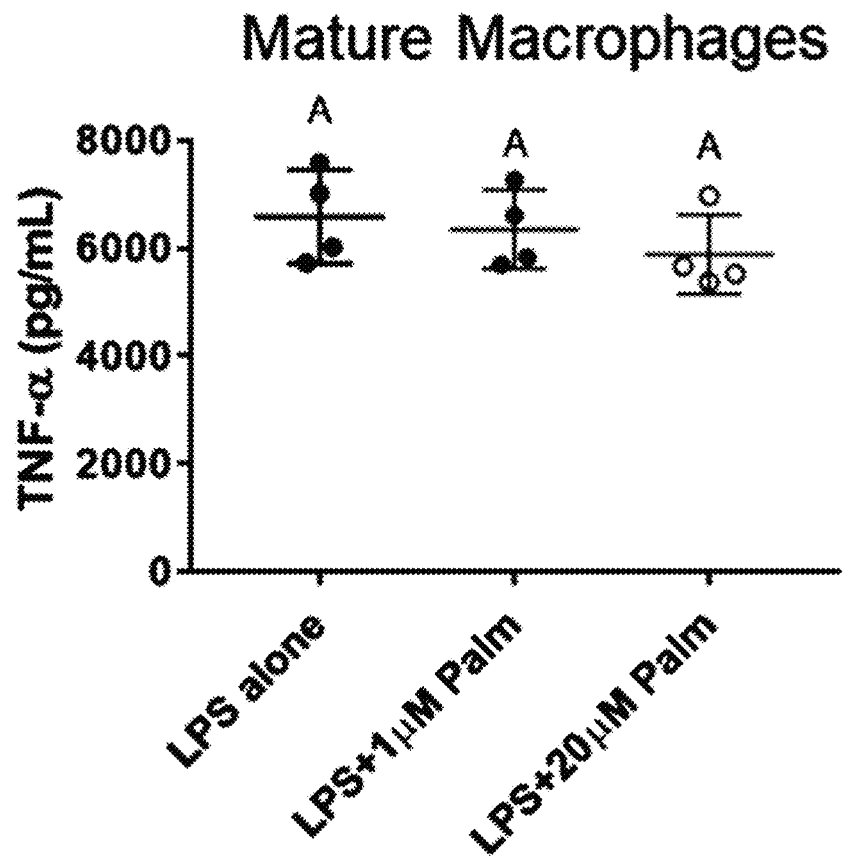
FIG. 42A, FIG. 42B, FIG. 42C, FIG. 42D, FIG. 42E, and FIG. 42F depict inflammatory signal regulation of the lipid moiety (i.e. palmitic acid—Palm). TNF-α secretion from MOs or DCs, as well as CD86 expression from DCs evaluated in the presence (FIG. 42A, FIG. 42B, FIG. 42C) or absence (FIG. 42D, FIG. 42E, FIG. 42F) of LPS. Palm was found to have no impact on regulating TNF-α secretion or CD86 expression for cells both at mature stages (FIG. 42A, FIG. 42B, FIG. 42C) or immature stages (FIG. 42D, FIG. 42E, FIG. 42F). Within a graph, groups that possess different letters have statistically significant differences in mean ($p \leq 0.05$) whereas those that possess the same letter are similar ($p > 0.05$).
Figure 42B:
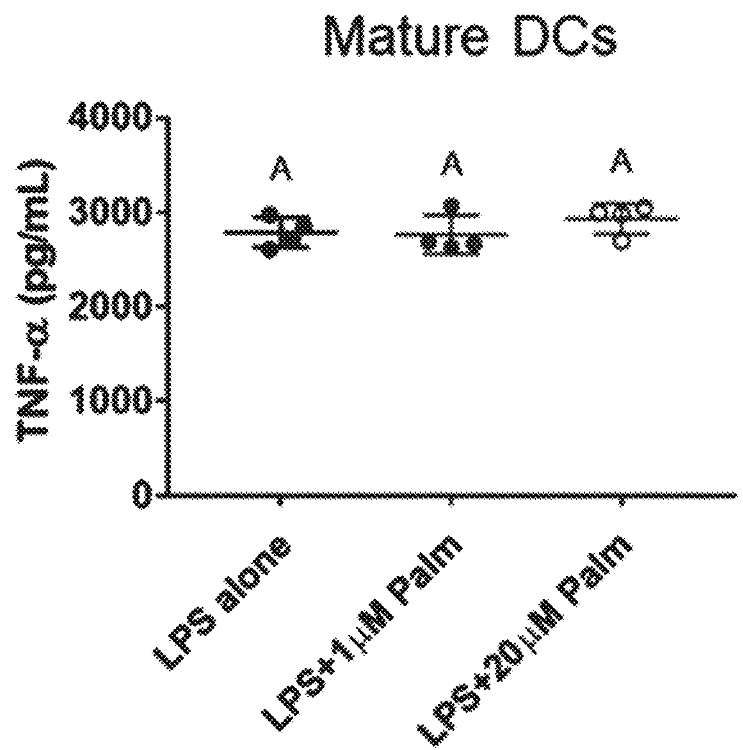
Figure 42C:
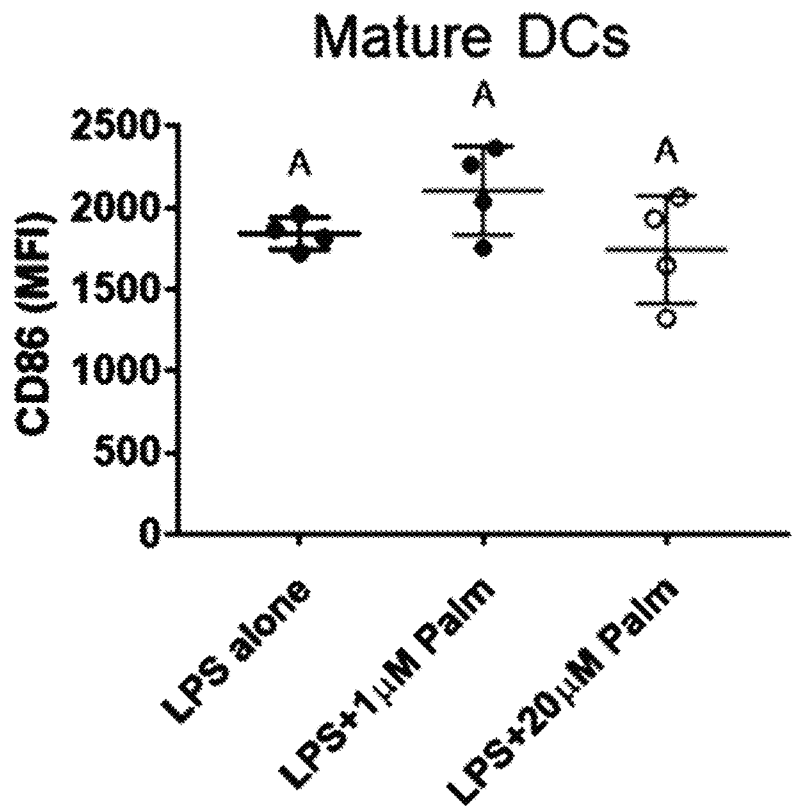
Figure 42D:
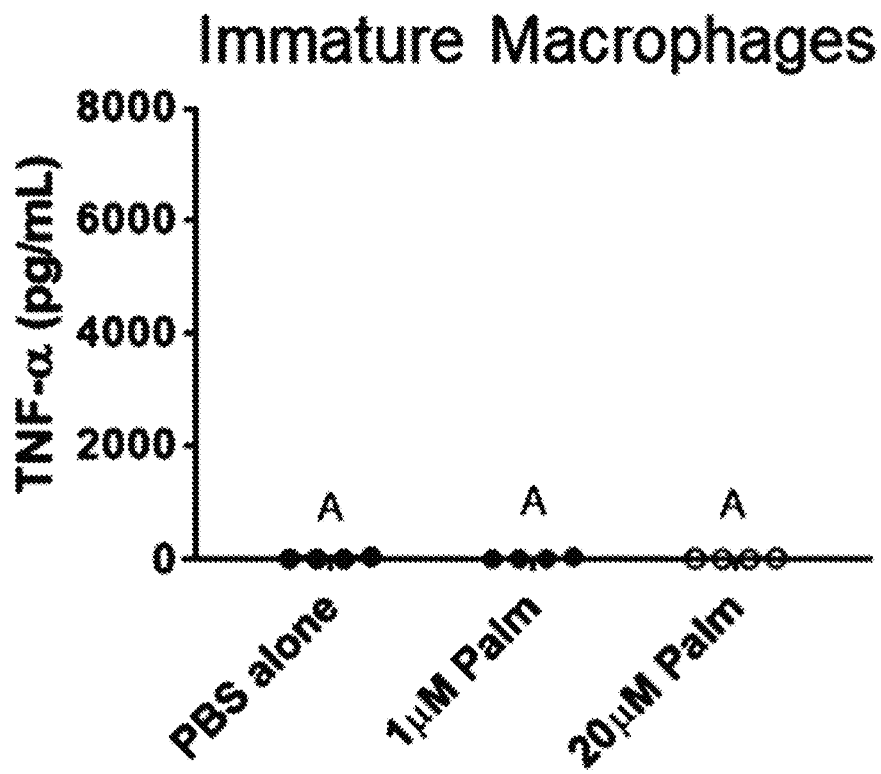
Figure 42E:
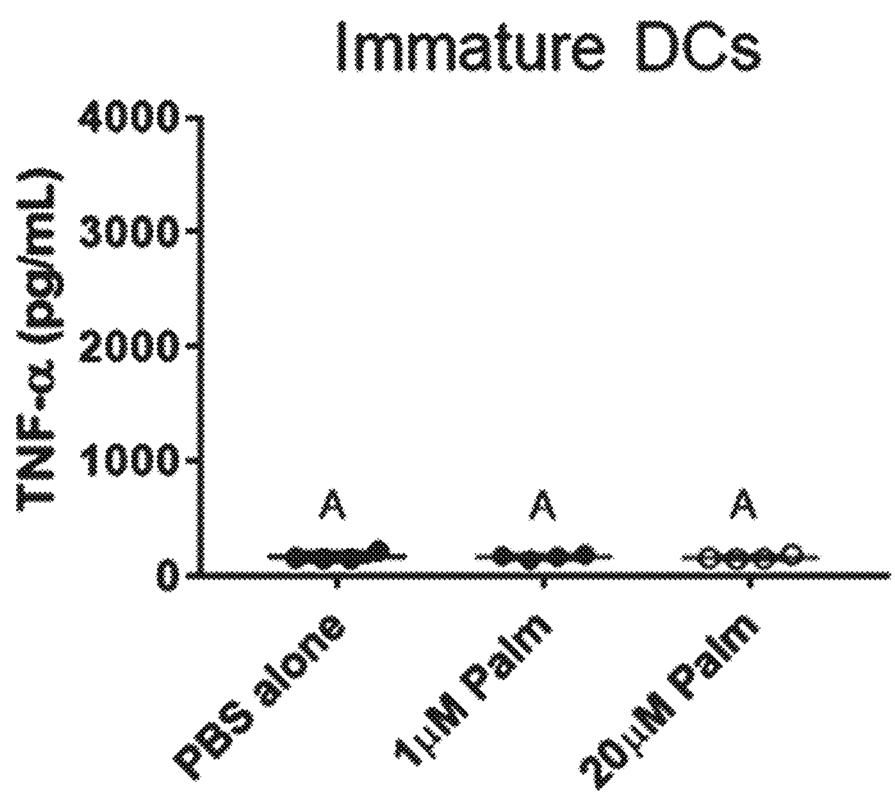
Figure 42F:
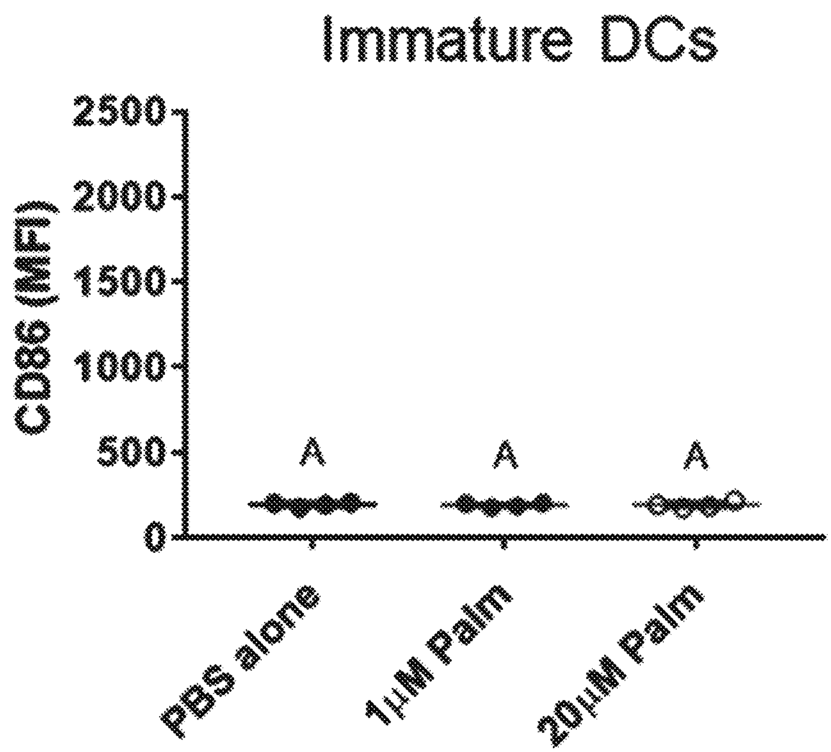

VIPAM Structure-Bioactivity Relationships: Interestingly, VIP is known to modulate TNF-α, CD86, and CCL22 expression through the same receptor (i.e. VPAC1), indicating that formulation chemistry and structure is very directly impacting peptide bioactivity. In specific, VIP/VPAC interactions are known to be dependent on a number of factors including VIP concentration, amino acid availability, and conformation. One of the major differences with peptide amphiphiles compared to peptides is their capacity to enhance peptide-cell interactions due to their lipid content. Therefore, both pVIPA and pzVIPA are expected to yield greater VIP concentrations at the cell surface. Additionally, the N-terminal amino acid of VIP (i.e. histidine) is known to play an important role in VIP/VPAC binding affinity. With the N-terminal histidine on pVIPA being directly lipidated, it is likely to be closer to the membrane and more rigid than pzVIPA which possesses a somewhat flexible linker (i.e. $(KE)_4$) between the lipid and VIP. Previous studies have demonstrated VIP α-helicity enhances peptide association with VPAC. Interestingly, CD analysis revealed that pzVIPA had more abundant α-helical conformation than both VIP and pVIPA (FIG. 41A and FIG. 41B). These factors may impact interactions between pzVIPA and VPAC leading to the enhanced TNF-α and CD86 suppression activity observed (FIG. 42A, FIG. 42B, and FIG. 42C).

Although both pVIPA and pzVIPA enhanced CCL22 induction from immature DCs (FIG. 43A), the magnitude of this response was significantly different. DC CCL22 induction is related to different factors including VIP/VPAC engagement and DC activation state. pzVIPA is likely engaging VPAC, but without activating the DCs as no increase in CD86 cell surface expression was detected (FIG. 43C). In contrast, high concentration pVIPA significantly increased CD86 expression in immature DCs (FIG. 43C) without altering other stimulatory markers like CD40 expression and TNF-α production (data not shown) providing evidence of a semi-mature DC state similar to previous work exploring VIP. This VIP-stimulated DC phenotype was found to directly correspond to more elevated levels of CCL22 production. An across the board increase in CCL22 production for mature DCs (FIG. 43B) is unsurprising since the production of this chemokine has been shown to be enhanced by LPS stimulation. The further increased CCL22 production by the exposure of mature DCs to high concentration pVIPA may be directly tied to the TNF-α results observed. In specific, prior research has shown that the presence of TNF-α can potentiate the cytokine-inducing capacity of VIP. For LPS-stimulated DCs, pVIPA does not downregulate TNF-α production (FIG. 42B) though moderates CD86 expression (FIG. 42C) similar to longer VIP exposure has been previously shown to do. Together these effects provide a strong foundational explanation for why these interesting CCL22 results were detected.

Conclusion

The results shown provide significant evidence that VIP amphiphile chemistry has a profound impact on micelle shape and bioactivity. Though pVIPA and pzVIPA both readily form micelles within the established VIP therapeutic window, each facilitates the formation of a different micellar shape (i.e. cylinders or braids). Interestingly, the two VIPAs induced quite different immunomodulatory effects with pzVIPAM braids suppressing the pro-inflammatory behavior of mature MOs and DCs and pVIPAM cylinders stimulating significant CCL22 production from both immature and mature DCs. These data indicate a significant relationship exists between micelle shape and bioactivity.

Example 3. Prophetic Example—Peptide Amphiphile Micelles as Modular Vaccines and Therapeutics Background and Significance Influenza is a common and highly communicable respiratory disease whose impact varies from year to year but is always incredibly significant as evidenced by data generated by the United States Center for Disease Control. For October 2011-April 2012, the influenza virus was estimated to be responsible for 9.2 million seasonal illnesses, 4.3 million medical visits, and 139,000 hospitalizations, numbers that are on the low end for seasonal disease. By comparison, the following season (i.e. October 2012-April 2013) was one of the worst ones recently with approximately 35.6 million seasonal illnesses, 16.6 million hospital visits, and 593,000 hospitalizations. This infectious disease is not only responsible for significant losses in productivity, but can also be quite lethal as evidenced by the approximately 291,000-646,000 worldwide deaths influenza is responsible for each year. The highly mutable nature of the influenza virus can also yield a pathogenic pandemic strain that can emerge at any time similar to the one that was responsible for more than 500 million illnesses and 50-100 million deaths worldwide from 1918 to 1920.

In response to the pandemic a century ago, researchers worked tirelessly to create a vaccine against influenza. Through improvements in viral culturing methods in the 1940s employing chicken egg embryos, inactivated influenza vaccines were able to be mass produced and used to vaccinate the armed forces followed by immunizing the general public. 4 Considerable efforts to improve the influenza vaccine have been made, the most significant of which focused on the development of an intranasally-delivered, live attenuated vaccine. In specific, presenting a weakened version of the virus directly to the primary site of infection (i.e. respiratory track) is hoped to be able to induce more durable and completely protective host immunity. 5 Extensive research on this product led to the FDA clearance of the first live attenuated vaccine formulation trademarked FluMist in 2003 which received considerable widespread use in the proceeding decade. While at first promising, uneven protectiveness against different strains of influenza have led to the CDC not recommending its use for the 2016-2017 and 2017-2018 seasons though it has been endorsed again for the 2018-2019 season.

Regardless of whether an inactivated or live attenuated vaccine is used, both have been found to significantly blunt the overall population-wide impact of influenza pathogenesis. Though promising, these strategies are still quite suboptimal as they convey only modest, short-term seasonal effectiveness of 10%-60% depending on the year. The limits of these traditional vaccines is their make-up and production methods. Formulations mostly consist of a small number of viruses (i.e. 3 for trivalent and 4 for quadrivalent). As influenza vaccines are still cultured in chicken eggs where mass production takes 5-6 months, predictions regarding the specific viruses to be included are made before the season begins using global disease surveillance programs. Due to this considerable lead time and strain differences, the variability in vaccine effectiveness is unsurprising. The limitations of this approach will be even further magnified during an influenza pandemic where a highly transmittable and fatal strain will have the potential to overcome the vaccine and cause extensive widespread disease and death. The 1957-1959 and 1968-1970 outbreaks which, despite the availability of some vaccines and relatively low lethality rates, still caused a combined 1.75-2.5 million deaths worldwide. More recently, the 2009 pandemic was of great public health concern since the dominant influenza virus was a modified H1N1 subtype for which the seasonal vaccine held no protective capacity. This strain was thankfully found to be much less lethal than prior pandemic outbreaks and even most seasonal strains for which a protective vaccine was able to be produced by the end of the calendar year. While fortunate, genetic recombination of H1N1 subtype influenza within an animal vector (e.g. avian or swine) could lead to a mutated influenza strain with a high transmission rate and significant lethality in the near future.

With these concerns in mind, the National Institute of Allergy and Infectious Disease has published a new plan committed to the development of a universal influenza vaccine to better control seasonal influenza and prevent a pandemic influenza outbreak. The criteria of such a vaccine would include the capacity to be highly effective against symptomatic infections, protect against both groups of influenza A, and last at least a year. While many objectives to achieve this high-minded goal were put forth, two of particular importance were the design of new cross-protective immunogens and the creation of novel adjuvants capable of facilitating durable immune responses. Recent advancements in rational influenza vaccine design have identified a variety of highly specific B cell, CD4 T cell, and CD8 T cell peptide epitopes which are conserved across many influenza sub-types. While promising, peptide antigens tend to be very weak immunogens requiring large dosages and significant adjuvant supplementation to be effective.

Biomaterials-based carriers have emerged as promising systems capable of improving peptide vaccine immunogenicity. While many systems have shown utility for this application, peptide amphiphiles (PAs) are unique biomaterials comprised of covalently coupled hydrophilic peptides and lipid-like hydrophobic tails which self-assemble into micellar nanoparticles in water.

These peptide amphiphile micelles (PAMs) have been shown capable of increasing localized concentration, enhancing intracellular delivery, controlling peptide secondary structure, and facilitating cell-specific targeting which have been shown to synergistically lead to self-adjuvanting immune responses to B cell and CD8 T cell epitopes. To enhance immunogenicity, peptide antigens are often delivered with adjuvants. For over 70 years aluminum salts were the only adjuvants FDA cleared for human use until monophosphoryl lipid A (MPLA) and Squalene/α-Tocopherol/polysorbate80 (AS03) were cleared as adjuvants for the human papillomavirus vaccine in 2009 and the H5N1 influenza virus vaccine in 2012, respectively. AS03 is an oil-in-water emulsion adjuvant that has been profoundly effective in inducing highly immunogenic, long-lasting immune responses to influenza, but is believed to be responsible for increased incidents of narcolepsy among children receiving the adjuvant. MPLA is the non-toxic portion of the bacterial endotoxin lipopolysaccharide (LPS) which has been found to be a Toll-like receptor-4 (TLR-4) agonist. Also, MPLA is hydrophobic allowing for it to be readily entrapped within the peptide amphiphile micelle (PAM) core. Other TLR agonists such dipalmitoylglycerylcysteinylserinyltetralysine ($P_2CSK_4$) for TLR-2, polyriboinosinic:polyriboctidylic acid (poly(I:C)) for TLR-3, and CpG oligodeoxynucleotides (CpG ODNs) for TLR-9 are attractive molecular adjuvant candidates as well. Hydrophobic $P_2C$ can be entrapped within the PAM core similarly to MPLA whereas negatively-charged poly(I:C) and CpG ODN can be complexed to short positively-charged oligolysine repeats (i.e. $K_8$). Prior research has demonstrated that the hydrophobic association of MPLA and $P_2CSK_4$ within PAMs facilitated enhanced antibody titers against a micelle-incorporated B cell peptide antigen against Group A *Streptococcus*.

While post-infection antiviral treatments like Oseltamivir (Tamiflu) and Zanamivir (Relenza) have shown some moderate effects, they are used sparingly in only high-risk patients and individuals within 48 hours of symptom onset to prevent the development of pathogenic resistance. The most effective method found to manage influenza is through vaccine prophylaxis.

Approach

Specific Aim 1) Heterogeneous B Cell/Universal Helper T Cell Epitope Amphiphile Micelle Vaccines for Influenza Inhibition and/or Neutralization 1A) Design B cell targeting micelles that also enhance micelle-associated $P_2C$ adjuvanticity.

B Cell Targeting Peptide—CD21-Specific P1—RMWPSSTVNLSAGRR (SEQ ID NO: 43)

B Cell Targeting Peptide—CD21-Specific B1—YILIHRN (SEQ ID NO: 44)

Alternative B Cell Targeting Peptide—CD21-Specific P2—PNLDFSPTCSFRFGC (SEQ ID NO: 45)

Alternative B Cell Targeting Peptide—CD21-Specific B2—PTLDPLP (SEQ ID NO: 46)

Alternative B Cell Targeting Peptide—A20-1 BCR—SAKTAVSQRVWLPSHRGGEP (SEQ ID NO: 47)

Alternative B Cell Targeting Peptide—A2036 BCR—EYVNCDNLVGNCVI (SEQ ID NO: 48)

Alternative B Cell Targeting Aptamer—CD19 Aptamer

B Cell Epitope Peptide—$M2_{(1)2-24}$—(M) SLLTEVETPIRNEWGCRCNDS SD (SEQ ID NO: 49)

B Cell Epitope Peptide—$HA2_{1-14(((16)20)23)}$—GLFGAIAGFIENGW (((EG) MIDG) WYG) (SEQ ID NO: 50)

B Cell Epitope Peptide—$NA_{222-230}$—ILRTQSEC (SEQ ID NO: 51)

Alternative B Cell Epitope Peptide—$NP_{147-155}$—TYQRTRALV (SEQ ID NO: 52)

Alternative B Cell Epitope Peptide—$NP_{243-251}$—RESRNPGNA (SEQ ID NO: 53)

Alternative B Cell Epitope Peptide—$HA2_{68-84}$—KEFSEVEGRIQDLEKYV (SEQ ID NO: 54)

Universal Helper T Cell Epitope Peptide—$HBsAg_{19-33}$—FFLLTRILTIPQSLD (SEQ ID NO: 55)

Universal Helper T Cell Epitope Peptide—TpD—ILMQYIKANSKFIGIPMGLPQSIALSSLMVAQ (SEQ ID NO: 56)

Alternative Helper T Cell Epitope Peptide—PADRE—A(a) KF(X)VAAWTLKAAA(a) (SEQ ID NO: 57)

Alternative Helper T Cell Epitope Peptide—$Pol_{711}$—EKVYLAWVPAHKGIG (SEQ ID NO: 58)

1B) Investigate the immunogenicity of B cell targeting, $P_2C$ associated, heterogeneous antigen micelles.

1C) Determine the influenza inhibition and neutralization capacity of vaccine-induced antibodies.

1D) Evaluate the short-term and long-term protective ability of composite linked recognition antigen micelles.

Specific Aim 2) Cytotoxic T Cell Epitope Amphiphile Micelle Vaccines for Clearing Influenza Infected Host Cells 2A) Produce DC targeting micelles that also enhance micelle-associated CpG adjuvanticity.

DC Targeting Peptide—NW—NWYLPWLGTNDW (SEQ ID NO: 59)

DC Targeting Peptide—h11c—ATPEDNGRSFS (SEQ ID NO: 60)

Alternative DC Targeting Peptide—WH—WPRFHSSVFHTH (SEQ ID NO: 61)

Alternative DC Targeting Peptide—TP—TPAFRYS[8] (SEQ ID NO: 62)

Cytotoxic T Cell Epitope Peptide—$PB1_{590-599}$—LVSDGGPNLY (SEQ ID NO: 63)

Cytotoxic T Cell Epitope Peptide—$NP_{39-47}$—FYIQMCTEL (SEQ ID NO: 64)

Cytotoxic T Cell Epitope Peptide—$NP_{366-374}$—ASNENMETM (SEQ ID NO: 65)

Cytotoxic T Cell Epitope Peptide—$PA_{224-233}$—SSLENFRAYV (SEQ ID NO: 66)

Alternative T Cell Epitope Peptide—$M1_{58-66}$—GILGFVFTL (SEQ ID NO: 67)

Alternative T Cell Epitope Peptide—$PA_{46-54}$—FMYSDFHFI (SEQ ID NO: 68)

Alternative T Cell Epitope Peptide—$NS1_{122-130}$—AIMDKNIIL (SEQ ID NO: 69)

2B) Explore the immunogenicity of DC Targeting, CpG associated, heterogeneous antigen micelles.

2C) Observe the influenza infected host cell killing capacity of vaccine-induced cytotoxic T cells.

2D) Assess the short-term and long-term protective ability of composite cytotoxic T cell antigen micelles.

Specific Aim 3) Anti-Viral Peptide Amphiphile Micelles for Influenza Post-Exposure Treatment 3A) Generate epithelial cell targeting micelles that also enhance micelle-associated anti-viral bioactivity.

Epithelial Cell Targeting Peptide—Peptide E—SERSMNF (SEQ ID NO: 70)

Epithelial Cell Targeting Peptide—Peptide Y—YGLPHKF (SEQ ID NO: 71)

Alternative Epithelial Cell Targeting Peptide—Peptide G—PSGAARA (SEQ ID NO: 72)

Alternative Epithelial Cell Targeting Peptide—Peptide EPI—THALWHT (SEQ ID NO: 73)

Anti-Viral Peptide—FluPep4—RRKKWLVFFVIFYFFR (SEQ ID NO: 74)

Anti-Viral Peptide—LF C-$Lobe_{553-563}$—NGESSADWAKN (SEQ ID NO: 75)

Anti-Viral Peptide—$PB1_{1-25}$—MDVNPTLLFLKVPAQNAISTTFPYT (SEQ ID NO: 76)

Alternative Anti-Viral Peptide—FluPep3—WLVFFVIFYFFRRRKK (SEQ ID NO: 77)

Alternative Anti-Viral Peptide—LF C-$Lobe_{418-429}$—SKHSSLDCVLRP (SEQ ID NO: 78)

Alternative Anti-Viral Peptide—Derived EB Peptide—RRKKLAVLLALLA (SEQ ID NO: 79)

Alternative Anti-Viral Peptide—Peptide 6—CATCEQIADSQHRSHRQMV (SEQ ID NO: 80)

3B) Ascertain the infected host cell intracellular influenza disruption activity of anti-viral loaded micelles.

3C) Measure immediate post-exposure treatment ability of composite anti-viral micelles.

Specific Aim 4) Immunomodulatory Amphiphile Micelles for Influenza Associated Sequelae Symptom Management 4A) Create macrophage targeting micelles that also enhance micelle-associated anti-inflammatory bioactivity.

Macrophage Targeting Peptide—MCP-1—YNFTNRKISVQRLASYRRITSSK (SEQ ID NO: 81)

Macrophage Targeting Peptide—LL-37—LLGDFFRKSKEKIGKEFKRIVQRIKDFLRNLVPRTES (SEQ ID NO: 82)

Alternative Macrophage Targeting Peptide—CD206—CSPGAKVRC (SEQ ID NO: 83)

Alternative Macrophage Targeting Peptide—fMLP—fMLP (SEQ ID NO: 84)

Immunomodulatory Peptide—VIP—HSDAVFTDNYTRLRKQMAVKKYLNSILN (SEQ ID NO: 3)

Immunomodulatory Peptide—AF10847 (IL-1 RANT)—ETPFTWEESNAYYWQPYALPL (SEQ ID NO: 85)

Immunomodulatory Peptide—IDR-1018—VRLIVAVRIWRR (SEQ ID NO: 86)

Alternative Immunomodulatory Peptide—KAF—KAFAKLAARLYRKALARQLGVAA (SEQ ID NO: 87)

Alternative Immunomodulatory Peptide—WP9QY—YCWSQYLCY (SEQ ID NO: 88)

4B) Uncover the influenza-associated activated macrophage modulation activity of anti-inflammatory micelles.

4C) Quantify the delayed post-exposure treatment ability of composite vasoactive intestinal peptide micelles.

REFERENCES (1) Bemdt, P.; Fields, G. B.; Tirrell, M. Synthetic lipidation of peptides and amino acids: monolayer structure and properties. *J. Am. Chem. Soc.* 1995, 117 (37), 9515-9522.

(2) Black, M.; Trent, A.; Kostenko, Y.; Lee, J. S.; Olive, C.; Tirrell, M. Self-Assembled Peptide Amphiphile Micelles Containing a Cytotoxic T-Cell Epitope Promote a Protective Immune Response In Vivo. *Adv. Mater.* 2012, 24 (28), 3845-3849.

(3) Cheetham, A. G.; Zhang, P.; Lin, Y.-a.; Lock, L. L.; Cui, H. Supramolecular nanostructures formed by anticancer drug assembly. *J. Am. Chem. Soc.* 2013, 135 (8), 2907-2910.

(4) Trent, A.; Ulery, B. D.; Black, M. J.; Barrett, J. C.; Liang, S.; Kostenko, Y.; David, N. A.; Tirrell, M. V. Peptide amphiphile micelles self-adjuvant group A streptococcal vaccination. *AAPSJ.* 2015, 17 (2), 380-388.

(5) Barrett, J. C.; Ulery, B. D.; Trent, A.; Liang, S.; David, N. A.; Tirrell, M. Modular peptide amphiphile micelles improve an antibody-mediated immune response to Group A *Streptococcus. ACS Biomater. Sci. Eng* 2017, 3 (2), 144-152.

(6) Zhang, R.; Ulery, B. D. Synthetic Vaccine Characterization and Design. *J. Bionanosci.* 2018, 12 (1), 1-11.

(7) Hartgerink, J. D.; Beniash, E.; Stupp, S. I. Self-assembly and mineralization of peptide-amphiphile nanofibers. *Science* 2001, 294 (5547), 1684-1688.

(8) Trent, A.; Marullo, R.; Lin, B.; Black, M.; Tirrell, M. Structural properties of soluble peptide amphiphile micelles. *Soft Matter* 2011, 7 (20), 9572-9582.

(9) Chung, E. J.; Mlinar, L. B.; Nord, K.; Sugimoto, M. J.; Wonder, E.; Alenghat, F. J.; Fang, Y.; Tirrell, M. Monocyte-Targeting Supramolecular Micellar Assemblies: A Molecular Diagnostic Tool for Atherosclerosis. *Adv. Healthcare Mater.* 2015, 4 (3), 367-376.

(10) Nagaraj an, R. Molecular packing parameter and surfactant self-assembly: the neglected role of the surfactant tail. *Langmuir* 2002, 18 (1), 31-38.

(11) Herb, C. A.; Chen, L. B.; Sun, W. M. Correlation of Viscoelastic Properties with Critical Packing Parameter for Mixed Surfactant Solutions in the $L_1$ Region. In *Structure and Flow in Surfactant Solutions*; ACS Syposium Series; American Chemical Society: Washington, D.C., 1994. Vol. 578, Chapter 19, pp 153-156; DOI: 10.1021/bk-1994-0578.ch010.

(12) Truong, N. P.; Quinn, J. F.; Anastasaki, A.; Haddleton, D. M.; Whittaker, M. R.; Davis, T. P. Facile access to thermoresponsive filomicelles with tuneable cores. *Chem. Commun.* 2016, 52 (24), 4497-4500.

(13) Shimada, T.; Lee, S.; Bates, F. S.; Hotta, A.; Tirrell, M. Wormlike Micelle Formation in Peptide-Lipid Conjugates Driven by Secondary Structure Transformation of the Headgroupst. *J. Phys. Chem. B* 2009, 113 (42), 13711-13714.

(14) Paramonov, S. E.; Jun, H.-W.; Hartgerink, J. D. Self-assembly of peptide-amphiphile nanofibers: the roles of hydrogen bonding and amphiphilic packing. *J. Am. Chem. Soc.* 2006, 128 (22), 7291-7298.

(15) Cui, H.; Webber, M. J.; Stupp, S. I. Self-assembly of peptide amphiphiles: From molecules to nanostructures to biomaterials. *Biopolymers* 2010, 94 (1), 1-18.

(16) Sahoo, J. K.; Nazareth, C.; VandenBerg, M. A.; Webber, M. J. Self-assembly of amphiphilic tripeptides with sequence-dependent nanostructure. *Biomater. Sci.* 2017, 5, 1526.

(17) Missirlis, D.; Chworos, A.; Fu, C. J.; Khant, H. A.; Krogstad, D. V.; Tirrell, M. Effect of the peptide secondary structure on the peptide amphiphile supramolecular structure and interactions. *Langmuir* 2011, 27 (10), 6163-6170.

(18) Tsai, W.-W.; Li, L.-s.; Cui, H.; Jiang, H.; Stupp, S. I. Self-assembly of amphiphiles with terthiophene and tripeptide segments into helical nanostructures. *Tetrahedron* 2008, 64 (36), 8504-8514.

(19) Zhang, P.; Chiu, Y.-C.; Tostanoski, L. H.; Jewell, C. M. Polyelectrolyte multilayers assembled entirely from immune signals on gold nanoparticle templates promote antigen-specific T cell response. *ACS Nano* 2015, 9 (6), 6465-6477.

(20) Correa, S.; Dreaden, E. C.; Gu, L.; Hammond, P. T. Engineering nanolayered particles for modular drug delivery. *J. Controlled Release* 2016, 240, 364.

(21) Kalsin, A. M.; Fialkowski, M.; Paszewski, M.; Smoukov, S. K.; Bishop, K. J.; Grzybowski, B. A. Electrostatic self-assembly of binary nanoparticle crystals with a diamond-like lattice. *Science* 2006, 312 (5772), 420-424.

(22) Whitesides, G. M.; Mathias, J. P.; Seto, C. T. Molecular self-assembly and nanochemistry: a chemical strategy for the synthesis of nanostructures. *Science* 1991, 254, 1312-1319.

(23) Levicky, R.; Herne, T. M.; Tarlov, M. J.; Satija, S. K. Using self-assembly to control the structure of DNA monolayers on gold: a neutron reflectivity study. *J. Am. Chem. Soc.* 1998, 120 (38), 9787-9792.

(24) Berger, R.; Delamarche, E.; Lang, H. P.; Gerber, C.; Gimzewski, J. K.; Meyer, E.; Güntherodt, H.-J. Surface stress in the self-assembly of alkanethiols on gold. *Science* 1997, 276 (5321), 2021-2024.

(25) Faul, C. F.; Antonietti, M. Ionic self-assembly: Facile synthesis of supramolecular materials. *Adv. Mater.* 2003, 15 (9), 673-683.

(26) Vauthey, S.; Santoso, S.; Gong, H.; Watson, N.; Zhang, S. Molecular self-assembly of surfactant-like peptides to form nanotubes and nanovesicles. *Proc. Natl. Acad. Sci.* U S. A. 2002, 99 (8), 5355-5360.

(27) Tsonchev, S.; Schatz, G. C.; Ratner, M. A. Electrostatically-directed self-assembly of cylindrical peptide amphiphile nanostruc-tures. *J. Phys. Chem. B* 2004, 108 (26), 8817-8822.

(28) Tsonchev, S.; Troisi, A.; Schatz, G. C.; Ratner, M. A. All-atom numerical studies of self-assembly of zwitterionic peptide amphiphiles. *J. Phys. Chem. B* 2004, 108 (39), 15278-15284.

(29) O'Leary, L. E.; Fallas, J. A.; Bakota, E. L.; Kang, M. K; Hartgerink, J. D. Multi-hierarchical self-assembly of a collagen mimetic peptide from triple helix to nanofibre and hydrogel. *Nat. Chem.* 2011, 3 (10), 821-828.

(30) Tayi, A. S.; Kaeser, A.; Matsumoto, M.; Aida, T.; Stupp, S. I. Supramolecular ferroelectrics. *Nat. Chem.* 2015, 7 (4), 281-294.

(31) Hudalla, G. A.; Modica, J. A.; Tian, Y. F.; Rudra, J. S.; Chong, A. S.; Sun, T.; Mrksich, M.; Collier, J. H. A Self-Adjuvanting Supramolecular Vaccine Carrying a Folded Protein Antigen. *Adv. Healthcare Mater.* 2013, 2 (8), 1114-1119.

(32) Hudalla, G. A.; Sun, T.; Gasiorowski, J. Z.; Han, H.; Tian, Y. F.; Chong, A. S.; Collier, J. H. Gradated assembly of multiple proteins into supramolecular nanomaterials. *Nat. Mater.* 2014, 13 (8), 829.

(33) Andrews, C. D.; Provoda, C. J.; Ott, G.; Lee, K-D. Conjugation of lipid and CpG-containing oligonucleotide yields an efficient method for liposome incorporation. *Bioconjugate Chem.* 2011, 22 (7), 1279-1286.

(34) Jalan, A. A.; Jochim, K A.; Hartgerink, J. D. Rational design of a non-canonical "sticky-ended" collagen triple helix. *J. Am. Chem. Soc.* 2014, 136 (21), 7535-7538.

(35) Tanrikulu, I. C.; Forticaux, A.; Jin, S.; Raines, R. T. Peptide tessellation yields micrometre-scale collagen triple helices. *Nat. Chem.* 2016, 8 (11), 1008.

(36) Wiradharma, N.; Tong, Y. W.; Yang, Y. Y. Design and evaluation of peptide amphiphiles with different hydrophobic blocks for simultaneous delivery of drugs and genes. *Macromol. Rapid Commun.* 2010, 31 (13), 1212-1217.

(37) Thota, N.; Jiang, J. Self-assembly of amphiphilic peptide (AF) 6H5K15 derivatives: roles of hydrophilic and hydrophobic residues. *J. Phys. Chem. B* 2014, 118 (10), 2683-2692.

(38) Palmer, L. C.; Stupp, S. I. Molecular self-assembly into one-dimensional nanostructures. *Acc. Chem. Res.* 2008, 41 (12), 1674-1684.

(39) Gunkel-Grabole, G.; Sigg, S.; Lomora, M.; Lorcher, S.; Palivan, C.; Meier, W. Polymeric 3D nano-architectures for transport and delivery of therapeutically relevant biomacromolecules. *Biomater. Sci.* 2015, 3 (1), 25-40.

(40) Bulut, S.; Erkal, T. S.; Toksoz, S.; Tekinay, A. B.; Tekinay, T.; Guler, M. O. Slow release and delivery of antisense oligonucleotide drug by self-assembled peptide amphiphile nanofibers. *Biomacromole-cules* 2011, 12 (8), 3007-3014.

(41) Nasrolahi Shirazi, A.; Oh, D.; Tiwari, R. K; Sullivan, B.; Gupta, A.; Bothun, G. D.; Parang, K Peptide amphiphile containing arginine and fatty acyl chains as molecular transporters. *Mol. Pharmaceutics* 2013, 10 (12), 4717-4727.

(42) Liu, L.; Xu, K.; Wang, H.; Tan, P. J.; Fan, W.; Venkatraman, S. S.; Li, L.; Yang, Y.-Y. Self-assembled cationic peptide nanoparticles as an efficient antimicrobial agent. *Nat. Nanotechnol.* 2009, 4 (7), 457.

(43) Jiménez, Z. A.; Yoshida, R. Temperature driven self-assembly of a zwitterionic block copolymer that exhibits triple thermoresponsivity and pH sensitivity. Macromolecules 2015, 48 (13), 4599-4606.

(44) Shao, Q.; Jiang, S. Molecular understanding and design of zwitterionic materials. *Adv. Mater.* 2015, 27 (1), 15-26.

(45) Wyman, I. W.; Liu, G. Micellar structures of linear triblock terpolymers: Three blocks but many possibilities. *Polymer* 2013, 54 (8), 1950-1978.

(46) Gallon, E.; Matini, T.; Sasso, L.; Mantovani, G.; Armifian de Benito, A.; Sanchis, J.; Caliceti, P.; Alexander, C.; Vicent, M. J.; Salmaso, S. Triblock copolymer nanovesicles for pH-responsive targeted delivery and controlled release of siRNA to cancer cells. *Biomacromolecules* 2015, 16 (7), 1924-1937.

(47) Zhao, D.; Huo, Q.; Feng, J.; Chmelka, B. F.; Stucky, G. D. Nonionic triblock and star diblock copolymer and oligomeric surfactant syntheses of highly ordered, hydrothermally stable, mesoporous silica structures. *J. Am. Chem. Soc.* 1998, 120 (24), 6024-6036.

(48) Mata, J.; Majhi, P.; Guo, C.; Liu, H.; Bahadur, P. Concentration, temperature, and salt-induced micellization of a triblock copolymer Pluronic L64 in aqueous media. *J. Colloid Interface Sci.* 2005, 292 (2), 548-556.

(49) Sun, T.; Han, H.; Hudalla, G. A.; Wen, Y.; Pompano, R. R.; Collier, J. H. Thermal stability of self-assembled peptide vaccine materials. *Acta Biomater.* 2016, 30, 62-71.

(50) Rudra, J. S.; Tian, Y. F.; Jung, J. P.; Collier, J. H. A self-assembling peptide acting as an immune adjuvant. *Proc. Natl. Acad. Sci*. U S. A. 2010, 107 (2), 622-627.

(51) Trimaille, T.; Verrier, B. Micelle-based adjuvants for subunit vaccine delivery. *Vaccines* 2015, 3 (4), 803-813.

(52) Kremer, J. R.; Mastronarde, D. N.; McIntosh, J. R. Computer visualization of three-dimensional image data using IMOD. *J. Struct Biol.* 1996, 116 (1), 71-76.

(53) Nowinski, A. K; White, A. D.; Keefe, A. J.; Jiang, S. Biologically inspired stealth peptide-capped gold nanoparticles. *Langmuir* 2014, 30 (7), 1864-1870.

(54) Mahmoud, Z. N.; Grundy, D. J.; Channon, K J.; Woolfson, D. N. The non-covalent decoration of self-assembling protein fibers. Biomaterials 2010, 31 (29), 7468-7474.

(55) Takeuchi, H.; Hanamura, N.; Hayasaka, H.; Harada, I. B-Z transition of poly(dG-m$^5$ dC) induced by binding of Lys-containing peptides. *FEBS Lett.* 1991, 279 (2), 253-255.

(56) Kim, Y. G.; Park, H. J.; Kim, K K; Lowenhaupt, K; Rich, A. A peptide with alternating lysines can act as a highly specific Z-DNA binding domain. *Nucleic Acids Res.* 2006, 34 (17), 4937-4942.

(57) Stein, P. E.; Leslie, A. G. W.; Finch, J. T.; Carrell, R. W. Crystal structure of uncleaved ovalbumin at 1.95 Å resolution. *J. Mol. Biol.* 1991, 221 (3), 941-959.

(58) Qiao, Y.; Lin, Y.; Wang, Y.; Yang, Z.; Liu, J.; Zhou, J.; Yan, Y.; Huang, J. Metal-driven hierarchical self-assembled one-dimensional nanohelices. *Nano Lett.* 2009, 9 (12), 4500-4504.

(59) Parker, A.; Fieber, W. Viscoelasticity of anionic wormlike micelles: effects of ionic strength and small hydrophobic molecules. *Soft Matter* 2013, 9 (4), 1203-1213.

(60) Borisova, O.; Billon, L.; Zaremski, M.; Grassl, B.; Bakaeva, Z.; Lapp, A.; Stepanek, P.; Borisov, O. pH-triggered reversible sol-gel transition in aqueous solutions of amphiphilic gradient copolymers. *Soft Matter* 2011, 7 (22), 10824-10833.

(61) Priftis, D.; Leon, L.; Song, Z.; Perry, S. L.; Margossian, K O.; Tropnikova, A.; Cheng, J.; Tirrell, M. Self-Assembly of α-Helical Polypeptides Driven by Complex Coacervation. *Angew. Chem.* 2015, 127 (38), 11280-11284.

(62) Perry, S. L.; Sing, C. E. Prism-based theory of complex coacervation: Excluded volume versus chain correlation. *Macromolecules* 2015, 48 (14), 5040-5053.

(63) Missirlis, D.; Teesalu, T.; Black, M.; Tirrell, M. The non-peptidic part determines the internalization mechanism and intracellular trafficking of peptide amphiphiles. *PLoS One* 2013, 8 (1), e54611.

(64) Liu, S.; Jiang, S. Zwitterionic polymer-protein conjugates reduce polymer-specific antibody response. *Nano Today* 2016, 11, 285.

(65) Zhang, P.; Sun, F.; Liu, S.; Jiang, S. Anti-PEG antibodies in the clinic: Current issues and beyond PEGylation. *J. Controlled Release* 2016, 244, 184.

(66) Zhang, P.; Jain, P.; Tsao, C.; Sinclair, A.; Sun, F.; Hung, H.-C.; Bai, T.; Wu, K; Jiang, S. Butyrylcholinesterase nanocapsule as a long circulating bioscavenger with reduced immune response. *J. Controlled Release* 2016, 230, 73-78.

(67) Zhang, P.; Sun, F.; Tsao, C.; Liu, S.; Jain, P.; Sinclair, A.; Hung, H.-C.; Bai, T.; Wu, K; Jiang, S. Zwitterionic gel encapsulation promotes protein stability, enhances pharmacokinetics, and reduces immunogenicity. *Proc. Natl. Acad. Sci*. U S. A. 2015, 112 (39), 12046-12051.

(68) Y.-V. Tan, C. Abad, Y. Wang, R. Lopez and J. A. Waschek, *Brain, behavior, and immunity,* 2015, 44, 167-175.

(69) M. Delgado, E. J. Munoz-Elias, R. P. Gomariz and D. Ganea, *The Journal of Immunology,* 1999, 162, 1707-1716.

(70) M. Delgado and D. Ganea, *Amino acids,* 2013, 45, 25-39.

(71) M. Delgado, C. Abad, C. Martinez, J. Leceta and R. P. Gomariz, *Nature medicine,* 2001, 7, 563-568.

(72) M. Delgado and D. Ganea, *Brain, behavior, and immunity,* 2008, 22, 1146-1151.

(73) A. Fernandez-Martin, E. Gonzalez-Rey, A. Chomy, J. Martin, D. Pozo, D. Ganea and M. Delgado, *Annals of the New York Academy of Sciences,* 2006, 1070, 276-281.

(74) M. G. Toscano, M. Delgado, W. Kong, F. Martin, M. Skarica and D. Ganea, *Molecular Therapy,* 2010, 18, 1035-1045.

(75) R. Jimeno, R. P. Gomariz, I. Gutierrez-Callas, C. Martinez, Y. Juarranz and J. Leceta, *Immunology and cell biology,* 2010, 88, 734-745.

(76) R. Yu, H. Zhang, L. Huang, X. Liu and J. Chen, *Peptides,* 2011, 32, 216-222.

(77) H. Cui, M. J. Webber and S. I. Stupp, *Peptide Science,* 2010, 94, 1-18.

(78) J. D. Hartgerink, E. Beniash and S. I. Stupp, *Science,* 2001, 294, 1684-1688.

(79) M. P. Hendricks, K Sato, L. C. Palmer and S. I. Stupp, *Accounts of chemical research,* 2017, 50, 2440-2448.

(80) A. Mata, Y. Geng, K J. Henrikson, C. Aparicio, S. R. Stock, R. L. Satcher and S. I. Stupp, *Biomaterials,* 2010, 31, 6004-6012.

(81) W.-W. Tsai, L.-s. Li, H. Cui, H. Jiang and S. I. Stupp, *Tetrahedron,* 2008, 64, 8504-8514.

(82) M. J. Webber, J. B. Matson, V. K Tamboli and S. I. Stupp, *Biomaterials,* 2012, 33, 6823-6832.

(83) R. H. Zha, S. Sur and S. I. Stupp, *Advanced healthcare materials,* 2013, 2, 126-133.

(84) D. Peters, M. Kastantin, V. R Kotamraju, P. P. Karmali, K Gujraty, M. Tirrell and E. Ruoslahti, *Proceedings of the National Academy of Sciences,* 2009, 106, 9815-9819.

(85) E. J. Chung, L. B. Mlinar, M. J. Sugimoto, K Nord, B. B. Roman and M. Tirrell, *Nanomedicine: Nanotechnology, Biology and Medicine,* 2015, 11, 479-487.

(86) J. C. Barrett, B. D. Ulery, A. Trent, S. Liang, N. A. David and M. Tirrell, *ACS Biomaterials Science & Engineering,* 2016, 3, 144-152.

(87) D. Missirlis, T. Teesalu, M. Black and M. Tirrell, *PloS one,* 2013, 8, e54611.

(88) L. B. Mlinar, E. J. Chung, E. A. Wonder and M. Tirrell, *Biomaterials,* 2014, 35, 8678-8686.

(89) M. J. Webber, J. Kessler and S. Stupp, *Journal of internal medicine,* 2010, 267, 71-88.

(90) M. Black, A. Trent, Y. Kostenko, J. S. Lee, C. Olive and M. Tirrell, *Advanced Materials,* 2012, 24, 3845-3849.

(91) A. Trent, R. Marullo, B. Lin, M. Black and M. Tirrell, *Soft Matter,* 2011, 7, 9572-9582.

(92) R. Zhang and B. D. Ulery, *Journal of Bionanoscience,* 2018, 12, 1-11.

(93) R. Zhang, S. Kramer Jake, J. D. Smith, B. Allen, N, C. Leeper, N, X. Li, L. D. Morton and B. D. Ulery, *the AAPS journal,* 2018.

(94) R Zhang, L. D. Morton, J. D. Smith, F. Gallazzi, T. A. White and B. D. Ulery, *ACS Biomaterials Science & Engineering,* 2018.

(95) M. A. Moretton, R. J. Glisoni, D. A. Chiappetta and A. Sosnik, *Colloids and Surfaces B: Biointerfaces,* 2010, 79, 467-479.

(96) A. Trent, B. D. Ulery, M. J. Black, J. C. Barrett, S. Liang, Y. Kostenko, N. A. David and M. V. Tirrell, *The AAPS journal,* 2015, 17, 380-388.

(97) M. F. Bachmann and G. T. Jennings, *Nature Reviews Immunology,* 2010, 10, 787-796.

(98) D. J. Irvine, M. A. Swartz and G. L. Szeto, *Nature materials,* 2013, 12, 978-990.

(99) J. Conde, N. Oliva, Y. Zhang and N. Artzi, *Nature materials,* 2016, 15, 1128-1138.

(100) R Zhang, J. D. Smith, S. Kramer Jake, B. Allen, N, S. Martin and B. D. Ulery, *ACS Biomaterials Science & Engineering,* 2018.

(101) H. A. Behanna, J. J. Dormers, A. C. Gordon and S. I. Stupp, *Journal of the American Chemical Society,* 2005, 127, 1193-1200.

(102) T. Shimada, N. Sakamoto, R. Motokawa, S. Koizumi and M. Tirrell, *The Journal of Physical Chemistry B,* 2011, 116, 240-243.

(103) S. E. Paramonov, H. W. Jun and J. D. Hartgerink, *Biomacromolecules,* 2006, 7, 24-26.

(104) J. Li, T. Wang, D. Wu, X. Zhang, J. Yan, S. Du, Y. Guo, J. Wang and A. Zhang, *Biomacromolecules,* 2008, 9, 2670-2676.

(105) R. M. Strider, S. L. Kunkel and R. C. Bone, *Critical care medicine,* 1993, 21, S447.

(106) O. Takeuchi, K Hoshino, T. Kawai, H. Sanjo, H. Takada, T. Ogawa, K Takeda and S. Akira, *Immunity,* 1999, 11, 443-451.

(107) M. Yoshizumi, M. A. Perrella, J. C. Burnett and M. E. Lee, *Circulation research,* 1993, 73, 205-209.

(108) M. Linderholm, C. Ahlm, B. Settergren, A. Waage and A. Tamvik, *The Journal of infectious diseases,* 1996, 173, 38-43.

(109) D. J. Lenschow, T. L. Walunas and J. A. Bluestone, *Annual review of immunology,* 1996, 14, 233-258.

(110) K Pletinckx, A Dohler, V. Pavlovic and M. B. Lutz, *Frontiers in immunology,* 2011, 2, 39.

(111) M. H. Sayegh and L. A. Turka, *New England Journal of Medicine,* 1998, 338, 1813-1821.

(112) S. Jhunjhunwala, G. Raimondi, A. J. Glowacki, S. J. Hall, D. Maskarinec, S. H. Thome, A. W. Thomson and S. R. Little, *Advanced materials,* 2012, 24, 4735-4738.

(113) M. Delgado, E. Gonzalez-Rey and D. Ganea, *The FASEB journal,* 2004, 18, 1453-1455.

(114) X. Jiang, H. Jing and D. Ganea, *Journal of neuroimmunology,* 2002, 133, 81-94.

(115) B. Arellano, D. J. Graber and C. L. Sentman, *Discovery medicine,* 2016, 22, 73.

(116) M.-G. Roncarolo and M. Battaglia, *Nature Reviews Immunology,* 2007, 7, nri2138.

(117) K S. Smigiel, S. Srivastava, J. M. Stolley and D. J. Campbell, *Immunological reviews,* 2014, 259, 40-59.

(118) M. Delgado, A Reduta, V. Sharma and D. Ganea, *Journal of leukocyte biology,* 2004, 75, 1122-1130.

(119) M. Delgado and D. Ganea, *The Journal of Immunology,* 2001, 167, 966-975.

(120) I. Langer, British journal of *pharmacology,* 2012, 166, 79-84.

(121) M. O'Donnell, R. Garippa, N. O'Neill, D. Bolin and J. Cottrell, *Journal of Biological Chemistry,* 1991, 266, 6389-6392.

(122) D. Missirlis, D. V. Krogstad and M. Tirrell, *Molecular pharmaceutics,* 2010, 7, 2173-2184.

(123) K Kato, C. Itoh, T. Yasukouchi and T. Nagamune, *Biotechnology progress,* 2004, 20, 897-904.

(124) T.-y. Wang, R. Leventis and J. R. Silvius, *Journal of Biological Chemistry,* 2005, 280, 22839-22846.

(125) S. Onoue, A. Matsumoto, Y. Nagano, K Ohshima, Y. Ohmori, S. Yamada, R. Kimura, T. Yajima and K Kashimoto, *European journal of pharmacology,* 2004, 485, 307-316.

(126) A. Chomy, E. Gonzalez-Rey, A. Fernandez-Martin, D. Pozo, D. Ganea and M. Delgado, *Proceedings of the National Academy of Sciences of the United States of America,* 2005, 102, 13562-13567.

(127) M. Vulcano, C. Albanesi, A. Stoppacciaro, R. Bagnati, G. D'Amico, S. Struyf, P. Transidico, R. Bonecchi, A. Del Prete and P. Allavena, *European journal of immunology,* 2001, 31, 812-822.

(128) Ding, H.; Prodinger, W. M.; Kopecek, J., Identification of CD21-Binding Peptides with Phage Display and Investigation of Binding Properties of HPMA Copolymer-Peptide Conjugates. Bioconjugate Chemistry 2006, 17 (2), 514-523.

(129) Ding, H.; Prodinger, W. M.; Kopecek, J., Two-Step Fluorescence Screening of CD21-Binding Peptides with One-Bead One-Compound Library and Investigation of Binding Properties of N-(2-Hydroxypropyl)methacrylamide Copolymer-Peptide Conjugates. Biomacromolecules 2006, 7 (11), 3037-3046.

(130) McGuire, M. J.; Samli, K N.; Chang, Y. C.; Brown, K C., Novel ligands for cancer diagnosis: Selection of peptide ligands for identification and isolation of B-cell lymphomas. Experimental Hematology 2006, 34 (4), 443-452.

(131) Martucci, N. M.; Migliaccio, N.; Ruggiero, I.; Albano, F.; Cali, G.; Romano, S.; Terracciano, M.; Rea, I.; Arcari, P.; Lamberti, A., Nanoparticle-based strategy for personalized B-cell lymphoma therapy. International Journal of Nanomedicine 2016, 11, 6089-6101.

(132) Tutykhina, I.; Esmagambetov, I.; Bagaev, A.; Pichugin, A.; Lysenko, A; Shcherbinin, D.; Sedova, E.; Logunov, D.; Shmarov, M.; Ataullakhanov, R.; Naroditsky, B.; Gintsburg, A., Vaccination potential of B and T epitope-enriched NP and M2 against Influenza A viruses from different dales and hosts. PLoS One 2018, 13 (1), e0191574.

(133) Fiers, W.; De Filette, M.; Birkett, A.; Neirynck, S.; Min Jou, W., A "universal" human influenza A vaccine. Virus Research 2004, 103 (1-2), 173-176.

(134) Stanekova, Z.; Vareckova, E., Conserved epitopes of influenza A virus inducing protective immunity and their prospects for universal vaccine development. Virology Journal 2010, 7, 351.

(135) Wolf, A. I.; Mozdzanowska, K; Williams, K L.; Singer, D.; Richter, M.; Hoffman, R.; Caton, A. J.; Otvos, L.; Erikson, J., Vaccination with M2e-Vased Multiple Antigenic Peptides: Characterization of the B Cell Response and Protection Efficacy in Inbred and Outbred Mice. *PLoS One* 2011, 6 (12), e28445.
(136) Chun, S.; Li, C.; Van Domselaar, G.; Wang, J.; Farnsworth, A.; Cui, X.; Rode, H.; Cyr,
T. D.; He, R.; Li, X., Universal antibodies and their applications to the quantitative determination of virtually all subtypes of the influenza A viral hemagglutinins. Vaccine 2008, 26 (48), 6068-6076.
(137) Rosendahl Huber, S. K; Camps, M. G. M.; Jacobi, R. H. J.; Mouthaan, J.; van Dijken, H.; van Beek, J.; Ossendorp, F.; de Jonge, J., Synthetic long peptide influenza vaccine containing conserved T and B cell epitopes reduces viral load in lungs of mice and ferrets. PLoS One 2015, 10 (6), e0127969.
(138) Vaccaro, L.; Cross, K J.; Kleinjung, J.; Straus, S. K; Thomas, D. J.; Wharton, S. A.; Skehel, J. J.; Fratemali, F., Plastic of influenza haemagglutinin fusion peptide and their interaction with lipid bilayers. Biophysical Journal 2005, 88 (1), 25-36.
(139) Esbjomer, E. K; Oglecka, K; Lincoln, P.; Graslund, A.; Norden, B., Membrane Binding of pH-Sensitive Influenza Fusion Peptides. Positioning, Configuration, and Induced Leakage in a Lipid Vesicle Model. Biochemistry 2007, 46 (47), 13490-13504.
(140) Doyle, T. M.; Jaentschke, B.; Van Domselaar, G.; Hashem, A. M.; Farnsworth, A.; Borbes, N. E.; Li, C.; Wang, J.; He, R.; Brown, E. G.; Li, X., The Universal Epitope of Influenza A Viral Neuraminidase Fundamentally Contributes to Enzyme Activity and Viral Replication. The Journal of Biological Chemistry 2013, 288 (25), 18283-18289.
(141) Doyle, T. M.; Hashem, A. M.; Li, C.; Van Domselaar, G.; Larocque, L.; Wang, J.; Smith, D.; Cyr, T.; Farnsworth, A.; He, R; Hurt, A. C.; Brown, E. G.; Li, X, Universal anti-neuraminidase antibody inhibiting all influenza A subtypes. Antiviral Research 2013, 100 (2), 567-574.
(142) Wu, K-W.; Chien, C.-Y.; Li, S.-W.; King, C.-C.; Chang, C.-H., Highly conserved influenza A virus epitope sequences as candidates of H3N2 flu vaccine targets. Genomics 2012, 100 (2), 102-109.
(143) Falugi, F.; Petracca, R.; Mariani, M.; Luzzi, E.; MAncianti, S.; Carinci, V.; Melli, M. L.; Finco, O.; Wack, A.; Di Tommaso, A.; De Magistris, M. T.; Costantino, P.; Del Guidice, G.; Abrignani, S.; Rappuoli, R.; Grandi, G., Rationally designed strings of promiscuous CD4+ T cell epitopes provide help to Haemohilus influenzae type b oligosaccharide: a model for new conjugate vaccines. European Journal of Immunology 2001, 31 (12), 3816-3824.
(144) Greenstein, J. L.; Schad, V. C.; Goodwin, W. H.; Brauer, A. B.; Bollinger, B. K; Chin, R. D.; Kuo, M. C., A universal T cell epitope-containing peptide from hepatitis B surface antigen can enhance antibody specific for HIV gp 120. Journal of Immunology 1992, 148 (12), 3970-3977.
(145) Fraser, C. C.; Altreuter, D. H.; Ilyinskii, P.; Pittet, L.; LaMothe, R. A.; Keegan, M.; Johnston, L.; Kishimoto, T. K, Generation of a universal CD4 memory T cell recall peptide effective in humans, mice and non-human primates. Vaccine 2014, 32 (24), 2896-2903.
(146) Park, H.-Y.; Tan, P. S.; Kavishna, R.; Ker, A.; Lu, J.; Chan, C. E. Z.; Hanson, B. J.; MacAry, P. A.; Caminschi, I.; Shot iman, K; Alonso, S.; Lahoud, M. H., Enhancing vaccine antibody responses by targeting Clec9A on dendritic cells. npj Vaccines 2017, 2, 31.
(147) Alexander, J.; Sidney, J.; Southwood, S.; Ruppert, J.; Oseroff, C.; Maewal, A.; Snoke, K; Serra, H. M.; Kubo, R. T.; Sette, A.; Grey, H. M., Development of high potency universal DR-restricted helper epitopes by modification of high affinity DR-blocking peptides. Immunity 1994, 1 (9), 751-761.
(148) Alexander, J.; Del Guercio, M. F.; Maewal, A.; Qiao, L.; Fikes, J.; Chesnut, R. W.; Paulson, J.; Bundle, D. R.; DeFrees, S.; Sette, A., Linear PADRE T helper epitope and carbohydrate B cell epitope conjugates induce specific high titer IgG antibody responses. Journal of Immunology 2000, 164 (3), 1625-1633.
(149) Pompano, R P.; Chen, J.; Verbus, E. A.; Han, H.; Fridman, A.; McNeely, T.; Collier, J. H.; Chong, A. S., Titrating T cell Epitopes within Self-Assembled Vaccines Optimizes CD4+ Helper T Cell and Antibody Outputs. Advanced Healthcare Materials 2014, 3 (11), 1898-1908.
(150) Kashi, V. P.; Jacob, R. A.; Shamanna, R. A.; Menon, M.; Balasiddaiah, A.; Varghese, R. K; Bachu, M.; Ranga, U., The grafting of universal T-helper epitopes enhances immunogenicity of HIV-1 Tat concurrently improving its safety profile. PLoS One 2014, 9 (12), e114155.
(151) Sioud, M.; Skorstad, G.; Mobergslien, A.; Saeboe-Larssen, S., A novel peptide carrier for efficient targeting of antigens and nucleic acids to dendritic cells. The FASEB Journal 2012, 27 (8), 3272-3283.
(152) Akazawa, T.; Ohashi, T.; Nakajima, H.; Nishizawa, Y.; Kodama, K; Sugiura, K; Inaba, T.; Inoue, N., Development of a dendritic cell-targeting lipopeptide as an immunoadjuvant that inhibits tumor growth without inducing local inflammation. International Journal of Cancer 2014, 135 (12), 2847-2856.
(153) De Silva, N. H.; Akazawa, T.; Wijewardana, W.; Inoue, N.; Oyamada, M.; Ohta, A.; Tachibana, Y.; Wijesekera, D. P. H.; Kuwamura, M.; Nishizawa, Y.; Itoh, K; Izawa, T.; Hatoya, S.; Hasegawa, T.; Yamate, J.; Inaba, T.; Sugiura, K, Development of effective tumor immunotherapy using a novel dendritic cell-targeting Toll-like receptor ligand. PLoS One 2017, 12 (11), e0188738.
(154) Yan, Z.; Wu, Y.; Du, J.; Li, G.; Wang, S.; Cao, W.; Zhou, X.; Wu, C.; Zhang, D.; Jing, X.; Li, Y.; Wang, H.; Gao, Y.; Qi, Y., A novel peptide targeting Clec9a on dendritic cell for cancer immunotherapy. Oncotarget 2016, 7 (26), 40437-40450.
(155) Zeng, B.; Middelberg, A. P.; Gemiarto, A.; MacDonald, K; Baxter, A. G.; Talekar, M.; Moi, D.; Tullett, K M.; Caminschi, I.; Lahoud, M. H.; Mazzieri, R.; Dolcetti, R.; Thomas, R., Self-adjuvanting nanoemulsion targeting dendritic cell receptor Clec9A enables antigen-specific immunotherapy. Journal of Clinical Investigation 2018, 128 (5), 1971-1984.
(156) Jung, S. N.; Kang, S. K; Yeo, G. H.; Li, H. Y.; Jiang, T.; Nah, J. W.; Bok, J. D.; Cho, C. S.; Choi, Y. J., Targeted delivery of vaccine to dendritic cells by chitosan nanoparticles conjugated with a targeting peptide ligand selected by phage display technique. Macromolecular Bioscience 2015, 15 (3), 395-404.
(157) Alexander, J.; Bisel, P.; del Guercio, M. F.; Marinkovic-Petrovic, A.; Southwood, S.; Stewart, S.; Ishioka, G.; Kotturi, M. F.; Batten, J.; Sidney, J.; Newman, M.; Sette, A., Identification of broad binding class I HLA supertype epitopes to provide universal converage of influenza A virus. Human Immunology 2010, 71 (5), 468-474.
(158) Stambas, J.; Doherty, P. C.; Turner, S. J., An In Vivo Cytotoxicity Threshold for Influenza A Virus-Specific Effector and Memoory CD8+ T Cells. Journal of Immunology 2007, 178 (3), 1285-1292.

(159) Si, Y.; Wen, Y.; Kelly, S. H.; Chong, A. S.; Collier, J. H., Intranasal delivery of adjuvant-free peptide nanofibers elicits resident CD8+ T cell responses. Journal of Controlled Release 2018, S0169-3659 (18), 30216-5.

(160) Tan, A. C. L.; Deliyannis, G.; Bharadwaj, M.; Brown, L. E.; Zeng, W.; Jackson, D. C., The design and proof of concept for a CD8+ T cell-based vaccine inducing cross-subtype protection against influenza A virus. Immunology and Cell Biology 2012, 91 (1), 96-104.

(161) Writer, M. J.; Marshall, B.; Pilkington-Miksa, M. A.; Barker, S. E.; Jacobsen, M.; Kritz, A.; Bell, P. C.; Lester, D. H.; Tabor, A. B.; Hailes, H. C.; Klein, N.; Hart, S. L., Targeted gene delivery to human airway epithelial cells with synthetic vectors incorporating novel targeting peptide selected by phage display. Journal of Drug Targeting 2004, 12 (4), 185-193.

(162) Manunta, M. D. I.; Tagalakis, A. D.; Attwood, M.; Aldossary, A. M.; Barnes, J. L.; Munye, M. M.; Weng, A.; McAnulty, R J.; Hart, S. L., Delivery of ENaC siRNA to epithelial cells mediated by a targeted nanocomplex: A therapeutic strategy for cystic fibrosis. Scientific Reports 2017 7(1), 700.

(163) Jost, P. J.; Harbottle, R. P.; Knight, A.; Miller, A. D.; Coutelle, C.; Schneider, H., A novel peptide, THALWHT, for the targeting of human airway epithelia. FEBS Letters 2001, 489 (2-3), 263-269.

(164) Nicol, M. Q.; Ligertwood, Y.; Bacon, M. N.; Dutia, B. M.; Nash, A. A., A novel family family of peptides with potent activity against influenza A viruses. Journal of General Virology 2012, 93 (Pt 5), 980-986.

(165) Ammendolia, M. G.; Agamennone, M.; Pietrantoni, A.; Lannutti, F.; Siciliano, R. A.; De Giulio, B.; Amici, C.; Superti, F., Bovine lactoferrin-derived peptides as novel broad-spectrum inhibitors of influenza virus. Pathogens and Global Health 2012, 106 (1), 12-19.

(166) Ghanem, A.; Mayer, D.; Chase, G.; Tegge, W.; Frank, R; Kochs, G.; Garcia-Sastre, A.; Schwemmle, M., Peptide-Mediated Interference with Influenza A Virus Polymerase. Journal of Virology 2007, 81 (14), 7801-7804.

(167) Wunderlich, K; Mayer, D.; Ranadheera, C.; Holler, A.-S.; Manz, B.; Martin, A.; Chase, G.; Tegge, W.; Frank, R.; Kessler, U.; Schwemmle, M., Identification of a PA-Binding Peptide with Inhibitory Activity against Influenza A and B Virus Replication. PLoS One 2009, 4 (10), e7517.

(168) Jones, J. C.; Settles, E. W.; Brandt, C. R.; Schultz-Cherry, S., Identification of the Minimal Active Sequence of an Anti-Influenza Virus Peptide. Antimicrobial Agents and Chemotherapy 2011, 55 (4), 1810-1813.

(169) Nasser, E. H.; Judd, A. K; Sanchez, A.; Anastasiou, D.; Bucher, D. J., Antiviral Activity of Influenza Virus M1 Zinc Finger Peptides. Journal of Virology 1996, 70 (12), 8639-8644.

(170) Judd, A. K; Sanchez, A.; Bucher, D.; Huff Iran, J. H.; Bailey, K; Sidwell, R. W., In Vivo Anti-Influenza Virus Activity of a Zinc Finger Peptide. Antimicrobial Agents and Chemotherapy 1997, 41 (3), 687-692.

(171) Chung, E. J.; Nord, K; Sugimoto, M. J.; Wonder, E.; Tirrell, M., Monocyte-Targeting Supramolecular Micellar Assemblies: A Molecular Diagnostic Tool for Atherosclerosis. Advanced Healthcare Materials 2015, 4 (3), 367-376.

(172) Poon, C.; Chowdhuri, S.; Kuo, C.-H.; Fang, Y.; Alenghat, F. J.; Hyatt, D.; Kani, K; Gross, M. E.; Chung, E. J., Protein mimetic and anticancer properties of monocyte-targeting peptide amphiphile micelles. ACS Biomaterials Science & Engineering 2017, 3 (12), 3273-3282.

(173) Zhang, X.; Bajic, G.; Andersen, G. R.; Christiansen, S. H.; Vorup-Jensen, T., The cationic pepitde LL-37 binds Mac-1 (CD11b/CD18) with a low dissociation rate and promotes phagocytosis. Biochimica et Biphysica Acta 2016, 1864 (5), 471-478.

(174) Lishko, V. K; Moreno, B.; Podolnikova, N. P.; Ugarova, T. P., Identification of Human Cathelicidin Peptide LL-37 as a Ligand for Macrophage Integrin αMβ2 (Mac-1, CD11b/CD18) that Promotes Phagocytosis by Opsonizing Bacteria. Research and Reports in Biochemistry 2016, 2016 (6), 39-55.

(175) Scodeller, P.; Simon-Gracia, L.; Kopanchuk, S.; Tobi, A.; Kilk, K; Saalik, P.; Kurm, K; Squadrito, M. L.; Kotamraju, V. R; Rinken, A.; De Palma, M.; Ruoslahti, E.; Teesalu, T., Precision Targeting of Tumor Macrophages with a CD206 Binding Peptide. Scientific Reports 2017, 7, 14655.

(176) Banerjee, G.; Medda, S.; Basu, M. K, A Novel Peptide-Grafted Liposomal Delivery System Targeted to Macrophages. 42 1998, 2 (348-351).

(177) Delgado, M.; Munoz-Elias, E. J.; Gomariz, R. P.; Ganea, D., Vasoactive Intestinal Peptide and Pituitary Adenylate Cyclase-Activating Polypeptide Enhance IL-10 PRoduction by Murine Macrophages: In Vitro and In Vivo Studies. Journal of Immunology 1999, 162 (3), 1707-1716.

(178) Tan, Y.-V.; Abad, C.; Wang, Y.; Lopez, R.; Waschek, J. A., VPAC2 (vasoactive intestinal peptide receptor type 2) receptor deficient mice develop exacerbated experimental autoimmuno encephalomyelitis with increased Th1/Th17 and reduced Th2/Treg responses. Brain, Behavior, and Immunity 2015, 44, 167-175.

(179) Yanofsky, S. D.; Baldwin, D. N.; Butler, J. H.; Holden, F. R.; Jacobs, J. W.; Balasubramanian, P.; Chinn, J. P.; Cwirla, S. E.; Peters-Bhatt, E.; Whitehorn, E. A.; Tate, E. H.; Akeson, A.; Bowlin, T. L.; Dower, W. J.; Barrett, R W., High affinity type I interleukin 1 receptor antagonists discovered by screening recombinant peptide libraries. Proceedings of the National Academy of Sciences 1996, 93 (14), 7381-7386.

(180) Fok, E.; Sandeman, S. R.; Guildford, A L.; Martin, Y. H., The Use of an IL-1 Receptor Antagonist Peptide to Control Inflammation in the Treatment of Corneal Limbal Epithelial Stem Cell Deficiency. BioMed Research International 2015, 2015, 516318.

(181) Pena, 0. M.; Afacan, N.; Pistolic, J.; Chen, C.; Madera, L.; Falsafi, R.; Fjell, C. D.; Hancock, R. E. W., Synthetic Cationic Peptide IDR-1018 Modulates Human Macrophage Differentiation. PLoS One 2013, 2013 (8), 1.

(182) Freitas, C. G.; Lima, S. M. F.; Freire, M. S.; Cantuaria, A. P. C.; Junior, N. G. O.; Santos, T. S.; Folha, J. S.; Ribeiro, S. M.; Dias, S. C.; Rezende, T. M. B.; Albuquerque, P.; Nicola, A. M.; de la Fuente-Nunez, C.; Hancock, R. E. W.; Franco, O. L.; Felipe, M. S. S., An Immunomodulatory Peptide Confers Protection in an Experimental Candidemia Murine Model. Antimicrobial Agents and Chemotherapy 2017, 61 (8), e02518-16.

(183) Brugnano, J. L.; Chan, B. K; Seal, B. L.; Panitch, A., Cell-penetrating peptides can confer biological function: regulation of inflammatory cytokines in human monocytes by MK2 inhibitor peptides. Journal of Controlled Release 2011, 155 (2), 128-133.

(184) Poh, S.; Lin, J. B.; Panitch, A., Release of Anti-inflammatory Peptides from Thermosensitive Nanoparticles with Degradable Cross-Links Suppresses Pro-inflammatory Cytokine Production. Biomacromolecules 2015, 16 (4), 1191-1200.

(185) Aoki, K; Saito, H.; Itzstein, C.; Ishiguro, M.; Shibata, T.; Blangue, R.; Mian, A. H.; Takahashi, M.; Suzuki, Y.; Yoshimatsu, M.; Yamaguchi, A.; Deprez, P.; Mollat, P.; Murali, R.; Ohya, K; Home, W. C.; Baron, R., A TNF receptor loop peptide mimic blocks RANK ligand-induced signaling, bone resorption, and bone loss. Journal of Clinical Investigation 2006, 116 (6), 1525-1534.

(186) Saito, H.; Kohima, T.; Takahashi, M.; Home, W. C.; Baron, R; Amagasa, T.; Ohya, K; Aoki, K, A tumor necrosis factor receptor loop peptide mimic inhibits bone destruction to the same extent as anti-tumor necrosis monoclonal antibody in murine collagen-induced arthritis. Arthritis and Rheumatism 2007, 56 (4), 1164-1174.

Whereas particular embodiments have been described above for purposes of illustration, it will be appreciated by those skilled in the art that numerous variations of the details may be made without departing from the disclosure as described in the appended claims.

We claim:

1. A triblock peptide of the formula:

A-B-C wherein

A is a lipid moiety, wherein the lipid moiety is PalmK or Palm2K; and

B and C are independently a peptide block or a zwitterion-like block, wherein one of B and C is a peptide block and the other of B and C is a zwitterion-like block;

wherein the peptide block is selected from the group consisting of SEQ ID NO: 1, SEQ ID NO: 2, SEQ ID NO: 3, or SEQ ID NO: 4;

wherein the zwitterion-like block is $(EK)_4$ or $(KE)_4$; and wherein the triblock peptide assembles into a micelle when in a liquid.

2. The triblock peptide of claim 1, wherein the peptide block has a molecular weight from 75 g/mol to 80,000 g/mol.

3. The triblock peptide of claim 1, wherein the zwitterion-like block has a molecular weight from 200 g/mol to 60,000 g/mol.

4. A triblock peptide of formula A-B-C, wherein one of A, B, and C is a lipid moiety, one of A, B, and C is a peptide block, and one of A, B, and C is a zwitterion-like block; wherein A, B, and C are in an arrangement selected from the group consisting of lipid-peptide-zwitterion, lipid-zwitterion-peptide, peptide-lipid-zwitterion, peptide-zwitterion-lipid, zwitterion-lipid-peptide, and zwitterion-peptide-lipid;

wherein the lipid moiety is PalmK or Palm2K;

wherein the peptide block is selected from the group consisting of SEQ ID NO: 1, SEQ ID NO: 2, SEQ ID NO: 3, or SEQ ID NO: 4;

wherein the zwitterion-like block is $(EK)_4$ or $(KE)_4$; and wherein the triblock peptide assembles into a micelle when in a liquid.

5. The triblock peptide of claim 1, wherein the micelles are from 4 nm to 100 μm in greatest dimension.

6. The triblock peptide of claim 1, wherein the micelles form structures selected from the group consisting of spheres, cylinders, worm-like structures and combinations thereof.

7. The triblock peptide of claim 1, wherein the micelles form higher-order structures.

8. The triblock peptide of claim 7, wherein the higher-order structures are selected from the group consisting of clusters, twines, braids, nets and combinations thereof.

9. The triblock peptide of claim 7, wherein the higher-order structures are from 10 nm to 100 μm in greatest dimension.

10. The triblock peptide of claim 1, wherein the peptides confined within the micelles form secondary structures.

11. The triblock peptide of claim 10, wherein the secondary structures are selected from the group consisting of α-helix, β-sheet, triple helix, 3-10 helix, random coil and combinations thereof.

12. A pharmaceutical composition, the composition comprising a triblock peptide of the formula:

A-B-C wherein

A is a lipid moiety, wherein the lipid moiety is PalmK or Palm2K; and

B and C are independently a peptide block or a zwitterion-like block, wherein one of B and C is a peptide block and the other of B and C is a zwitterion-like block;

wherein the peptide block is selected from the group consisting of SEQ ID NO: 1, SEQ ID NO: 2, SEQ ID NO: 3, or SEQ ID NO: 4; and the zwitterion-like block is $(EK)_4$ or $(KE)_4$; and a pharmaceutically acceptable carrier, wherein the triblock peptide is arranged in a micelle.

13. The pharmaceutical composition of claim 12, wherein the composition is a vaccine composition and further comprises an immune effective amount of an adjuvant.

14. The pharmaceutical composition of claim 13, wherein the adjuvant is selected from the group consisting of analgesic adjuvant, an inorganic compound, a mineral oil, a bacterial product, a delivery system, a cytokine, a food-based oil, a nonbacterial organic compound, an oligonucleotide, a plant based saponin and combinations thereof.

15. The pharmaceutical composition of claim 13, wherein the adjuvant is selected from the group consisting of an aluminium salt, aluminium hydroxide, aluminium phosphate, a salt of calcium, iron or zinc, an insoluble suspension of acylated tyrosine or acylated sugars, cationically or anionically derivatised saccharides, polyphosphazenes, biodegradable microspheres, ceramide, monophosphoryl lipid A (MPLA), lipid A derivatives (e.g., of reduced toxicity), 3-O-deacylated MPL [3D-MPL], quit A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, poly(I:C), bioadhesives and mucoadhesives, microparticles, liposomes, polyoxyethylene ether formulations, polyoxyethylene ester formulations, muramyl peptides, squalamine and its derivatives, squalene and its derivatives, or imidazoquinolone compounds (e.g., imiquamod and its homologues), human immunomodulators, cytokines, interleukins (e.g., IL-1, IL-2, IL-4, IL-5, IL-6, IL-7, IL-12, etc.), macrophage colony stimulating factor (M-CSF), tumour necrosis factor (TNF), granulocyte, macrophage colony stimulating factor (GM-CSF) and combinations thereof.

16. The pharmaceutical composition of claim 12, wherein the composition is selected from the group consisting of immunogenic compositions immunomodulatory compositions, and anti-cancer compositions.

17. The pharmaceutical composition of claim 12, wherein the micelles are from 4 nm to 100 μm in greatest dimension.

18. The pharmaceutical composition of claim 12, wherein the micelles form structures selected from the group consisting of spheres, cylinders, worm-like structures and combinations thereof.

19. The pharmaceutical composition of claim 12, wherein the micelles form higher-order structures.

20. The pharmaceutical composition of claim 19, wherein the higher-order structures are selected from the group consisting of clusters, twines, braids, nets and combinations thereof.

21. The pharmaceutical composition of claim 19, wherein the higher-order structures are from 10 nm to 100 μm in greatest dimension.

22. The pharmaceutical composition of claim 12, wherein the peptides confined within the micelles form secondary structures.

23. The pharmaceutical composition of claim 22, wherein the secondary structures are selected from the group consisting of α-helix, β-sheet, triple helix, 3-10 helix, random coil and combinations thereof.

24. The triblock peptide of claim 1, wherein the micelles form spheres.

25. The triblock peptide of claim 1, wherein triblock peptide comprises double fatty acid lipid conjugation.

26. The triblock peptide of claim 1, wherein the lipid moiety is PalmK.

27. The triblock peptide of claim 1, wherein the lipid moiety is Palm2K.

28. The triblock peptide of claim 4, wherein the lipid moiety is PalmK.

29. The triblock peptide of claim 4, wherein the lipid moiety is Palm2K.

30. The pharmaceutical composition of claim 12, wherein the lipid moiety is PalmK.

31. The pharmaceutical composition of claim 12, wherein the lipid moiety is Palm2K.

32. The triblock peptide of claim 1, wherein the peptide is selected from SEQ ID NO: 1 and SEQ ID NO: 2.

33. The triblock peptide of claim 4, wherein the peptide is selected from SEQ ID NO: 1 and SEQ ID NO: 2.

34. The pharmaceutical composition of claim 12, wherein the peptide is selected from SEQ ID NO: 1 and SEQ ID NO: 2.

* * * * *

SEQUENCE LISTING

```
<160> NUMBER OF SEQ ID NOS: 89

<210> SEQ ID NO 1
<211> LENGTH: 22
<212> TYPE: PRT
<213> ORGANISM: Artificial Sequence
<220> FEATURE:
<223> OTHER INFORMATION: Synthetic

<400> SEQUENCE: 1

Glu Ser Leu Lys Ile Ser Gln Ala Val His Ala Ala His Ala Glu Ile
1               5                   10                  15

Asn Glu Ala Gly Arg Glu
            20


<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Glu Gln Leu Glu Ser Ile Ile Asn Phe Glu Lys Leu Thr Glu
1               5                   10


<210> SEQ ID NO 3
<211> LENGTH: 28
<212> TYPE: PRT
<213> ORGANISM: Artificial Sequence
<220> FEATURE:
<223> OTHER INFORMATION: Synthetic

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25


<210> SEQ ID NO 4
<211> LENGTH: 37
<212> TYPE: PRT
<213> ORGANISM: Artificial Sequence
<220> FEATURE:
<223> OTHER INFORMATION: Synthetic

<400> SEQUENCE: 4

Lys Glu Lys Glu Lys Glu Lys Glu Lys His Ser Asp Ala Val Phe Thr
1               5                   10                  15

Asp Asn Tyr Thr Arg Leu Arg Lys Gln Met Ala Val Lys Lys Tyr Leu
            20                  25                  30

Asn Ser Ile Leu Asn
        35
```

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Ile Met Tyr Asn Tyr Pro Ala Met
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Gln Gln Trp Asn Phe Ala Gly Ile
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Phe Gln Asp Ala Tyr Asn Ala Ala Gly Gly His Asn Ala Val Phe
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Asn Ala Asn Pro Asn Ala Asn Pro Asn Ala Asn Pro
1               5                   10

<210> SEQ ID NO 9
<211> LENGTH: 21
<212> TYPE: PRT
<213> ORGANISM: Artificial Sequence
<220> FEATURE:
<223> OTHER INFORMATION: Synthetic

<400> SEQUENCE: 9

Met Glu Val Gly Trp Tyr Arg Ser Pro Phe Ser Arg Val Val His Leu
1               5                   10                  15

Tyr Arg Asn Gly Lys
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Ser Ser Gln Asn Ser Ser Asp Lys Pro Val Ala His Val Val Ala Asn
1               5                   10                  15

```
His Gln Val Glu
            20


<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

Gly Val Thr Ser Ala Pro Asp Thr Arg Pro Ala Pro Gly Ser Thr Ala
1               5                   10                  15

Pro Pro Ala His
            20


<210> SEQ ID NO 12
<211> LENGTH: 21
<212> TYPE: PRT
<213> ORGANISM: Artificial Sequence
<220> FEATURE:
<223> OTHER INFORMATION: Synthetic

<400> SEQUENCE: 12

Phe Leu Leu His His Ala Phe Val Asp Ser Ile Phe Glu Gln Trp Leu
1               5                   10                  15

Gln Arg His Arg Pro
            20


<210> SEQ ID NO 13
<211> LENGTH: 23
<212> TYPE: PRT
<213> ORGANISM: Artificial Sequence
<220> FEATURE:
<223> OTHER INFORMATION: Synthetic

<400> SEQUENCE: 13

Arg Asn Gly Tyr Arg Ala Leu Met Asp Lys Ser Leu His Val Gly Thr
1               5                   10                  15

Gln Cys Ala Leu Thr Arg Arg
            20


<210> SEQ ID NO 14
<211> LENGTH: 16
<212> TYPE: PRT
<213> ORGANISM: Artificial Sequence
<220> FEATURE:
<223> OTHER INFORMATION: Synthetic

<400> SEQUENCE: 14

Trp Asn Arg Gln Leu Tyr Pro Glu Trp Thr Glu Ala Gln Arg Leu Asp
1               5                   10                  15


<210> SEQ ID NO 15
<211> LENGTH: 16
<212> TYPE: PRT
<213> ORGANISM: Artificial Sequence
<220> FEATURE:
<223> OTHER INFORMATION: Synthetic

<400> SEQUENCE: 15

Ala Gln Asn Ile Leu Leu Ser Asn Ala Pro Leu Gly Pro Gln Phe Pro
1               5                   10                  15
```

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Thr Ser Tyr Val Lys Val Leu His His Met Val Lys Ile Ser Gly
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Leu Leu Lys Tyr Arg Ala Arg Glu Pro Val Thr Lys Ala Glu
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Lys Ile Met Asp Gln Val Gln Gln Ala
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Arg Leu Gln Glu Asp Pro Pro Ala Gly Val
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Lys Leu Asp Val Gly Asn Ala Glu Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Tyr Leu Met Asp Thr Ser Gly Lys Val
1               5

<210> SEQ ID NO 22

<211> LENGTH: 9
<212> TYPE: PRT
<213> ORGANISM: Artificial Sequence
<220> FEATURE:
<223> OTHER INFORMATION: Synthetic

<400> SEQUENCE: 22

Ile Leu Asp Asp Ile Gly His Gly Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Leu Leu Asp Arg Phe Leu Ala Thr Val
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Phe Leu Tyr Asp Asp Asn Gln Arg Val
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ala Leu Met Glu Gln Gln His Tyr Val
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Leu Leu Ile Asp Asp Lys Gly Thr Ile Lys Leu
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Tyr Leu Ile Glu Leu Ile Asp Arg Val
1               5

<210> SEQ ID NO 28
<211> LENGTH: 9

<212> TYPE: PRT
<213> ORGANISM: Artificial Sequence
<220> FEATURE:
<223> OTHER INFORMATION: Synthetic

<400> SEQUENCE: 28

Asn Leu Met Glu Gln Pro Ile Lys Val
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Phe Leu Ala Glu Asp Ala Leu Asn Thr Val
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Ser Leu Leu Met Trp Ile Thr Gln Val
1               5

<210> SEQ ID NO 31
<211> LENGTH: 19
<212> TYPE: PRT
<213> ORGANISM: Artificial Sequence
<220> FEATURE:
<223> OTHER INFORMATION: Synthetic

<400> SEQUENCE: 31

Asp Thr Cys Pro Pro Leu Met Leu Tyr Asn Pro Thr Thr Tyr Gln Met
1               5                   10                  15

Asp Val Asn

<210> SEQ ID NO 32
<211> LENGTH: 19
<212> TYPE: PRT
<213> ORGANISM: Artificial Sequence
<220> FEATURE:
<223> OTHER INFORMATION: Synthetic

<400> SEQUENCE: 32

Leu His Cys Pro Ala Leu Val Thr Tyr Asn Thr Asp Thr Phe Glu Ser
1               5                   10                  15

Met Pro Asn

<210> SEQ ID NO 33
<211> LENGTH: 19
<212> TYPE: PRT
<213> ORGANISM: Artificial Sequence
<220> FEATURE:
<223> OTHER INFORMATION: Synthetic

<400> SEQUENCE: 33

Pro Arg Cys Pro Gln Pro Leu Val Tyr Asn Lys Leu Thr Phe Gln Leu
1               5                   10                  15

Glu Pro Asn

<210> SEQ ID NO 34
<211> LENGTH: 19
<212> TYPE: PRT
<213> ORGANISM: Artificial Sequence
<220> FEATURE:
<223> OTHER INFORMATION: Synthetic

<400> SEQUENCE: 34

Thr Gln Cys Pro Gln Thr Phe Val Tyr Asn Pro Thr Thr Phe Gln Leu
1 5 10 15

Glu His Asn

<210> SEQ ID NO 35
<211> LENGTH: 13
<212> TYPE: PRT
<213> ORGANISM: Artificial Sequence
<220> FEATURE:
<223> OTHER INFORMATION: Synthetic

<400> SEQUENCE: 35

Met Leu Tyr Asn Pro Thr Thr Tyr Gln Met Asp Val Asn
1 5 10

<210> SEQ ID NO 36
<211> LENGTH: 13
<212> TYPE: PRT
<213> ORGANISM: Artificial Sequence
<220> FEATURE:
<223> OTHER INFORMATION: Synthetic

<400> SEQUENCE: 36

Val Thr Tyr Asn Thr Asp Thr Phe Glu Ser Met Pro Asn
1 5 10

<210> SEQ ID NO 37
<211> LENGTH: 13
<212> TYPE: PRT
<213> ORGANISM: Artificial Sequence
<220> FEATURE:
<223> OTHER INFORMATION: Synthetic

<400> SEQUENCE: 37

Leu Val Tyr Asn Lys Leu Thr Phe Gln Leu Glu Pro Asn
1 5 10

<210> SEQ ID NO 38
<211> LENGTH: 13
<212> TYPE: PRT
<213> ORGANISM: Artificial Sequence
<220> FEATURE:
<223> OTHER INFORMATION: Synthetic

<400> SEQUENCE: 38

Phe Val Tyr Asn Pro Thr Thr Phe Gln Leu Glu His Asn
1 5 10

<210> SEQ ID NO 39
<211> LENGTH: 16
<212> TYPE: PRT
<213> ORGANISM: Artificial Sequence
<220> FEATURE:
<223> OTHER INFORMATION: Synthetic

<400> SEQUENCE: 39

Asp Thr Cys Pro Pro Leu Met Leu Tyr Asn Pro Thr Thr Tyr Gln Met
1 5 10 15

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Leu His Cys Pro Ala Leu Val Thr Tyr Asn Thr Asp Thr Phe Glu Ser
1 5 10 15

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Pro Arg Cys Pro Gln Pro Leu Val Tyr Asn Lys Leu Thr Phe Gln Leu
1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Thr Gln Cys Pro Gln Thr Phe Val Tyr Asn Pro Thr Thr Phe Gln Leu
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: Synthetic

<400> SEQUENCE: 43

Arg Met Trp Pro Ser Ser Thr Val Asn Leu Ser Ala Gly Arg Arg
1 5 10 15

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Tyr Ile Leu Ile His Arg Asn
1 5

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

Pro Asn Leu Asp Phe Ser Pro Thr Cys Ser Phe Arg Phe Gly Cys

```
1               5                   10                  15


<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Pro Thr Leu Asp Pro Leu Pro
1               5


<210> SEQ ID NO 47
<211> LENGTH: 20
<212> TYPE: PRT
<213> ORGANISM: Artificial Sequence
<220> FEATURE:
<223> OTHER INFORMATION: Synthetic

<400> SEQUENCE: 47

Ser Ala Lys Thr Ala Val Ser Gln Arg Val Trp Leu Pro Ser His Arg
1               5                   10                  15

Gly Gly Glu Pro
            20


<210> SEQ ID NO 48
<211> LENGTH: 14
<212> TYPE: PRT
<213> ORGANISM: Artificial Sequence
<220> FEATURE:
<223> OTHER INFORMATION: Synthetic

<400> SEQUENCE: 48

Glu Tyr Val Asn Cys Asp Asn Leu Val Gly Asn Cys Val Ile
1               5                   10


<210> SEQ ID NO 49
<211> LENGTH: 24
<212> TYPE: PRT
<213> ORGANISM: Artificial Sequence
<220> FEATURE:
<223> OTHER INFORMATION: Synthetic

<400> SEQUENCE: 49

Met Ser Leu Leu Thr Glu Val Glu Thr Pro Ile Arg Asn Glu Trp Gly
1               5                   10                  15

Cys Arg Cys Asn Asp Ser Ser Asp
            20


<210> SEQ ID NO 50
<211> LENGTH: 23
<212> TYPE: PRT
<213> ORGANISM: Artificial Sequence
<220> FEATURE:
<223> OTHER INFORMATION: Synthetic

<400> SEQUENCE: 50

Gly Leu Phe Gly Ala Ile Ala Gly Phe Ile Glu Asn Gly Trp Glu Gly
1               5                   10                  15

Met Ile Asp Gly Trp Tyr Gly
            20


<210> SEQ ID NO 51
<211> LENGTH: 8
```

<212> TYPE: PRT
<213> ORGANISM: Artificial Sequence
<220> FEATURE:
<223> OTHER INFORMATION: Synthetic

<400> SEQUENCE: 51

```
Ile Leu Arg Thr Gln Ser Glu Cys
1               5
```

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

```
Thr Tyr Gln Arg Thr Arg Ala Leu Val
1               5
```

<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

```
Arg Glu Ser Arg Asn Pro Gly Asn Ala
1               5
```

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

```
Lys Glu Phe Ser Glu Val Glu Gly Arg Ile Gln Asp Leu Glu Lys Tyr
1               5                   10                  15

Val
```

<210> SEQ ID NO 55
<211> LENGTH: 15
<212> TYPE: PRT
<213> ORGANISM: Artificial Sequence
<220> FEATURE:
<223> OTHER INFORMATION: Synthetic

<400> SEQUENCE: 55

```
Phe Phe Leu Leu Thr Arg Ile Leu Thr Ile Pro Gln Ser Leu Asp
1               5                   10                  15
```

<210> SEQ ID NO 56
<211> LENGTH: 32
<212> TYPE: PRT
<213> ORGANISM: Artificial Sequence
<220> FEATURE:
<223> OTHER INFORMATION: Synthetic

<400> SEQUENCE: 56

```
Ile Leu Met Gln Tyr Ile Lys Ala Asn Ser Lys Phe Ile Gly Ile Pro
1               5                   10                  15

Met Gly Leu Pro Gln Ser Ile Ala Leu Ser Ser Leu Met Val Ala Gln
            20                  25                  30
```

<210> SEQ ID NO 57
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: UNSURE
<222> LOCATION: (5)..(5)
<223> OTHER INFORMATION: Xaa = unknown

<400> SEQUENCE: 57

Ala Ala Lys Phe Xaa Val Ala Ala Trp Thr Leu Lys Ala Ala Ala Ala
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: Synthetic

<400> SEQUENCE: 58

Glu Lys Val Tyr Leu Ala Trp Val Pro Ala His Lys Gly Ile Gly
1 5 10 15

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Asn Trp Tyr Leu Pro Trp Leu Gly Thr Asn Asp Trp
1 5 10

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Ala Thr Pro Glu Asp Asn Gly Arg Ser Phe Ser
1 5 10

<210> SEQ ID NO 61
<211> LENGTH: 12
<212> TYPE: PRT
<213> ORGANISM: Artificial Sequence
<220> FEATURE:
<223> OTHER INFORMATION: Synthetic

<400> SEQUENCE: 61

Trp Pro Arg Phe His Ser Ser Val Phe His Thr His
1 5 10

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Thr Pro Ala Phe Arg Tyr Ser
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Leu Val Ser Asp Gly Gly Pro Asn Leu Tyr
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Phe Tyr Ile Gln Met Cys Thr Glu Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Ala Ser Asn Glu Asn Met Glu Thr Met
1               5

<210> SEQ ID NO 66
<211> LENGTH: 10
<212> TYPE: PRT
<213> ORGANISM: Artificial Sequence
<220> FEATURE:
<223> OTHER INFORMATION: Synthetic

<400> SEQUENCE: 66

Ser Ser Leu Glu Asn Phe Arg Ala Tyr Val
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic

<400> SEQUENCE: 67

Gly Ile Leu Gly Phe Val Phe Thr Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Phe Met Tyr Ser Asp Phe His Phe Ile
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Ala Ile Met Asp Lys Asn Ile Ile Leu
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ser Glu Arg Ser Met Asn Phe
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic

<400> SEQUENCE: 71

Tyr Gly Leu Pro His Lys Phe
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic

<400> SEQUENCE: 72

Pro Ser Gly Ala Ala Arg Ala
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic

<400> SEQUENCE: 73

Thr His Ala Leu Trp His Thr
1               5

<210> SEQ ID NO 74
<211> LENGTH: 16
<212> TYPE: PRT
<213> ORGANISM: Artificial Sequence
<220> FEATURE:
<223> OTHER INFORMATION: Synthetic

<400> SEQUENCE: 74

Arg Arg Lys Lys Trp Leu Val Phe Phe Val Ile Phe Tyr Phe Phe Arg

```
1               5                   10                  15


<210> SEQ ID NO 75
<211> LENGTH: 11
<212> TYPE: PRT
<213> ORGANISM: Artificial Sequence
<220> FEATURE:
<223> OTHER INFORMATION: Synthetic

<400> SEQUENCE: 75

Asn Gly Glu Ser Ser Ala Asp Trp Ala Lys Asn
1               5                   10


<210> SEQ ID NO 76
<211> LENGTH: 25
<212> TYPE: PRT
<213> ORGANISM: Artificial Sequence
<220> FEATURE:
<223> OTHER INFORMATION: Synthetic

<400> SEQUENCE: 76

Met Asp Val Asn Pro Thr Leu Leu Phe Leu Lys Val Pro Ala Gln Asn
1               5                   10                  15

Ala Ile Ser Thr Thr Phe Pro Tyr Thr
            20                  25


<210> SEQ ID NO 77
<211> LENGTH: 16
<212> TYPE: PRT
<213> ORGANISM: Artificial Sequence
<220> FEATURE:
<223> OTHER INFORMATION: Synthetic

<400> SEQUENCE: 77

Trp Leu Val Phe Phe Val Ile Phe Tyr Phe Phe Arg Arg Arg Lys Lys
1               5                   10                  15


<210> SEQ ID NO 78
<211> LENGTH: 12
<212> TYPE: PRT
<213> ORGANISM: Artificial Sequence
<220> FEATURE:
<223> OTHER INFORMATION: Synthetic

<400> SEQUENCE: 78

Ser Lys His Ser Ser Leu Asp Cys Val Leu Arg Pro
1               5                   10


<210> SEQ ID NO 79
<211> LENGTH: 13
<212> TYPE: PRT
<213> ORGANISM: Artificial Sequence
<220> FEATURE:
<223> OTHER INFORMATION: Synthetic

<400> SEQUENCE: 79

Arg Arg Lys Lys Leu Ala Val Leu Leu Ala Leu Leu Ala
1               5                   10


<210> SEQ ID NO 80
<211> LENGTH: 19
<212> TYPE: PRT
<213> ORGANISM: Artificial Sequence
<220> FEATURE:
<223> OTHER INFORMATION: Synthetic

<400> SEQUENCE: 80
```

Cys Ala Thr Cys Glu Gln Ile Ala Asp Ser Gln His Arg Ser His Arg
1 5 10 15

Gln Met Val

<210> SEQ ID NO 81
<211> LENGTH: 23
<212> TYPE: PRT
<213> ORGANISM: Artificial Sequence
<220> FEATURE:
<223> OTHER INFORMATION: Synthetic

<400> SEQUENCE: 81

Tyr Asn Phe Thr Asn Arg Lys Ile Ser Val Gln Arg Leu Ala Ser Tyr
1 5 10 15

Arg Arg Ile Thr Ser Ser Lys
20

<210> SEQ ID NO 82
<211> LENGTH: 37
<212> TYPE: PRT
<213> ORGANISM: Artificial Sequence
<220> FEATURE:
<223> OTHER INFORMATION: Synthetic

<400> SEQUENCE: 82

Leu Leu Gly Asp Phe Phe Arg Lys Ser Lys Glu Lys Ile Gly Lys Glu
1 5 10 15

Phe Lys Arg Ile Val Gln Arg Ile Lys Asp Phe Leu Arg Asn Leu Val
20 25 30

Pro Arg Thr Glu Ser
35

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Cys Ser Pro Gly Ala Lys Val Arg Cys
1 5

<210> SEQ ID NO 84
<211> LENGTH: 4
<212> TYPE: PRT
<213> ORGANISM: Artificial Sequence
<220> FEATURE:
<223> OTHER INFORMATION: Synthetic

<400> SEQUENCE: 84

Phe Met Leu Pro
1

<210> SEQ ID NO 85
<211> LENGTH: 21
<212> TYPE: PRT
<213> ORGANISM: Artificial Sequence
<220> FEATURE:
<223> OTHER INFORMATION: Synthetic

<400> SEQUENCE: 85

Glu Thr Pro Phe Thr Trp Glu Glu Ser Asn Ala Tyr Tyr Trp Gln Pro
1 5 10 15

```
Tyr Ala Leu Pro Leu
            20


<210> SEQ ID NO 86
<211> LENGTH: 12
<212> TYPE: PRT
<213> ORGANISM: Artificial Sequence
<220> FEATURE:
<223> OTHER INFORMATION: Synthetic

<400> SEQUENCE: 86

Val Arg Leu Ile Val Ala Val Arg Ile Trp Arg Arg
1               5                   10


<210> SEQ ID NO 87
<211> LENGTH: 23
<212> TYPE: PRT
<213> ORGANISM: Artificial Sequence
<220> FEATURE:
<223> OTHER INFORMATION: Synthetic

<400> SEQUENCE: 87

Lys Ala Phe Ala Lys Leu Ala Ala Arg Leu Tyr Arg Lys Ala Leu Ala
1               5                   10                  15

Arg Gln Leu Gly Val Ala Ala
            20


<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Tyr Cys Trp Ser Gln Tyr Leu Cys Tyr
1               5


<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Lys Glu Lys Glu Lys Glu Lys Glu
1               5
```